US012646586B2

(12) United States Patent
Nakamura et al.

(10) Patent No.: US 12,646,586 B2
(45) Date of Patent: *Jun. 2, 2026

(54) METHOD FOR DESIGNING RNA BINDING PROTEIN UTILIZING PPR MOTIF, AND USE THEREOF

(71) Applicant: KYUSHU UNIVERSITY, NATIONAL UNIVERSITY CORPORATION, Fukuoka (JP)

(72) Inventors: Takahiro Nakamura, Fukuoka (JP); Yusuke Yagi, Fukuoka (JP); Keiko Kobayashi, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/221,440

(22) Filed: Jul. 13, 2023

(65) Prior Publication Data

US 2024/0047005 A1    Feb. 8, 2024
US 2026/0134942 A9    May 14, 2026

Related U.S. Application Data

(60) Division of application No. 17/195,449, filed on Mar. 8, 2021, now Pat. No. 11,742,056, which is a division of application No. 16/894,295, filed on Jun. 5, 2020, now Pat. No. 10,943,671, which is a continuation of application No. 16/431,429, filed on Jun. 4, 2019, now Pat. No. 10,679,731, which is a division of application No. 15/962,127, filed on Apr. 25, 2018, now Pat. No. 10,340,028, which is a division of (Continued)

(51) Int. Cl.
| | |
|---|---|
| *G16B 15/00* | (2019.01) |
| *C07K 14/415* | (2006.01) |
| *C12N 15/82* | (2006.01) |
| *C12Q 1/68* | (2018.01) |
| *G01N 33/53* | (2006.01) |
| *G16B 20/30* | (2019.01) |
| *G16B 20/50* | (2019.01) |
| *G16B 30/00* | (2019.01) |
| *G16B 30/10* | (2019.01) |
| *G16B 35/00* | (2019.01) |
| *G16C 20/60* | (2019.01) |
| *G16B 20/00* | (2019.01) |

(52) U.S. Cl.
CPC ............ *G16B 15/00* (2019.02); *C07K 14/415* (2013.01); *C12N 15/8216* (2013.01); *C12N 15/8287* (2013.01); *C12N 15/8289* (2013.01); *C12Q 1/68* (2013.01); *G01N 33/5308* (2013.01); *G16B 20/30* (2019.02); *G16B 20/50* (2019.02); *G16B 30/00* (2019.02); *G16B 30/10* (2019.02); *G16B 35/00*

(2019.02); *G16C 20/60* (2019.02); *C07K 2319/85* (2013.01); *C12Q 2522/101* (2013.01); *G16B 20/00* (2019.02)

(58) Field of Classification Search
CPC ........ G16B 15/00; G16B 20/30; G16B 30/00; C12N 15/8216; C12Q 1/68; C12Q 2522/101; G01N 33/5308; C07K 2319/85
See application file for complete search history.

(56) References Cited

U.S. PATENT DOCUMENTS

| | | | |
|---|---|---|---|
| 2004/0088749 A1 | 5/2004 | Imamura et al. | |
| 2004/0117868 A1 | 6/2004 | Mamura et al. | |

(Continued)

FOREIGN PATENT DOCUMENTS

| | | |
|---|---|---|
| EP | 1382612 A1 | 1/2004 |
| EP | 1 586 652 A1 | 10/2005 |

(Continued)

OTHER PUBLICATIONS

Fuji et al. PNAS, Jan. 25, 2011, vol. 108, No. 4; pp. 1723-1728.*

(Continued)

*Primary Examiner* — Jeanette M Lieb
(74) *Attorney, Agent, or Firm* — WHDA, LLP

(57)    ABSTRACT

A method for designing a protein capable of binding in an RNA base selective manner or RNA base sequence specific manner is provided. The protein of the present invention is a protein containing one or more of PPR motifs (preferably 2 to 14 PPR motifs) each consisting of a polypeptide of 30- to 38-amino acid length represented by the formula 1 (wherein Helix A is a moiety of 12-amino acid length capable of forming an α-helix structure, and is represented by the formula 2, wherein, in the formula 2, $A_1$ to $A_{12}$ independently represent an amino acid; X does not exist, or is a moiety of 1- to 9-amino acid length; Helix B is a moiety of 11- to 13-amino acid length capable of forming an α-helix structure; and L is a moiety of 2- to 7-amino acid length represented by the formula 3, wherein, in the formula 3, the amino acids are numbered "i" (−1), "ii" (−2), and so on from the C-terminus side, provided that $L_{iii}$ to $L_{vii}$ may not exist), and combination of three amino acids $A_1$, $A_4$ and $L_{ii}$, or combination of two amino acids $A_4$, and $L_{ii}$ is a combination corresponding to a target RNA base or base sequence.

9 Claims, 67 Drawing Sheets

Specification includes a Sequence Listing.

Related U.S. Application Data application No. 15/335,243, filed on Oct. 26, 2016, now Pat. No. 9,984,202, which is a division of application No. 14/352,697, filed as application No. PCT/JP2012/077274 on Oct. 22, 2012, now Pat. No. 9,513,283.

(56) References Cited

U.S. PATENT DOCUMENTS

| | | |
|---|---|---|
| 2010/0199376 A1 | 8/2010 | Imamura et al. |
| 2011/0060033 A1 | 3/2011 | Toriyama et al. |

FOREIGN PATENT DOCUMENTS

| | | | |
|---|---|---|---|
| EP | 2258165 A1 | 12/2010 |
| JP | 2002355041 A | 12/2002 |
| JP | 2003-289879 A | 10/2003 |
| WO | 2002/088179 A1 | 11/2002 |
| WO | 2009/113249 A1 | 9/2009 |
| WO | 2011072246 A2 | 3/2011 |
| WO | 2011/111829 A1 | 9/2011 |
| WO | 2013/058404 A1 | 4/2013 |
| WO | 2013155555 A1 | 10/2013 |

OTHER PUBLICATIONS

Small and Peeters. The PPR motif—a TPR-related motif prevalent in plant organellar proteins. Protein Motifs, Station de Génétique, INRA, Tibs 25, Feb. 2000, p. 47-48.*

Morgan L Maeder et al. Rapid "Open-Source" Engineering of Customized Zinc-Finger Nucleases for Highly Efficient Gene Modification. Molecular Cell 31, pp. 294-301, Jul. 25, 2008.

Jeffrey C Miller et al. A Tale nuclease architecture for efficient genome editing, Nature Biotechnology, Feb. 2007, vol. 29, No. 2. (8 pages).

Xiaoqiang Wang et al. Modular Recognition of RNA by a Human Pumilio-Homology Domain, Cell, vol. 110, pp. 501-512, Aug. 23, 2002, Plant Biology Division, The Noble Foundation, Ardmore, Oklahoma 73402.

Jason D. Gillman et al., The petunia restorer of fertility protein is part of a large mitochondrial complex that interacts with transcripts of the CMS-associated locus, Plant J., 2007, vol. 49 No. 2, pp. 217-227.

Sota Fukii et al., Selection patterns on restorer-like genes reveal a conflict between nuclear and mitochondrial genomes throughout angiosperm evolution, Proc. Natl. Acad. Sci. USA, Jan. 25, 2011, vol. 108, No. 4, pp. 1723-1723.

Shuyun Dong et al., Specific and modular binding code for cytosine recognition in Pumilio/FBF (PUF) Rna-binding domains, J. Biol. Cem., Jul. 29, 2011, vol. 286, No. 30, pp. 26732-26742.

Nobuya Koizuka et al., Genetic characterization of a pentatricopeptide repeat protein gene, orf687, that restores fertilit in the cytoplasmic male-sterile kosena radish, Plant j., 2003, vol. 34 No. 4, pp. 407-415.

Alice Barkan et al., A combinatorial amino acid code for RNA recognition by pentatricopeptide repeat proteins, PloS Genet., Aug. 16, 2012, vol. 8 No. 8, e1002910.

Keiko Kobayashi et al., Identification and caracterizaiton of the RNA binding surface of the pentaricopeptide repeat protein, Nucleic Acids REs., Mar. 2012., vol. 40, No. 6, pp. 2712-2723, Epub. Nov. 29, 2011.

Takahiro Nakamura et., Mechanistic insight into pentatricopeptide repeat proteins as sequence-specific RNA-Binding proteins for organellar RNAs in plants, Plant Cell Physiol., Jul. 2012, vol. 53, No. 7, pp. 1171-1179, Epub. Sep. 5, 2012.

International Preliminary Report on Patentability (Chapter II of the Patent Coperation Treaty) (Form PCT/IPEA/416) of the International Application No. PCT/JP2012/077274 mailed Feb. 25, 2014 with form PCT/IPEA/409. (24 pages).

Office Action dated Mar. 26, 2021, issued in counterpart Australian Patent Application No. 20219280013 (4 pages; English).

Cheom-Gil Ceong et al., Engineering RNA sequence specificity of Pumilio repeats, PNAS, Sep. 12, 2006, vol. 103, No. 37 pp. 13635-13639.

Jan D. Small et al., The PPR motif-a TPR-related motif prevalent in plant organellar proteins, TIBS Feb. 25, 2000, Station de Genetiquem INRA, Route de st-Cyr.

Jesse D Woodson et al. Coordination of gene expression between organellar and nuclear genomes, Nature Reviews Genetics, vol. 9, May 2008.

Sophie Desloire et al., "Identification of the fertility restoration locus, Rfo, in radish, as a member od the pentatricopeptide-repeat protein family", Jun. 1, 2003, EMBO reports vol. 4, No. 6, pp. 558-594, cited in Extended European Search Report dated Jun. 2, 2015.

Extended European Search Report dated Jun. 2, 2015, issued in corresponding Patent Application No. 12841435.6 (7 pages).

Office Action dated Mar. 21, 2017, issued in counterpart European Application No. 12 841 435.6. (5 pages).

Office Action dated Mar. 31, 2017, issued in counterpart Australian Application No. 2012326971. (4 pages).

Office Action dated Aug. 1, 2017, issued in counterpart Japanese Application No. 2017-112765, with English translation (6 pages).

Office Action dated Aug. 1, 2017, issued in counterpart Japanese Application No. 2017-112764, with English translation (9 pages).

Office Action dated Nov. 30, 2017, issued in counterpart European Application No. 12 841 435.6 (5 pages).

English machine translation of WO2011/111289, cited in specification and international search report, previously filed with English abstract only on Oct. 26, 2016.

International Search Report dated Jan. 22, 2013, issued in corresponding International Application No. PCT/JP2012/077274, with forms PCT/ISA/210, PCT/ISA/237 and English translation, (13 pages).

Examination Report date Jan. 3, 2019, issued in counterpart Australian application No. 2017254874. (3 pages).

Office Action dated Jan. 8, 2019, issued in counterpart Japanese application No. 2017-244766, with English translation. (12 pages).

Office Action dated May 17, 2022, issued in counterpart JP application No. 2021-086108, with English translation. (9 pages).

Office action ated Mar. 23, 2021, issued in the counterpart Japanese Patent Application No. 2017-244766 (18 pages; w/ English machine translation).

* cited by examiner

FIG. 1A
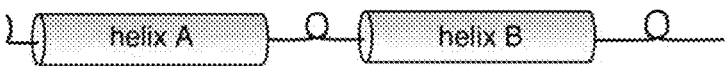
```
                       10 12 14 16 18 20 22 24 26 28 vii  v  iii  i
                  123456789 11 13 15 17 19 21 23 25 27 29  vi  iv  ii
      P   vtYntlIsglckaGrleeAlelfeeMkek-GiaPdv
      S   vvynaLidmYaKcGdleeArkvFdeMper-----dv
      L1  fTlasvLkACaslgaLslGkqiHgyviKs-Gfdsde
      L2  vTFlgVLsACSHsGLVeeGLeyFesMkekYGIePde
          *    *                                      *
```
FIG. 1B
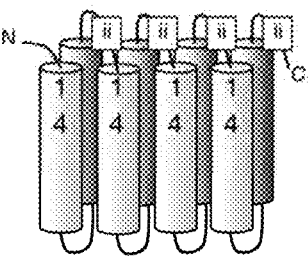
FIG. 1C
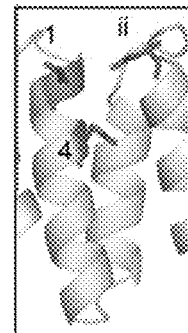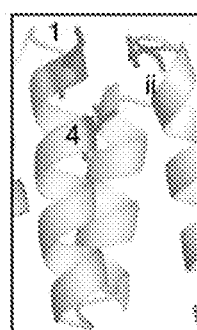

FIG. 2

| Name | AGI number | Localization | PPR code | Target RNA sequence | Editing site | ref* |
|------|-----------|--------------|----------|---------------------|--------------|------|
| AHG11 | At2g44880 | – | FND-FTD-YTS-VTD-VNT-ITN-VND-VLK-KTQ-AND-ILK-EGN | – | Unknown* | – |
| CLB19 | At1g05750 | Chl | VTN-IIH-MTN-VNW-AND-VIN-RNT-VND-VTR-EGI | acacgugcaa<br>agaagcccaa | rpoA(78691)<br>clpP(69942) | [1] |
| CRR21 | At5g55740 | Chl | EGN-YTN-FAD-FPC-FSN-VNT-VSD-ITD-VND-VAD-VSD-INN-INN-ITN-FTL-STE-PND-ITC-EGD | auguacagcggucaaauag | ndhD(116785) | [2] |
| CRR22 | At1g11290 | Chl | FTL-VHV-YTD-FTD-VNS-IVL-NTN-VNT-VMN-SNT-VND-FVN-FTH-TNN-VLS-DGA | aagcuuucccuagccc<br>uaugcagcuucaacau<br>auuaucuauucuaguuc | ndhB(96419)<br>ndhD(116281)<br>rpoB(25779) | [3] |
| CRR28 | At1g59720 | Chl | FGS-FND-HPD-YNS-VND-YQD-LND-ANN-VVA-EGD | aucuuuguag<br>aumuaugcag | ndhB(96698)<br>ndhD(116290) | [3] |
| CRR4 | At2g45350 | Chl | FND-FSD-FND-VNN-IND-INW-TDD-VND-TVG-KVS-DND-IVR-QGN | uaucuugucuuua | ndhD(117166) | [4] |
| LOI1 | At4g14850 | Mt | DGP-FNN-VTN-FPD-FCN-ENN-ICD-SNW-SAS-FST-FSN-VNN-MVG-EST | ugauacgauuaauu<br>uaauaccuuauuc<br>uaauuauugacou | nad4(161816)<br>cox3(218701)<br>ccb203(257133) | [5] |
| LPA66 | At5g48910 | Chl | LAN-FNN-FPD-FSE-VNS-VNN-VVD-VSN-ISS-VIR-EGD | uguaccuaccg | psbF(63985) | [6] |
| MEF1 | At5g52630 | Mt | NCI-LNS-TSD-HPD-FSN-VSN-YSS-FSN-GNN-ILT-KAW | accuacucauu<br>acagaagguuu<br>aacgaauccua | rps4(82161)<br>nad7(137931)<br>nad2(329886) | [7] |
| MEF9 | At1g62260 | Mt | VNW-TSD-FNW-ATA-VLL-YNN-VND-INW-MSH-VND-HTD-PNE-INS-IVQ-ESD | uucaagcuuuaccuu | nad7(133233) | [8] |
| MEF14 | At3g26780 | Mt | FNT-SPD-FSI-SSD-MVG-SND-VNN-ISD-ITN-RTN-IVG-EGG | aguacuccaaagcu | matR(144418) | [9] |
| MEF18 | At5g19020 | Mt | RVN-YND-ANS-VTN-VAR-FTN-VND-VGS-VVY-FAH-AND-FND-IVN-NAT-SNN-IVD-KGD | uccauaaauuucucg | nad4(167599) | [10] |
| MEF19 | At3g05240 | Mt | ISS-YND-FPN-YTN-VGN-TVN-ITT-VND-VLD-ACD-ITD-ILT-EGN | uuauugauugguu | ccb206(209125) | [10] |
| MEF20 | At3g18970 | Mt | RVS-LTW-AGT-TVD-FTN-FTN-ITV-EGD | cacgaaag | rps4(82691) | [10] |
| MEF21 | At2g20540 | Mt | FTN-FND-FPH-VND-INW-ASD-IIQ-GND-ISN-ILK-EGD | acuucgauaug | cox3(218536) | [10] |
| MEF22 | At3g12770 | Mt | FTQ-FND-FPD-FNT-VTD-VVE-DIN-IND-ITD-FSD-VSN-VLQ-QAG | uguggguucgauc | nad3(260858) | [10] |
| otp80 | At5g59200 | Chl | FFN-YTN-VSS-SLD-VTD-VTN-FVS-FND-INN-VVQ-EGD | ugucgaaucag | rpl23(86055) | [11] |
| otp81 | At2g29760 | Chl | FNN-YPD-FND-VNS-VVN-TND-VTW-ASN-IVN-HSD-FSN-VTE-KAS | auucuuuuugaaa | rps12(69553) | [11] |
| otp82 | At1g08070 | Chl | LNN-YPD-YTY-AKD-VND-SVN-KND-INN-VLA-STS-SND-IVK-EGD | uuaguuuuucugg<br>guagcugcuucag | ndhG(118858)<br>ndhB(95644) | [11]<br>[11] |
| otp84 | At3g57430 | Chl | EID-YPS-TNN-VNS-FVN-FND-VND-FSN-FSW-AAN-TAD-FNW-TTN-IMD-ASN-INN-VIS-DAN | auccacuuacuucuauua<br>uugcauuaauuauuacuu<br>gugugauagcaucoacua | ndhF(112349)<br>psbZ(35800)<br>ndhB(94999) | [11]<br>[11]<br>[11] |
| otp85 | At2g02980 | Chl | VND-YND-YPC-VNN-ILY-KTD-QSD-ILS-KGL | uugccguca | ndhD(116494) | [11] |
| otp86 | At3g63370 | Chl | FGT-FNG-SPT-FND-VNN-YVE-YND-VND-VTN-QND-ITD-MGD-VND-VTD-VLE-SVG-LTD-ILW-EVT | uaucauuugauucgucgau | rps14(37161) | [11] |
| otp87 | At1g74600 | Mt | FKD-NGY-IGY-VSN-YND-YSD-FTS-VTN-CTD-SAR-NND-FCD-TSD-AAD-SAG-DSD-VSD-FSE-SSD-ITD-VVE-RVW | ccaugacgacuaggaaaaggca<br>accuccgaauaaugaguaggua | nad7(132094)<br>atp1(82180) | [12] |
| SLO1 | At2g22410 | Mt | FND-FPV-HND-VND-VIT-PNT-VTW-AGD-IIN-ATN-LTD-IIQ-KSD | uuucccgaaagcg<br>auuuccaucagcc | nad4(162141)<br>nad9(23908) | [13] |
| YS1 | At3g22690 | Chl | FND-YPD-FNW-SCN-VVN-LSN-DND-ILW-NNT-VNW-TSD-VMD-RTD-STD-VVE-VGN | augaauucccuaggaa | rpoB(25779) | [14] |
| PpPPR_56 | – | Mt | FVN-HNS-ANN-GMD-RTD-ITN-IVD-RTD-VND-ILD-RTN-VND-VVD-SND | uuuggaagucaccu<br>uauagacgguaucu | nad3eU230S<br>nad4eU272S | [15]<br>[15] |
| PpPPR_71 | – | Mt | RVN-YNT-VNS-ILD-RTD-SNN-ILD-RTD-VTD-IMD-LTD-VSD-VIH-PND-INN-VVT-KGD | uuccacaggugcuccuu | ccmFCeU122SF | [16] |
| PpPPR_77 | – | Mt | AVD-FND-INN-IID-RND-VND-VID-RTD-VNN-TLD-QND-ING-VLN-HND-IND-IAD-NND-MTV-SSD-GND-VNN-FVD-RAN-VND-STT-EGN | caauuacuaucaaagcuauuggacau<br>acuuuggcuuugaagcagcugcuugg | cox2eU270RW<br>cox3eU733RW | [15]<br>[15] |
| PpPPR_78 | – | Mt | SMD-YNT-HND-TMD-KNS-VTN-IID-ATD-INN-IVD-GND-ITN-VTD-HND-VND-VID-SNN-IND-VVT-EGN | uccugaggucuauauucuaa<br>acguuaugaauauuuuuaa | cox1eU755SL<br>rps14eU137SL | [17] |
| PpPPR_79 | – | Mt | YVN-YNS-VND-FVD-TND-VTS-IMD-RTD-IND-ATD-RND-VTN-IMD-AND-VNN-AVT-KAN | acuuuucgacuauuuu | nad5eU598RC | [17] |
| PpPPR_91 | – | Mt | SGN-NGD-YND-VSN-ILD-ATN-VTN-VVD-INS-MGN-VMD-STN-VTN-VND-VID-VTD-VNN-ITR-QGD | ugcacaaauaggauugcau | nad5eU730RW | [15] |

*[References]
1. Chateigner-Boutin, A.L., et al., Plant J., 2008, 56:590-602.
2. Okuda, K., et al., Proc. Natl. Acad. Sci. USA, 2007, 104:8178-8183.
3. Okuda, K., et al., Plant Cell, 2009, 21:146-156.
4. Kotera, E., M. Tasaka, and T. Shikanai, Nature, 2005, 433: p. 326-330.
5. Tang, J., et al., Plant J., 2010, 61:456-466.
6. Cai, W., et al., Plant Physiol., 2009, 150:1260-1271.
7. Zehrmann, A., et al., Plant Cell, 2009, 21:558-567.
8. Takenaka, M., Plant Physiol., 2009, 152:939-947.
9. Verbitskiy, D., et al., FEBS Lett., 2011, 585:700-704.
10. Takenaka, M., et al., J. Biol. Chem., 2010, 285:27122-27129.
11. Hammani, K., et al., Plant Cell, 2009, 21:3686-3699.
12. Hammani, K., et al., J. Biol. Chem., 2011, 286:21361-21371.
13. Sung, T.-Y., et al., Plant J., 2010, 63:499-511.
14. Zhou, W., et al., Plant J., 2009, 58: 82-96.
15. Ohtani, S., et al., Plant Cell Physiol., 2010, 51:1942-1949.
16. Tasaki, E., et al., Plant J., 2010, 62:560-570.
17. Uchida, M., et al., FEBS Lett., 2011, 585:2367-2371.

Alignment P4, Amino acid 3
Measured value

P values
Theoretical values (Median)      5.128E-07

| | total | A | U | G | C |
|---|---|---|---|---|---|
| A | 16.00 | 4.33 | 5.50 | 3.00 | 3.17 |
| C | 5.99 | 4.00 | 0.33 | 1.33 | 0.33 |
| D | 1.00 | 0.00 | 0.00 | 1.00 | 0.00 |
| F | 1.00 | 0.00 | 1.00 | 0.00 | 0.00 |
| G | 25.00 | 8.00 | 6.83 | 8.00 | 2.17 |
| H | 1.00 | 0.67 | 0.33 | 0.00 | 0.00 |
| I | 10.00 | 1.83 | 2.83 | 0.83 | 4.50 |
| K | 2.00 | 0.50 | 0.00 | 1.00 | 0.50 |
| L | 15.00 | 2.33 | 8.33 | 0.00 | 4.33 |
| N | 98.96 | 10.66 | 41.66 | 11.33 | 35.32 |
| M | 3.00 | 0.00 | 2.67 | 0.00 | 0.33 |
| P | 17.00 | 1.00 | 13.83 | 1.67 | 0.50 |
| Q | 1.00 | 0.00 | 1.00 | 0.00 | 0.00 |
| R | 1.00 | 1.00 | 0.00 | 0.00 | 0.00 |
| S | 41.99 | 15.83 | 12.33 | 8.83 | 5.00 |
| T | 53.99 | 26.67 | 7.17 | 16.17 | 4.00 |
| V | 33.00 | 9.50 | 13.17 | 2.83 | 7.50 |
| total | 326.92 | 86.32 | 116.98 | 55.98 | 67.64 |

| | total | A | U | G | C |
|---|---|---|---|---|---|
| | 16.00 | 4.22 | 5.72 | 2.74 | 3.31 |
| | 5.99 | 1.58 | 2.14 | 1.03 | 1.24 |
| | 1.00 | 0.26 | 0.36 | 0.17 | 0.21 |
| | 1.00 | 0.26 | 0.36 | 0.17 | 0.21 |
| | 25.00 | 6.60 | 8.94 | 4.28 | 5.17 |
| | 1.00 | 0.26 | 0.36 | 0.17 | 0.21 |
| | 10.00 | 2.64 | 3.58 | 1.71 | 2.07 |
| | 2.00 | 0.53 | 0.72 | 0.34 | 0.41 |
| | 15.00 | 3.96 | 5.37 | 2.57 | 3.10 |
| | 98.96 | 26.12 | 35.40 | 16.94 | 20.47 |
| | 3.00 | 0.79 | 1.07 | 0.51 | 0.62 |
| | 17.00 | 4.49 | 6.08 | 2.91 | 3.52 |
| | 1.00 | 0.26 | 0.36 | 0.17 | 0.21 |
| | 1.00 | 0.26 | 0.36 | 0.17 | 0.21 |
| | 41.99 | 11.08 | 15.02 | 7.19 | 8.69 |
| | 53.99 | 14.25 | 19.32 | 9.24 | 11.17 |
| | 33.00 | 8.71 | 11.80 | 5.65 | 6.83 |
| | 326.92 | 86.30 | 116.95 | 55.97 | 67.63 |

Alignment P4, Amino acid 3
Measured value

P values
Theoretical values (Median)      0.739419764

| | total | A | U | G | C |
|---|---|---|---|---|---|
| A | 73.979 | 13.165 | 28.658 | 15.662 | 16.494 |
| C | 26.995 | 7.666 | 9.499 | 8 | 1.83 |
| D | 3.999 | 2.333 | 0.333 | 1.333 | 0 |
| E | 4 | 1 | 2 | 0 | 1 |
| F | 6 | 0 | 4.5 | 0 | 1.5 |
| G | 34.984 | 8.329 | 12.331 | 6.163 | 8.161 |
| H | 2 | 0.5 | 1 | 0 | 0.5 |
| I | 5 | 1 | 1 | 0.5 | 2.5 |
| K | 6.999 | 2.666 | 2.333 | 0 | 1 |
| L | 5 | 1 | 1 | 1 | 2 |
| N | 7.999 | 4.333 | 2 | 0 | 1.666 |
| S | 94.974 | 28.494 | 34.992 | 10.995 | 20.493 |
| T | 40.995 | 11.332 | 11.665 | 9.166 | 8.832 |
| V | 10.999 | 2.5 | 4.333 | 2.5 | 1.666 |
| Y | 2.995 | 1.999 | 0.333 | 0.663 | 0 |
| total | 326.92 | 86.317 | 116.98 | 55.982 | 67.642 |

| | total | A | U | G | C |
|---|---|---|---|---|---|
| | 73.979 | 19.528 | 26.464 | 12.665 | 15.303 |
| | 26.995 | 7.1258 | 9.6569 | 4.6215 | 5.5841 |
| | 3.999 | 1.0556 | 1.4306 | 0.6846 | 0.8272 |
| | 4 | 1.0559 | 1.4309 | 0.6848 | 0.8274 |
| | 6 | 1.5838 | 2.1464 | 1.0272 | 1.2411 |
| | 34.984 | 9.2346 | 12.515 | 5.9892 | 7.2367 |
| | 2 | 0.5279 | 0.7155 | 0.3424 | 0.4137 |
| | 5 | 1.3198 | 1.7886 | 0.856 | 1.0343 |
| | 6.999 | 1.8475 | 2.5037 | 1.1982 | 1.4478 |
| | 5 | 1.3198 | 1.7886 | 0.856 | 1.0343 |
| | 7.999 | 2.1115 | 2.8615 | 1.3694 | 1.6546 |
| | 94.974 | 25.07 | 33.975 | 16.259 | 19.646 |
| | 40.995 | 10.821 | 14.665 | 7.0183 | 8.4801 |
| | 10.999 | 2.9034 | 3.9346 | 1.883 | 2.2752 |
| | 2.995 | 0.7906 | 1.0714 | 0.5127 | 0.6195 |
| | 326.92 | 86.30 | 116.95 | 55.97 | 67.63 |

FIG. 8

| PPR code | occurrence of the code | Nucleotide occurrence frequency | | | | Scoring matrix | | | | Probability matrix (for MEME) | | | |
|---|---|---|---|---|---|---|---|---|---|---|---|---|---|
| | | A | G | U | C | A | G | U | C | A | G | U | C |
| VND | 16 | 0.50 | 0.00 | 10.17 | 5.33 | -3.74 | -2.75 | 4.42 | 2.01 | 0.03 | 0.00 | 0.64 | 0.33 |
| FND | 12 | 1.83 | 1.00 | 6.83 | 2.33 | -1.34 | -1.06 | 2.53 | -0.16 | 0.15 | 0.08 | 0.57 | 0.19 |
| EGD | 7 | 0.00 | 7.00 | 0.00 | 0.00 | -1.85 | 5.80 | -2.51 | -1.45 | 0.00 | 1.00 | 0.00 | 0.00 |
| VNN | 7 | 1.33 | 0.00 | 0.33 | 5.33 | -0.52 | -1.20 | -2.18 | 3.88 | 0.19 | 0.00 | 0.05 | 0.76 |
| FSN | 6 | 4.67 | 0.33 | 0.33 | 0.67 | 3.08 | -0.70 | -1.82 | -0.58 | 0.78 | 0.06 | 0.06 | 0.11 |
| VTN | 6 | 3.50 | 1.50 | 0.00 | 1.00 | 1.91 | 0.47 | -2.15 | -0.24 | 0.58 | 0.25 | 0.00 | 0.17 |
| INN | 5 | 0.00 | 0.00 | 1.83 | 3.17 | -1.32 | -0.86 | 0.04 | 2.13 | 0.00 | 0.00 | 0.37 | 0.63 |
| ITD | 5 | 0.00 | 3.00 | 1.00 | 1.00 | -1.32 | 2.14 | -0.79 | -0.04 | 0.00 | 0.60 | 0.20 | 0.20 |
| FTN | 4 | 4.00 | 0.00 | 0.00 | 0.00 | 2.94 | -0.69 | -1.44 | -0.83 | 1.00 | 0.00 | 0.00 | 0.00 |
| TSD | 4 | 0.33 | 0.50 | 2.50 | 0.67 | -0.73 | -0.19 | 1.06 | -0.16 | 0.08 | 0.13 | 0.63 | 0.17 |
| VNS | 4 | 0.00 | 0.00 | 0.67 | 3.33 | -1.06 | -0.69 | -0.77 | 2.50 | 0.00 | 0.00 | 0.17 | 0.83 |
| VSN | 4 | 2.67 | 0.00 | 1.00 | 0.33 | 1.61 | -0.69 | -0.44 | -0.50 | 0.67 | 0.00 | 0.25 | 0.08 |
| YND | 4 | 0.00 | 0.50 | 3.00 | 0.50 | -1.06 | -0.19 | 1.56 | -0.33 | 0.00 | 0.13 | 0.75 | 0.13 |
| FNN | 3 | 1.67 | 1.33 | 0.00 | 0.00 | 0.87 | 0.81 | -1.08 | -0.62 | 0.56 | 0.44 | 0.00 | 0.00 |
| FNW | 3 | 0.33 | 1.00 | 0.67 | 1.00 | -0.46 | 0.48 | -0.41 | 0.38 | 0.11 | 0.33 | 0.22 | 0.33 |
| FPD | 3 | 0.00 | 0.00 | 3.00 | 0.00 | -0.79 | -0.52 | 1.92 | -0.62 | 0.00 | 0.00 | 1.00 | 0.00 |
| INW | 3 | 0.00 | 0.00 | 2.00 | 1.00 | -0.79 | -0.52 | 0.92 | 0.38 | 0.00 | 0.00 | 0.67 | 0.33 |
| VNW | 3 | 0.50 | 0.00 | 1.00 | 1.50 | -0.29 | -0.52 | -0.08 | 0.88 | 0.17 | 0.00 | 0.33 | 0.50 |
| VSD | 3 | 1.50 | 1.00 | 0.50 | 0.00 | 0.71 | 0.48 | -0.58 | -0.62 | 0.50 | 0.33 | 0.17 | 0.00 |
| VTD | 3 | 0.00 | 3.00 | 0.00 | 0.00 | -0.79 | 2.48 | -1.08 | -0.62 | 0.00 | 1.00 | 0.00 | 0.00 |
| VVE | 3 | 1.00 | 0.00 | 1.50 | 0.50 | 0.21 | -0.52 | 0.42 | -0.12 | 0.33 | 0.00 | 0.50 | 0.17 |
| YPD | 3 | 0.00 | 0.00 | 3.00 | 0.00 | -0.79 | -0.52 | 1.92 | -0.62 | 0.00 | 0.00 | 1.00 | 0.00 |
| YTN | 3 | 0.00 | 1.00 | 2.00 | 0.00 | -0.79 | 0.48 | 0.92 | -0.62 | 0.00 | 0.33 | 0.67 | 0.00 |
| ND | 48 | 3.83 | 5.00 | 30.50 | 8.67 | -8.84 | -3.22 | 13.32 | -1.27 | 0.08 | 0.10 | 0.64 | 0.18 |
| NN | 23 | 3.33 | 3.50 | 4.16 | 11.99 | -2.74 | -0.44 | -4.07 | 7.24 | 0.14 | 0.15 | 0.18 | 0.52 |
| TN | 20 | 12.83 | 2.83 | 2.67 | 1.67 | 7.55 | -0.59 | -4.49 | -2.47 | 0.64 | 0.14 | 0.13 | 0.08 |
| SD | 19 | 4.83 | 6.50 | 5.00 | 2.67 | -0.18 | 3.25 | -1.80 | -1.27 | 0.25 | 0.34 | 0.26 | 0.14 |
| TD | 17 | 2.33 | 11.67 | 1.67 | 1.33 | -2.16 | 8.75 | -4.42 | -2.18 | 0.14 | 0.69 | 0.10 | 0.08 |
| SN | 14 | 9.33 | 0.33 | 3.33 | 1.00 | 5.64 | -2.06 | -1.68 | -1.90 | 0.67 | 0.02 | 0.24 | 0.07 |
| GD | 10 | 0.50 | 8.00 | 1.50 | 0.00 | -2.14 | 6.29 | -2.08 | -2.07 | 0.05 | 0.80 | 0.15 | 0.00 |
| NW | 10 | 1.16 | 1.33 | 3.67 | 3.83 | -1.48 | -0.38 | 0.09 | 1.76 | 0.12 | 0.13 | 0.37 | 0.38 |
| PD | 9 | 0.00 | 0.67 | 7.83 | 0.50 | -2.38 | -0.88 | 4.61 | -1.36 | 0.00 | 0.07 | 0.87 | 0.06 |
| VN | 9 | 2.67 | 1.33 | 3.00 | 2.00 | 0.29 | -0.21 | -0.22 | 0.14 | 0.30 | 0.15 | 0.33 | 0.22 |
| NS | 8 | 0.33 | 0.00 | 2.67 | 5.00 | -1.78 | -1.37 | -0.20 | 3.34 | 0.04 | 0.00 | 0.33 | 0.62 |
| NT | 8 | 1.00 | 1.50 | 0.67 | 4.83 | -1.11 | 0.13 | -2.20 | 3.18 | 0.13 | 0.19 | 0.08 | 0.60 |
| GN | 5 | 3.00 | 0.00 | 2.00 | 0.00 | 1.68 | -0.86 | 0.21 | -1.03 | 0.60 | 0.00 | 0.40 | 0.00 |
| VG | 5 | 1.00 | 0.00 | 1.00 | 3.00 | -0.32 | -0.86 | -0.79 | 1.97 | 0.20 | 0.00 | 0.20 | 0.60 |
| AD | 4 | 0.33 | 3.00 | 0.67 | 0.00 | -0.72 | 2.32 | -0.77 | -0.83 | 0.08 | 0.75 | 0.17 | 0.00 |
| SS | 4 | 0.00 | 0.33 | 2.67 | 1.00 | -1.06 | -0.35 | 1.23 | 0.17 | 0.00 | 0.08 | 0.67 | 0.25 |
| VE | 4 | 1.00 | 0.00 | 2.50 | 0.50 | -0.06 | -0.68 | 1.07 | -0.33 | 0.25 | 0.00 | 0.63 | 0.13 |
| AN | 3 | 0.67 | 0.00 | 1.67 | 0.67 | -0.13 | -0.51 | 0.59 | 0.05 | 0.22 | 0.00 | 0.56 | 0.22 |
| CD | 3 | 1.00 | 1.33 | 0.33 | 0.33 | 0.21 | 0.82 | -0.74 | -0.29 | 0.33 | 0.44 | 0.11 | 0.11 |
| IN | 3 | 0.50 | 0.00 | 1.50 | 1.00 | -0.29 | -0.51 | 0.43 | 0.38 | 0.17 | 0.00 | 0.50 | 0.33 |
| TW | 3 | 1.50 | 0.50 | 1.00 | 0.00 | 0.71 | -0.01 | -0.07 | -0.62 | 0.50 | 0.17 | 0.33 | 0.00 |
| VD | 3 | 0.00 | 1.00 | 1.00 | 1.00 | -0.79 | 0.49 | -0.07 | 0.38 | 0.00 | 0.33 | 0.33 | 0.33 |
| VS | 3 | 1.00 | 0.00 | 1.00 | 1.00 | 0.21 | -0.51 | -0.07 | 0.38 | 0.33 | 0.00 | 0.33 | 0.33 |
| ¹ Background frequency | | 0.26 | 0.17 | 0.36 | 0.21 | 0.00 | 0.00 | 0.00 | 0.00 | 0.26 | 0.17 | 0.36 | 0.21 |

¹ The value indicates a probability of nucleotide occurrence for all RNA sequences surrounding the RNA editing sites used to construct the PPR code.
² The scoring matrix is estimated by a subtraction of the background frequency from the nucleotide occurrence frequency of the PPR code.
³ The probability matrix is obtained from the nucleotide occurrence frequency.

| | PpPPR_71 | PpPPR_79 | PpPPR_91 | PpPPR_78 | PpPPR_56 | PpPPR_77-1 |
|---|---|---|---|---|---|---|
| ccmFCeU122SF | | 8.2E-02 | 1.3E-01 | 1.1E-01 | 3.9E-03 | 2.4E-01 |
| nad5eU598RC | 7.9E-02 | 2.3E-03 | 4.0E-01 | 1.6E-01 | 7.3E-02 | 6.5E-02 |
| nad5eU730RW | 1.8E-03 | 1.8E-01 | | 1.1E-01 | 6.0E-02 | 3.4E-01 |
| cox1eU755SL | 4.1E-01 | 8.1E-01 | 2.5E-01 | 2.6E-03 | 8.3E-02 | 4.8E-02 |
| rps14eU137SL | 1.8E-01 | 3.5E-01 | 9.0E-01 | 1.5E-03 | 5.5E-02 | 3.6E-02 |
| nad5eU235SL | 2.0E-01 | 3.5E-01 | 1.4E-01 | 5.2E-02 | | 1.1E-01 |
| nad4eU272SL | 3.0E-01 | 7.4E-01 | 8.0E-01 | 1.6E-01 | 1.8E-03 | 1.4E-01 |
| cox2eU379RW | 2.5E-01 | 3.8E-01 | 3.0E-01 | 1.4E-01 | 8.4E-02 | 1.0E-01 |
| cox3eU733RW | 2.3E-02 | 2.5E-01 | 6.0E-02 | 8.8E-02 | 4.4E-01 | 1.0E-01 |
| ccmFCeU103PS | 4.3E-01 | 7.1E-02 | 8.8E-01 | 1.1E-01 | 8.3E-02 | 2.0E-01 |
| atp9eU82SL | 5.9E-01 | 1.9E-01 | 3.8E-02 | 1.1E-01 | 6.9E-02 | 7.2E-01 |
| rps14(cp)eU-1 | 8.3E-01 | 1.5E-01 | 1.3E-01 | 4.2E-01 | 5.0E-01 | 5.3E-01 |
| rps14(cp)eU2TM | 8.7E-01 | 1.1E-01 | 6.1E-01 | 9.4E-01 | 5.2E-01 | 9.0E-01 |

< 1.0E-03    < 5.0E-02

FIG. 13A
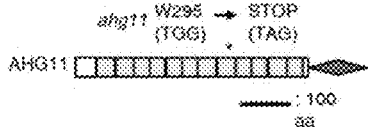
FIG. 13B
| Rank | Editing site | P-value | Editing status |
|---|---|---|---|
| 1 | nad4_1172 | 5.5E-04 | E |
| 2 | orf240_199 | 6.8E-04 | E |
| 3 | orf240A_115 | 6.8E-04 | E |
| 4 | rps3_64 | 6.8E-04 | E |
| 5 | nad4_877 | 1.1E-03 | E |
| 6 | nad5_609 | 1.4E-03 | E |
| 7 | nad4_376 | 1.7E-03 | Un |
| 8 | ccb8c_406 | 1.8E-03 | E |
| 9 | petL(65716) | 2.3E-03 | E |
| 10 | nad5_863 | 2.7E-03 | E |
FIG. 13C
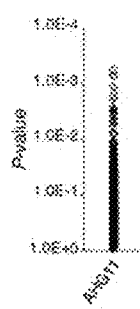
FIG. 13D
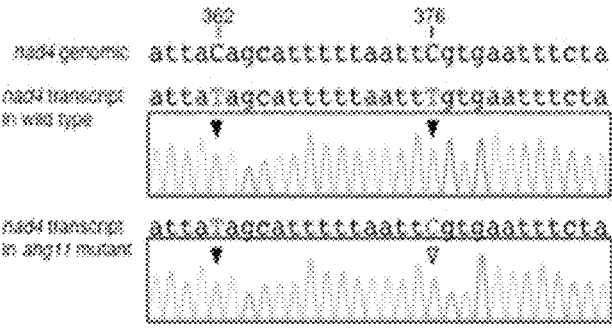

FIG. 14

| Protein | At code | | At + Pp code* | |
| | P-value | Rank | P-value | Rank |
| --- | --- | --- | --- | --- |
| CRR21 | 5.0e-8 | 1 | 1.0e-7 | 1 |
| CRR4 | 6.0e-6 | 1 | 6.0e-6 | 1 |
| LPA66 | 9.0e-5 | 21 | 4.0e-5 | 11 |
| OTP80 | >1.0e-5 | ND | 2.0e-5 | 8 |
| OTP81 | 9.0e-5 | 74 | 5.0e-5 | 45 |
| YS1 | 4.0e-5 | 21 | 3.0e-6 | 2 |

ND, not determined

FIG. 15

Table S5. List of scoring matrix for PPR code extracted from 414 PPR motifs in 24 *Arabidopsis* PPR proteins and 5 *Physcomitrella* PPR proteins

| PPR code | occurrence of the code | Nucleotide occurrence frequency | | | | Scoring matrix | | | | Probability matrix (for MEME) | | | | P (m) | P (RY) | P (WS) |
|---|---|---|---|---|---|---|---|---|---|---|---|---|---|---|---|---|
| | | A | G | U | C | A | G | U | C | A | G | U | C | | | |
| VND | 21 | 0.50 | 0.50 | 14.17 | 5.83 | 0.24 | 0.33 | 13.80 | 5.63 | 0.02 | 0.02 | 0.67 | 0.28 | | | 6.5.E-02 |
| FND | 12 | 1.83 | 1.00 | 6.83 | 2.33 | -3.65 | -2.53 | -0.84 | -1.87 | 0.15 | 0.08 | 0.57 | 0.19 | 7.7.E-02 | 8.8.E-02 | 1.2.E-01 |
| VTN | 10 | 7.50 | 1.50 | 0.00 | 1.00 | 4.37 | -0.52 | -4.39 | -1.46 | 0.75 | 0.15 | 0.00 | 0.10 | | | 1.1.E-01 |
| VNN | 9 | 1.33 | 0.00 | 1.33 | 6.33 | -1.28 | -1.68 | -2.33 | 4.28 | 0.15 | 0.00 | 0.15 | 0.70 | | | 2.2.E-01 |
| EGD | 7 | 0.00 | 7.00 | 0.00 | 0.00 | -2.35 | 5.49 | -3.29 | -1.84 | 0.00 | 1.00 | 0.00 | 0.00 | | | |
| INN | 7 | 0.50 | 0.00 | 2.33 | 4.17 | -1.33 | -1.18 | -0.33 | 2.73 | 0.07 | 0.00 | 0.33 | 0.60 | 1.0.E-01 | | 6.1.E-01 |
| VTD | 6 | 0.00 | 5.00 | 1.00 | 0.00 | -1.83 | 3.82 | -1.36 | -1.43 | 0.00 | 0.83 | 0.17 | 0.00 | | 1.6.E-01 | 1.0.E-01 |
| RTD | 6 | 1.00 | 5.00 | 0.00 | 0.00 | -0.57 | 3.99 | -8.19 | -1.23 | 0.17 | 0.83 | 0.00 | 0.00 | | | 1.0.E-01 |
| FSN | 6 | 4.67 | 0.33 | 0.33 | 0.67 | 3.10 | -0.68 | -1.86 | -0.56 | 0.78 | 0.06 | 0.06 | 0.11 | | 1.0.E-01 | 1.0.E-01 |
| ITD | 5 | 0.00 | 3.00 | 1.00 | 1.00 | -1.57 | 1.99 | -1.19 | -0.23 | 0.00 | 0.60 | 0.20 | 0.20 | 2.6.E-01 | 6.5.E-01 | 1.8.E-01 |
| YND | 5 | 0.00 | 0.50 | 3.00 | 1.50 | -1.31 | -0.34 | 1.17 | 0.48 | 0.00 | 0.10 | 0.60 | 0.30 | 2.4.E-01 | 7.4.E-02 | 8.5.E-01 |
| VSN | 5 | 3.67 | 0.00 | 1.00 | 0.33 | 2.36 | -0.84 | -0.83 | -0.69 | 0.73 | 0.00 | 0.20 | 0.07 | 8.4.E-02 | 3.6.E-01 | 5.3.E-02 |
| VNS | 5 | 0.00 | 0.00 | 0.67 | 4.33 | -1.31 | -0.84 | -1.16 | 3.31 | 0.00 | 0.00 | 0.13 | 0.87 | | | 1.0.E-01 |
| FTN | 4 | 4.00 | 0.00 | 0.00 | 0.00 | 2.69 | -0.84 | -1.83 | -1.02 | 1.00 | 0.00 | 0.00 | 0.00 | | | |
| VSD | 4 | 1.50 | 1.00 | 0.50 | 1.00 | 0.46 | 0.33 | -0.36 | 0.18 | 0.38 | 0.25 | 0.13 | 0.25 | 9.2.E-01 | 6.2.E-01 | 1.0.E+00 |
| IND | 4 | 1.00 | 0.00 | 3.00 | 0.00 | -0.04 | -0.67 | 1.54 | -0.82 | 0.25 | 0.00 | 0.75 | 0.00 | 1.1.E-01 | 3.2.E-01 | |
| ITN | 4 | 4.00 | 0.00 | 0.00 | 0.00 | 2.96 | -0.67 | -1.48 | -0.82 | 1.00 | 0.00 | 0.00 | 0.00 | | | |
| IMD | 4 | 0.00 | 0.00 | 3.00 | 1.00 | -1.04 | -0.67 | 1.54 | 0.18 | 0.00 | 0.00 | 0.75 | 0.25 | 1.1.E-01 | | 3.2.E-01 |
| TSD | 4 | 0.33 | 0.50 | 2.50 | 0.67 | -0.71 | -0.17 | 1.04 | -0.16 | 0.08 | 0.13 | 0.63 | 0.17 | 3.8.E-01 | 2.4.E-01 | 4.0.E-01 |
| FPD | 3 | 0.00 | 0.00 | 3.00 | 0.00 | -1.04 | -0.67 | 1.54 | -0.82 | 0.00 | 0.00 | 1.00 | 0.00 | | 8.3.E-02 | 8.3.E-02 |
| INW | 3 | 0.00 | 0.00 | 2.00 | 1.00 | -0.78 | -0.50 | 0.90 | 0.39 | 0.00 | 0.00 | 0.67 | 0.33 | 3.0.E-01 | 8.3.E-02 | 5.8.E-01 |
| VNW | 3 | 0.50 | 0.00 | 1.00 | 1.50 | -0.28 | -0.50 | -0.19 | 0.89 | 0.17 | 0.00 | 0.33 | 0.50 | 6.4.E-01 | 2.5.E-01 | 1.0.E+00 |
| VVE | 3 | 1.00 | 0.00 | 1.50 | 0.50 | 0.22 | -0.50 | 0.40 | -0.11 | 0.33 | 0.00 | 0.50 | 0.17 | 6.4.E-01 | 5.8.E-01 | 2.5.E-01 |
| YPD | 3 | 0.00 | 0.00 | 3.00 | 0.00 | -0.78 | -0.50 | 1.90 | -0.61 | 0.00 | 0.00 | 1.00 | 0.00 | | 8.3.E-02 | 8.3.E-02 |
| YTN | 3 | 0.00 | 1.00 | 2.00 | 0.00 | -0.78 | 0.50 | 0.90 | -0.61 | 0.00 | 0.33 | 0.67 | 0.00 | 3.0.E-01 | 5.8.E-01 | 5.8.E-01 |
| EGN | 3 | 2.00 | 0.00 | 1.00 | 0.00 | 1.22 | -0.50 | -0.10 | -0.61 | 0.67 | 0.00 | 0.33 | 0.00 | 3.0.E-01 | 5.8.E-01 | 8.3.E-02 |
| LTD | 3 | 0.00 | 3.00 | 0.00 | 0.00 | -0.78 | 2.50 | -1.10 | -0.61 | 0.00 | 1.00 | 0.00 | 0.00 | | 8.3.E-02 | 6.3.E-02 |
| SND | 3 | 0.00 | 1.00 | 1.50 | 0.50 | -0.78 | 0.50 | 0.40 | -0.11 | 0.00 | 0.33 | 0.50 | 0.17 | 6.4.E-01 | 5.8.E-01 | 1.0.E+00 |
| HND | 3 | 0.50 | 0.50 | 1.50 | 0.50 | -0.28 | 0.00 | 0.40 | -0.11 | 0.17 | 0.17 | 0.50 | 0.17 | 8.0.E-01 | 5.8.E-01 | 5.6.E-01 |
| IVD | 3 | 1.00 | 0.00 | 0.00 | 2.00 | 0.22 | -0.50 | -1.10 | 1.39 | 0.33 | 0.00 | 0.00 | 0.67 | 3.6.E-01 | 5.8.E-01 | 5.6.E-01 |
| SNN | 3 | 0.00 | 0.00 | 0.50 | 2.50 | -0.78 | -0.50 | -0.60 | 1.89 | 0.00 | 0.00 | 0.17 | 0.83 | 1.3.E-01 | 8.3.E-02 | 2.5.E-01 |
| VVD | 3 | 1.00 | 0.00 | 1.00 | 1.00 | 0.22 | -0.50 | -0.10 | 0.39 | 0.33 | 0.00 | 0.33 | 0.33 | 8.0.E-01 | 5.8.E-01 | 5.8.E-01 |
| FNW | 3 | 0.33 | 1.00 | 0.67 | 1.00 | -0.45 | 0.50 | -0.43 | 0.39 | 0.11 | 0.33 | 0.22 | 0.33 | 9.4.E-01 | 8.5.E-01 | 5.8.E-01 |
| FVN | 3 | 1.67 | 0.33 | 1.00 | 0.00 | 0.88 | -0.17 | -0.10 | -0.61 | 0.56 | 0.11 | 0.33 | 0.00 | 6.3.E-01 | 5.8.E-01 | 1.8.E-01 |
| FNN | 3 | 1.67 | 1.33 | 0.00 | 0.00 | 0.88 | 0.83 | -1.10 | -0.61 | 0.56 | 0.44 | 0.00 | 0.00 | 3.6.E-01 | 8.3.E-02 | 8.5.E-01 |
| ND | 57 | 5.33 | 6.00 | 40.00 | 11.67 | -9.55 | -3.59 | 19.15 | -0.02 | 0.09 | 0.11 | 0.70 | 0.20 | | | |
| NN | 27 | 3.83 | 3.50 | 7.16 | 15.49 | -3.22 | -1.05 | -2.71 | 9.96 | 0.14 | 0.13 | 0.27 | 0.57 | | | 1.0.E-01 |
| TN | 25 | 20.83 | 3.83 | 2.67 | 1.67 | 14.31 | -0.37 | -6.47 | -3.48 | 0.83 | 0.15 | 0.11 | 0.07 | | | |
| TD | 21 | 3.33 | 19.67 | 2.67 | 2.33 | -2.15 | 16.13 | -5.03 | -1.97 | 0.16 | 0.94 | 0.13 | 0.11 | | | |
| SD | 20 | 4.83 | 6.50 | 5.00 | 3.67 | -0.39 | 3.13 | -2.31 | -0.43 | 0.24 | 0.33 | 0.25 | 0.18 | 8.5.E-01 | 5.5.E-01 | 8.4.E-01 |
| SN | 15 | 10.33 | 0.33 | 3.33 | 1.00 | 6.42 | -2.19 | -2.15 | -3.05 | 0.69 | 0.02 | 0.22 | 0.07 | | 1.0.E-01 | |
| GD | 13 | 0.50 | 9.00 | 3.50 | 0.00 | -2.89 | 6.81 | -1.25 | -3.66 | 0.04 | 0.69 | 0.27 | 0.00 | | 9.6.E-02 | 1.7.E-01 |
| NS | 13 | 0.83 | 0.50 | 4.67 | 7.00 | -2.56 | -1.69 | -0.09 | 4.33 | 0.06 | 0.04 | 0.36 | 0.54 | | | 5.8.E-01 |
| VN | 12 | 3.67 | 1.33 | 5.00 | 2.00 | 0.53 | -0.69 | 0.61 | -0.48 | 0.31 | 0.11 | 0.42 | 0.17 | 4.3.E-01 | 5.8.E-01 | 1.2.E-01 |
| NW | 10 | 1.16 | 1.33 | 3.67 | 3.83 | -1.45 | -0.35 | 0.01 | 1.78 | 0.12 | 0.13 | 0.37 | 0.38 | 4.7.E-01 | 1.1.E-01 | 9.2.E-01 |
| PD | 9 | 0.00 | 0.67 | 7.83 | 0.50 | -2.35 | -0.85 | 4.54 | -1.34 | 0.00 | 0.07 | 0.87 | 0.06 | | | |
| NT | 9 | 1.00 | 1.50 | 1.67 | 5.83 | -1.35 | -0.01 | -1.62 | 3.99 | 0.11 | 0.17 | 0.19 | 0.65 | 7.9.E-02 | 8.8.E-02 | 1.1.E-01 |
| GN | 8 | 5.00 | 0.00 | 3.00 | 0.00 | 2.91 | -1.35 | 0.07 | -1.64 | 0.63 | 0.00 | 0.38 | 0.00 | | 4.8.E-01 | |
| MD | 7 | 1.00 | 1.50 | 5.50 | 1.00 | -0.83 | 0.32 | 2.94 | -0.43 | 0.14 | 0.21 | 0.79 | 0.14 | | 9.1.E-02 | 9.1.E-02 |
| VD | 6 | 2.00 | 1.00 | 2.00 | 3.00 | 0.43 | -0.01 | -0.13 | 1.77 | 0.33 | 0.17 | 0.33 | 0.50 | 3.7.E-01 | 2.5.E-01 | 4.1.E-01 |
| VG | 5 | 1.00 | 0.00 | 1.00 | 3.00 | -0.31 | -0.84 | -0.83 | 1.98 | 0.20 | 0.00 | 0.20 | 0.60 | 2.8.E-01 | 1.8.E-01 | 6.5.E-01 |
| AD | 4 | 0.33 | 3.00 | 0.67 | 0.00 | -0.71 | 2.33 | -0.80 | -0.82 | 0.08 | 0.75 | 0.17 | 0.00 | 1.4.E-01 | 1.8.E-01 | 3.2.E-01 |
| SS | 4 | 0.00 | 0.33 | 2.67 | 1.00 | -1.04 | -0.34 | 1.20 | 0.18 | 0.00 | 0.08 | 0.67 | 0.25 | 2.4.E-01 | 9.6.E-02 | 5.1.E-01 |
| VE | 4 | 1.00 | 0.00 | 2.50 | 0.50 | -0.04 | -0.67 | 1.04 | -0.32 | 0.25 | 0.00 | 0.63 | 0.13 | 3.2.E-01 | 3.2.E-01 | 1.3.E-01 |
| AN | 4 | 0.67 | 0.00 | 2.67 | 0.67 | -0.38 | -0.67 | 1.20 | -0.15 | 0.17 | 0.00 | 0.67 | 0.17 | 2.6.E-01 | 1.8.E-01 | 1.8.E-01 |
| CD | 3 | 1.00 | 1.33 | 0.33 | 0.33 | 0.22 | 0.83 | -0.77 | -0.28 | 0.33 | 0.44 | 0.11 | 0.11 | 8.0.E-01 | 3.3.E-01 | 8.5.E-01 |
| IN | 3 | 0.50 | 0.00 | 1.50 | 1.00 | -0.28 | -0.50 | 0.40 | 0.39 | 0.17 | 0.00 | 0.50 | 0.33 | 6.4.E-01 | 2.5.E-01 | 5.6.E-01 |
| TW | 3 | 1.50 | 0.50 | 1.00 | 0.00 | 0.72 | 0.00 | -0.10 | -0.61 | 0.50 | 0.17 | 0.33 | 0.00 | 6.4.E-01 | 5.6.E-01 | 2.5.E-01 |
| VS | 3 | 1.00 | 0.00 | 1.00 | 1.00 | 0.22 | -0.50 | -0.10 | 0.39 | 0.33 | 0.00 | 0.33 | 0.33 | 8.0.E-01 | 5.8.E-01 | 5.8.E-01 |
| LD | 3 | 1.00 | 0.00 | 1.50 | 3.50 | 0.22 | -0.50 | 0.40 | 2.89 | 0.33 | 0.00 | 0.50 | 1.17 | | | 6.8.E-02 |
| TS | 3 | 0.00 | 0.50 | 1.50 | 1.00 | -0.78 | 0.00 | 0.40 | 0.39 | 0.00 | 0.17 | 0.50 | 0.33 | 6.4.E-01 | 2.5.E-01 | 1.0.E+00 |
| ID | 3 | 0.33 | 0.83 | 2.83 | 0.00 | -0.45 | 0.33 | 1.74 | -0.61 | 0.11 | 0.28 | 0.94 | 0.00 | 7.9.E-02 | 2.8.E-01 | 1.4.E-01 |
| VT | 3 | 1.00 | 0.00 | 3.00 | 0.00 | 0.22 | -0.50 | 1.90 | -0.61 | 0.33 | 0.00 | 1.00 | 0.00 | | 2.0.E-01 | |
| Background frequency | | 0.26 | 0.17 | 0.37 | 0.20 | 0.00 | 0.00 | 0.00 | 0.00 | 0.26 | 0.17 | 0.37 | 0.20 | | | |

¹ The value indicates a probability of nucleotide occurrence for all RNA sequences surrounding the RNA editing sites used to construct the PPR code.
² The scoring matrix is estimated by a subtraction of the background frequency from the nucleotide occurrence frequency of the PPR code.
³ The probability matrix is obtained from the nucleotide occurrence frequency.

| | | | | | | | |
|---|---|---|---|---|---|---|---|
| SEQ ID NO.:10 | MEF14 (At5g26742) | Arabidopsis thaliana PPT protein | | Amino acid | 655 | a.a. | MKVPSKKALPCSVSRLLHTERHTERDRLTTLPNKYVDKTDVFSKNSVAIDLAKSGDGAELALLAFSSMRKLSLYPTRSSPPCAIKACSSLFDIFSCKGTNCSGAPVFGVGDCFVSSALVARYSTCGKLEDGARNVFDEFNKRKVSWTTSMPGYSLNGNGLDAVSLPKDLLVDENDDCCAMRLDSMGLYSYSACSMVPAKGLTESHGFVKRGPDRGVSVSNTLLDAYAKGSSEGGVAVARKIFDQNVDKDRVSYNSMSVYAQSGMSNEAFEVFRRLVKNKVVTFNAITLSTVLLAYGHSGALRIGKCHDQVRRLGLEDGVVGTSHDMYCKCGRYETARAHDRRKNAVYKSVHKMKALYGSHKDAAAKLSLFHAMDSGVRHVNTHTYGYLKACDSHAGLHVEGNYKNHNAMKGHSGVEKVLHYGCNVDLLGRAGPLQKAYDLIGRMKMKPDSHVSSLLAACRHKNVLEADGVYARLPELGDSGNCDYYNKLSHHYADAGPYKDVERVRNHKAKRGLVKPPDFSLLELRDSVHVFLGDESPGRQREKVYEFLAELNRRLLEACYYSHTVSSVCHKNVDEEEKEMTLRVHSEKLAAKPDMNTVPGSTYNVKKNLRVCSDCHRHVKLIGKHVDREGFVVRDAARRPHHPKDGCSCSCGDYYW |
| SEQ ID NO.:11 | MEF18 (At5g19020) | Arabidopsis thaliana PPT protein | | Amino acid | 685 | a.a. | MKLRRFPRSHRCWVISLQAARCFSAPSRTHRDFSQEESQTPMALVRKLGSCKBSNGVTGCRGHNCRVLRKGLCSSKCYGNGVLNRYAKCRLLLGDAESVPRDHAKLGSAGFRMMVDRTYRSSRLKDALKLFTKVMPERSSCVGKTTLRKGVACKRGNVWSEAKSLPRKMRNLGRKSEVTLATVRACSHLGGRRCRMKLGSLKRLKLESGFVPSTNLLHMYSLCLGLKDARKLPDEMPERNLVTIWRVSKLNGVSKRLLEGAESLPDGITSRDVSWGTRMDGCLRKKGLDEALVYYTEMLRCGMRKPSEVMVGLLLSASARSICSSKGLLGLRGTVKRPGTDYQRLGATRHFYAVSGNCLRLCLQTFSASLGSLEECKRAHCYVLNFSTPPNDKLTAAKDMYAKCGSRTALNFHKGTKNSGSTIGPHNACGSATHHGHAKLALGLYSGLGSLPNPNSDTPVGVLSACCHAGLVELGKTYFESRKSDHSGEPDKNHYGLMVGLLGRAGRLGEAKLGEEAKELHHKAMPVKADVHKVGSRLLSASRTHGNVEGAELAATELAADPGHGGCKVMSLSNVYADAGRHYSDVALVREEKMRTRDVESGRAFTGVV |
| SEQ ID NO.:12 | MEF19 (At5g05340) | Arabidopsis thaliana PPT protein | | Amino acid | 505 | a.a. | MKMKKHVKPRLSGLENCRSLVELNGGLHGLMKGSVRRMVRVPLSRLDRFCITCPETMRRLGYARSVFESRDCPGVVYDMNSMRPGVGNGPMPDKALLPVLQEMLRKGYSRPDVFTSRPYVDKAGSRLRDKGFGSCVHRFVVRTGFEVNMIVVSTCLLHMYMCCGEMVGVGLRVTEDRPQVMVVAWGSRLISQFVNNRHFSQAREAPREMGSNKDVKANETMVGLLVACDRCKDDVDKWVHGRLLQRLWRDPVFGSKVDPNVBAILSLDMYAKCGQRLRTAPVLFDDSMPERTLVSWNSRITGYSGNGDAEEALCMRLDRLDLRLSHAPGKVTPLSVRRASMRDGCDKDLGGSRKVYSRATCRVKSAAPVCALVRKKVAKTCGDAESAKKAPEDLEKKLTHANTIVMGLASSHGHHEALSPRRGMKKGVVATPGSTYVLGVLVACSHGLVSEGGORYFAEMRRCLRGEPTVEHYCMCVDLSRAGRFEEAERVKTRPVKPNHVWKGALLNGCCMHEALRELTDRRRGSMVASPRSLGSCGHVYLLSRYAKAGRWACDKLRRESRDKSKPVOKDLGRRSKVETMF |
| SEQ ID NO.:13 | MEF20 (At5g18570) | Arabidopsis thaliana PPT protein | | Amino acid | 472 | a.a. | MGSVFPGPRFLSLLGQNSKTLRQAKGRHAQLVNGCHGNSLFGRLGHYCSKPSTESSSKLAHLLVPRFGHPDKRLFNTLLKCSKPEDGRRIPANYASKSGLLYLRGRTFVFVLGACARGASSGALRVGPRVGMVKKLGFLVESELIGTTLLHFYAKNGDLRYSRNVFDERMPERTISVYSWNAMIGGYCGHRDKGHNRNNARKIARRLPRRPSLCCGGSGYRPTPTTTMVCVLSAMSGTGLLERGSLVHGYRKLGFTPEVGVFRGTALVGKMYSKCGGLNRAPSMVFSELSMVKKVPTWTSRRATGLALMGRGNETPNLLNRMAESSMKPNGRTTSLLSAVRHGGLVEEGIELPKSRMKTRFGVTPVSEHVGCNVDLLGKAGRLGEEATYGPILAMPKPDAELLRSLCMRCGVYGETVRAGEEGKALLRSPEDGRKLSGGSCRDTYVALSNVLAHRGKWVEVEKLRSESRKSERRRKTRPGYSFV |
| SEQ ID NO.:14 | MEF21 (At5g20540) | Arabidopsis thaliana PPT protein | | Amino acid | 534 | a.a. | MAFKRGRREVENYPPFRLQRVKSRNEWKKNNASHHGLSGSSFMVTKMVGFCGKKEDMGYATRLFNGVGNPHVFLYNGRGAYTHRSLVCDVRRITKGLLRKDPELPGRPTFPFMFNSCASLDSCVLGNGYHGHLCKRGPRFHVVVTSNLKRTYMFDRLVDAHKVPDEMSRDVSWNSLLGGYARLGSMKRAKGLFRLMLGNTIVSWTAMSGYTGGCYVEAMGRFGEMDKLAGIEFDEISLSNLPSCAKLGSLRLGKKWRKYAERRGFLNGTGVCHALSKCGVSDAKGLFGCMKGYHGHLLKFKDPPRHHVTVGMAMDAHETPNEMGRAKVKPNGTFLGLLSACSHVGMAVDGQLFYFDMMRCDYGSEPKEHVGCLLCVLARACRLSERAVETRNTMPRKPDSRVVGSLLSSCRTPGRLDVALVAARDHLVSLEPEDKMGNYVLLANGYACKCKWEDVSRLRKARRKNENMKKTPGGSLLEVNNHVCEFVSGDNSKPPVPTERSPVLQLFTSRCRDQDVTRNRNALAPFQIV |
| SEQ ID NO.:15 | MEF22 (At5g17770) | Arabidopsis thaliana PPT protein | | Amino acid | 634 | a.a. | MSSASCLASPLLVTNHCGHSGGSFYASLRDSATHKACKLKGHARPLLVLGLGKSGGFKUTKLHAASSRFGDITSARGVFSDLPRFCRPPKNARRGTSRRKNNFPQGALLMYSNMGLKRVSPDSFTTPFRLLNACSDLSHKGMGRFVHAGVFRLGFVGNGLAVLYAKCRRLGSARTVFSGRLPLPSRTHSWVTAWSAVANGGFRMEALSFSGMRRMDVKFPGNNVALVSVLNAFTGLGGLKHGRSHADVVKMGLGRETDLLSLNTMYAKCGVSATAKLFDRMKSPNLKLVHAMSGVYARNGYAREACDMFHSKMKHVRRPDTSRTGARSACACVGSLSGARGMYSYVGRSGVYRGDVFSSGLSMVFPRMAGHHKRYGQLPRHAHRFGSKCCGEMEGRRRFHSMKLKRSKYTHANGRGSCRGCRPGGFGVDYKHKFGGEETLGSHGRMKATGLSRTPGGTPLRGTKNLRACVNGHAATNLGKLVGRRHVQRGTNRFHHRKDGVCSCGCTYWLRLMACNRSSGRRSQGHVKFSRDMMGDHKRFRSDCRVCLVGGLGRAGRLDGAYEGKAVRVGHNKEKGLNKDVGCSKVSVGRSLRGRLEAFVNGDKSHPRYEEBSRGVEYHERLRKESGFVHRDAGSLHGLSDEEAEETLGSHGRSRKKATGLSRTPGGTPLRTKNLRACVNGHAATNLGKLVGRRHVQRGTNRFHHPKDGVCSCGCTYW |
| SEQ ID NO.:16 | MEF3 (At1g62260) | Arabidopsis thaliana PPT protein | | Amino acid | 655 | a.a. | MRCRSVLLFPKVLYGGGSCLKCLLGAGFSTSVSGSLGFRATNKELNGMRRSGVAEAARDIFEKLEAGNTVTYKNTMISGYVRRREMNGARKLPVMRPKGCVVTWSTVMRGGYVSGGGRFLEEGARKLPDEMPSRDSFSRVNTMSSGYVAKNRRGEALLLFEKMMPERNAVSRSSAMFSHCGNGVVDSKAFVLFSKMMPVKDSSPLCAVLVSGLMNRSRSEAAKVSLLGGYGSLGSRRDLVYKAYHTLSVGVYGRRGVGEAARCLPDGPDLLCGDCNKGGFRREPCSNVVGMNSMKALKVGDVSAARLLPDQMNKMRRDTGVMRMRGWVSRGSRMEDAPALFSEMPHSRDAHSWNRMMSGVASVGSVELARHVFEKTPEKHTVSYNGSRAAYEKNNDYKEAVDLPSRMKEGGKPFGHRRTLSSLSASTTLKNLRLGMNRHGFVNKTVPDVPVHNALSTAVSRCCGSMEGRRFUSMKLKRSKYTHANGRGSCRGFRKLGHPPHHVTVGVLSALGRGAGRVDEAKGFVSHMSVVKEFGMSHVSSLVNVTSGGLGGFRSAAMVGTSMPPEDVKTYMGALLGACRYFNNVGLARMVAAEAMSRLEPESSTPVVLLYNMYASMGVWGEASGVRNNMSSMSRFRKKERDSSVYDSST |
| SEQ ID NO.:17 | cb06 (At5g59200) | Arabidopsis thaliana PPT protein | | Amino acid | 544 | a.a. | MGSLAAYSGPSTFSRDFGSNTLRLSRFKTLSSVLRSCKRNAHVPSRHAKSRTFHSGDDAFVVFELIRVCSRLDSVDKAYDVFSKVGNPNVVRLYTAMSGSVSGCRSGRDAVSSRKDVNRRMNHVLPGGYVRFCRSHAGLHLGLGFDSRSRGVKLKMMVGVGKGSRGKVLGACSDLGALELGVSNVARRGVRMRLSRVGNALSNMYSRCCGNNEAFKRGVRNMRMSGLAMHGASVSANKEPRDMVSRGFRRHGYRTLVALLNACSHGGLLDIGLEVYSRMINDYGLGPSGKDVLTSSACAGVGGLGPVRMVMTGRGYNDMSGLAMHGASVSANKEPRDMVSRGFRRHGYRTLVALLNACSHAGLGTLLSAGKKHGNMELGEKKANRLFEDENPDSGTYVLLSRLVASGGRWKESTSRRESKRSPDSGIEKEPGCSTHSDRGHERLVGDKMPHSEAYGRLGELNRLSFKENGRGRMGF |
| SEQ ID NO.:18 | cc31 (At5g23760) | Arabidopsis thaliana PPT protein | | Amino acid | 738 | a.a. | MAHFSTAGRLSLRRHFHKSNFNGFTTNNERSRMRLSRCVSLRGLKGTHGRHMRTGTFSGPVSAAKSPFAAAAKLSPFASRLEYARKTPDEPSRKPNGFAAVRTLGRAYASGPSPVLSMVARLGMVSEGDGVFRKYFPPFLRKAAAEVGSLSLGRGLHGMAMRSAMGSDGFPVAHSLPGYSGCCGQLGRACKVFTTRKENDVSRRNNGFVRKGSPDKALELFKKMRSEDVKGRSHFKGASMVTMVGVLSACRGRHLGFRGRGSYKEENRVRVANLRLANARLDRRTKDGGRRDAKRLPDRMRERDNVTWTTMLDGYAGEDVREAAFERLKDRMRGRGVRVSPRTKGRMMFHVTSALHGMVSKCGDLKDGRKVRNSRKREDVVRWSSAMSGLRMVACGGREAVDRFYRSMSRMKPNGVTPTVPLRCACSHTGGLVGEAESLRHDRMERRVGKVRREKHRYRCIKDVLRGRGYRLRKAVRFERMPRSTSVVWGALSGCKKHMRLNLAEDRRACTRLRLEPKRMDGRAHVLLSRYAKLSGKWERVSRELRRNKRMVTGLSKEEGRGSRSGRAHFRSSGDHAGRMMKRAVYGRLHEVMERLRSNGYEPKSRGVLRREEKMRSESLRLRSEKRLRKVGIRTEAPKVNRVRKRKKRCGDCHGVAKLISGRVDRESGRDRYRRFHVRFRNGGCSCKDPYV |

FIG. 16C

| SEQ ID NO. | ID or name | remark 1 | remark 2 | Type | Length | Unit | Sequence |
|---|---|---|---|---|---|---|---|
| SEQ ID NO.:19 | otp82 (At3g68570) | Arabidopsis thaliana PPT protein | | Amino acid | 731 | a.a. | *[sequence illegible]* |
| SEQ ID NO.:20 | cfp84 (At3g74430) | Arabidopsis thaliana PPT protein | | Amino acid | 890 | a.a. | *[sequence illegible]* |
| SEQ ID NO.:21 | cfp85 (At2g00940) | Arabidopsis thaliana PPT protein | | Amino acid | 603 | a.a. | *[sequence illegible]* |
| SEQ ID NO.:22 | otp86 (At5g83375) | Arabidopsis thaliana PPT protein | | Amino acid | 980 | a.a. | *[sequence illegible]* |
| SEQ ID NO.:23 | cfp87 (At5g74690) | Arabidopsis thaliana PPT protein | | Amino acid | 895 | a.a. | *[sequence illegible]* |
| SEQ ID NO.:24 | SLO1 (At2g22410) | Arabidopsis thaliana PPT protein | | Amino acid | 691 | a.a. | *[sequence illegible]* |
| SEQ ID NO.:25 | YS1 (At5g22800) | Arabidopsis thaliana PPT protein | | Amino acid | 842 | a.a. | *[sequence illegible]* |

FIG. 16D

| | | | | | | |
|---|---|---|---|---|---|---|
| SEQ ID NO: 26 | PpPPR_59 | Physcomitrella patens PPR Protein | Amino acid | 659 | a.a. | (illegible amino acid sequence) |
| SEQ ID NO: 27 | PpPPR_71 | Physcomitrella patens PPR Protein | Amino acid | 815 | a.a. | (illegible amino acid sequence) |
| SEQ ID NO: 28 | PpPPR_77 | Physcomitrella patens PPR Protein | Amino acid | 1264 | a.a. | (illegible amino acid sequence) |
| SEQ ID NO: 29 | PpPPR_78 | Physcomitrella patens PPR Protein | Amino acid | 1042 | a.a. | (illegible amino acid sequence) |
| SEQ ID NO: 30 | PpPPR_79 | Physcomitrella patens PPR Protein | Amino acid | 604 | a.a. | (illegible amino acid sequence) |
| SEQ ID NO: 31 | PpPPR_91 | Physcomitrella patens PPR Protein | Amino acid | 890 | a.a. | (illegible amino acid sequence) |

FIG. 16E

| SEQ ID NO. | ID or notes | remark 1 | remark 2 | Type | Length | Unit | Sequence |
|---|---|---|---|---|---|---|---|
| SEQ ID NO. 32 | atpbeU02SL | Physcomitrella patens RNA-editing site | | RNA | 31 | mer | cuuuaagguauauggaaacguauuuuaguucuuc |
| SEQ ID NO. 33 | ccmFCeU103P6 | Physcomitrella patens RNA-editing site | | RNA | 31 | mer | ccaucucuaauggaugguaagaugaaugauc |
| SEQ ID NO. 34 | ccmFCeU1029P | Physcomitrella patens RNA-editing site | for PpPPR_71 | RNA | 31 | mer | gcugggaugccuccccaauggacgcccuccucuc |
| SEQ ID NO. 35 | coxieU758SL | Physcomitrella patens RNA-editing site | for PpPPR_75 | RNA | 31 | mer | aauccccaguccuggaguccucuccuccucuc |
| SEQ ID NO. 36 | coxiieU270RW | Physcomitrella patens RNA-editing site | for PpPPR_77 | RNA | 31 | mer | acuauuacucucaaugucuc.auggacaucaac |
| SEQ ID NO. 37 | coxiieU733RW | Physcomitrella patens RNA-editing site | for PpPPR_77 | RNA | 31 | mer | cacauuugguuucaagucugcuguucugguuac |
| SEQ ID NO. 38 | nad3eU23SL | Physcomitrella patens RNA-editing site | for PpPPR_56 | RNA | 31 | mer | ccuaucucuccucgaucuggacgcccuuuucuc |
| SEQ ID NO. 39 | nad4eU272SL | Physcomitrella patens RNA-editing site | for PpPPR_58 | RNA | 31 | mer | aucccuccuccgcguaaugcgcgguucuucuc |
| SEQ ID NO. 40 | nad5eU598RC | Physcomitrella patens RNA-editing site | for PpPPR_79 | RNA | 31 | mer | ccaaucaguacgacucccuuga'cucuauccucgcuc |
| SEQ ID NO. 41 | nad5eU730RW | Physcomitrella patens RNA-editing site | for PpPPR_81 | RNA | 31 | mer | gguaacucucugccucaacuaggucuuguauucuc |
| SEQ ID NO. 42 | rps14cpeU-1 | Physcomitrella patens RNA-editing site | | RNA | 31 | mer | ccuaacaaacaucucaauucucucaaacaauc |
| SEQ ID NO. 43 | rps14cceU2TM | Physcomitrella patens RNA-editing site | | RNA | 31 | mer | acaacaacaucucaucaucucaacaacaac |
| SEQ ID NO. 44 | rps14eU137SL | Physcomitrella patens RNA-editing site | for PpPPR_78 | RNA | 31 | mer | aucaaaacacgcaucgaacuacaacuuuuaagcu |
| SEQ ID NO. 45 | accD(57868) | Arabidopsis thaliana chloroplasts RNA-editing site | | RNA | 31 | mer | caaucugcuagccuccgaacgacuggaccuucc |
| SEQ ID NO. 46 | accD(56642) | Arabidopsis thaliana chloroplasts RNA-editing site | | RNA | 31 | mer | cccucuaacaucgacuccucgccucaucacuc |
| SEQ ID NO. 47 | atpf(12707) | Arabidopsis thaliana chloroplasts RNA-editing site | | RNA | 31 | mer | gacucucccucccgaucccuagcaacaaucc |
| SEQ ID NO. 48 | clpP(69842) | Arabidopsis thaliana chloroplasts RNA-editing site | for CLB19 | RNA | 31 | mer | cuccucccguccgccacagacgccccuagcuc |
| SEQ ID NO. 49 | matK(2031) | Arabidopsis thaliana chloroplasts RNA-editing site | | RNA | 31 | mer | ccaaggcuuuaucuucagaccuuauauaauucuc |
| SEQ ID NO. 50 | ndhB(94998) | Arabidopsis thaliana chloroplasts RNA-editing site | for clpP4 | RNA | 31 | mer | ugaucuguugugugauacaucucuuauucuc |
| SEQ ID NO. 51 | ndhB(95226) | Arabidopsis thaliana chloroplasts RNA-editing site | | RNA | 31 | mer | ccaucacuagucagguuaacuauggaaacucc |
| SEQ ID NO. 52 | ndhB(95408) | Arabidopsis thaliana chloroplasts RNA-editing site | | RNA | 31 | mer | ccggaauuaucgaagaaccuuuuuuacuucuc |
| SEQ ID NO. 53 | ndhB(95644) | Arabidopsis thaliana chloroplasts RNA-editing site | for clpP2 | RNA | 31 | mer | ccgucuccuccgaacgacgcuggucuagcucc |
| SEQ ID NO. 54 | ndhB(95860) | Arabidopsis thaliana chloroplasts RNA-editing site | | RNA | 31 | mer | ccuccuccugcuaucucugaacucacgcccuc |
| SEQ ID NO. 55 | ndhB(96419) | Arabidopsis thaliana chloroplasts RNA-editing site | for CRR22 | RNA | 31 | mer | gaacugggcuucaaggcuucccuaagcccuuc |

FIG. 16F

| SEQ ID NO. 56 | ndhB(96579) | Arabidopsis thaliana chloroplasts RNA-editing site | | RNA | 31 | mer | auggjuggjugbadgcdduducuaucugguuc |
| SEQ ID NO. 57 | ndhB(96868) | Arabidopsis thaliana chloroplasts RNA-editing site | for CRR28 | RNA | 31 | mer | |
| SEQ ID NO. 58 | ndhB(97016) | Arabidopsis thaliana chloroplasts RNA-editing site | | RNA | 31 | mer | |
| SEQ ID NO. 59 | ndhD(116261) | Arabidopsis thaliana chloroplasts RNA-editing site | for CRR22 | RNA | 31 | mer | |
| SEQ ID NO. 60 | ndhD(116290) | Arabidopsis thaliana chloroplasts RNA-editing site | for CRR28 | RNA | 31 | mer | |
| SEQ ID NO. 61 | ndhD(116494) | Arabidopsis thaliana chloroplasts RNA-editing site | for otp85 | RNA | 31 | mer | |
| SEQ ID NO. 62 | ndhD(116785) | Arabidopsis thaliana chloroplasts RNA-editing site | for CRR21 | RNA | 31 | mer | |
| SEQ ID NO. 63 | ndhD(117180) | Arabidopsis thaliana chloroplasts RNA-editing site | for CRR4 | RNA | 31 | mer | |
| SEQ ID NO. 64 | ndhF(112346) | Arabidopsis thaliana chloroplasts RNA-editing site | for otp84 | RNA | 31 | mer | |
| SEQ ID NO. 65 | ndhG(118858) | Arabidopsis thaliana chloroplasts RNA-editing site | for otp82 | RNA | 31 | mer | |
| SEQ ID NO. 66 | psbE(65718) | Arabidopsis thaliana chloroplasts RNA-editing site | | RNA | 31 | mer | |
| SEQ ID NO. 67 | psbE(64109) | Arabidopsis thaliana chloroplasts RNA-editing site | | RNA | 31 | mer | ggcaucuccaaacaaacaggcgccguuuugauc |
| SEQ ID NO. 68 | psbF(63985) | Arabidopsis thaliana chloroplasts RNA-editing site | for LPA66 | RNA | 31 | mer | |
| SEQ ID NO. 69 | psbZ(35800) | Arabidopsis thaliana chloroplasts RNA-editing site | for otp84 | RNA | 31 | mer | |
| SEQ ID NO. 70 | rpl23(86056) | Arabidopsis thaliana chloroplasts RNA-editing site | for otp80 | RNA | 31 | mer | |
| SEQ ID NO. 71 | rpoA(79631) | Arabidopsis thaliana chloroplasts RNA-editing site | for CLB19 | RNA | 31 | mer | |
| SEQ ID NO. 72 | rpoB(23898) | Arabidopsis thaliana chloroplasts RNA-editing site | | RNA | 31 | mer | |
| SEQ ID NO. 73 | rpoB(25779) | Arabidopsis thaliana chloroplasts RNA-editing site | for CRR22 | RNA | 31 | mer | |
| SEQ ID NO. 74 | rpoB(25992) | Arabidopsis thaliana chloroplasts RNA-editing site | for YS1 | RNA | 31 | mer | scaduuccuuaaaugaacuuccuuggaacuuc |
| SEQ ID NO. 75 | rpoC1(21806) | Arabidopsis thaliana chloroplasts RNA-editing site | | RNA | 31 | mer | |
| SEQ ID NO. 76 | rps12(combined83) | Arabidopsis thaliana chloroplasts RNA-editing site | for otp81 | RNA | 31 | mer | |
| SEQ ID NO. 77 | rps14(37082) | Arabidopsis thaliana chloroplasts RNA-editing site | | RNA | 31 | mer | aaugggaauauaauggaauaauuacaauuccc |

| SEQ ID NO. | ID or name | remark 1 | remark 2 | Type | Length | Unit | Sequence |
|---|---|---|---|---|---|---|---|
| SEQ ID NO.:100 | ccb2_181 | Arabidopsis thaliana mitochondria RNA-editing site | | RNA | 31 | mer | atbggdccdcggtgttbctttctc |
| SEQ ID NO.:101 | ccb2_189 | Arabidopsis thaliana mitochondria RNA-editing site | | RNA | 31 | mer | ccctcrgtgttcttctctctgcacc |
| SEQ ID NO.:102 | ccb2_193 | Arabidopsis thaliana mitochondria RNA-editing site | | RNA | 31 | mer | ccghgttccttccctgcaccttc |
| SEQ ID NO.:103 | ccb2_194 | Arabidopsis thaliana mitochondria RNA-editing site | | RNA | 31 | mer | cgtgttcctctcctgcacctttcc |
| SEQ ID NO.:104 | ccb2_26 | Arabidopsis thaliana mitochondria RNA-editing site | | RNA | 31 | mer | gaccgagacgcctttcttgtactatatc |
| SEQ ID NO.:105 | ccb2_286 | Arabidopsis thaliana mitochondria RNA-editing site | | RNA | 31 | mer | ccgatcctacttctacccttgcttggcctt |
| SEQ ID NO.:106 | ccb2_304 | Arabidopsis thaliana mitochondria RNA-editing site | | RNA | 31 | mer | ttggtgggttaccgggttcttcatccttb |
| SEQ ID NO.:107 | ccb2_338 | Arabidopsis thaliana mitochondria RNA-editing site | | RNA | 31 | mer | ttbtctggtttcccgtgttccacctttc |
| SEQ ID NO.:108 | ccb2_367 | Arabidopsis thaliana mitochondria RNA-editing site | | RNA | 31 | mer | ccgtcccactccgttcgatcccggaactgatc |
| SEQ ID NO.:109 | ccb2_378 | Arabidopsis thaliana mitochondria RNA-editing site | | RNA | 31 | mer | ggtcgatccggactgatcggtcaaccttc |
| SEQ ID NO.:110 | ccb2_386 | Arabidopsis thaliana mitochondria RNA-editing site | | RNA | 31 | mer | gtcgatccggactgatcggtccaacctbc |
| SEQ ID NO.:111 | ccb2_406 | Arabidopsis thaliana mitochondria RNA-editing site | | RNA | 31 | mer | atbcccttctcggagccctggcttctgaactctc |
| SEQ ID NO.:112 | ccb2_424 | Arabidopsis thaliana mitochondria RNA-editing site | | RNA | 31 | mer | ghcttgacccctctgtcgttgttcactbttc |
| SEQ ID NO.:113 | ccb2_429 | Arabidopsis thaliana mitochondria RNA-editing site | | RNA | 31 | mer | tgacttctcgghgttgctcacttccgtcc |
| SEQ ID NO.:114 | ccb2_467 | Arabidopsis thaliana mitochondria RNA-editing site | | RNA | 31 | mer | gaatccatcctccgacgtggttcgtccaccgatc |
| SEQ ID NO.:115 | ccb2_475 | Arabidopsis thaliana mitochondria RNA-editing site | | RNA | 31 | mer | tccagccgtgggttggaaccgccgtggcaaccttc |
| SEQ ID NO.:116 | ccb2_478 | Arabidopsis thaliana mitochondria RNA-editing site | | RNA | 31 | mer | tccgccagtgggttggaaccgctggcaaaatcc |
| SEQ ID NO.:117 | ccb2_485 | Arabidopsis thaliana mitochondria RNA-editing site | | RNA | 31 | mer | gttggaaccgctcgcaaaatcctaaccaattc |
| SEQ ID NO.:118 | ccb2_512 | Arabidopsis thaliana mitochondria RNA-editing site | | RNA | 31 | mer | cttcacctacttcattgcacccacagcgttc |
| SEQ ID NO.:119 | ccb2_514 | Arabidopsis thaliana mitochondria RNA-editing site | | RNA | 31 | mer | tcacctacttcattgcccccdaaccgtttctc |
| SEQ ID NO.:120 | ccb2_531 | Arabidopsis thaliana mitochondria RNA-editing site | | RNA | 31 | mer | ctctbgaaccagaactggtbctcgttctttc |

FIG. 16I

| SEQ ID NO.:121 | ccb2_554 | Arabidopsis thaliana mitochondria RNA-editing site | | RNA | 31 | mer | ttgaacacgtatggcttcatgtccttcatc |
|---|---|---|---|---|---|---|---|
| SEQ ID NO.:122 | ccb2_568 | Arabidopsis thaliana mitochondria RNA-editing site | for MEF19 | RNA | 31 | mer | ggatccatgtcctccatcgatcgctatc |
| SEQ ID NO.:123 | ccb3_589 | Arabidopsis thaliana mitochondria RNA-editing site | | RNA | 31 | mer | ttcaagtcatcatcgatcggtatccatc |
| SEQ ID NO.:124 | ccb3_71 | Arabidopsis thaliana mitochondria RNA-editing site | | RNA | 31 | mer | ttcatcctcaccatcatcgagtttcttc |
| SEQ ID NO.:125 | ccb3_75 | Arabidopsis thaliana mitochondria RNA-editing site | | RNA | 31 | mer | ttccacctcctcatccgagttcttcatc |
| SEQ ID NO.:126 | ccb3_78 | Arabidopsis thaliana mitochondria RNA-editing site | | RNA | 31 | mer | catcacccatcatcgagtttcttcatcatc |
| SEQ ID NO.:127 | ccb2_84 | Arabidopsis thaliana mitochondria RNA-editing site | | RNA | 31 | mer | cacccatcacgagtttcttcatcctc |
| SEQ ID NO.:128 | ccb4_505 | Arabidopsis thaliana mitochondria RNA-editing site | | RNA | 31 | mer | tctgagtgatctatccagcatgatgtcatc |
| SEQ ID NO.:129 | ccb3_160 | Arabidopsis thaliana mitochondria RNA-editing site | | RNA | 31 | mer | cattcaagtcatcgggatagacacaacatgatc |
| SEQ ID NO.:130 | ccb3_179 | Arabidopsis thaliana mitochondria RNA-editing site | | RNA | 31 | mer | atttccgatctcatcatgtacaagtcctgc |
| SEQ ID NO.:131 | ccb3_184 | Arabidopsis thaliana mitochondria RNA-editing site | | RNA | 31 | mer | ccgtatctcatcgtacaagttcctgcggatc |
| SEQ ID NO.:132 | ccb3_262 | Arabidopsis thaliana mitochondria RNA-editing site | | RNA | 31 | mer | ttcatcttaaccatcaccatcctctatctc |
| SEQ ID NO.:133 | ccb3_331 | Arabidopsis thaliana mitochondria RNA-editing site | | RNA | 31 | mer | aacgtcgttactcatcgttactggcgggttc |
| SEQ ID NO.:134 | ccb3_380 | Arabidopsis thaliana mitochondria RNA-editing site | | RNA | 31 | mer | ggacgatcgttcgacctcgtcatccatc |
| SEQ ID NO.:135 | ccb3_400 | Arabidopsis thaliana mitochondria RNA-editing site | | RNA | 31 | mer | gatcgtttgaacctcatgatcctctcgtttc |
| SEQ ID NO.:136 | ccb4_421 | Arabidopsis thaliana mitochondria RNA-editing site | | RNA | 31 | mer | atctcgtttccatctcacctgcggtgcactgc |
| SEQ ID NO.:137 | ccb3_445 | Arabidopsis thaliana mitochondria RNA-editing site | | RNA | 31 | mer | caatgtgttcatcaagtccctgcgtcagaacc |
| SEQ ID NO.:138 | ccb3_458 | Arabidopsis thaliana mitochondria RNA-editing site | | RNA | 31 | mer | aataagctccgtcgtcacccggatccaatc |
| SEQ ID NO.:139 | ccb3_463 | Arabidopsis thaliana mitochondria RNA-editing site | | RNA | 31 | mer | ctcccgtcgtcaccggctctcattcaattc |
| SEQ ID NO.:140 | ccb3_467 | Arabidopsis thaliana mitochondria RNA-editing site | | RNA | 31 | mer | ctgtccgtaaccggctctcattcaattcgtg |
| SEQ ID NO.:141 | ccb3_473 | Arabidopsis thaliana mitochondria RNA-editing site | | RNA | 31 | mer | aacccggctctctattcaattcgtgtggacc |
| SEQ ID NO.:142 | ccb3_477 | Arabidopsis thaliana mitochondria RNA-editing site | | RNA | 31 | mer | ggctctctattcaattcgtggtggaccgatc |

FIG. 16J

| SEQ ID NO:143 | ccb3_497 | Arabidopsis thaliana mitochondria RNA-editing site | | RNA | 31 | mer | ctggaccgatcgctatacccatactaccagtc |
| SEQ ID NO:144 | ccb3_521 | Arabidopsis thaliana mitochondria RNA-editing site | | RNA | 31 | mer | aaaagtcttcagtcaactggttggaatcacatc |
| SEQ ID NO:145 | ccb3_548 | Arabidopsis thaliana mitochondria RNA-editing site | | RNA | 31 | mer | caatggcatctaactcgggagcaatagcctgatc |
| SEQ ID NO:146 | ccb3_568 | Arabidopsis thaliana mitochondria RNA-editing site | | RNA | 31 | mer | attagccgatttggtaccatcaatacatgttc |
| SEQ ID NO:147 | ccb3_575 | Arabidopsis thaliana mitochondria RNA-editing site | | RNA | 31 | mer | gatatggtaccatcaatacatgttcatatgcc |
| SEQ ID NO:148 | ccb3_608 | Arabidopsis thaliana mitochondria RNA-editing site | | RNA | 31 | mer | ttcccccttgtctcaacttgctactctccc |
| SEQ ID NO:149 | ccb3_614 | Arabidopsis thaliana mitochondria RNA-editing site | | RNA | 31 | mer | ccttgtctaacttgctactctccctctc |
| SEQ ID NO:150 | ccb3_618 | Arabidopsis thaliana mitochondria RNA-editing site | | RNA | 31 | mer | gactaacttgctaactctcccctctacaaccc |
| SEQ ID NO:151 | ccb3_619 | Arabidopsis thaliana mitochondria RNA-editing site | | RNA | 31 | mer | tctaacttgctaactctccctctctcaaccc |
| SEQ ID NO:152 | ccb3_624 | Arabidopsis thaliana mitochondria RNA-editing site | | RNA | 31 | mer | cttgctaactctccctctctcaaccaggatc |
| SEQ ID NO:153 | ccb3_653 | Arabidopsis thaliana mitochondria RNA-editing site | | RNA | 31 | mer | gtatcttgttctctggaaaccacgcctct |
| SEQ ID NO:154 | ccb3_658 | Arabidopsis thaliana mitochondria RNA-editing site | | RNA | 31 | mer | tgttgttctggaaaccgctctactatcc |
| SEQ ID NO:155 | ccb3_673 | Arabidopsis thaliana mitochondria RNA-editing site | | RNA | 31 | mer | ccgtctcctattcacatctttctgacctct |
| SEQ ID NO:156 | ccb6c_103 | Arabidopsis thaliana mitochondria RNA-editing site | | RNA | 31 | mer | ctattgaaatggtcgtcagtagaggatgttc |
| SEQ ID NO:157 | ccb6c_1159 | Arabidopsis thaliana mitochondria RNA-editing site | | RNA | 31 | mer | ggcacggacgtgaagtgcctctcatacacaatc |
| SEQ ID NO:158 | ccb6c_1172 | Arabidopsis thaliana mitochondria RNA-editing site | | RNA | 31 | mer | atacccctctacttccagggttctatgcttc |
| SEQ ID NO:159 | ccb6c_1215 | Arabidopsis thaliana mitochondria RNA-editing site | | RNA | 31 | mer | aagttcctgaacagggagttgggtacctcc |
| SEQ ID NO:160 | ccb6c_122 | Arabidopsis thaliana mitochondria RNA-editing site | | RNA | 31 | mer | gtagagatgttcccaatggttgcccactcc |
| SEQ ID NO:161 | ccb6c_123 | Arabidopsis thaliana mitochondria RNA-editing site | | RNA | 31 | mer | agagatgttcccaacgggttgcccttttcc |
| SEQ ID NO:162 | ccb6c_1248 | Arabidopsis thaliana mitochondria RNA-editing site | | RNA | 31 | mer | ctaatgaaactgctttcttctctatctc |
| SEQ ID NO:163 | ccb6c_1256 | Arabidopsis thaliana mitochondria RNA-editing site | | RNA | 31 | mer | aactgatctgctttcttgttggaagagtc |
| SEQ ID NO:164 | ccb6c_1297 | Arabidopsis thaliana mitochondria RNA-editing site | | RNA | 31 | mer | cagctcctaacagggatctaagttgctggaatctc |

FIG. 16K

| SEQ ID NO:165 | ccrdq_198 | Arabidopsis thaliana mitochondria RNA-editing site | | RNA | 21 | nnn | cttttccccggcgcacicaaticgctattcc |
|---|---|---|---|---|---|---|---|
| SEQ ID NO:166 | ccdin_199 | Arabidopsis thaliana mitochondria RNA-editing site | | RNA | 21 | nnn | atggaactcacacatccccatctcctatctctctc |
| SEQ ID NO:167 | ccrdq_160 | Arabidopsis thaliana mitochondria RNA-editing site | | RNA | 21 | nnn | accacacctaccctcctcctctctctccccc |

FIG. 16L

| SEQ ID NO.: | ID of name | remark 1 | remark 2 | Type | Length | End | Sequence |
|---|---|---|---|---|---|---|---|
| SEQ ID NO.:168 | ccb6c_175 | Arabidopsis thaliana mitochondria RNA-editing site | | RNA | 31 | mer | (illegible) |
| SEQ ID NO.:169 | ccb6c_333 | Arabidopsis thaliana mitochondria RNA-editing site | | RNA | 31 | mer | (illegible) |
| SEQ ID NO.:170 | ccb6c_334 | Arabidopsis thaliana mitochondria RNA-editing site | | RNA | 31 | mer | (illegible) |
| SEQ ID NO.:171 | ccb6c_378 | Arabidopsis thaliana mitochondria RNA-editing site | | RNA | 31 | mer | (illegible) |
| SEQ ID NO.:172 | ccb6c_406 | Arabidopsis thaliana mitochondria RNA-editing site | | RNA | 31 | mer | (illegible) |
| SEQ ID NO.:173 | ccb6c_419 | Arabidopsis thaliana mitochondria RNA-editing site | | RNA | 31 | mer | (illegible) |
| SEQ ID NO.:174 | ccb6c_53 | Arabidopsis thaliana mitochondria RNA-editing site | | RNA | 31 | mer | (illegible) |
| SEQ ID NO.:175 | ccb6c_561 | Arabidopsis thaliana mitochondria RNA-editing site | | RNA | 31 | mer | (illegible) |
| SEQ ID NO.:176 | ccb6c_923 | Arabidopsis thaliana mitochondria RNA-editing site | | RNA | 31 | mer | (illegible) |
| SEQ ID NO.:177 | ccb6n-A_104 | Arabidopsis thaliana mitochondria RNA-editing site | | RNA | 31 | mer | (illegible) |
| SEQ ID NO.:178 | ccb6n-A_143 | Arabidopsis thaliana mitochondria RNA-editing site | | RNA | 31 | mer | (illegible) |
| SEQ ID NO.:179 | ccb6n-A_157 | Arabidopsis thaliana mitochondria RNA-editing site | | RNA | 31 | mer | (illegible) |
| SEQ ID NO.:180 | ccb6n-A_205 | Arabidopsis thaliana mitochondria RNA-editing site | | RNA | 31 | mer | (illegible) |
| SEQ ID NO.:181 | ccb6n-A_262 | Arabidopsis thaliana mitochondria RNA-editing site | | RNA | 31 | mer | (illegible) |
| SEQ ID NO.:182 | ccb6n-A_268 | Arabidopsis thaliana mitochondria RNA-editing site | | RNA | 31 | mer | (illegible) |
| SEQ ID NO.:183 | ccb6n-A_286 | Arabidopsis thaliana mitochondria RNA-editing site | | RNA | 31 | mer | (illegible) |
| SEQ ID NO.:184 | ccb6n-A_340 | Arabidopsis thaliana mitochondria RNA-editing site | | RNA | 31 | mer | (illegible) |
| SEQ ID NO.:185 | ccb6n-A_375 | Arabidopsis thaliana mitochondria RNA-editing site | | RNA | 31 | mer | (illegible) |
| SEQ ID NO.:186 | ccb6n-A_378 | Arabidopsis thaliana mitochondria RNA-editing site | | RNA | 31 | mer | (illegible) |
| SEQ ID NO.:187 | ccb6n-A_404 | Arabidopsis thaliana mitochondria RNA-editing site | | RNA | 31 | mer | (illegible) |
| SEQ ID NO.:188 | ccb6n-A_44 | Arabidopsis thaliana mitochondria RNA-editing site | | RNA | 31 | mer | (illegible) |

FIG. 16M

| | | | | | | | |
|---|---|---|---|---|---|---|---|
| SEQ ID NO.:188 | ccb6n-A_484 | Arabidopsis thaliana mitochondria RNA-editing site | | RNA | 31 | mer | gttctacgaaccctgtgatctgaacttc |
| SEQ ID NO.:189 | ccb6n-A_579 | Arabidopsis thaliana mitochondria RNA-editing site | | RNA | 31 | mer | gaaatctaacaaatcctctggatctgatggccgt |
| SEQ ID NO.:191 | ccb6n-A_591 | Arabidopsis thaliana mitochondria RNA-editing site | | RNA | 31 | mer | aaaatacaaacacbctcgatgatgctgatgcgtt |
| SEQ ID NO.:192 | ccb6n-A_709 | Arabidopsis thaliana mitochondria RNA-editing site | | RNA | 31 | mer | ggagctctggcatgcatctgatctctc |
| SEQ ID NO.:193 | ccb6n-A_710 | Arabidopsis thaliana mitochondria RNA-editing site | | RNA | 31 | mer | gacgctctgcatgctcgtctctc |
| SEQ ID NO.:194 | ccb6n-A_715 | Arabidopsis thaliana mitochondria RNA-editing site | | RNA | 31 | mer | gcattgctgtttctctcctttctctctt |
| SEQ ID NO.:195 | ccb6n-A_779 | Arabidopsis thaliana mitochondria RNA-editing site | | RNA | 31 | mer | tcttcttgtaccgaatcgctgcatgatc |
| SEQ ID NO.:196 | ccb6n-A_781 | Arabidopsis thaliana mitochondria RNA-editing site | | RNA | 31 | mer | cctgaatcgcctgcagaatcaaatctgtttcc |
| SEQ ID NO.:197 | ccb6n-A_806 | Arabidopsis thaliana mitochondria RNA-editing site | | RNA | 31 | mer | aatcaaatcctgtccacagatctatatc |
| SEQ ID NO.:198 | ccb6n-A_860 | Arabidopsis thaliana mitochondria RNA-editing site | | RNA | 31 | mer | gatgaagccgaaaagaatggaaacgctgctt |
| SEQ ID NO.:199 | ccb6n-B_176 | Arabidopsis thaliana mitochondria RNA-editing site | | RNA | 31 | mer | gttgagcgtttcaacgtaagccatctgcc |
| SEQ ID NO.:200 | ccb6n-B_200 | Arabidopsis thaliana mitochondria RNA-editing site | | RNA | 31 | mer | ggaaagtcgtcggcttctcatgaattaggtc |
| SEQ ID NO.:201 | ccb6n-B_228 | Arabidopsis thaliana mitochondria RNA-editing site | | RNA | 31 | mer | catgaatacgtcgggctgcggctgcgggttc |
| SEQ ID NO.:202 | ccb6n-B_255 | Arabidopsis thaliana mitochondria RNA-editing site | | RNA | 31 | mer | gatcccgacgaaacgctctctgcgctc |
| SEQ ID NO.:203 | ccb6n-B_277 | Arabidopsis thaliana mitochondria RNA-editing site | | RNA | 31 | mer | tcttctgctctctgggctctgcgaacacagctc |
| SEQ ID NO.:204 | ccb6n-B_301 | Arabidopsis thaliana mitochondria RNA-editing site | | RNA | 31 | mer | aaacgctctgctctctcatctgctaaattaccccc |
| SEQ ID NO.:205 | ccb6n-B_320 | Arabidopsis thaliana mitochondria RNA-editing site | | RNA | 31 | mer | taaattacaacctactcactcctggctctct |
| SEQ ID NO.:206 | ccb6n-B_344 | Arabidopsis thaliana mitochondria RNA-editing site | full | RNA | 31 | mer | ggaccbcgttctacatatgtgactctcc |
| SEQ ID NO.:207 | ccb6n-B_356 | Arabidopsis thaliana mitochondria RNA-editing site | | RNA | 31 | mer | tbaatactgtgacctaccatgctgtgtctc |
| SEQ ID NO.:208 | ccb6n-B_391 | Arabidopsis thaliana mitochondria RNA-editing site | | RNA | 31 | mer | accttcacatacgtccggactgctcagctc |
| SEQ ID NO.:209 | ccb6n-B_467 | Arabidopsis thaliana mitochondria RNA-editing site | | RNA | 31 | mer | gatgggtctcctctaaatgacgggctctc |
| SEQ ID NO.:210 | ccb6n-B_63 | Arabidopsis thaliana mitochondria RNA-editing site | | RNA | 31 | mer | tbcgtaatgcgaacgaacgcgaccacttacttc |

| SEQ ID NO. 233 | cox3_603 | Arabidopsis thaliana mitochondria RNA-editing site | | RNA | 31 | cox | ttcggaaagtattatggatccctttc |
| SEQ ID NO. 234 | cytc_1084 | Arabidopsis thaliana mitochondria RNA-editing site | | RNA | 31 | cox | gatccattgtactcattgganaacttttct |
| SEQ ID NO. 235 | cytb_215 | Arabidopsis thaliana mitochondria RNA-editing site | | RNA | 31 | cox | agccaatctcagttattgcttggagattcggtc |

FIG. 16P

| SEQ ID NO.: | ID or name | remark 1 | remark 2 | Type | Length | Unit | Sequence |
|---|---|---|---|---|---|---|---|
| SEQ ID NO.:236 | cytb_288 | Arabidopsis thaliana mitochondria RNA-editing site | | RNA | 31 | mer | catatgccatgctcacatgagcccaagtatgtttc |
| SEQ ID NO.:237 | cytb_326 | Arabidopsis thaliana mitochondria RNA-editing site | | RNA | 31 | mer | gtttacctcatcattcagtgggtcatatc |
| SEQ ID NO.:238 | cytb_508 | Arabidopsis thaliana mitochondria RNA-editing site | | RNA | 31 | mer | gcccacccttacatcgtttttttagctttcattc |
| SEQ ID NO.:239 | cytb_610 | Arabidopsis thaliana mitochondria RNA-editing site | | RNA | 31 | mer | ttttcattttagctaggaggccaagctttcttcatc |
| SEQ ID NO.:240 | cytb_853 | Arabidopsis thaliana mitochondria RNA-editing site | | RNA | 31 | mer | attcgtcgccggaatggtgtatttctttaccggatcc |
| SEQ ID NO.:241 | cytb_308 | Arabidopsis thaliana mitochondria RNA-editing site | | RNA | 31 | mer | gctcactgcgggtaggtgtgtcctcaaggtgcacc |
| SEQ ID NO.:242 | cytb_924 | Arabidopsis thaliana mitochondria RNA-editing site | | RNA | 31 | mer | tagcctgcaatatgtcaccaagttttcaaagtatc |
| SEQ ID NO.:243 | cytb_902 | Arabidopsis thaliana mitochondria RNA-editing site | | RNA | 31 | mer | aatgttgcgtagttcaaagtttcgtcacgatcc |
| SEQ ID NO.:244 | matR_1693 | Arabidopsis thaliana mitochondria RNA-editing site | | RNA | 31 | mer | accactgggtcggtgtgatcttcttagtcagtacagctc |
| SEQ ID NO.:245 | matR_1698 | Arabidopsis thaliana mitochondria RNA-editing site | | RNA | 31 | mer | cttgggctgggatcttatcaacagcggaattcacc |
| SEQ ID NO.:246 | matR_1670 | Arabidopsis thaliana mitochondria RNA-editing site | | RNA | 31 | mer | ggaaggatccattagcccgcaacgaaagacccttggcc |
| SEQ ID NO.:247 | matR_1723 | Arabidopsis thaliana mitochondria RNA-editing site | | RNA | 31 | mer | accgttcatgcgtagtcaaggatgggatcttttggatggctc |
| SEQ ID NO.:248 | matR_1731 | Arabidopsis thaliana mitochondria RNA-editing site | | RNA | 31 | mer | agtccatgacgaagaacgacctcgtcaatcggtcc |
| SEQ ID NO.:249 | matR_1734 | Arabidopsis thaliana mitochondria RNA-editing site | | RNA | 31 | mer | taaaatggtctcgggtgcatccgtgataaatggtcc |
| SEQ ID NO.:250 | matR_1771 | Arabidopsis thaliana mitochondria RNA-editing site | | RNA | 31 | mer | gacgataacgtcatcgtgtcctcaatcacccggctgcc |
| SEQ ID NO.:251 | matR_1807 | Arabidopsis thaliana mitochondria RNA-editing site | | RNA | 31 | mer | aaccattatcaagtccgaacgaacgattgctgcggacc |
| SEQ ID NO.:252 | matR_1899 | Arabidopsis thaliana mitochondria RNA-editing site | Rto MEF14 | RNA | 31 | mer | ttgaatatactctccaagtactcaaacagcatc |
| SEQ ID NO.:253 | matR_241 | Arabidopsis thaliana mitochondria RNA-editing site | | RNA | 31 | mer | tttcaccaccatcgaccgagcatcgactccatcc |
| SEQ ID NO.:254 | matR_264 | Arabidopsis thaliana mitochondria RNA-editing site | | RNA | 31 | mer | aagagatccgacgcatccaagtactctcctc |
| SEQ ID NO.:255 | matR_374 | Arabidopsis thaliana mitochondria RNA-editing site | | RNA | 31 | mer | cccaacacagtgtactcatcaagggccatcc |
| SEQ ID NO.:256 | matR_461 | Arabidopsis thaliana mitochondria RNA-editing site | | RNA | 31 | mer | accgaaatttccgattgctcaagtagagttattgatcc |

FIG. 16Q

| | | | | | | | |
|---|---|---|---|---|---|---|---|
| SEQ ID NO.:257 | nadR_80 | Arabidopsis thaliana mitochondria RNA-editing site | | RNA | 31 | mer | (illegible sequence) |
| SEQ ID NO.:258 | nad1_167 | Arabidopsis thaliana mitochondria RNA-editing site | | RNA | 31 | mer | (illegible sequence) |
| SEQ ID NO.:259 | nad1_2 | Arabidopsis thaliana mitochondria RNA-editing site | | RNA | 31 | mer | (illegible sequence) |
| SEQ ID NO.:260 | nad1_265 | Arabidopsis thaliana mitochondria RNA-editing site | | RNA | 31 | mer | (illegible sequence) |
| SEQ ID NO.:261 | nad1_307 | Arabidopsis thaliana mitochondria RNA-editing site | | RNA | 31 | mer | (illegible sequence) |
| SEQ ID NO.:262 | nad1_308 | Arabidopsis thaliana mitochondria RNA-editing site | | RNA | 31 | mer | (illegible sequence) |
| SEQ ID NO.:263 | nad1_376 | Arabidopsis thaliana mitochondria RNA-editing site | | RNA | 31 | mer | (illegible sequence) |
| SEQ ID NO.:264 | nad1_490 | Arabidopsis thaliana mitochondria RNA-editing site | | RNA | 31 | mer | (illegible sequence) |
| SEQ ID NO.:265 | nad1_493 | Arabidopsis thaliana mitochondria RNA-editing site | | RNA | 31 | mer | (illegible sequence) |
| SEQ ID NO.:266 | nad1_495 | Arabidopsis thaliana mitochondria RNA-editing site | | RNA | 31 | mer | (illegible sequence) |
| SEQ ID NO.:267 | nad1_500 | Arabidopsis thaliana mitochondria RNA-editing site | | RNA | 31 | mer | (illegible sequence) |
| SEQ ID NO.:268 | nad1_538 | Arabidopsis thaliana mitochondria RNA-editing site | | RNA | 31 | mer | (illegible sequence) |
| SEQ ID NO.:269 | nad1_546 | Arabidopsis thaliana mitochondria RNA-editing site | | RNA | 31 | mer | (illegible sequence) |
| SEQ ID NO.:270 | nad1_571 | Arabidopsis thaliana mitochondria RNA-editing site | | RNA | 31 | mer | (illegible sequence) |
| SEQ ID NO.:271 | nad1_586 | Arabidopsis thaliana mitochondria RNA-editing site | | RNA | 31 | mer | (illegible sequence) |
| SEQ ID NO.:272 | nad1_608 | Arabidopsis thaliana mitochondria RNA-editing site | | RNA | 31 | mer | (illegible sequence) |
| SEQ ID NO.:273 | nad1_674 | Arabidopsis thaliana mitochondria RNA-editing site | | RNA | 31 | mer | (illegible sequence) |
| SEQ ID NO.:274 | nad1_725 | Arabidopsis thaliana mitochondria RNA-editing site | | RNA | 31 | mer | (illegible sequence) |
| SEQ ID NO.:275 | nad1_743 | Arabidopsis thaliana mitochondria RNA-editing site | | RNA | 31 | mer | (illegible sequence) |
| SEQ ID NO.:276 | nad1_755 | Arabidopsis thaliana mitochondria RNA-editing site | | RNA | 31 | mer | (illegible sequence) |
| SEQ ID NO.:277 | nad1_783 | Arabidopsis thaliana mitochondria RNA-editing site | | RNA | 31 | mer | (illegible sequence) |
| SEQ ID NO.:278 | nad1_797 | Arabidopsis thaliana mitochondria RNA-editing site | | RNA | 31 | mer | (illegible sequence) |

FIG. 16R

| SEQ ID | | Arabidopsis thaliana mitochondria RNA-editing site | | | | | |
|---|---|---|---|---|---|---|---|
| SEQ ID NO: 279 | nad1_823 | Arabidopsis thaliana mitochondria RNA-editing site | | RNA | 31 | mer | gtcttgatctggttagtatoaaggttcttc |
| SEQ ID NO: 280 | nad1_698 | Arabidopsis thaliana mitochondria RNA-editing site | | RNA | 31 | mer | catgttatgatcaattaatggacttgtcc |
| SEQ ID NO: 281 | nad1_828 | Arabidopsis thaliana mitochondria RNA-editing site | | RNA | 31 | mer | cggaaaggtcttgcctcaaaccaaagctc |
| SEQ ID NO: 282 | nad1_907 | Arabidopsis thaliana mitochondria RNA-editing site | | RNA | 31 | mer | ttcttgatctcatcatcagctcgggtagtcc |
| SEQ ID NO: 283 | nad2_1081 | Arabidopsis thaliana mitochondria RNA-editing site | | RNA | 31 | mer | aatgacgcatggatgcaatcgccatcagttcc |
| SEQ ID NO: 284 | nad2_1160 | Arabidopsis thaliana mitochondria RNA-editing site | MEF1 | RNA | 31 | mer | ggggagctcagccaataacgaaatcctatttc |
| SEQ ID NO: 285 | nad2_1235 | Arabidopsis thaliana mitochondria RNA-editing site | | RNA | 31 | mer | accccccgttagccggcttttgagccaattc |
| SEQ ID NO: 286 | nad2_1279 | Arabidopsis thaliana mitochondria RNA-editing site | | RNA | 31 | mer | gcttggtgttgtggagcttacttctcagcctt |
| SEQ ID NO: 287 | nad2_1280 | Arabidopsis thaliana mitochondria RNA-editing site | | RNA | 31 | mer | cttaggttgtgggattcttctagcccc |
| SEQ ID NO: 288 | nad2_1305 | Arabidopsis thaliana mitochondria RNA-editing site | | RNA | 31 | mer | tccagtgggagtaggactagcgcatctaggcc |
| SEQ ID NO: 289 | nad2_1433 | Arabidopsis thaliana mitochondria RNA-editing site | | RNA | 31 | mer | tactcagtcaatgactccctttcattcattc |
| SEQ ID NO: 290 | nad2_1438 | Arabidopsis thaliana mitochondria RNA-editing site | | RNA | 31 | mer | cagtaaatgacttccttttcatttcactttcatc |
| SEQ ID NO: 291 | nad2_1490 | Arabidopsis thaliana mitochondria RNA-editing site | | RNA | 31 | mer | ttctcagctactcataaaattgccactcagttc |
| SEQ ID NO: 292 | nad2_288 | Arabidopsis thaliana mitochondria RNA-editing site | | RNA | 31 | mer | tcttcttaggttggggaccaatttttctcatttctcc |
| SEQ ID NO: 293 | nad2_341 | Arabidopsis thaliana mitochondria RNA-editing site | | RNA | 31 | mer | tcggctggtcaccattctgagcgtgtctctcgatttc |
| SEQ ID NO: 294 | nad2_344 | Arabidopsis thaliana mitochondria RNA-editing site | | RNA | 31 | mer | ctggtacccattctgatctggcttttcggaatcttc |
| SEQ ID NO: 295 | nad2_369 | Arabidopsis thaliana mitochondria RNA-editing site | | RNA | 31 | mer | tcgatgcttcgaatctcatttgaatttaatttc |
| SEQ ID NO: 296 | nad2_394 | Arabidopsis thaliana mitochondria RNA-editing site | | RNA | 31 | mer | gcttctgaatctcatcatgaatttaattcttctcaatttc |
| SEQ ID NO: 297 | nad2_400 | Arabidopsis thaliana mitochondria RNA-editing site | | RNA | 31 | mer | gaaatccatttgaatcatttccactcctactc |
| SEQ ID NO: 298 | nad2_427 | Arabidopsis thaliana mitochondria RNA-editing site | | RNA | 31 | mer | actcgcggttatgatctttatctctatgatcagacc |
| SEQ ID NO: 299 | nad2_445 | Arabidopsis thaliana mitochondria RNA-editing site | | RNA | 31 | mer | ctttcatgatctcggatcatgatttcattgtcc |
| SEQ ID NO: 300 | nad2_461 | Arabidopsis thaliana mitochondria RNA-editing site | | RNA | 31 | mer | gtttcaatgcccatcgaatttcgctatgagcc |

FIG. 16S

| SEQ ID NO: 301 | nad2_328 | Arabidopsis thaliana mitochondria RNA-editing site | | RNA | 31 | mrr | aagaaagtctgaatttcsscgyaagccggtc |
|---|---|---|---|---|---|---|---|
| SEQ ID NO: 302 | nad2_329 | Arabidopsis thaliana mitochondria RNA-editing site | | RNA | 31 | mrr | gaaagtctgaatttcsccgyaagccggtc |
| SEQ ID NO: 303 | nad2_358 | Arabidopsis thaliana mitochondria RNA-editing site | | RNA | 31 | mrr | ctcgaaaatattgatctacggtycattict |

FIG. 16T

| SEQ ID NO. | ID or name | remark 1 | remark 2 | Type | Length | Unit | Sequence |
|---|---|---|---|---|---|---|---|
| SEQ ID NO. 304 | nad2_585 | Arabidopsis thaliana mitochondria RNA-editing site | | RNA | 31 | mer | ttcctcgggaatattattgattggttgttcc |
| SEQ ID NO. 305 | nad2_59 | Arabidopsis thaliana mitochondria RNA-editing site | | RNA | 31 | mer | ccracacgtcaatcttttttagcggttic |
| SEQ ID NO. 306 | nad2_842 | Arabidopsis thaliana mitochondria RNA-editing site | | RNA | 31 | mer | cacctcttcgatccattcgcccagtcttgacc |
| SEQ ID NO. 307 | nad2_898 | Arabidopsis thaliana mitochondria RNA-editing site | | RNA | 31 | mer | gatctacgtcgtctttcttctgggcttccgtc |
| SEQ ID NO. 308 | nad2_823 | Arabidopsis thaliana mitochondria RNA-editing site | | RNA | 31 | mer | tcatttatatgcgcttaacatctcttatttc |
| SEQ ID NO. 309 | nad2_840 | Arabidopsis thaliana mitochondria RNA-editing site | | RNA | 31 | mer | tctctcttctgctcaaaatttacgtcgtttc |
| SEQ ID NO. 310 | nad2_89 | Arabidopsis thaliana mitochondria RNA-editing site | | RNA | 31 | mer | cccccagagatcttatcattccatgcaacctc |
| SEQ ID NO. 311 | nad2_90 | Arabidopsis thaliana mitochondria RNA-editing site | | RNA | 31 | mer | cccccagatcttaacaataagcaactccc |
| SEQ ID NO. 312 | nad2_958 | Arabidopsis thaliana mitochondria RNA-editing site | | RNA | 31 | mer | ccgtccatggtccccaaacgaacgtttcacccagacc |
| SEQ ID NO. 313 | nad2_981 | Arabidopsis thaliana mitochondria RNA-editing site | | RNA | 31 | mer | gccccctctacgaacgtccaaacgccctttacgcc |
| SEQ ID NO. 314 | nad2_991 | Arabidopsis thaliana mitochondria RNA-editing site | | RNA | 31 | mer | ccttcgtccattcggccccatgtcgggttttcttcc |
| SEQ ID NO. 315 | nad2_996 | Arabidopsis thaliana mitochondria RNA-editing site | | RNA | 31 | mer | gttcaatttcggcccacttctatggttcttatttcggccc |
| SEQ ID NO. 316 | nad3_149 | Arabidopsis thaliana mitochondria RNA-editing site | for-MEF22 | RNA | 31 | mer | tcgtacgtcctaacgaaatggggttccgaccctc |
| SEQ ID NO. 317 | nad3_211 | Arabidopsis thaliana mitochondria RNA-editing site | | RNA | 31 | mer | tttatctcgtttcaattatttttaatcc |
| SEQ ID NO. 318 | nad3_212 | Arabidopsis thaliana mitochondria RNA-editing site | | RNA | 31 | mer | gtatcacgttccatttctatttttcaatcc |
| SEQ ID NO. 319 | nad3_258 | Arabidopsis thaliana mitochondria RNA-editing site | | RNA | 31 | mer | gataagtaaacttttcctttcctttggcgaagtatc |
| SEQ ID NO. 320 | nad3_264 | Arabidopsis thaliana mitochondria RNA-editing site | | RNA | 31 | mer | taacccatttcctctttcctttgggaagtaccctcc |
| SEQ ID NO. 321 | nad3_26 | Arabidopsis thaliana mitochondria RNA-editing site | | RNA | 31 | mer | tctgacctcatgctcaacgactttgtacccaactcc |
| SEQ ID NO. 322 | nad3_347 | Arabidopsis thaliana mitochondria RNA-editing site | | RNA | 31 | mer | gacttctcttatctatctgtccaaacaacgggttctttgcttc |
| SEQ ID NO. 323 | nad3_352 | Arabidopsis thaliana mitochondria RNA-editing site | | RNA | 31 | mer | ctttatacgatcttgtacaaacgatgctgacttctgtaacc |
| SEQ ID NO. 324 | nad3_64 | Arabidopsis thaliana mitochondria RNA-editing site | | RNA | 31 | mer | ttaagtgaattaagctgctactagttttctttgatcc |

FIG. 16U

| SEQ ID NO. | | Arabidopsis thaliana mitochondria RNA-editing site | | RNA | 31 | mer | |
|---|---|---|---|---|---|---|---|
| SEQ ID NO.:325 | nad5_69 | Arabidopsis thaliana mitochondria RNA-editing site | | RNA | 31 | mer | gathagctgctagttcctgatcctactc |
| SEQ ID NO.:326 | nad3_5 | Arabidopsis thaliana mitochondria RNA-editing site | | RNA | 31 | mer | gccgagaacaaccaggtgggctgtaatgctgtc |
| SEQ ID NO.:327 | nad3_93 | Arabidopsis thaliana mitochondria RNA-editing site | | RNA | 31 | mer | ttcttgatcatactggggttccttttccc |
| SEQ ID NO.:328 | nad4_1010 | Arabidopsis thaliana mitochondria RNA-editing site | | RNA | 31 | mer | ctcatccaggaatggcgagctaggccatcctccc |
| SEQ ID NO.:329 | nad4_1033 | Arabidopsis thaliana mitochondria RNA-editing site | | RNA | 31 | mer | atctcccgcatgtaagtcatcgcatcgtgttc |
| SEQ ID NO.:330 | nad4_107 | Arabidopsis thaliana mitochondria RNA-editing site | | RNA | 31 | mer | tctttcattcacaatcatcagacatcgtcgtcc |
| SEQ ID NO.:331 | nad4_1101 | Arabidopsis thaliana mitochondria RNA-editing site | | RNA | 31 | mer | ccgacatcacgacctcgacctgttcgatcattcc |
| SEQ ID NO.:332 | nad4_1128 | Arabidopsis thaliana mitochondria RNA-editing site | | RNA | 31 | mer | tcccgcaggttagtgacgccctcctgccctgccatc |
| SEQ ID NO.:333 | nad4_1131 | Arabidopsis thaliana mitochondria RNA-editing site | | RNA | 31 | mer | ccgaggttagtgagcacccctgctgcattcc |
| SEQ ID NO.:334 | nad4_1132 | Arabidopsis thaliana mitochondria RNA-editing site | | RNA | 31 | mer | gaaggttagtgagcaccctgccgaacttctctc |
| SEQ ID NO.:335 | nad4_1148 | Arabidopsis thaliana mitochondria RNA-editing site | | RNA | 31 | mer | tcccatgccgaactctctcaccccatctcttttcc |
| SEQ ID NO.:336 | nad4_1172 | Arabidopsis thaliana mitochondria RNA-editing site | | RNA | 31 | mer | tcttttcctttacttcgtgccacatatgagttc |
| SEQ ID NO.:337 | nad4_1208 | Arabidopsis thaliana mitochondria RNA-editing site | | RNA | 31 | mer | tcggtactacgcagcttatcgtggcgggaattcatc |
| SEQ ID NO.:338 | nad4_124 | Arabidopsis thaliana mitochondria RNA-editing site | for L001 | RNA | 31 | mer | tccaagaatacgaccggatacgcttcctggtc |
| SEQ ID NO.:339 | nad4_1355 | Arabidopsis thaliana mitochondria RNA-editing site | for MEF18 | RNA | 31 | mer | caaacgatttctctctctctcaatctctccgattc |
| SEQ ID NO.:340 | nad4_1373 | Arabidopsis thaliana mitochondria RNA-editing site | | RNA | 31 | mer | aactctctgctttaaactgccacgagaagttc |
| SEQ ID NO.:341 | nad4_1401 | Arabidopsis thaliana mitochondria RNA-editing site | | RNA | 31 | mer | ttccatattatacctttctctgttggacc |
| SEQ ID NO.:342 | nad4_1405 | Arabidopsis thaliana mitochondria RNA-editing site | | RNA | 31 | mer | atattatacctttctgtggacccgac |
| SEQ ID NO.:343 | nad4_1417 | Arabidopsis thaliana mitochondria RNA-editing site | | RNA | 31 | mer | ttcttgttggaccactcggcatgggtgttc |
| SEQ ID NO.:344 | nad4_1452 | Arabidopsis thaliana mitochondria RNA-editing site | | RNA | 31 | mer | ttccgaatcgggttttaaccccaaaagtcgtcc |
| SEQ ID NO.:345 | nad4_158 | Arabidopsis thaliana mitochondria RNA-editing site | | RNA | 31 | mer | gttccccatcttacctttctgtatctccctc |
| SEQ ID NO.:346 | nad4_164 | Arabidopsis thaliana mitochondria RNA-editing site | | RNA | 31 | mer | ctctttctactttgtatctcctgttcc |

FIG. 16V

| | | | | | | | |
|---|---|---|---|---|---|---|---|
| SEQ ID NO: 347 | nad4_166 | Arabidopsis thaliana mitochondria RNA-editing site | | RNA | 31 | mer | ctiatacttitigtatirbcbpticctc |
| SEQ ID NO: 348 | nad4_197 | Arabidopsis thaliana mitochondria RNA-editing site | | RNA | 31 | mer | ggatacaattcgacidtcagggtcaastc |
| SEQ ID NO: 349 | nad4_23 | Arabidopsis thaliana mitochondria RNA-editing site | | RNA | 31 | mer | ctatgttggaacdtctgtgactgctatc |
| SEQ ID NO: 350 | nad4_317 | Arabidopsis thaliana mitochondria RNA-editing site | | RNA | 31 | mer | tgcccacattcgatccdatttgcattc |
| SEQ ID NO: 351 | nad4_362 | Arabidopsis thaliana mitochondria RNA-editing site | | RNA | 31 | mer | ctatgtgaagttctggaaagagtctattcc |
| SEQ ID NO: 352 | nad4_378 | Arabidopsis thaliana mitochondria RNA-editing site | | RNA | 31 | mer | gggaaatgagtatcttacatgcacttttcaatc |
| SEQ ID NO: 353 | nad4_402 | Arabidopsis thaliana mitochondria RNA-editing site | | RNA | 31 | mer | aatctgtgaatttcttaatgatcgcaggttatc |
| SEQ ID NO: 354 | nad4_403 | Arabidopsis thaliana mitochondria RNA-editing site | | RNA | 31 | mer | attcatgaattctcatgatcgcagggtcc |
| SEQ ID NO: 355 | nad4_418 | Arabidopsis thaliana mitochondria RNA-editing site | | RNA | 31 | mer | attcatcgatggttatcgcatctcgaattc |
| SEQ ID NO: 356 | nad4_436 | Arabidopsis thaliana mitochondria RNA-editing site | | RNA | 31 | mer | attcatagattctcatcatctcatgttttc |
| SEQ ID NO: 357 | nad4_437 | Arabidopsis thaliana mitochondria RNA-editing site | | RNA | 31 | mer | tgctatgatcctatcatatctcatgttttcc |
| SEQ ID NO: 358 | nad4_440 | Arabidopsis thaliana mitochondria RNA-editing site | Ref St.St | RNA | 31 | mer | tacdatttctatgtttccatgacactcggtgcc |
| SEQ ID NO: 359 | nad4_509 | Arabidopsis thaliana mitochondria RNA-editing site | | RNA | 31 | mer | ttcccaaatcatggaaccaccatgcattcaacatactc |
| SEQ ID NO: 360 | nad4_688 | Arabidopsis thaliana mitochondria RNA-editing site | | RNA | 31 | mer | tatcgttggccaaatcttttctatgggatgcatic |
| SEQ ID NO: 361 | nad4_74 | Arabidopsis thaliana mitochondria RNA-editing site | | RNA | 31 | mer | ttctatccgtgttctatcgttgccaggaaaagcattac |
| SEQ ID NO: 362 | nad4_767 | Arabidopsis thaliana mitochondria RNA-editing site | | RNA | 31 | mer | cggtcaaggatccgtcatctggatggagcattcc |
| SEQ ID NO: 363 | nad4_784 | Arabidopsis thaliana mitochondria RNA-editing site | | RNA | 31 | mer | tcgtgaaggatatccttaacaattggabaccc |
| SEQ ID NO: 364 | nad4_839 | Arabidopsis thaliana mitochondria RNA-editing site | | RNA | 31 | mer | aacccaatgttcccgaacgcgacattgcc |
| SEQ ID NO: 365 | nad4_84 | Arabidopsis thaliana mitochondria RNA-editing site | | RNA | 31 | mer | ccctggctcaggaagcatiactctctttc |
| SEQ ID NO: 366 | nad4_896 | Arabidopsis thaliana mitochondria RNA-editing site | | RNA | 31 | mer | tgctatcatatctcttgacgccatc |
| SEQ ID NO: 367 | nad4_977 | Arabidopsis thaliana mitochondria RNA-editing site | | RNA | 31 | mer | tgaatctcgttactatttgtatgtttatcjtcc |
| SEQ ID NO: 368 | nad4L_109 | Arabidopsis thaliana mitochondria RNA-editing site | | RNA | 31 | mer | aacagtacgaaacaatctcattctatgtcaatgc |

FIG. 16W

| SEQ ID NO: 369 | nad4L_110 | Arabidopsis thaliana mitochondria RNA-editing site | | RNA | 51 | rev | atstccctattatgtcaatgcaacttgaatc |
|---|---|---|---|---|---|---|---|
| SEQ ID NO: 370 | nad4L_131 | Arabidopsis thaliana mitochondria RNA-editing site | | RNA | 51 | rev | caattgaatcaatgtattagctggaatc |
| SEQ ID NO: 371 | nad4L_138 | Arabidopsis thaliana mitochondria RNA-editing site | | RNA | 51 | rev | atccgaactttggacttttccgtcatc |

FIG. 16X

| SEQ ID NO. | ID or name | remark 1 | remark 2 | Type | Length | Unit | Sequence |
|---|---|---|---|---|---|---|---|
| SEQ ID NO. 372 | nad4L_186 | Arabidopsis thaliana mitochondria RNA-editing site | | RNA | 31 | mer | ctgcatgaattgatggatcaagtatttgcttc |
| SEQ ID NO. 373 | nad4L_197 | Arabidopsis thaliana mitochondria RNA-editing site | | RNA | 31 | mer | tgatgggtcaagtatgcttcaatggttcc |
| SEQ ID NO. 374 | nad4L_41 | Arabidopsis thaliana mitochondria RNA-editing site | | RNA | 31 | mer | ccaaatattcaacatatctgatcatttc |
| SEQ ID NO. 375 | nad4L_55 | Arabidopsis thaliana mitochondria RNA-editing site | | RNA | 31 | mer | tttccgcacatccatttaggtattc |
| SEQ ID NO. 376 | nad4L_86 | Arabidopsis thaliana mitochondria RNA-editing site | | RNA | 31 | mer | gcgggaatcttcaatcagacgaaatattcc |
| SEQ ID NO. 377 | nad4L_95 | Arabidopsis thaliana mitochondria RNA-editing site | | RNA | 31 | mer | tcctttattagatcgaaatatttcattcatgtc |
| SEQ ID NO. 378 | nad5_1275 | Arabidopsis thaliana mitochondria RNA-editing site | | RNA | 31 | mer | tggaaatctgcattcgtggtgaacatggtc |
| SEQ ID NO. 379 | nad5_1498 | Arabidopsis thaliana mitochondria RNA-editing site | | RNA | 31 | mer | gtttagtaatcaattcggggtcaattccac |
| SEQ ID NO. 380 | nad5_155 | Arabidopsis thaliana mitochondria RNA-editing site | | RNA | 31 | mer | catcttgacttgcttttctatggaacgtcgcacc |
| SEQ ID NO. 381 | nad5_1550 | Arabidopsis thaliana mitochondria RNA-editing site | | RNA | 31 | mer | ccgaatacgagcttgctgctccaccatttcc |
| SEQ ID NO. 382 | nad5_1620 | Arabidopsis thaliana mitochondria RNA-editing site | | RNA | 31 | mer | ccaaaccaatacctatctgttagtatttc |
| SEQ ID NO. 383 | nad5_1819 | Arabidopsis thaliana mitochondria RNA-editing site | | RNA | 31 | mer | caaggtgcttgttgcgttatatgaaatatc |
| SEQ ID NO. 384 | nad5_1886 | Arabidopsis thaliana mitochondria RNA-editing site | | RNA | 31 | mer | attcaacctagtactttgtaatcgaatc |
| SEQ ID NO. 385 | nad5_1721 | Arabidopsis thaliana mitochondria RNA-editing site | | RNA | 31 | mer | agtttgaatgactttctagtcagatagtc |
| SEQ ID NO. 386 | nad5_1885 | Arabidopsis thaliana mitochondria RNA-editing site | | RNA | 31 | mer | atccatatgccatcgcaaagtactcgtc |
| SEQ ID NO. 387 | nad5_1918 | Arabidopsis thaliana mitochondria RNA-editing site | | RNA | 31 | mer | aactggttcaactcaattgtgcatcatc |
| SEQ ID NO. 388 | nad5_1918 | Arabidopsis thaliana mitochondria RNA-editing site | | RNA | 31 | mer | cttggtcaactctcatttgtaccttctc |
| SEQ ID NO. 389 | nad5_1929 | Arabidopsis thaliana mitochondria RNA-editing site | | RNA | 31 | mer | tcaaatgtgaaccttcatcgtcatgtggtgacc |
| SEQ ID NO. 390 | nad5_1958 | Arabidopsis thaliana mitochondria RNA-editing site | | RNA | 31 | mer | actctcaatcctcgggtagatcatcatgatc |
| SEQ ID NO. 391 | nad5_342 | Arabidopsis thaliana mitochondria RNA-editing site | | RNA | 31 | mer | atgattctgggatctttgttccagtagccc |
| SEQ ID NO. 392 | nad5_272 | Arabidopsis thaliana mitochondria RNA-editing site | | RNA | 31 | mer | tcgaatgctagtcgtcgttaatgtggtgaccc |

FIG. 16Y

| SEQ ID NO. 393 | nad5_338 | Arabidopsis thaliana mitochondria RNA-editing site | | RNA | 31 | mer | agccctcgattatgggtattatccattc |
| SEQ ID NO. 394 | nad5_324 | Arabidopsis thaliana mitochondria RNA-editing site | | RNA | 31 | mer | gtattatccatctactttcatgcc |
| SEQ ID NO. 395 | nad5_396 | Arabidopsis thaliana mitochondria RNA-editing site | | RNA | 31 | mer | tcatgccaatgtggtgactggagatatcctc |
| SEQ ID NO. 396 | nad5_484 | Arabidopsis thaliana mitochondria RNA-editing site | | RNA | 31 | mer | ttacatcgacttcaggccgcatcatcagcagctac |
| SEQ ID NO. 397 | nad5_548 | Arabidopsis thaliana mitochondria RNA-editing site | | RNA | 31 | mer | ttaggtgctttggattcgctctctgtttc |
| SEQ ID NO. 398 | nad5_563 | Arabidopsis thaliana mitochondria RNA-editing site | | RNA | 31 | mer | gattggattcagtcttgggatttcggatc |
| SEQ ID NO. 399 | nad5_588 | Arabidopsis thaliana mitochondria RNA-editing site | | RNA | 31 | mer | cttacatgagctttctaacctcttgttc |
| SEQ ID NO. 400 | nad5_806 | Arabidopsis thaliana mitochondria RNA-editing site | | RNA | 31 | mer | acttttcaccccattgtctcgtgctagtgc |
| SEQ ID NO. 401 | nad5_609 | Arabidopsis thaliana mitochondria RNA-editing site | | RNA | 31 | mer | cttctcaaccattgtatcgttcatagtgcc |
| SEQ ID NO. 402 | nad5_629 | Arabidopsis thaliana mitochondria RNA-editing site | | RNA | 31 | mer | gtgctagttgccctttagaactcttggattc |
| SEQ ID NO. 403 | nad5_679 | Arabidopsis thaliana mitochondria RNA-editing site | | RNA | 31 | mer | aatgcccataagctctattgttcttcattc |
| SEQ ID NO. 404 | nad5_713 | Arabidopsis thaliana mitochondria RNA-editing site | | RNA | 31 | mer | ggctctgatgggaattcagcgatgataggatc |
| SEQ ID NO. 405 | nad5_725 | Arabidopsis thaliana mitochondria RNA-editing site | | RNA | 31 | mer | aatcccgtcagataagcatagcctattggtc |
| SEQ ID NO. 406 | nad5_784 | Arabidopsis thaliana mitochondria RNA-editing site | | RNA | 31 | mer | ccatgtgaggtgttcaactccatgatttctgatc |
| SEQ ID NO. 407 | nad5_835 | Arabidopsis thaliana mitochondria RNA-editing site | | RNA | 31 | mer | ctagccaagtgtgtctccccatttcttgaatacc |
| SEQ ID NO. 408 | nad5_863 | Arabidopsis thaliana mitochondria RNA-editing site | | RNA | 31 | mer | acccaacctacggcttgaatgttattacttc |
| SEQ ID NO. 409 | nad5_875 | Arabidopsis thaliana mitochondria RNA-editing site | | RNA | 31 | mer | cttgattgtcattacttctgcacgg agctcc |
| SEQ ID NO. 410 | nad5_593 | Arabidopsis thaliana mitochondria RNA-editing site | | RNA | 31 | mer | ccatt cgtttgttcccaatcccagttcttc |
| SEQ ID NO. 411 | nad6_161 | Arabidopsis thaliana mitochondria RNA-editing site | | RNA | 31 | mer | tcaggttcgacttctcgtctagtatctccc |
| SEQ ID NO. 412 | nad6_109 | Arabidopsis thaliana mitochondria RNA-editing site | | RNA | 31 | mer | gactctcgctatgaacctccagttgttc |
| SEQ ID NO. 413 | nad6_131 | Arabidopsis thaliana mitochondria RNA-editing site | | RNA | 31 | mer | ccttgctagttcatatagagggctcaaagcccgttttc |
| SEQ ID NO. 414 | nad6_25 | Arabidopsis thaliana mitochondria RNA-editing site | | RNA | 31 | mer | gtacccatgatctctagtttgtcgagccc |

FIG. 16Z

| SEQ ID NO. 415 | nad8_446 | Arabidopsis thaliana mitochondria RNA-editing site | | RNA | 31 | mer | cattgggccattactctctactactattc |
| SEQ ID NO. 416 | nad8_463 | Arabidopsis thaliana mitochondria RNA-editing site | | RNA | 31 | mer | catcctactatctgctcgggtttc |
| SEQ ID NO. 417 | nad8_50 | Arabidopsis thaliana mitochondria RNA-editing site | | RNA | 31 | mer | gctcctgcctggttctcggttgct |
| SEQ ID NO. 418 | nad8_89 | Arabidopsis thaliana mitochondria RNA-editing site | | RNA | 31 | mer | gctctaaaatctcggctccatctcgtttgtttc |
| SEQ ID NO. 419 | nad8_96 | Arabidopsis thaliana mitochondria RNA-editing site | | RNA | 31 | mer | ctaaaaaatccggtaccatccgtttgttcc |
| SEQ ID NO. 420 | nad8_96 | Arabidopsis thaliana mitochondria RNA-editing site | | RNA | 31 | mer | gtccggtacctccgttgttctccaccccc |
| SEQ ID NO. 421 | nad7_1050 | Arabidopsis thaliana mitochondria RNA-editing site | | RNA | 31 | mer | cttccggtccgttcctggctaagccatctgtccc |
| SEQ ID NO. 422 | nad7_1052 | Arabidopsis thaliana mitochondria RNA-editing site | | RNA | 31 | mer | gtccggtcctggcacccacctcgtccctaccgt |
| SEQ ID NO. 423 | nad7_1078 | Arabidopsis thaliana mitochondria RNA-editing site | | RNA | 31 | mer | cctatccgtcgtatctaactaagcgcaccggctcc |
| SEQ ID NO. 424 | nad7_1082 | Arabidopsis thaliana mitochondria RNA-editing site | | RNA | 31 | mer | acccgtcgtaacctaagcgcacccggctctgct |
| SEQ ID NO. 425 | nad7_1098 | Arabidopsis thaliana mitochondria RNA-editing site | | RNA | 31 | mer | gctaaaactaagcgacgcacctggctctgctcctatctt |
| SEQ ID NO. 426 | nad7_1103 | Arabidopsis thaliana mitochondria RNA-editing site | | RNA | 31 | mer | ctcggctctgctcctctctaccaacgcatctctgatctt |
| SEQ ID NO. 427 | nad7_1124 | Arabidopsis thaliana mitochondria RNA-editing site | | RNA | 31 | mer | gactcgatctctctgtccaaactcatcacatgctt |
| SEQ ID NO. 428 | nad7_1137 | Arabidopsis thaliana mitochondria RNA-editing site | | RNA | 31 | mer | gtctaaactctcacctgcccggccaggtggtgtt |
| SEQ ID NO. 429 | nad7_137 | Arabidopsis thaliana mitochondria RNA-editing site | | RNA | 31 | mer | gggtgggtaccgtcgcggatccacacatattggatc |
| SEQ ID NO. 430 | nad7_200 | Arabidopsis thaliana mitochondria RNA-editing site | for NEK9 | RNA | 31 | mer | accaaatctatctctcaaggcattaacctattc |
| SEQ ID NO. 431 | nad7_209 | Arabidopsis thaliana mitochondria RNA-editing site | | RNA | 31 | mer | atctctaaacgctttacctatctctgatggtt |
| SEQ ID NO. 432 | nad7_213 | Arabidopsis thaliana mitochondria RNA-editing site | | RNA | 31 | mer | tctaaacgctttacctatctgatctgttctagac |
| SEQ ID NO. 433 | nad7_24 | Arabidopsis thaliana mitochondria RNA-editing site | for OTP87 | RNA | 31 | mer | ccttctctcatgatgactctggtgataaaggcaaatc |
| SEQ ID NO. 434 | nad7_344 | Arabidopsis thaliana mitochondria RNA-editing site | | RNA | 31 | mer | catgttctctgatggtcccaaga-ctcccgcbt |
| SEQ ID NO. 435 | nad7_251 | Arabidopsis thaliana mitochondria RNA-editing site | | RNA | 31 | mer | ctatgtatggcccaacgaacaacgctcatctctt |
| SEQ ID NO. 436 | nad7_316 | Arabidopsis thaliana mitochondria RNA-editing site | | RNA | 31 | mer | ttactgctctaaatctctctctgacgtgttattcc |

FIG. 16AA

| SEQ ID NO. 437 | nad7_333 | Arabidopsis thaliana mitochondria RNA-editing site | | RNA | 31 | noer | gaagtgtbatccgctgtaadcacdcggcattc |
| SEQ ID NO. 438 | nad7_344 | Arabidopsis thaliana mitochondria RNA-editing site | | RNA | 31 | noer | tccgtgaacataactcgaattcccaccactt |
| SEQ ID NO. 439 | nad7_38 | Arabidopsis thaliana mitochondria RNA-editing site | | RNA | 31 | noer | ctctaggaaacagganacatacacaactltactct |

FIG. 16BB

| SEQ ID NO. | ID or name | remark 1 | remark 2 | Type | Length | Unit | Sequence |
|---|---|---|---|---|---|---|---|
| SEQ ID NO. 440 | nad7_879 | Arabidopsis thaliana mitochondria RNA-editing site | | RNA | 31 | mer | |
| SEQ ID NO. 441 | nad7_879 | Arabidopsis thaliana mitochondria RNA-editing site | | RNA | 31 | mer | |
| SEQ ID NO. 442 | nad7_698 | Arabidopsis thaliana mitochondria RNA-editing site | | RNA | 31 | mer | |
| SEQ ID NO. 443 | nad7_728 | Arabidopsis thaliana mitochondria RNA-editing site | | RNA | 31 | mer | |
| SEQ ID NO. 444 | nad7_734 | Arabidopsis thaliana mitochondria RNA-editing site | | RNA | 31 | mer | |
| SEQ ID NO. 445 | nad7_759 | Arabidopsis thaliana mitochondria RNA-editing site | | RNA | 31 | mer | |
| SEQ ID NO. 446 | nad7_759 | Arabidopsis thaliana mitochondria RNA-editing site | | RNA | 31 | mer | |
| SEQ ID NO. 447 | nad7_77 | Arabidopsis thaliana mitochondria RNA-editing site | | RNA | 31 | mer | |
| SEQ ID NO. 448 | nad7_799 | Arabidopsis thaliana mitochondria RNA-editing site | | RNA | 31 | mer | |
| SEQ ID NO. 449 | nad7_799 | Arabidopsis thaliana mitochondria RNA-editing site | | RNA | 31 | mer | |
| SEQ ID NO. 450 | nad7_806 | Arabidopsis thaliana mitochondria RNA-editing site | | RNA | 31 | mer | |
| SEQ ID NO. 451 | nad7_863 | Arabidopsis thaliana mitochondria RNA-editing site | | RNA | 31 | mer | |
| SEQ ID NO. 452 | nad9_187 | Arabidopsis thaliana mitochondria RNA-editing site | | RNA | 31 | mer | |
| SEQ ID NO. 453 | nad9_190 | Arabidopsis thaliana mitochondria RNA-editing site | | RNA | 31 | mer | |
| SEQ ID NO. 454 | nad9_238 | Arabidopsis thaliana mitochondria RNA-editing site | | RNA | 31 | mer | |
| SEQ ID NO. 455 | nad9_328 | Arabidopsis thaliana mitochondria RNA-editing site | for SLO1 | RNA | 31 | mer | |
| SEQ ID NO. 456 | nad9_398 | Arabidopsis thaliana mitochondria RNA-editing site | | RNA | 31 | mer | |
| SEQ ID NO. 457 | nad9_439 | Arabidopsis thaliana mitochondria RNA-editing site | | RNA | 31 | mer | |
| SEQ ID NO. 458 | nad9_32 | Arabidopsis thaliana mitochondria RNA-editing site | | RNA | 31 | mer | |
| SEQ ID NO. 459 | orf240_199 | Arabidopsis thaliana mitochondria RNA-editing site | | RNA | 31 | mer | |
| SEQ ID NO. 460 | orf240A_115 | Arabidopsis thaliana mitochondria RNA-editing site | | RNA | 31 | mer | |

FIG. 16CC

| | | | | | | | |
|---|---|---|---|---|---|---|---|
| SEQ ID NO: 461 | orfX_144 | Arabidopsis thaliana mitochondria RNA-editing site | | RNA | 31 | mer | tggttgtcttggttttttttttattggttc |
| SEQ ID NO: 462 | orfX_145 | Arabidopsis thaliana mitochondria RNA-editing site | | RNA | 31 | mer | ggttgtttttttttttttttttttttggttc |
| SEQ ID NO: 463 | orfX_151 | Arabidopsis thaliana mitochondria RNA-editing site | | RNA | 31 | mer | tttttttttttttttttttttttttttttttt |
| SEQ ID NO: 464 | orfX_154 | Arabidopsis thaliana mitochondria RNA-editing site | | RNA | 31 | mer | gttttttttttttttttttttttttatatctcc |
| SEQ ID NO: 465 | orfX_173 | Arabidopsis thaliana mitochondria RNA-editing site | | RNA | 31 | mer | ttttttttttttttttttttttttcttttttttt |
| SEQ ID NO: 466 | orfX_177 | Arabidopsis thaliana mitochondria RNA-editing site | | RNA | 31 | mer | ggtttttttttttttttttttttttttttttt |
| SEQ ID NO: 467 | orfX_200 | Arabidopsis thaliana mitochondria RNA-editing site | | RNA | 31 | mer | tttttttttttttttttttttttttttttttt |
| SEQ ID NO: 468 | orfX_361 | Arabidopsis thaliana mitochondria RNA-editing site | | RNA | 31 | mer | ttttttttttttttttttttttttttttttttt |
| SEQ ID NO: 469 | orfX_364 | Arabidopsis thaliana mitochondria RNA-editing site | | RNA | 31 | mer | ttttttttttttttttttttttttttttttttt |
| SEQ ID NO: 470 | orfX_377 | Arabidopsis thaliana mitochondria RNA-editing site | | RNA | 31 | mer | ttttttttttttttttttttttttttttttttt |
| SEQ ID NO: 471 | orfX_379 | Arabidopsis thaliana mitochondria RNA-editing site | | RNA | 31 | mer | ttttttttttttttttttttttttttttttttt |
| SEQ ID NO: 472 | orfX_387 | Arabidopsis thaliana mitochondria RNA-editing site | | RNA | 31 | mer | ttttttttttttttttttttttttttttttttt |
| SEQ ID NO: 473 | orfX_406 | Arabidopsis thaliana mitochondria RNA-editing site | | RNA | 31 | mer | ttttttttttttttttttttttttttttttttt |
| SEQ ID NO: 474 | orfX_407 | Arabidopsis thaliana mitochondria RNA-editing site | | RNA | 31 | mer | ttttttttttttttttttttttttttttttttt |
| SEQ ID NO: 475 | orfX_409 | Arabidopsis thaliana mitochondria RNA-editing site | | RNA | 31 | mer | ttttttttttttttttttttttttttttttttt |
| SEQ ID NO: 476 | orfX_412 | Arabidopsis thaliana mitochondria RNA-editing site | | RNA | 31 | mer | ttttttttttttttttttttttttttttttttt |
| SEQ ID NO: 477 | orfX_440 | Arabidopsis thaliana mitochondria RNA-editing site | | RNA | 31 | mer | ttttttttttttttttttttttttttttttttt |
| SEQ ID NO: 478 | orfX_474 | Arabidopsis thaliana mitochondria RNA-editing site | | RNA | 31 | mer | ttttttttttttttttttttttttttttttttt |
| SEQ ID NO: 479 | orfX_509 | Arabidopsis thaliana mitochondria RNA-editing site | | RNA | 31 | mer | atgttttttttttttttttttttatctatgacc |
| SEQ ID NO: 480 | orfX_530 | Arabidopsis thaliana mitochondria RNA-editing site | | RNA | 31 | mer | ttttttttttttttttttttttttttttttttt |
| SEQ ID NO: 481 | orfX_538 | Arabidopsis thaliana mitochondria RNA-editing site | | RNA | 31 | mer | ttttttttttttttttttttttttttttttttt |
| SEQ ID NO: 482 | orfX_550 | Arabidopsis thaliana mitochondria RNA-editing site | | RNA | 31 | mer | ttttttttttttttttttttttttttgtgctcc |

FIG. 16DD

| SEQ ID NO. | Name | Description | | Type | Length | | Sequence |
|---|---|---|---|---|---|---|---|
| SEQ ID NO.:483 | orfX_581 | Arabidopsis thaliana mitochondria RNA-editing site | | RNA | 31 | mer | cccagcacctgtacctgggcctgtttgcc |
| SEQ ID NO.:484 | orfX_596 | Arabidopsis thaliana mitochondria RNA-editing site | | RNA | 31 | mer | gacctgtaacggtgatctgttgcccgacc |
| SEQ ID NO.:485 | orfX_587 | Arabidopsis thaliana mitochondria RNA-editing site | | RNA | 31 | mer | tatcctgtactgtgatcgtggccagcatc |
| SEQ ID NO.:486 | orfX_59 | Arabidopsis thaliana mitochondria RNA-editing site | | RNA | 31 | mer | tctatctctctcctggactcacttcgcatc |
| SEQ ID NO.:487 | orfX_643 | Arabidopsis thaliana mitochondria RNA-editing site | | RNA | 31 | mer | acgaaccaacgtcgtttgatggttttc |
| SEQ ID NO.:488 | orfX_649 | Arabidopsis thaliana mitochondria RNA-editing site | | RNA | 31 | mer | aacatgccgctttgatggctttccggctc |
| SEQ ID NO.:489 | orfX_695 | Arabidopsis thaliana mitochondria RNA-editing site | | RNA | 31 | mer | tggtttccgctctccacagctcgctcttc |
| SEQ ID NO.:490 | orfX_669 | Arabidopsis thaliana mitochondria RNA-editing site | | RNA | 31 | mer | gcgtcttccgctctccacagctgctctctc |
| SEQ ID NO.:491 | orfX_693 | Arabidopsis thaliana mitochondria RNA-editing site | | RNA | 31 | mer | ttccacacctcggatcatctgctgccacatc |
| SEQ ID NO.:492 | orfX_700 | Arabidopsis thaliana mitochondria RNA-editing site | | RNA | 31 | mer | gctccggatcctctggcccaaatcgtcgcc |
| SEQ ID NO.:493 | orfX_705 | Arabidopsis thaliana mitochondria RNA-editing site | | RNA | 31 | mer | ggatctctggctccaaatcgtctccggttc |
| SEQ ID NO.:494 | orfX_746 | Arabidopsis thaliana mitochondria RNA-editing site | | RNA | 31 | mer | ttgatcatacagtggtcctttgttgggcatc |
| SEQ ID NO.:495 | orfX_97 | Arabidopsis thaliana mitochondria RNA-editing site | | RNA | 31 | mer | atttctagtggagacagttcgaatccgttccgttc |
| SEQ ID NO.:496 | pseudo-rps14_160 | Arabidopsis thaliana mitochondria RNA-editing site | | RNA | 31 | mer | ccttcgaacgagtccagtaaacccgagtgattc |
| SEQ ID NO.:497 | pseudo-rps14_27 | Arabidopsis thaliana mitochondria RNA-editing site | | RNA | 31 | mer | aaacgccttctccaagctctttgtccaaagatccc |
| SEQ ID NO.:498 | rps16_200 | Arabidopsis thaliana mitochondria RNA-editing site | | RNA | 31 | mer | gtactaaactggcgtttctgaacgcttggtcatc |
| SEQ ID NO.:499 | rps16_228 | Arabidopsis thaliana mitochondria RNA-editing site | | RNA | 31 | mer | agatctctggcactcaagtctctaaagcccgctc |
| SEQ ID NO.:500 | rps16_24 | Arabidopsis thaliana mitochondria RNA-editing site | | RNA | 31 | mer | tcttcacccaaccaacccgtctcgccttgc |
| SEQ ID NO.:501 | rps16_93 | Arabidopsis thaliana mitochondria RNA-editing site | | RNA | 31 | mer | ataaaatcgcttctgctctacccggaagtatc |
| SEQ ID NO.:502 | rps16_440 | Arabidopsis thaliana mitochondria RNA-editing site | | RNA | 31 | mer | ggatcgctcgtgtgtcctccaccggggcaaaccc |
| SEQ ID NO.:503 | rps16_506 | Arabidopsis thaliana mitochondria RNA-editing site | | RNA | 31 | mer | gaacagccgctccattacgcgacatacaccc |
| SEQ ID NO.:504 | rps16_513 | Arabidopsis thaliana mitochondria RNA-editing site | | RNA | 31 | mer | ccgctacattacgcgctcataaaccatgttc |

FIG. 16EE

| SEQ ID NO: 505 | rpl16_61 | Arabidopsis thaliana mitochondria RNA-editing site | | RNA | 31 | rna | ccgcggaagjtabdacbpt6cggaatcb: |
| SEQ ID NO: 506 | rpl2_212 | Arabidopsis thaliana mitochondria RNA-editing site | | RNA | 31 | rna | abgacctcatbgtbctcbagatbgatcc |
| SEQ ID NO: 507 | rpl2_209 | Arabidopsis thaliana mitochondria RNA-editing site | | RNA | 31 | rna | aagtbcgabcgtcgcgcaaagabtcbgacc |

FIG. 16FF

| SEQ ID NO. | ID or name | remark 1 | remark 2 | Type | Length | Unit | Sequence |
|---|---|---|---|---|---|---|---|
| SEQ ID NO. 506 | rps2_711 | Arabidopsis thaliana mitochondria RNA-editing site | | RNA | 31 | mer | oangccccgccctbctcgcggcccataggatc |
| SEQ ID NO. 508 | rps5_189 | Arabidopsis thaliana mitochondria RNA-editing site | | RNA | 31 | mer | kaadetggdkaaftgdtdtgagatlccqtc |
| SEQ ID NO. 510 | rps5_317 | Arabidopsis thaliana mitochondria RNA-editing site | | RNA | 31 | mer | ctchccgagggcaatggcatgtctcattltc |
| SEQ ID NO. 511 | rps5_329 | Arabidopsis thaliana mitochondria RNA-editing site | | RNA | 31 | mer | atggacdgtctcctttccggtctagacttc |
| SEQ ID NO. 512 | rps5_38 | Arabidopsis thaliana mitochondria RNA-editing site | | RNA | 31 | mer | ttcccctcaatttbcctcctgaagatgtatc |
| SEQ ID NO. 513 | rps5_47 | Arabidopsis thaliana mitochondria RNA-editing site | | RNA | 31 | mer | ttcaftccgaagatgtatctccgfctagadc |
| SEQ ID NO. 514 | rps5_512 | Arabidopsis thaliana mitochondria RNA-editing site | | RNA | 31 | mer | cttcggccaaccctccaagcpagtggcctttcc |
| SEQ ID NO. 515 | rps5_58 | Arabidopsis thaliana mitochondria RNA-editing site | | RNA | 31 | mer | gacfgaaccagtcaagctccgcgctcccaccc |
| SEQ ID NO. 516 | rps5_58 | Arabidopsis thaliana mitochondria RNA-editing site | | RNA | 31 | mer | atgtatccgtccaagatccgtctctcccaacc |
| SEQ ID NO. 517 | rps5_64 | Arabidopsis thaliana mitochondria RNA-editing site | | RNA | 31 | mer | ttcaagtccaagatccgttcctccaaccqaatc |
| SEQ ID NO. 518 | rps5_52 | Arabidopsis thaliana mitochondria RNA-editing site | | RNA | 31 | mer | ctccccgcccccgttctgacagttcccggatc |
| SEQ ID NO. 519 | rps12_184 | Arabidopsis thaliana mitochondria RNA-editing site | | RNA | 31 | mer | atacctgtccctagaaccacggagtatgctc |
| SEQ ID NO. 520 | rps12_146 | Arabidopsis thaliana mitochondria RNA-editing site | | RNA | 31 | mer | cctgtgatcaccgaataaccctcatccccttc |
| SEQ ID NO. 521 | rps12_199 | Arabidopsis thaliana mitochondria RNA-editing site | | RNA | 31 | mer | cgtttgagccaaccgacatgcccatttgctc |
| SEQ ID NO. 522 | rps12_321 | Arabidopsis thaliana mitochondria RNA-editing site | | RNA | 31 | mer | ttgcccatccccggcgtggagggttcatacttc |
| SEQ ID NO. 523 | rps12_266 | Arabidopsis thaliana mitochondria RNA-editing site | | RNA | 31 | mer | tgttacttcagcagcagatgcgcpccacpgatc |
| SEQ ID NO. 524 | rps12_284 | Arabidopsis thaliana mitochondria RNA-editing site | | RNA | 31 | mer | gttagagttgaaacpatcgcccacgcpgcatccttc |
| SEQ ID NO. 525 | rps12_285 | Arabidopsis thaliana mitochondria RNA-editing site | | RNA | 31 | mer | tagagtgaaatgaatccgccacgcpgttcaaacctc |
| SEQ ID NO. 526 | rps12_64 | Arabidopsis thaliana mitochondria RNA-editing site | | RNA | 31 | mer | agacccctacccgactccgtctggaataagctacc |
| SEQ ID NO. 527 | rps3_1110 | Arabidopsis thaliana mitochondria RNA-editing site | | RNA | 31 | mer | ccatccaattaaggctccaatatgtcgggaaaccc |
| SEQ ID NO. 528 | rps3_1244 | Arabidopsis thaliana mitochondria RNA-editing site | | RNA | 31 | mer | gcccacgagagtgctccfcccggaccggtcaaaccttc |

FIG. 16GG

| SEQ ID NO. 529 | rps3_128 | Arabidopsis thaliana mitochondria RNA-editing site | | RNA | 31 | mer | gtatcaatgatgtccatctgagggdcttatttc |
|---|---|---|---|---|---|---|---|
| SEQ ID NO. 530 | rps3_1266 | Arabidopsis thaliana mitochondria RNA-editing site | | RNA | 31 | mer | gtaccaggtaccactctaattttcacgaagtc |
| SEQ ID NO. 531 | rps3_1278 | Arabidopsis thaliana mitochondria RNA-editing site | | RNA | 31 | mer | ttttcacgaaggtcaasaaatgcgatcttc |
| SEQ ID NO. 532 | rps3_1344 | Arabidopsis thaliana mitochondria RNA-editing site | | RNA | 31 | mer | gtccagtcaaatctaaatctcgttatcaaagg |
| SEQ ID NO. 533 | rps3_1351 | Arabidopsis thaliana mitochondria RNA-editing site | | RNA | 31 | mer | aaatcaaaatctgttatcaaagcgtcgtctc |
| SEQ ID NO. 534 | rps3_1362 | Arabidopsis thaliana mitochondria RNA-editing site | | RNA | 31 | mer | aaatcaaatctgttatcaaagcgctcc |
| SEQ ID NO. 535 | rps3_1479 | Arabidopsis thaliana mitochondria RNA-editing site | | RNA | 31 | mer | acgggtgagctgggcctcggtatttgtttcc |
| SEQ ID NO. 536 | rps3_1532 | Arabidopsis thaliana mitochondria RNA-editing site | | RNA | 31 | mer | aaactaaatgctctaggcatcgaaaaactc |
| SEQ ID NO. 537 | rps3_1534 | Arabidopsis thaliana mitochondria RNA-editing site | | RNA | 31 | mer | actaaatgctctaggcatcgaaaaatctc |
| SEQ ID NO. 538 | rps3_1571 | Arabidopsis thaliana mitochondria RNA-editing site | | RNA | 31 | mer | cattcaaccataaaatcgatctgctcctgc |
| SEQ ID NO. 539 | rps3_1580 | Arabidopsis thaliana mitochondria RNA-editing site | | RNA | 31 | mer | ataaaatcgatctgctcctcgtccggaatctc |
| SEQ ID NO. 540 | rps3_1598 | Arabidopsis thaliana mitochondria RNA-editing site | | RNA | 31 | mer | ctgtgaaggtatctactcgtccggaatctc |
| SEQ ID NO. 541 | rps3_427 | Arabidopsis thaliana mitochondria RNA-editing site | | RNA | 31 | mer | ttcggatttgtctcgtaggtgtatatc |
| SEQ ID NO. 542 | rps3_508 | Arabidopsis thaliana mitochondria RNA-editing site | | RNA | 31 | mer | acccgatctccctgtaccgaagggdttc |
| SEQ ID NO. 543 | rps3_548 | Arabidopsis thaliana mitochondria RNA-editing site | | RNA | 31 | mer | aaccctcgctaaagaagaatctttctaaatc |
| SEQ ID NO. 544 | rps3_809 | Arabidopsis thaliana mitochondria RNA-editing site | | RNA | 31 | mer | agcgtccgatggaaaatgacgactcctc |
| SEQ ID NO. 545 | rps3_84 | Arabidopsis thaliana mitochondria RNA-editing site | | RNA | 31 | mer | ctcggtaaaaatctgcgtccagatctaagtc |
| SEQ ID NO. 546 | rps3_897 | Arabidopsis thaliana mitochondria RNA-editing site | | RNA | 31 | mer | gctctcgtctcgctttttcgtagaaacgttc |
| SEQ ID NO. 547 | rps4_1043 | Arabidopsis thaliana mitochondria RNA-editing site | | RNA | 31 | mer | cctatcctccacgacatcagattaaaagatc |
| SEQ ID NO. 548 | rps4_1043 | Arabidopsis thaliana mitochondria RNA-editing site | | RNA | 31 | mer | atatcctccacgtcctaagatcaaagatctcg |
| SEQ ID NO. 549 | rps4_1052 | Arabidopsis thaliana mitochondria RNA-editing site | | RNA | 31 | mer | actgactaaagataaagatctccaaatctcc |
| SEQ ID NO. 550 | rps4_1057 | Arabidopsis thaliana mitochondria RNA-editing site | | RNA | 31 | mer | ctaagataaagatgtcccaaacctctcttc |

FIG. 16HH

| SEQ ID NO.:551 | rps4_176 | Arabidopsis thaliana mitochondria RNA-editing site | | RNA | 31 | noe | aagagatctattaagaagagaaaagattatc |
|---|---|---|---|---|---|---|---|
| SEQ ID NO.:552 | rps4_206 | Arabidopsis thaliana mitochondria RNA-editing site | for MEF20 | RNA | 31 | noe | tatatccaataccaactccaugaaagtgc |
| SEQ ID NO.:553 | rps4_228 | Arabidopsis thaliana mitochondria RNA-editing site | | RNA | 31 | noe | ctccaataccaactacacgaaagtgccct |
| SEQ ID NO.:554 | rps4_235 | Arabidopsis thaliana mitochondria RNA-editing site | | RNA | 31 | noe | ttacaaactcccgaaagtgccccttttc |
| SEQ ID NO.:555 | rps4_290 | Arabidopsis thaliana mitochondria RNA-editing site | | RNA | 31 | noe | gaaacaaacgaacticatata acctttcc |
| SEQ ID NO.:556 | rps4_308 | Arabidopsis thaliana mitochondria RNA-editing site | | RNA | 31 | noe | gaacttcatatacccttccacttaatcc |
| SEQ ID NO.:557 | rps4_332 | Arabidopsis thaliana mitochondria RNA-editing site | | RNA | 31 | noe | ttacttccgaaacaacgatgcaacgttcc |
| SEQ ID NO.:558 | rps4_343 | Arabidopsis thaliana mitochondria RNA-editing site | | RNA | 31 | noe | ctcaagatcgatcgtactccgcttcgctcc |
| SEQ ID NO.:559 | rps4_377 | Arabidopsis thaliana mitochondria RNA-editing site | | RNA | 31 | noe | ttcttgaacttcatttcccccaagccaaggtttttcc |
| SEQ ID NO.:560 | rps4_52N | Arabidopsis thaliana mitochondria RNA-editing site | | RNA | 31 | noe | aaaattaaggagatctitcfatataacatgtaacctt |
| SEQ ID NO.:561 | rps4_77 | Arabidopsis thaliana mitochondria RNA-editing site | | RNA | 31 | noe | cattaagattcaaacttgtcgtcaacttt |
| SEQ ID NO.:562 | rps4_82 | Arabidopsis thaliana mitochondria RNA-editing site | | RNA | 31 | noe | ccaaacttgccgctccttctttggaaaagttc |
| SEQ ID NO.:563 | rps4_958 | Arabidopsis thaliana mitochondria RNA-editing site | for MEF1 | RNA | 31 | noe | ttcaaaacggatcgaactccactccataatc |
| SEQ ID NO.:564 | rps4_967 | Arabidopsis thaliana mitochondria RNA-editing site | | RNA | 31 | noe | gaacfaactacttcattttcgtcaagtctaactc |
| SEQ ID NO.:565 | rps4_992 | Arabidopsis thaliana mitochondria RNA-editing site | | RNA | 31 | noe | ttcattaatagaacacacaataaaagtctgtgtttatc |
| SEQ ID NO.:566 | rps7_282 | Arabidopsis thaliana mitochondria RNA-editing site | | RNA | 31 | noe | ttaagctatagatacgacagctttcgacgaaaatgttc |

FIG. 18A
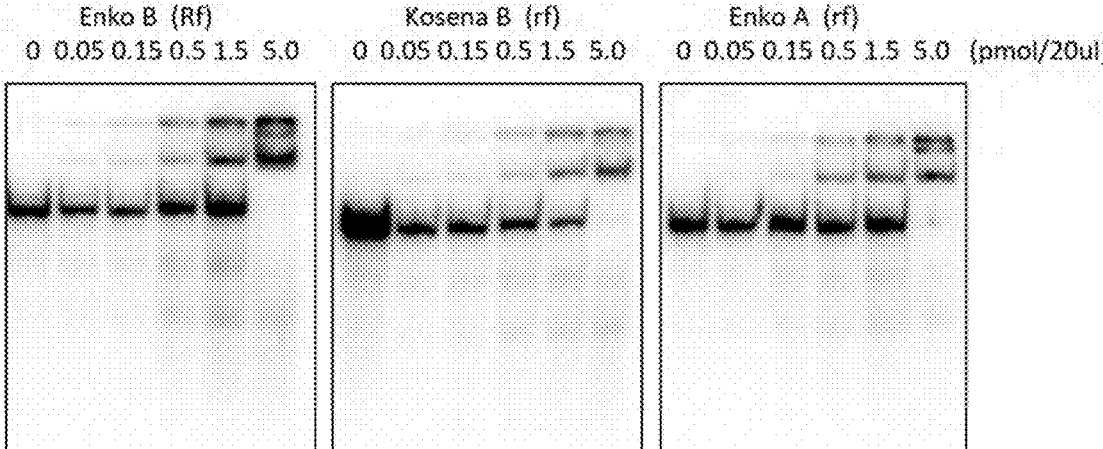
FIG. 18B
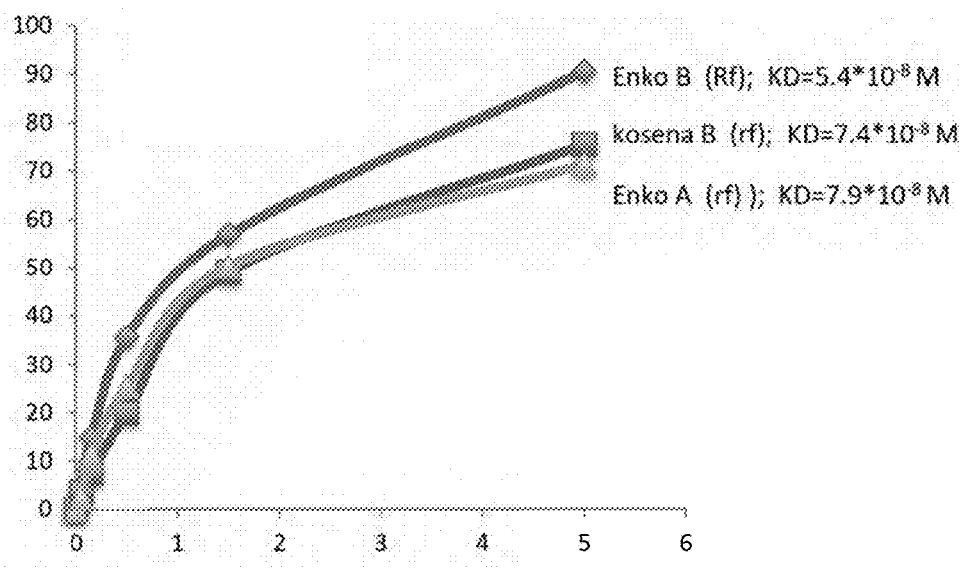
FIG. 18C
| | EnkoB | kosenaB | EnkoA |
|---|---|---|---|
| 208 | 8.399.E-06 | 4.620.E-04 | 6.299.E-02 |
| 316 | 2.702.E-04 | 2.667.E-04 | 2.630.E-04 |
| 352 | 1.372.E-04 | 7.168.E-03 | 3.535.E-01 |
| 373 | 2.711.E-04 | 5.013.E-03 | 4.007.E-01 |

FIG. 19A
large Rf (enko B)
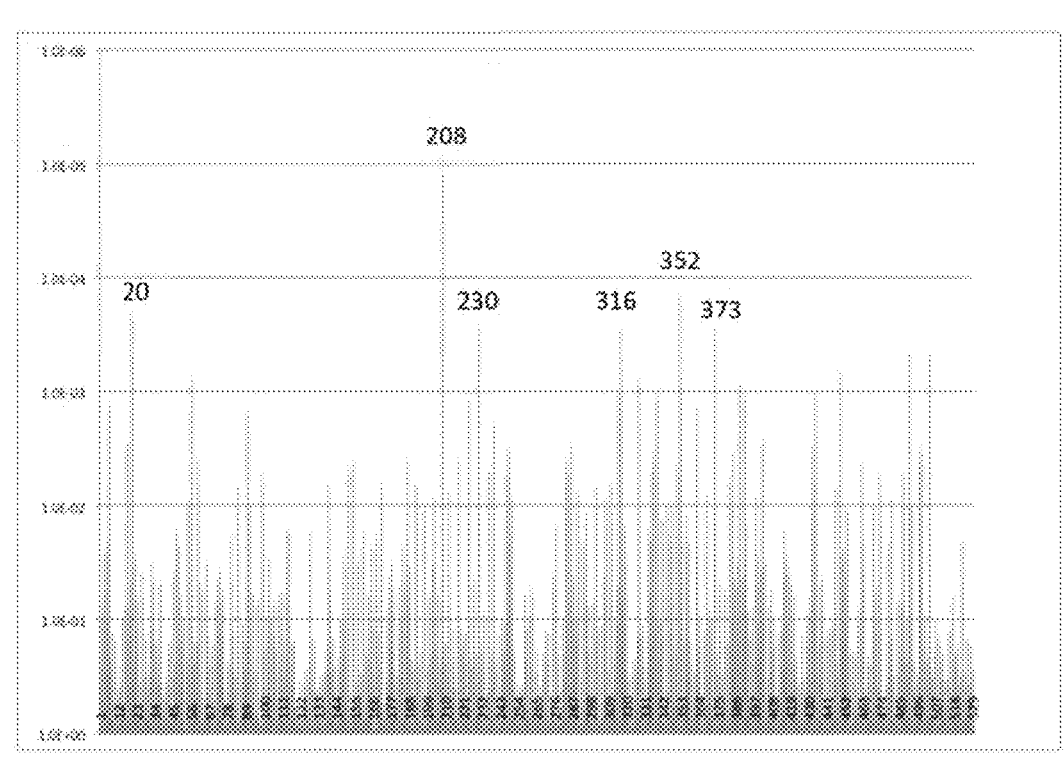
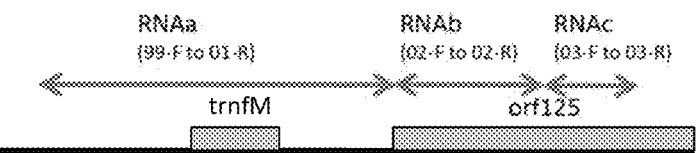

PPR motif No.

Amino acid

Enko B (Rf; ND)

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | V | Y | V | V | I | V | F | V | I | I | T | V | Q | I | V | I |
| 4 | C | N | T | T | G | S | N | N | S | N | N | D | N | S | T | I |
| ii | D | D | N | T | N | D | D | N | N | D | D | D | D | N | N | D |

Kosena B (rf; 99.4%)

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | V | Y | V | V | I | V | F | V | I | I | T | V | Q | I | V | I |
| 4 | C | T | N | T | G | S | N | N | S | N | N | D | N | S | T | I |
| ii | D | D | N | T | N | D | D | N | N | D | D | D | D | N | N | D |

Comet B (Rf; 98.0%)

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | V | Y | V | V | I | V | F | V | I | I | T | V | Q | I | V | I |
| 4 | C | N | T | T | G | S | N | N | S | N | N | D | N | S | T | I |
| ii | D | D | N | T | N | D | D | N | N | D | D | D | D | N | N | D |

Enko A (rf; 85.7%)

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | I | Y | V | L | I | V | V | V | I | F | V | V | L | I | V | I |
| 4 | N | T | T | T | G | S | N | N | N | T | N | N | N | S | N | I |
| ii | D | D | D | D | N | N | N | N | D | N | D | D | D | N | N | D |

Comet A (rf; 87.6%)

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | I | Y | V | V | I | V | V | V | I | F | T | V | L | I | V | I |
| 4 | N | T | T | T | G | S | N | N | N | N | N | N | N | S | N | I |
| ii | D | D | N | D | N | N | N | N | D | D | D | D | D | N | N | D |

Icicle CA (rf; 85.8%)

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | I | Y | V | V | I | V | F | V | I | F | V | V | L | I | V | I |
| 4 | C | T | N | T | G | S | S | N | S | N | T | N | N | S | N | I |
| ii | N | D | N | N | D | D | D | N | D | N | N | D | D | N | N | D | rrORF690-1 (?; 87.2%)

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | I | Y | A | I | I | V | F | V | V | I | T | V | L | F | V | I |
| 4 | N | N | N | T | G | S | T | S | S | N | N | N | N | N | N | I |
| ii | D | D | N | D | N | N | N | S | N | D | D | D | D | N | N | D | rrORF690-2 (?; 86.6%)

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | I | Y | A | I | I | V | F | V | V | I | T | V | L | V | V | I |
| 4 | N | N | N | T | G | S | T | S | S | N | N | N | N | N | N | I |
| ii | D | D | N | D | N | N | N | S | N | D | D | D | D | N | N | D |

PC_PPR-A (?; 85.8%)

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | V | Y | V | L | I | V | V | V | I | F | V | V | L | I | V | I |
| 4 | F | T | T | T | G | S | N | N | N | T | N | N | N | S | N | I |
| ii | D | D | N | D | N | D | N | N | D | N | D | D | D | N | D | D |

PC_PPR-BL (?; 82.8%)

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | V | Y | V | I | I | V | F | V | I | I | I | V | Q | I | V | I |
| 4 | F | T | S | T | G | S | N | S | N | S | T | N | N | N | T | R |
| ii | N | S | N | N | N | N | N | N | D | N | N | D | D | D | N | D |

METHOD FOR DESIGNING RNA BINDING PROTEIN UTILIZING PPR MOTIF, AND USE THEREOF

CROSS-REFERENCE TO RELATED APPLICATION

This application is a Divisional of U.S. patent application Ser. No. 17/195,449, filed on Mar. 8, 2021, which is a Divisional of U.S. patent application Ser. No. 16/894,295, filed on Jun. 5, 2020 (issued as U.S. Pat. No. 10,943,671), which is a Divisional of U.S. patent application Ser. No. 16/431,429, filed on Jun. 4, 2019 (issued as U.S. Pat. No. 10,679,731), which is a Divisional of U.S. patent application Ser. No. 15/962,127, filed on Apr. 25, 2018, which is a Divisional of U.S. patent application Ser. No. 15/335,243, filed on Oct. 26, 2016 (issued as U.S. Pat. No. 9,984,202), which is a Divisional of U.S. patent application Ser. No. 14/352,697, filed on Jul. 22, 2014 (issued as U.S. Pat. No. 9,513,283), which is a U.S. National Stage entry of International Application No. PCT/JP2012/077274, filed on Oct. 22, 2012, which claims priority to Japanese Patent Application No. 2011-231346, filed on Oct. 21, 2011. The entirety of each of the foregoing is incorporated herein by reference.

The sequence listing that is submitted in the present application in a computer readable form under the name of "P24436US06_Sequence_Listing.xml" and is hereby incorporated by reference into the present application, the file size of which is 555 K bytes was created on Oct. 13, 2023.

TECHNICAL FIELD

The present invention relates to a protein capable of selectively or specifically binding to an intended RNA base or RNA sequence. According to the present invention, a pentatricopeptide repeat (PPR) motif is used. The present invention can be used for identification and design of an RNA binding protein, identification of a target RNA of a PPR protein, as well as functional control of RNA. The present invention is useful in the medical field, agricultural field, and so forth.

BACKGROUND ART

In recent years, techniques of binding nucleic acid binding protein factors elucidated by various analyses to an intended sequence have been established and utilized. By using such a sequence-specific binding, it is becoming possible to analyze intracellular localization of a target nucleic acid (DNA or RNA), eliminate a target DNA sequence, or control (activate or inactivate) expression of a gene coding for a protein existing downstream from such a target sequence.

Although there are being conducted research and development utilizing zinc finger proteins (Non-patent document 1) and TAL effectors (Non-patent document 2, Patent document 1), which are protein factors that act on DNA, as protein engineering materials, development of protein factors that specifically act on RNA is still extremely limited. This is because any general correspondence between affinity to RNA of amino acid sequences constituting proteins and bindable RNA sequences has been scarcely elucidated, or there is no such correspondence. Concerning the pumilio protein constituted by repetition of two or more puf motifs each consisting of 38 amino acids, it has been exceptionally demonstrated that one puf motif binds to one RNA base (Non-patent document 3), and it is being attempted to develop a novel protein having an RNA binding property and a technique of modifying RNA binding property by using the pumilio proteins (Non-patent document 4). However, the puf motifs are highly conserved, and exist only in an extremely small number. Therefore, they are used only for creation of a protein factor that interacts with a limited RNA sequence.

The PPR proteins (proteins having the pentatricopeptide repeat (PPR) motif) have been identified on the basis of genome sequence information (Non-patent document 5), which proteins constitute such a large family consisting of about 500 members only for plants. Although the PPR proteins are nuclear-encoded, they chiefly act for control of organelles (chloroplasts and mitochondria) at the RNA level, cleavage, translation, splicing, editing, and stability of RNA in a gene-specific manner. The PPR proteins typically have a structure comprising about 10 contiguous poorly conserved 35-amino acid motifs, i.e., PPR motifs, and it is considered that the combination of the PPR motifs is responsible for the sequence-selective binding with RNA. Almost all the PPR proteins consist of only the repeats of about 10 PPR motifs, and in many cases, any domain required for expression of catalytic action cannot be found in them. Therefore, it is considered that the identity of the PPR proteins is an RNA adapter (Non-patent document 6).

The inventors of the present invention proposed a method for modifying an RNA-binding protein using this PPR motif (Patent document 2).

PRIOR ART REFERENCES

Patent Documents

Patent document 1: WO2011/072246
Patent document 2: WO2011/111829

Non-Patent Documents

Non-patent document 1: Maeder, M. L., Thibodeau-Beganny, S., Osiak, A., Wright, D. A., Anthony, R. M., Eichtinger, M., Jiang, T., Foley, J. E., Winfrey, R. J., Townsend, J. A., et al. (2008), Rapid "open-source" engineering of customized zinc-finger nucleases for highly efficient gene modification, Mol. Cell, 31, 294-301

Non-patent document 2: Miller, J. C., Tan, S., Qiao, G., Barlow, K. A., Wang, J., Xia, D. F., Meng, X., Paschon, D. E., Leung, E., Hinkley, S. J., et al. (2011), A TALE nuclease architecture for efficient genome editing, Nature Biotech., 29, 143-148.

Non-patent document 3: Wang, X., McLachlan, J., Zamore, P. D., and Hall, T. M. (2002), Modular recognition of RNA by a human pumilio-homology domain, Cell, 110, 501-512

Non-patent document 4: Cheong, C. G., and Hall, T. M. (2006), Engineering RNA sequence specificity of Pumilio repeats, Proc. Natl. Acad. Sci. USA, 103, 13635-13639

Non-patent document 5: Small, I. D., and Peeters, N. (2000), The PPR motif—a TPR-related motif prevalent in plant organellar proteins, Trends Biochem. Sci., 25, 46-47

Non-patent document 6: Woodson, J. D., and Chory, J. (2008), Coordination of gene expression between organellar and nuclear genomes, Nature Rev. Genet., 9, 383-395

SUMMARY OF THE INVENTION

Object to be Achieved by the Invention

The properties of the PPR proteins as an RNA adapter are expected to be determined by the properties of the PPR motifs constituting the PPR proteins and combination of a plurality of the PPR motifs. However, correlation of the amino acid constitution and function thereof are scarcely clarified. If amino acids that function when the PPR motifs exhibit the RNA-binding property are identified, and relation between structure of a PPR motif and a target base is elucidated, a protein capable of binging to an RNA having arbitrary sequence and length may be constructed by artificially manipulating structure of a PPR motif or combination of a plurality of PPR motifs.

Means for Achieving the Object

In order to achieve the aforementioned object, the inventors of the present invention examined genetically analyzed PPR proteins, especially such PPR proteins involved in the RNA editing (modification of genetic information at the RNA level, especially conversion from cytosine (henceforth abbreviated as C) to uracil (henceforth abbreviated as U)), and target RNA sequences thereof, and elucidated that three amino acids in the PPR motifs (amino acids 1, 4, and "ii" (−2)) comprise information responsible for binding to a specific RNA base by using computational scientific techniques. More precisely, the inventors of the present invention found that the binding RNA base selectivity (also referred to as specificity) of the PPR motif is determined by three amino acids, i.e., the first and fourth amino acids contained in the first helix among two of the α-helix structures constituting the motif, as well as the second ("ii" (−2)) amino acid from the end (C-terminus side) in the moiety that can form a loop structure after the second helix, and accomplished the present invention.

The present invention thus provides the followings.

[1] A method for designing a protein that can bind to an RNA molecule in an RNA base-selective or RNA base sequence-specific manner, wherein:

the protein is a protein containing one or more of PPR motifs (preferably 2 to 14 PPR motifs) each consisting of a polypeptide of 30- to 38-amino acid length represented by the formula 1:

[F1]

$$(HelixA)\text{-}X\text{-}(HelixB)\text{-}L \qquad \text{(Formula 1)}$$

(wherein:

Helix A is a moiety of 12-amino acid length capable of forming an α-helix structure, and is represented by the formula 2:

[F2]

$$A_1\text{-}A_2\text{-}A_3\text{-}A_4\text{-}A_5\text{-}A_6\text{-}A_7\text{-}A_8\text{-}A_9\text{-}A_{10}\text{-}A_{11}\text{-}A_{12} \qquad \text{(Formula 2)}$$

wherein, in the formula 2, $A_1$ to $A_{12}$ independently represent an amino acid;

X does not exist, or is a moiety of 1- to 9-amino acid length;

Helix B is a moiety of 11- to 13-amino acid length capable of forming an α-helix structure; and L is a moiety of 2- to 7-amino acid length represented by the formula 3;

[F3]

$$L_{vii}\text{-}L_{vi}\text{-}L_v\text{-}L_{iv}\text{-}L_{iii}\text{-}L_{ii}\text{-}L_i \qquad \text{(Formula 3)}$$

wherein, in the formula 3, the amino acids are numbered "i" (−1), "ii" (−2), and so on from the C-terminus side, provided that $L_{iii}$ to $L_{vii}$ may not exist), and combination of three amino acids $A_1$, $A_4$ and $L_{ii}$, or combination of two amino acids $A_4$, and $L_{ii}$ is a combination corresponding to a target RNA base or base sequence.

[2] The method according to [1], wherein the combination of the three amino acids $A_1$, $A_4$ and $L_{ii}$ is a combination corresponding to the target RNA base or base sequence, and the combination of the amino acids is determined according to any one of the following propositions:

(3-1) when the three amino acids $A_1$, $A_4$, and $L_{ii}$ are valine, asparagine, and aspartic acid, respectively, the PPR motif can selectively bind to U (uracil);

(3-2) when the three amino acids $A_1$, $A_4$, and $L_{ii}$ are valine, threonine, and asparagine, respectively, the PPR motif can selectively bind to A (adenine);

(3-3) when the three amino acids $A_1$, $A_4$, and $L_{ii}$ are valine, asparagine, and asparagine, respectively, the PPR motif can selectively bind to C (cytosine);

(3-4) when the three amino acids $A_1$, $A_4$, and $L_{ii}$ are glutamic acid, glycine, and aspartic acid, respectively, the PPR motif can selectively bind to G (guanine);

(3-5) when the three amino acids $A_1$, $A_4$, and $L_{ii}$ are isoleucine, asparagine, and asparagine, respectively, the PPR motif can selectively bind to C or U;

(3-6) when the three amino acids $A_1$, $A_4$, and $L_{ii}$ are valine, threonine, and aspartic acid, respectively, the PPR motif can selectively bind to G;

(3-7) when the three amino acids $A_1$, $A_4$, and $L_{ii}$ are lysine, threonine, and aspartic acid, respectively, the PPR motif can selectively bind to G;

(3-8) when the three amino acids $A_1$, $A_4$, and $L_{ii}$ are phenylalanine, serine, and asparagine, respectively, the PPR motif can selectively bind to A;

(3-9) when the three amino acids $A_1$, $A_4$, and $L_{ii}$ are valine, asparagine, and serine, respectively, the PPR motif can selectively bind to C;

(3-10) when the three amino acids $A_1$, $A_4$, and $L_{ii}$ are phenylalanine, threonine, and asparagine, respectively, the PPR motif can selectively bind to A;

(3-11) when the three amino acids $A_1$, $A_4$, and $L_{ii}$ are isoleucine, asparagine, and aspartic acid, respectively, the PPR motif can selectively bind to U or A;

(3-12) when the three amino acids $A_1$, $A_4$, and $L_{ii}$ are threonine, threonine, and asparagine, respectively, the PPR motif can selectively bind to A;

(3-13) when the three amino acids $A_1$, $A_4$, and $L_{ii}$ are isoleucine, methionine, and aspartic acid, respectively, the PPR motif can selectively bind to U or C;

(3-14) when the three amino acids $A_1$, $A_4$, and $L_{ii}$ are phenylalanine, proline, and aspartic acid, respectively, the PPR motif can selectively bind to U;

(3-15) when the three amino acids $A_1$, $A_4$, and $L_{ii}$ are tyrosine, proline, and aspartic acid, respectively, the PPR motif can selectively bind to U; and (3-16) when the three amino acids $A_1$, $A_4$, and $L_{ii}$ are leucine, threonine, and aspartic acid, respectively, the PPR motif can selectively bind to G.

[3] The method according to [1], wherein the combination of the two amino acids $A_4$ and $L_{ii}$ is a combination corresponding to the target RNA base or base sequence, and the combination of the amino acids is determined according to any one of the following propositions:

(2-1) when $A_4$ and $L_{ii}$ are asparagine and aspartic acid, respectively, the motif can selectively bind to U;

(2-2) when $A_4$ and $L_{ii}$ are asparagine and asparagine, respectively, the motif can selectively bind to C;

(2-3) when $A_4$ and $L_{ii}$ are threonine and asparagine, respectively, the motif can selectively bind to A;

(2-4) when $A_4$ and $L_{ii}$ are threonine and aspartic acid, respectively, the motif can selectively bind to G;

(2-5) when $A_4$ and $L_{ii}$ are serine and asparagine, respectively, the motif can selectively bind to A;

(2-6) when $A_4$ and $L_{ii}$ are glycine and aspartic acid, respectively, the motif can selectively bind to G;

(2-7) when $A_4$ and $L_{ii}$ are asparagine and serine, respectively, the motif can selectively bind to C;

(2-8) when $A_4$ and $L_{ii}$ are proline and aspartic acid, respectively, the motif can selectively bind to U;

(2-9) when $A_4$ and $L_{ii}$ are glycine and asparagine, respectively, the motif can selectively bind to A;

(2-10) when $A_4$ and $L_{ii}$ are methionine and aspartic acid, respectively, the motif can selectively bind to U;

(2-11) when $A_4$ and $L_{ii}$ are leucine and aspartic acid, respectively, the motif can selectively bind to C; and (2-12) when $A_4$ and $L_{ii}$ are valine and threonine, respectively, the motif can selectively bind to U.

[4] A method for identifying a target base or base sequence for an RNA-binding protein comprising one or more (preferably 2 to 14) of the PPR motifs defined in [1], wherein:

the base or base sequence is identified by determining presence or absence of a base corresponding to a combination of the three amino acids $A_1$, $A_4$ and $L_{ii}$ of the PPR motifs, or a combination of the two amino acids $A_4$ and $L_{ii}$ of the PPR motifs on the basis of any of the propositions (3-1) to (3-16) mentioned in [2], or any of the propositions (2-1) to (2-12) mentioned in [3].

[5] A method for identifying a PPR protein that comprises one or more (preferably 2 to 14) of the PPR motifs defined in [1], and can bind to a target RNA base or a target RNA having a specific base sequence, wherein:

the PPR protein is identified by determining presence or absence of a combination of the three amino acids $A_1$, $A_4$ and $L_{ii}$ of the PPR motifs corresponding to the target RNA base or a specific base constituting the target RNA on the basis of any of the propositions (3-1) to (3-16) mentioned in [2], or any of the propositions (2-1) to (2-12) mentioned in [3].

[6] A method for controlling a function of RNA, comprising using a protein designed by the method according to [1].

[7] A complex comprising a region consisting of a protein designed by the method according to [1] and a functional region, which have been linked together.

[8] A method for modifying a cellular genetic material, which comprises the following steps:

preparing a cell containing an RNA having a target sequence; and introducing the complex according to [7] into the cell, so that the protein region of the complex binds to the RNA having the target sequence, and therefore the functional region modifies the target sequence.

[9] A method for judging fertility of a gene of a PPR protein, which comprises:

the step of detecting amino acid polymorphism observed among various varieties for a gene of a PPR protein that functions as a fertility restoration factor for cytoplasmic male sterility;

the step of specifying relation of the polymorphism and the fertility for the gene; and the step of specifying a base sequence of a gene of a PPR protein obtained from a test sample, and determining fertility of the test sample.

[10] The method according to [9], wherein the PPR protein is a protein comprising one or more (preferably 2 to 16) of PPR motifs each consisting of a polypeptide of 30- to 38-amino acid length represented by the formula 1 defined in [1].

[11] The method according to [9] or [10], wherein the amino acid polymorphism is specified as polymorphism observed in units of the PPR motifs.

[12] The method according to any one of [9] to [11], wherein the polymorphism observed in the PPR motifs is identified by a combination of the three amino acids $A_1$, $A_4$ and $L_{ii}$, or a combination of the two amino acids $A_4$ and $L_{ii}$ of the motif of the formula 1.

[13] The method according to [12], wherein the polymorphism observed in the PPR motifs is identified as polymorphism of amino acid 4 ($A_4$) in the motifs of the formula 1.

[14] The method according to [13], wherein the fertility is indicated by the fact that amino acids 4 in all of the PPR motifs in the PPR protein are the same as amino acids 4 in all of the corresponding PPR motifs of Enko B, or the fact that the amino acids "ii" in all of the PPR motifs in the PPR protein are the same as the amino acids "ii" in all of the corresponding PPR motifs of Enko B.

[15] The method according to any one of [9] to [14], wherein the gene of the PPR protein is a family gene carried at the same locus as that of the "ORF687 gene" coding for Enko B, a gene coding for a protein showing an amino acid identity of 90% or higher to Enko B, or a gene showing a nucleotide sequence identity of 90% or higher to the "ORF687 gene" coding for Enko B.

[16] The method according to any one of [9] to [15], wherein the proteins encoded by the or %87-like genes of various varieties are any of the proteins of SEQ ID NOS: 576 to 578 and 585 to 591.

Effect of the Invention

According to the present invention, a PPR motif capable of binding to a target RNA base and a protein containing it can be provided. By using a plurality of PPR motifs, a protein capable of binding to a target RNA having an arbitrary sequence or length can be provided.

According to the present invention, a target RNA of an arbitrary PPR protein can be predicted and identified, and conversely, a PPR protein capable of binding to an arbitrary RNA can be predicted and identified. Prediction of such a target RNA sequence enhances the possibility of elucidating the genetic identity thereof and using it. For example, in the case of considering fertility as a function of the PPR protein according to the present invention, for an industrially useful gene of PPR protein such as those capable of functioning as a restoration factor for cytoplasmic male sterility, functionalities of various homologous genes thereof providing proteins that show amino acid polymorphism can be determined on the basis of the difference of the target RNA sequences thereof.

Further, a functional region can be bound to a PPR motif or PPR protein provided by the present invention to prepare a complex.

The present invention can further be utilized for a method of delivering the aforementioned complex to a living body and allowing it to function, preparation of a transformant using a nucleic acid sequence (DNA or RNA) coding for a protein obtained by the present invention, as well as specific modification, control, and impartation of a function in various scenes in organisms (cells, tissues, and individuals).

BRIEF DESCRIPTION OF THE DRAWINGS

FIGS. 1A-1C show the conserved sequences and amino acid numbers of the PPR motif. FIG. 1A shows the amino acids constituting the PPR motif defined in the present invention, and the amino acid numbers thereof. FIG. 1B shows the positions of the three amino acids (1, 4, and "ii" (−2)) that control the binding base selecting property on the putative structure. FIG. 1C shows the positions of the amino acids on the putative structure. By using the total amino acid sequences of *Arabidopsis thaliana* CRR4 (SEQ ID NO: 6) and CRR21 (SEQ ID NO: 3) as the query sequences for the program PHYRE (http://www.sbg.bio.ic.ac.uk/phyre/), the putative structures were analyzed. As a result, the structures were predicted with high scores using O-GlucNAc transferase (1w3b) as the template (4.3e-17 and 4.7e-16, for CRR4 and CRR21). Among the structures, the 5th PPR motif of CRR4 (left figure), and the 8th PPR motif of CRR21 (right figure) are shown. The positions 1, 4, and "ii" (−2) are shown as sticks in magenta color (dark gray in monochromatic indication).

FIG. 2 shows the RNA-editing PPR proteins analyzed so far and the RNA-editing sites as targets thereof.

FIG. 3A shows the PPR motif sequences and amino acid numbers of *Arabidopsis thaliana* RNA-editing PPR proteins.

FIGS. 3B-3H each shows continuation of FIG. 3A.

FIG. 4A shows identification of amino acids having a binding nucleotide specifying capacity in the PPR motif. The PPR motifs of RNA-editing PPR protein are aligned with an RNA-editing site upstream sequence in various positions. The alignment was performed by arranging the sequences at a 1-motif to 1-nucleotide correspondence, in a contiguous linear manner. The alignment P1 was obtained by fitting the last PPR motif of the protein to the base 1 nucleotide before the editable C. The base sequence was then moved toward the right, 1 base at a time, to obtain the alignments P2 to P6. The squares represent PPR motifs, and the diamond represents additional motifs (E, E+, DYW) on the C terminus side. If amino acids at specific sites in the motif (for example, amino acids of the motifs indicated in green (dark gray in monochromatic indication)) are responsible for the RNA base recognition, low randomness can be expected for corresponding nucleotides in a specific alignment (lower figure on the right). Otherwise, high randomness is expected (upper figure on the right). FIG. 4B shows binding RNA base specifying capacities of amino acids 1, 4, and "ii" (−2). Low randomness between the amino acid and the base in each alignment is shown in terms of a P value. FIG. 4C shows binding RNA base specifying capacities of amino acids 1, 4, and "ii" (−2) for various classifications of nucleic acids. They are indicated in a similar manner to that of FIG. 4B. The nucleic acids are classified according to type of nucleobase, purine or pyrimidine (RY, A & G or U & C), and presence or absence of hydrogen bond groups (WS, A & U or G & C). FIG. 4D shows results of further detailed analysis of the binding base specifying capacities of the RNA recognition amino acids in the PPR motifs shown in FIG. 4C mentioned above. It was demonstrated that, in addition to that amino acid 4 mainly determines the type of the binding base, purine or pyrimidine (RY), the amino acid "ii" (−2) functions to determine the form of the nucleotide, amino form (A and C)

or keto form (G and U) (MK) (FIG. 4D). FIG. 4E shows examples of RNA recognition codes (PPR codes) of several PPR motifs. The white letters indicates types of amino acids 1, 4, and "ii" (−2). The occurrence frequencies of the codes are indicated in the row of "No.", and the occurrence frequencies of the corresponding nucleic acids are indicated in the rows of "Nucleotide frequency".

FIG. 5 shows identification (examples) of the amino acids in the PPR motifs involved in the RNA recognition. The amino acids involved in the RNA recognition were searched for by using data sets of RNA bases corresponding the PPR motifs in each alignment. For example, by using data of RNA bases corresponding the PPR motifs in alignment P4, the binding RNA base specifying capacities of amino acids 4 and 5 were analyzed. For each alignment, data were first sorted according to the types of the amino acids, and the numbers of the RNA bases contained were calculated (upper left table). Then, theoretical values of the numbers were prepared on the basis of the medians of the occurrence frequencies of all the RNA bases contained in the data sets (upper right table). By the chi square test using these two kinds of data, P values were calculated. The upper tables show the analysis results for amino acid 4 in alignment P4, for which significant P values were obtained, and the lower tables show the analysis results for the amino acid 5 in alignment P4, for which significant P values were not obtained.

FIGS. 6A and 6B show P values for low randomness between the type of amino acid and the occurrence frequency of base calculated for the amino acids of all the positions in the alignments P1 to P6. The amino acids that showed significant P values (P<0.01) are indicated in magenta color (dark gray in monochromatic indication). The lines (horizontal lines in the graphs) in cyan color (dark gray in monochromatic indication) indicate P value of 0.01.

FIG. 6C shows the summary of the low randomness for each alignment. A product of the P values of the amino acids of the positions shown in FIGS. 6A-6B for each alignment is shown as a total value of the low randomness for that alignment.

FIG. 8 shows the RNA recognition codes of the PPR motifs extracted from *Arabidopsis thaliana*.

FIG. 11A shows the matching scores for the RNA-editing sites of the triPPR or the diPPR codes obtained by conversion of amino acids 1, 4, and "ii" (−2) extracted from the moss PPR proteins as shown in FIG. 10, which values are shown in terms of P values. As the RNA-editing sites, 13 RNA-editing sites of the moss were used, and as reference sequences, 34 RNA-editing sites of *Arabidopsis thaliana* chloroplast were used. In the drawing, only the matching scores for the 13 RNA-editing sites of the moss are shown. The diamonds indicate matching scores of the proteins for the respective editing sites. The correct editing sites are shown in magenta color (solid gray in monochromatic indication). FIG. 11B shows the P values shown in FIG. 11A in the form of table.

FIG. 12A shows prediction of RNA-editing sites of 13 known PPR proteins with respect to the total 34 chloroplast RNA-editing sites. The diamonds indicate the matching scores between the proteins and the RNA-editing site sequences. The correct RNA-editing sites are shown in magenta color (solid gray in monochromatic indication). FIG. 12B shows prediction of RNA-editing sites of 11 known PPR proteins with respect to the total 488 mitochondria RNA-editing sites.

FIGS. 13A-13D show prediction of the target RNA editing sites of *Arabidopsis thaliana* PPR protein AHG11, and experimental verification thereof. FIG. 13A shows the motif structure of AHG11. It has a typical structure of RNA-editing PPR protein comprising 12 PPR motifs and the additional motifs (E, E+, DYW) on the C terminus side. In Ahg11 mutants, there can be found a new translation stop codon in the coding region generated by the point mutation at the position indicated with the asterisk (295 Trp). FIG. 13B shows prediction of the target RNA-editing sites using all the RNA-editing sites contained in the chloroplasts and mitochondria of *Arabidopsis thaliana*. The top ten editing sites that showed the highest P values are shown. Presence or absence of the RNA editing in wild strain and mutant strain was experimentally verified, and the results are shown in the column of Editing status. The sites for which RNA editing was detected in both the wild strain and the mutant strain are indicated as E, and the site for which RNA editing could not be observed only in the mutant strain is indicated as Un. FIG. 13C shows the results of the prediction in the form of graph. FIG. 13D shows experimental verification of the target RNA-editing sites of AHG11. There are shown the results of the sequence analysis of the region containing the mitochondria nad4. RNAs were extracted from the wild strain and the ahg11 mutant strain, cDNAs were prepared by reverse transcription, and nucleotide sequence analysis of them was conducted. There are two RNA-editing sites (nsd4_362 and _376) in this region. The edited sites are indicated with black arrows, and the non-edited site is indicated with a white arrow.

FIG. 14 shows prediction of the target sites in the chloroplast genome sequence. The target sites were predicted in the *Arabidopsis thaliana* chloroplast total genome sequence (154,478 bp) by using six PPR proteins. For the prediction, the codes extracted from *Arabidopsis thaliana* (At codes) or the codes extracted from *Arabidopsis thaliana* and the moss (At+Pp codes) were used.

FIG. 15 shows the RNA recognition codes of the PPR motifs extracted from *Arabidopsis thaliana* and *Physcomitrella patens* subsp. *patens*.

FIGS. 16A-16HH show amino acid sequences or nucleotide sequences that are referenced in the present disclosure and/or relevant to the present invention.

FIG. 17A shows a schematic diagram around the mitochondrial orf125, and also schematically shows the regions of RNAa, RNAbc, RNAb, and RNAc used in the binding experiment. FIG. 17B shows binding of the Enko B protein and RNA. Enko B protein (1.4 nmol) and $^{32}$P-labeled RNAbc (0.1 ng) were reacted in the presence of non-labeled RNAa, RNAbc, RNAb, and RNAc (×5 and ×10 w/w with respect to RNAbc, used as a competitive inhibition substance) in 20 μL of a reaction mixture to perform the gel shift competition experiment.

FIGS. 18A-18C show binding of the ORF687-like proteins and RNA. FIG. 18A shows the results of analysis of RNA binding characteristics of ORF687-like proteins performed by gel shift assay for binding of Enko B (Rf), Kosena B (if), and Enko A (if) with RNAb. FIG. 18B is shows the results of FIG. 18A in the form of graph, and dissociation constants (KD) of the proteins representing the RNA binding capacities thereof were calculated on the basis of this graph. FIG. 18C shows the results of calculation of the matching scores of Enko B (Rf), Kosena B (if), and Enko A (if), and potential binding sites thereof performed in the same manner as that used for obtaining the results shown in FIGS. 19A-19B.

FIGS. 19A and 19B show prediction of binding sequence of the fertility restoration factor that acts on Ogura-type cytoplasm. FIG. 19A shows the results for prediction of binding of the Enko B protein using the PPR codes, and the structure of RNA containing the CMS gene orf125 is shown in the lower diagram of FIG. 19A. As for the regions from RNAa to RNAc shown in FIG. 19A, refer to FIGS. 17A-17B. In FIG. 19A, the regions of Nos. 208, 230, 316, 352 and 373 are focused on, among the regions that showed a significantly high P value (FIG. 19A).

FIG. 20A shows the secondary structure of the region including the region of No. 306 and the predicted binding sites for the ORF687-like protein, and shows PPR motifs with boxes together with the corresponding bases. The 2nd and 3rd PPR motifs for which Enko B (Rf) and Kosena B (if) show a remarkable difference are emphasized. FIG. 20B shows the secondary structure of the region including the regions of Nos. 352 and 373 and the predicted binding sites for the ORF687-like protein. FIG. 20C shows results indicating structural change of RNAb induced by Enko B, which were obtained by mixing RNAb and Enko B protein, and then adding a double-strand selective RNase (RNase VD).

FIG. 21A shows alignment of ORF687-like proteins.

FIG. 21B shows alignment of ORF687-like proteins.

FIG. 22 shows a list of the base specifying amino acids of ORF687-like proteins contained in various radish varieties.

DESCRIPTION OF EMBODIMENTS

[PPR Motif and PPR Protein]

Figure 3C:
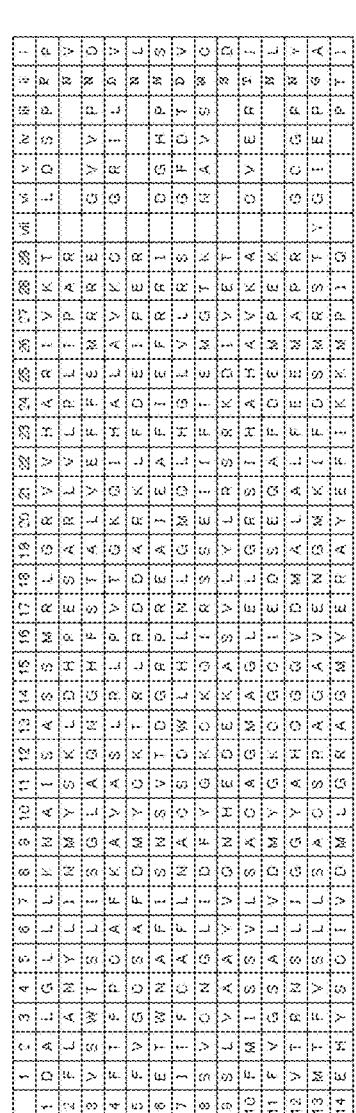
Figure 3D:
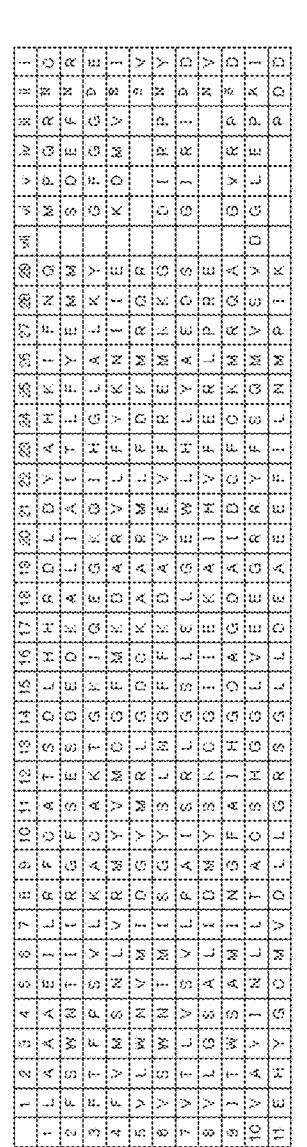
Figure 3E:
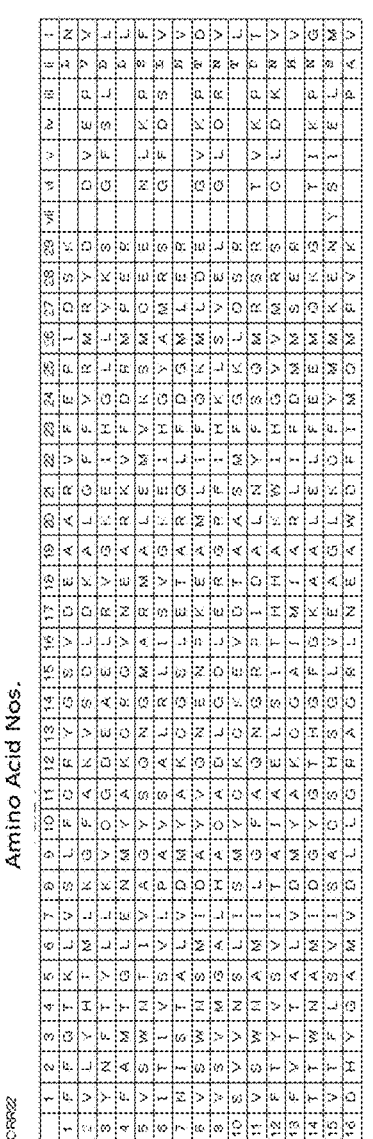

The term "PPR motif" used in the present invention refers to a polypeptide consisting of 30 to 38 amino acids and having an amino acid sequence showing an E value determined by amino acid sequence analysis using a protein domain search program on the Web, i.e., an E value obtained by using Pfam, PF01535, or Prosite, PS51375, not larger than a predetermined value (desirably E 03), unless especially indicated. The position numbers of amino acids constituting the PPR motif defined in the present invention are substantially synonymous with those obtainable with PF01535, but they correspond to those obtained by subtracting 2 from the numbers of the amino acid positions obtained with PS51375 (for example, the position 1 referred to in the present invention is the position 3 obtained with PS51375). Further, the amino acid "ii" (−2) is the second amino acid from the end (C-terminus side) of the amino acids constituting the PPR motif, or the second amino acid towards the N-terminus side from the first amino acid of the following PPR motif, i.e., −2nd amino acid (FIG. 1). When the following PPR motif is not definitely identified, the amino acid 2 amino acids before the first amino acid of the following helical structure is the amino acid "ii". For Pfam, http://pfam.sanger.ac.uk/ can be referred to, and for Prosite, http://www.expasy.org/prosite/ can be referred to.

Although the conservativeness of the conserved amino acid sequence of the PPR motif is low at the amino acid level, two of the α-helixes as the secondary structure are well conserved. Although a typical PPR motif is constituted by 35 amino acids, the length thereof is as variable as 30 to 38 amino acids.

More specifically, the PPR motif referred to in the present invention consists of a polypeptide of a 30- to 38-amino acid length represented by the formula 1.

[F4]

$$\text{(HelixA)-X-(HelixB)-L} \qquad \text{(Formula 1)}$$

In the formula:

Helix A is a moiety of 12-amino acid length capable of forming an α-helix structure, and is represented by the formula 2;

[F5]

$$A_1\text{-}A_2\text{-}A_3\text{-}A_4\text{-}A_5\text{-}A_6\text{-}A_7\text{-}A_8\text{-}A_9\text{-}A_{10}\text{-}A_{11}\text{-}A_{12} \qquad \text{(Formula 2)}$$

wherein, in the formula 2, $A_1$ to $A_{12}$ independently represent an amino acid;

X does not exist, or is a moiety of 1- to 9-amino acid length;

Helix B is a moiety of 11- to 13-amino acid length capable of forming an α-helix structure; and L is a moiety of 2- to 7-amino acid length represented by the formula 3;

[F6]

$$L_{vii}\text{-}L_{vi}\text{-}L_{v}\text{-}L_{iv}\text{-}L_{iii}\text{-}L_{ii}\text{-}L_{i} \qquad \text{(Formula 3)}$$

wherein, in the formula 3, the amino acids are numbered "i" (−1), "ii" (−2), and so on from the C-terminus side, provided that $L_{iii}$ to $L_{vii}$ may not exist.

The term "PPR protein" used in the present invention refers to a PPR protein comprising one or more, preferably two or more, of the above-mentioned PPR motifs, unless especially indicated. The term "protein" used in this specification refers to any substance consisting of a polypeptide (chain consisting of a plurality of amino acids bound via peptide bonds), unless especially indicated, and includes those consisting of a polypeptide of a comparatively low molecular weight. The term "amino acid" used in the present invention refers to a usual amino acid molecule, and also refers to an amino acid residue constituting a peptide chain. Which one is referred to shall be clear to those skilled in the art from the context.

Many kinds of PPR proteins exist in plants, and in the case of *Arabidopsis thaliana*, about 500 kinds of proteins and about 5000 kinds of the motifs can be found. Also in many land plants, such as rice plant, poplar, and selaginella, PPR motifs and PPR proteins of various amino acid sequences exist. It is known that some PPR proteins are important factors for obtaining F1 seeds for hybrid vigor as a fertility restoration factor that works for pollen (male gamete) formation. As an action analogous to the fertility restoration, it has been clarified that some PPR proteins work for speciation. It has also been clarified that most of PPR proteins act on RNA in mitochondria or chloroplasts.

For animals, it is known that anomaly of the PPR protein identified as LRPPRC causes Leigh syndrome French Canadian type (LSFC, Leigh's syndrome, subacute necrotizing encephalomyelopathy).

The term "selectively" used in the present invention concerning the binding property of the PPR motif with RNA base means that the binding activity for one base among the RNA bases is higher than the binding activities for the other bases, unless otherwise indicated. Concerning this selectivity, those skilled in the art can plan and conduct an experiment for confirming it, and it can also be obtained by calculation as disclosed in the examples described in this specification. The term RNA base used in the present invention refers to a base of a ribonucleotide constituting RNA, specifically, any one of adenine (A), guanine (G), cytosine (C), and uracil (U). The PPR protein may have selectivity for a base in RNA, but it does not bind to a nucleic acid monomer. Although the sequence searching method for the conserved amino acids as the PPR motif had been established before the present invention was accomplished, the correspondence between the amino acid and the selective binding with RNA base was not discovered at all.

The present invention provides the following findings.

(I) Information concerning positions of amino acids important for the selective binding: Specifically, combination of the three amino acids, amino acids 1, 4, and "ii" (−1) ($A_1$, $A_4$, $L_{ii}$), or combination of the two amino acids, amino acids 4 and "ii" (−1) ($A_4$, $L_{ii}$), is important for the selective binding with an RNA base, and to which RNA base the motif binds is determined by such a combination.

The present invention is based on the findings concerning combination of the three amino acids $A_1$, $A_4$, and $L_{ii}$, and/or combination of the two amino acids $A_4$, and $L_{ii}$ found by the inventors of the present invention.

(II) Information concerning the correspondence of combination of the three amino acids of $A_1$, $A_4$, and $L_{ii}$ and RNA base: Specifically, the followings are mentioned.

(3-1) When the combination of the three amino acids of $A_1$, $A_4$, and $L_{ii}$ is a combination of valine, asparagine, and aspartic acid as $A_1$, $A_4$, and $L_{ii}$, respectively, the PPR motif has a selective RNA base binding capacity that it strongly binds to U, less strongly binds to C, and still less strongly binds to A or G.

(3-2) When the combination of the three amino acids of $A_1$, $A_4$, and $L_{ii}$ is a combination of valine, threonine, and asparagine as $A_1$, $A_4$, and $L_{ii}$, respectively, the PPR motif has a selective RNA base binding capacity that it strongly binds to A, less strongly binds to G, and still less strongly binds to C, but does not binds to U.

(3-3) When the combination of the three amino acids of $A_1$, $A_4$, and $L_{ii}$ is a combination of valine, asparagine, and asparagine as $A_1$, $A_4$, and $L_{ii}$, respectively, the PPR motif has a selective RNA base binding capacity that it strongly binds to C, and less strongly binds to A or U, but does not bind to G.

(3-4) When the combination of the three amino acids of $A_1$, $A_4$, and $L_{ii}$ is a combination of glutamic acid, glycine, and aspartic acid as $A_1$, $A_4$, and $L_{ii}$, respectively, the PPR motif has a selective RNA base binding capacity that it strongly binds to G, but does not bind to A, U, and C.

(3-5) When the combination of the three amino acids of $A_1$, $A_4$, and $L_{ii}$ is a combination of isoleucine, asparagine, and asparagine as $A_1$, $A_4$, and $L_{ii}$, respectively, the PPR motif has a selective RNA base binding capacity that it strongly binds to C, less strongly binds to U, and still less strongly binds to A, but does not bind to G.

(3-6) When the combination of the three amino acids of $A_1$, $A_4$, and $L_{ii}$ is a combination of valine, threonine, and aspartic acid as $A_1$, $A_4$, and $L_{ii}$, respectively, the PPR motif has a selective RNA base binding capacity that it strongly binds to G, and less strongly binds to U, but does not bind to A and C.

(3-7) When the combination of the three amino acids of $A_1$, $A_4$, and $L_{ii}$ is a combination of lysine, threonine, and aspartic acid as $A_1$, $A_4$, and $L_{ii}$, respectively, the PPR motif has a selective RNA base binding capacity that it strongly binds to G, and less strongly binds to A, but does not bind to U and C.

(3-8) When the combination of the three amino acids of $A_1$, $A_4$, and $L_{ii}$ is a combination of phenylalanine, serine, and asparagine as $A_1$, $A_4$, and $L_{ii}$, respectively, the PPR motif has a selective RNA base binding capacity that it strongly binds to A, less strongly binds to C, and still less strongly binds to G and U.

(3-9) When the combination of the three amino acids of $A_1$, $A_4$, and $L_{ii}$ is a combination of valine, asparagine, and serine as $A_1$, $A_4$, and $L_{ii}$, respectively, the PPR motif has a selective RNA base binding capacity that it strongly binds to C, and less strongly binds to U, but does not bind to A and G.

(3-10) When the combination of the three amino acids of $A_1$, $A_4$, and $L_{ii}$ is a combination of phenylalanine, threonine, and asparagine as $A_1$, $A_4$, and $L_{ii}$, respectively, the PPR motif has a selective RNA base binding capacity that it strongly binds to A, but does not bind to G, U, and C.

(3-11) When the combination of the three amino acids of $A_1$, $A_4$, and $L_{ii}$ is a combination of isoleucine, asparagine, and aspartic acid as $A_1$, $A_4$, and $L_{ii}$, respectively, the PPR motif has a selective RNA base binding capacity that it strongly binds to U, and less strongly binds to A, but does not bind to G and C.

(3-12) When the combination of the three amino acids of $A_1$, $A_4$, and $L_{ii}$ is a combination of threonine, threonine, and asparagine as $A_1$, $A_4$, and $L_{ii}$, respectively, the PPR motif has a selective RNA base binding capacity that it strongly binds to A, but does not bind to G, U, and C.

(3-13) When the combination of the three amino acids of $A_1$, $A_4$, and $L_{ii}$ is a combination of isoleucine, methionine, and aspartic acid as $A_1$, $A_4$, and $L_{ii}$, respectively, the PPR motif has a selective RNA base binding capacity that it strongly binds to U, and less strongly binds to C, but does not bind to A and G.

(3-14) When the combination of the three amino acids of $A_1$, $A_4$, and $L_{ii}$ is a combination of phenylalanine, proline, and aspartic acid as $A_1$, $A_4$, and $L_{ii}$, respectively, the PPR motif has a selective RNA base binding capacity that it strongly binds to U, and less strongly binds to C, but does not bind to A and G.

(3-15) When the combination of the three amino acids of $A_1$, $A_4$, and $L_{ii}$ is a combination of tyrosine, proline, and aspartic acid as $A_1$, $A_4$, and $L_{ii}$, respectively, the PPR motif has a selective RNA base binding capacity that it strongly binds to U, but does not bind to A, G, and C.

(3-16) When the combination of the three amino acids of $A_1$, $A_4$, and $L_{ii}$ is a combination of leucine, threonine, and aspartic acid as $A_1$, $A_4$, and $L_{ii}$, respectively, the PPR motif has a selective RNA base binding capacity that it strongly binds to G, but does not bind to A, U, and C.

(II) Information concerning the correspondence of combination of the two amino acids of $A_4$, and $L_{ii}$ and RNA base: Specifically, the followings are mentioned.

(2-1) When $A_4$ and $L_{ii}$ are asparagine and aspartic acid, respectively, the PPR motif has a selective RNA base binding capacity that it strongly binds to U, less strongly binds to C, and still less strongly binds to A and G.

(2-2) When $A_4$ and $L_{ii}$ are asparagine and asparagine, respectively, the PPR motif has a selective RNA base binding capacity that it strongly binds to C, less strongly binds to U, and still less strongly binds to A and G.

(2-3) When $A_4$ and $L_{ii}$ are threonine and asparagine, respectively, the PPR motif has a selective RNA base binding capacity that it strongly binds to A, and weakly binds to G, U, and C.

(2-4) When $A_4$ and $L_{ii}$ are threonine and aspartic acid, respectively, the PPR motif has a selective RNA base binding capacity that it strongly binds to G, and weakly binds to A, U, and C.

(2-5) When $A_4$ and $L_{ii}$ are serine and asparagine, respectively, the PPR motif has a selective RNA base binding capacity that it strongly binds to A, and less strongly binds to G, U, and C.

(2-6) When $A_4$ and $L_{ii}$ are glycine and aspartic acid, respectively, the PPR motif has a selective RNA base binding capacity that it strongly binds to G, less strongly binds to U, and still less strongly binds to A, but does not bind to C.

(2-7) When $A_4$ and $L_{ii}$ are asparagine and serine, respectively, the PPR motif has a selective RNA base binding capacity that it strongly binds to C, less strongly binds to U, and still less strongly binds to A and G.

(2-8) When $A_4$ and $L_{ii}$ are proline and aspartic acid, respectively, the PPR motif has a selective RNA base binding capacity that it strongly binds to U, and less strongly binds to G and C, but does not bind to A.

(2-9) When $A_4$ and $L_{ii}$ are glycine and asparagine, respectively, the PPR motif has a selective RNA base binding capacity that it strongly binds to A, and less strongly binds to G, but does not bind to C and U.

(2-10) When $A_4$ and $L_{ii}$ are methionine and aspartic acid, respectively, the PPR motif has a selective RNA base binding capacity that it strongly binds to U, and weakly binds to A, G, and C.

(2-11) When $A_4$ and $L_{ii}$ are leucine and aspartic acid, respectively, the PPR motif has a selective RNA base binding capacity that it strongly binds to C, and less strongly binds to U, but does not bind to A and G.

(2-12) When $A_4$ and $L_{ii}$ are valine and threonine, respectively, the PPR motif has a selective RNA base binding capacity that it strongly binds to U, and less strongly binds to A, but does not bind to G and C.

In the examples described in this specification, binding of proteins partially analyzed genetically or molecular biologically and potential RNA target sequences thereof are further analyzed by computational science techniques to obtain the aforementioned findings. More precisely, binding or selective binding of the proteins and RNA is analyzed on the basis of P value (probability) as an index. According to the present invention, when the P value is 0.05 or smaller (contingency of 5% or less), which means a generally significant level, preferably when the P value is 0.01 or smaller (contingency of 1% or less), more preferably when a more significant P value compared with the foregoing levels is calculated, it is evaluated that the probability for binding of the protein and RNA is sufficiently high. Such judgment based on the P value can fully be understood by those skilled in the art.

Binding property of a specific combination of amino acids at specific positions for an RNA base can be experimentally confirmed. Experiments for such a purpose include preparation of a PPR motif or a protein containing a plurality of PPR motifs, preparation of a substrate RNA, and test for the binding property (for example, gel shift assay). These experiments are well known to those skilled in the art, and for specific procedures and conditions for them, Patent document 2, for example, can be referred to.

[Use of PPR Motif and PPR Protein]
Identification and Design:

One PPR motif can recognize a specific base of RNA. Further, according to the present invention, by choosing amino acids of specific positions, PPR motifs that selectively recognize each of A, U, G, and C can be selected or designed, and a protein containing an appropriate series of such PPR motifs can recognize a corresponding specific sequence. Therefore, according to the present invention, a natural PPR protein that selectively binds to RNA having a specific base sequence can be predicted and identified, and conversely, RNA that serves as a target of binding of a PPR protein can be predicted and identified. The prediction and identification of such a target is useful for elucidating genetic identity thereof, and expands availability of the target. Further, according to the present invention, a PPR motif that can selectively bind to a desired RNA base, and a protein comprising a plurality of PPR motifs that can sequence-specifically bind to a desired RNA can be designed. For designing moieties other than the amino acids of the important positions in the PPR motif, sequence information of natural PPR motifs can be referred to. Further, such a PPR motif or protein as mentioned above can also be designed by replacing only the amino acids of the positions of interest in the whole sequence of a natural PPR motif or protein. Although the number of repetition times of the PPR motif can be appropriately chosen depending on the target sequence, it may be, for example, 2 or more, or 2 to 20.

At the time of the designing, types of amino acids other than those of the combination of amino acids 1, 4, and "ii"

or amino acids 4, and "ii" maybe taken into consideration. For example, types of the 8th and 12th amino acids described in Patent document 2 mentioned above may be important for expression of the RNA binding activity. According to the study of the inventors of the present invention, $A_8$ of a certain PPR motif and $A_{12}$ of the same PPR motif may cooperate for binding to RNA. $A_8$ may be a basic amino acid, preferably lysine, or an acidic amino acid, preferably aspartic acid, and $A_{12}$ may be a basic amino acid, a neutral amino acid, or a hydrophobic amino acid.

The designed motif or protein can be prepared by the methods well known to those skilled in the art. That is, the present invention provides a PPR motif that selectively binds to a specific RNA base, and a PPR protein that specifically binds to RNA having a specific sequence, which are designed by paying attention to the combination of amino acids 1, 4, and "ii" or the combination of amino acids 4 and "ii". In particular, it was found that, for the action on fertility as a function of the PPR protein, amino acid 4 ($A_4$) and the amino acid "ii" are effective for both the cases of the aforementioned combination of three amino acids and combination of two amino acids. Such a motif and protein can be prepared by the methods well known to those skilled in the art, even in a relatively large amount, and such methods may comprise determining a nucleic acid sequence coding for an amino acid sequence of an objective motif or protein from that amino acid sequence, cloning it, and preparing a transformant that produces the objective motif or protein.
Preparation of Complex and Use Thereof:

The PPR motif or PPR protein provided by the present invention can be made into a complex by binding a functional region. The functional region means a moiety having a specific biological function such as enzymatic function, catalytic function, inhibition function, and promotion function exerted in living bodies or cells, or a moiety having a function as a marker. Such a region consists of, for example, a protein, peptide, nucleic acid, physiologically active substance, or drug. Examples of protein as the functional region include ribonuclease (RNase). Examples of RNase include RNase A (for example, bovine pancreatic ribonuclease A, PDB 2AAS) and RNase H. Such a complex does not exist in the nature, and it is a novel substance.

Further, the complex provided by the present invention may be able to deliver the functional region to a living body or cell in an RNA sequence-specific manner, and allow it to function. It may be therefore able to modify or disrupt RNA, or impart a novel function to RNA, in a living body or cell in an RNA sequence-specific manner, like the zinc finger proteins (Non-patent document 1 mentioned above) or TAL effector (Non-patent document 2 and Patent document 1 mentioned above). Furthermore, it may be able to deliver a drug to RNA in an RNA sequence-specific manner. Therefore, the present invention provides a method for delivering a functional material in an RNA sequence-specific manner.

It is known that some PPR proteins are important for obtaining F1 seeds for hybrid vigor as a fertility restoration factor that works for pollen (male gamete) formation. It is expected that a fertility restoration factor not identified yet can be identified, and a technique for highly utilize such a factor can be developed by the present invention. For example, as elucidated in the examples described in this specification, if amino acid polymorphism is detected for a gene for a specific PPR motif in a PPR protein that works as a fertility restoration factor for cytoplasmic male sterility, and relation of the polymorphism and fertility is established for the gene, it can be judged whether the gene of the PPR protein in a test sample has a genotype relating to fertility or a genotype relating to sterility. Examples of the gene of the PPR protein in which the polymorphism is detected in such a case as mentioned above include, for example, in the case of radish, a family gene locating at the same locus as that of the "OFR687 gene" coding for the OFR687 protein of Enko (named Enko B), a gene coding for a protein showing an amino acid identity of 90% or higher to Enko B, and a gene showing a nucleotide sequence identity of 90% or higher to the "ORF687 gene" coding for Enko B. The family gene locating at the same locus as that of the "OFR687 gene" coding for the OFR687 protein of Enko (named Enko B) includes all the genes shown in FIGS. 21A-21B and 22 (Kosena B, Comet B, Enko A, Comet A, Icicle CA, rrORF690-1, rrORF690-2, PC PPR-A, PC PPR-BL), but it is not limited to these. The gene coding for a protein showing an amino acid identity of 90% or higher to Enko B, and the gene showing a nucleotide sequence identity of 90% or higher to the "ORF687 gene" coding for Enko B can be obtained by searching gene databases, and the species as the origin thereof is not limited to those of radish. The PPR motif is a PPR motif consisting of a polypeptide of 30- to 38-amino acid length represented by the formula 1 mentioned above, and the PPR protein may comprise one or more of such PPR motifs (preferably 2 to 16 motifs). As the polymorphism in the PPR motif, there can be used polymorphism of the combination of amino acids 1, 4, and "ii" or the combination of amino acids 4 and "ii", which was elucidated to be responsible for the binding of PPR motif to RNA by the present invention. As seen from the P values shown in FIG. 4B or 4D, among the amino acids of the combinations responsible for the binding of the PPR motif to RNA, amino acid 4 plays the most important role, and the amino acid "ii" plays the secondarily important role. It was further elucidated that, in comparison with the PPR protein of Enko B, the fact that amino acids 4 of all the PPR motifs in a protein encoded by a gene as a test subject are the same as those of Enko B, or the fact that the amino acids "ii" in all the corresponding PPR motifs are the same as those of Enko B is important for the function as a fertility restoration factor. Further, it was also elucidated that, similarly to the fertility restoration, some PPR proteins act on speciation. It is expected that identification and modification of a target RNA of the PPR protein enable mating of species, of which mating has so far been impossible. Further, since most of the PPR proteins act on RNA in mitochondria and chloroplasts, the novel PPR proteins provided by the present invention will contribute to modification and improvement of the functions concerning photosynthesis, respiration, and synthesis of useful metabolites.

Further, for animals, it is known that anomaly of the PPR protein identified as LRPPRC causes Leigh syndrome French Canadian type (LSFC, Leigh's syndrome, subacute necrotizing encephalomyelopathy). The present invention can contribute to the treatment (prophylactic treatment, therapeutic treatment, suppression of advance) of LSFC.

Further, the PPR proteins are involved in all the steps of RNA processing seen in organelles, digestion, RNA editing, translation, splicing, and RNA stability. According to the present invention, it can be expected that, by modifying the binding base selectivity of a PPR motif, expression of a desired RNA can be modified.

The PPR proteins used in the present invention as materials mainly function for specification of the editing site of RNA editing (conversion of genetic information on RNA, C to U in many cases) (refer to References 2 and 3 mentioned later). The PPR proteins of this type have an additional motif suggested to interact with an RNA editing enzyme existing on the C-terminus side. It can be expected that, by using a PPR protein having such a structure, nucleotide polymorphism can be introduced, and a disease or condition induced by nucleotide polymorphism can be treated.

Further, a part of PPR proteins have an RNA cleavage enzyme on the C-terminus side. By modifying the binding RNA base selectivity of the PPR motif on the N terminus side of such a PPR protein, an RNA sequence-specific RNA cleaving enzyme can be constituted. Furthermore, a complex having a marker moiety such as GFP bound to a PPR protein can be used for visualizing a desired RNA in a living body.

Further, the existing PPR proteins include those that act on DNA. It has been reported that one of them is the transcription activator of a mitochondrial gene, and another one is a transcription activator localizing in the nucleus. Therefore, it may also be possible to design a protein factor that binds to a desired DNA sequence on the basis of the findings obtained by the present invention.

EXAMPLES

Example 1: Collection of PPR Proteins Involved in RNA Editing and Target Sequences Thereof With reference to the information shown in FIG. 2, the PPR proteins of *Arabidopsis thaliana* involved in RNA editing so far analyzed (SEQ II) NOS: 2 to 24, see FIGS. 16A-16HH) were collected from the *Arabidopsis* Malian genome information database (MATDB: http://mips.gsf.de/proj/thal/db/index.html), and sequences around RNA-editing sites that serve as a target (SEQ ID NOS: 48, 50, 53, 55, 57, 59, 60, 61, 62, 63, 64, 65, 68, 69, 70, 71, 73, 74, 76, 78, 80, 122, 206, 228, 232, 252, 284, 316, 338, 339, 358, 430, 433, 455, 552 and 563 (see FIGS. 16A-16HH)) were collected from the RNA-editing database (http://biologia.unical.it/py_script/overview.html). As the RNA sequences, those of 31 nucleotides upstream from the editable C (cytosine) residue including that C were collected. All the collected proteins and RNA-editing sites corresponding to the proteins are shown in FIG. 2.

To the PPR motif structures in the proteins, the amino acid numbers defined in the present invention, as well as the information of the Uniprot database (http://www.uniprot.org/) are imparted. The PPR motifs contained in 24 of the *Arabidopsis thalianas* PPR proteins (SEQ ID NOS: 2 to 25, see FIGS. 16A-16HH) used for the experiments and amino acid numbers thereof are shown in FIGS. 3A-3H.

Figure 4A:
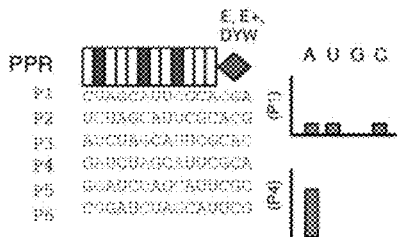
FIGS. 4A-4E show the amino acids in the PPR motifs involved in the RNA recognition.

Example 2: Identification of Amino Acids that Impart Binding Base Selectivity The researches so far elucidated that the PPR proteins involved in RNA editing have a motif having a specific conserved amino acid sequence on the C-terminus side (E, E+ and DYW motifs, provided that DYW motif often does not exist). It has been suggested that more than ten amino acids in the E+ motif are required for the conversion from C (cytosine) to U (uracil), not for the selective binding to RNA (Reference 3). Further, it has also suggested in the past non-patent paper that the information required for recognition of the editable C is included in the 20 upstream nucleotides and 5 downstream nucleotides thereof. That is, it can be predicted that a plurality of PPR motifs in the PPR protein recognize "somewhere" of the upstream sequence of the editable C, and the E+ motif locates near the editable C. Furthermore, there is considered a possibility that specific amino acids in the PPR motif may recognize the RNA residue of the upstream sequence to which they bind (FIG. 4A).

This possibility was verified by using the 24 RNA-editing PPR proteins of *Arabidopsis thaliana* and target RNA sequences thereof described in Example 1. First, all the PPR motifs of the PPR protein were aligned with the corresponding RNA residues by arranging the last PPR motif in the protein at the first nucleotide from the editable C with 1-motif to 1-nucleotide correspondence in linear contiguity (FIG. 4A, alignment P1). Then, the RNA sequence was moved toward the right, 1 nucleotide at a time, to obtain the alignments P2 to P6. In the data set for each of these alignments P1 to P6, the information on the RNA residues corresponding to the PPR motifs was collected.

For a PPR protein that works for a single editing site, a score of 1 was given to each occurrence of the RNA nucleotide (A, U, G or C). For PPR proteins that work for 2 and 3 editing sites, scores of 0.5 and 0.3 were given to each occurrence of the RNA nucleotide, respectively. Then, the sets of PPR motifs and nucleotides were sorted according to types of amino acids for each of the amino acid numbers in the PPR motifs. It can generally be predicted that amino acids and RNA residues randomly appear for the types thereof (high-randomness or high-entropy) (an example is shown in the upper graph on the right side in FIG. 4A). However, if an amino acid of a specific position has binding RNA base selecting capacity, it is predicted that the corresponding RNA base is converged to one kind or limited kinds of them in correct alignments (P1 to P6 mentioned above) (low randomness or low entropy, an example is shown in the lower graph on the right side in FIG. 4A).

The aforementioned low randomness was calculated for all the amino acid numbers of the PPR motifs for the data sets of the alignments P1 to P6 created above. The low randomness was calculated by the chi square test based on a theoretical value (average of occurrence frequencies of all the nucleotides) (examples are shown in FIG. 5).

Figure 4C:
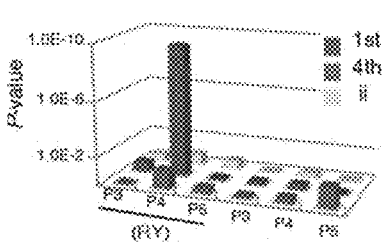
Figure 4B:
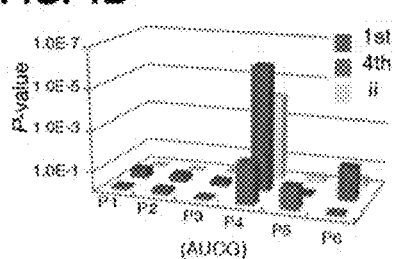
Figure 4D:
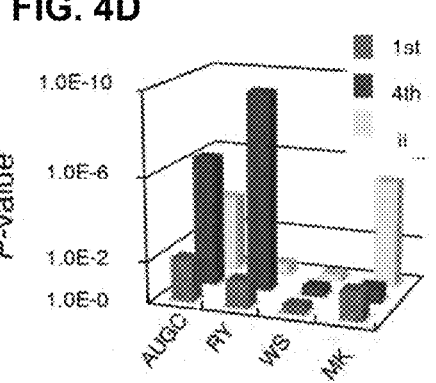
Figure 6A:
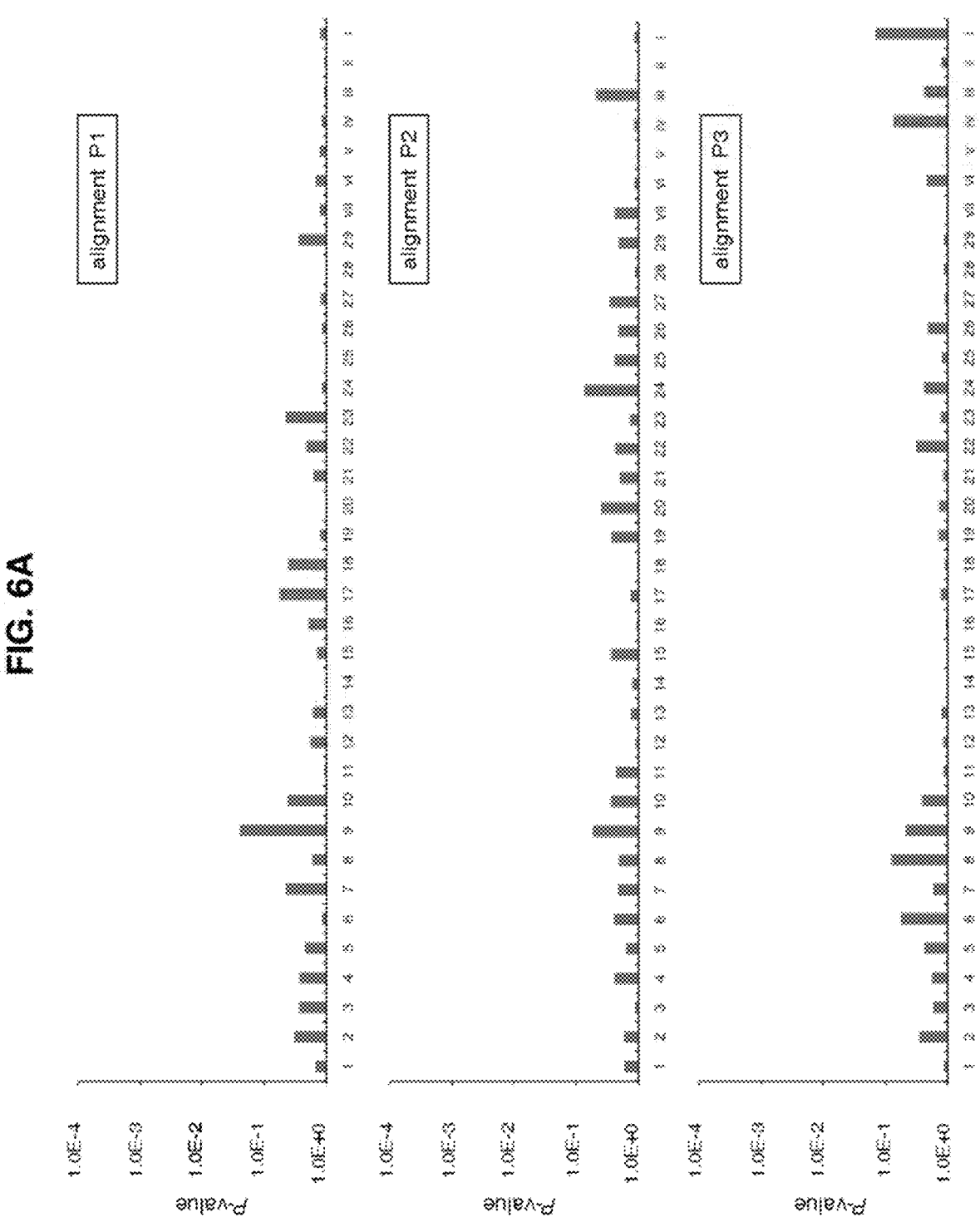
FIGS. 6A-6C show results of search for the amino acids responsible for the RNA base specifying capacity.
Figure 6B:
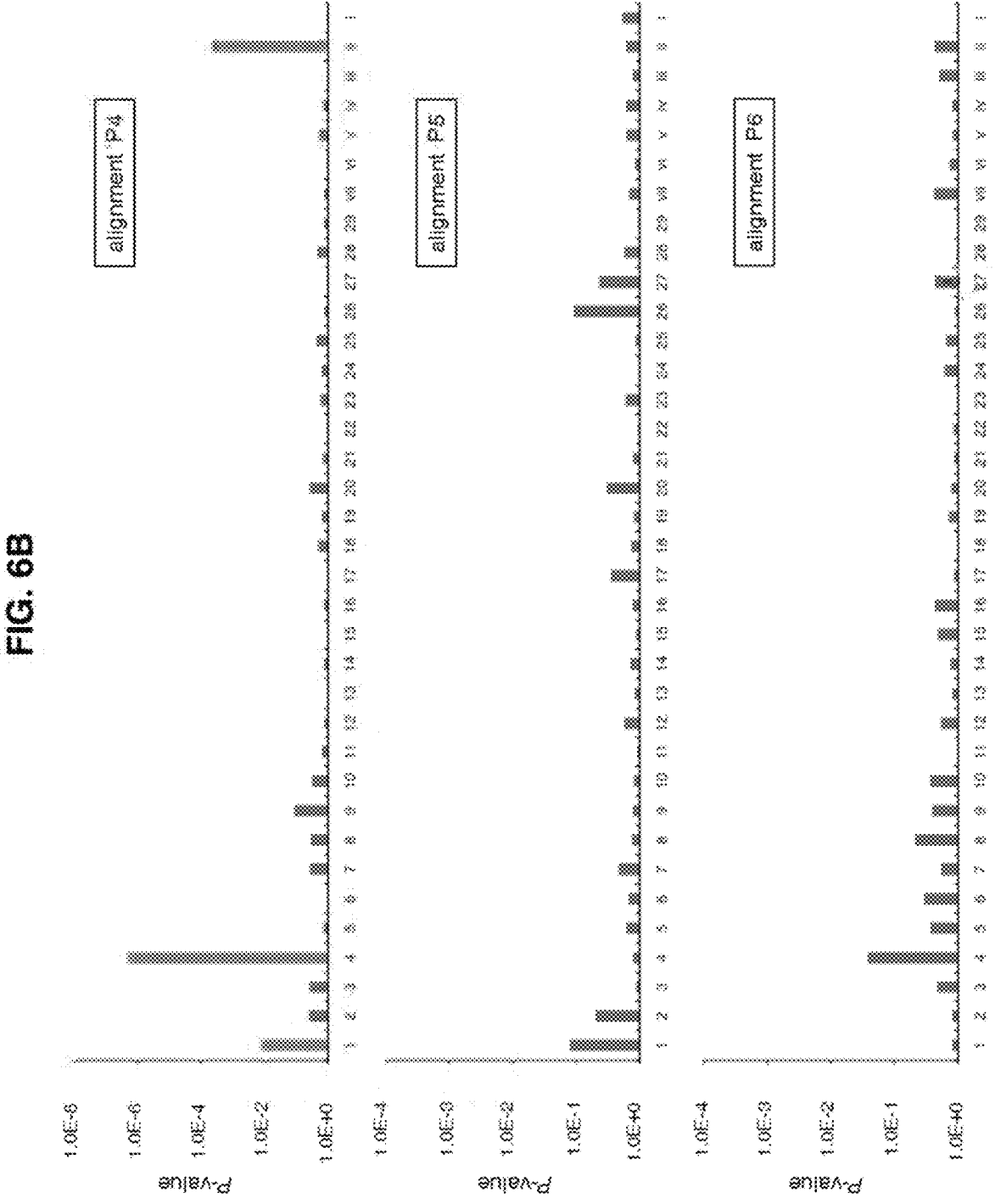
Figure 6C:
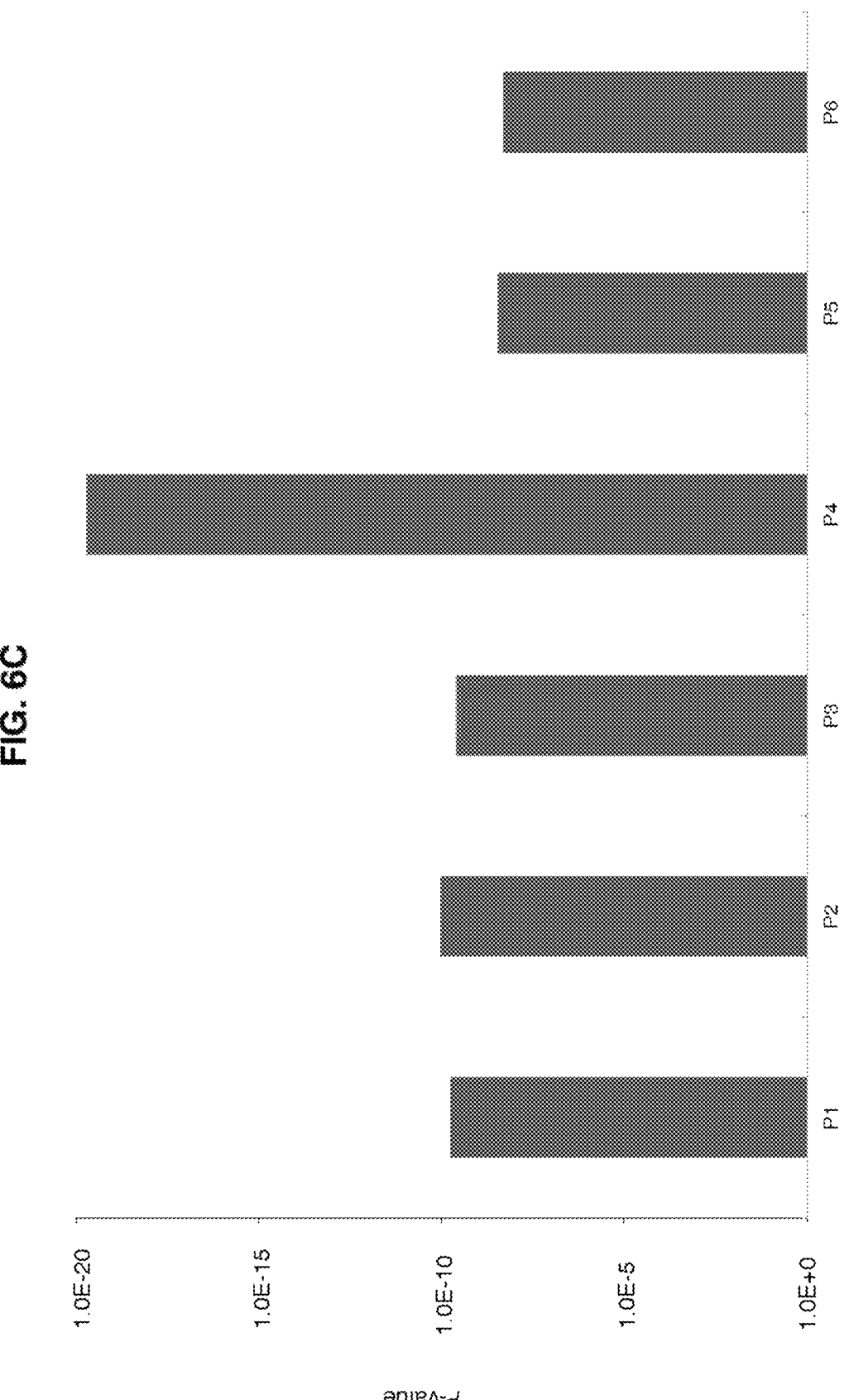

As a result, for amino acids 1, 4 and "ii" (−2) in alignment P4, it was determined that the significance value P is smaller than 0.01 (probability lower than 1%) (FIG. 4B). That is, it was revealed that the last PPR motif in the RNA-editing PPR protein is arranged at the base 4 nucleotides before the editable C, and the three amino acids (1, 4, and "ii") are responsible for the binding RNA base selection. Further, because any significant P value was not calculated for the alignments P3 and P5, it was revealed that there is no interference from the PPR motifs of both sides, i.e., one PPR motif recognizes one RNA residue, and the binding does not depends on the constitution of the motifs. For the other amino acids in alignment P4, and all the amino acids of the other alignments, any significant P value was not obtained (FIGS. 6A-6C). Further, the RNA bases were classified into those of purine (A and G) or pyrimidine (C and U) (RY), and the same calculation was performed. As a result, an extremely significant P value (P<0.01) was obtained only for amino acid 4 (FIG. 4C). This indicates that amino acid 4 mainly determines which one of purine and pyrimidine is the RNA base to be bound. The binding base specifying capacity of the RNA recognition amino acids in the PPR motif shown in FIG. 4C was analyzed in more detail. As a result, in addition to that amino acid 4 mainly distinguishes the type of the base to which it binds, purine or pyrimidine (RY), it was found that the amino acid "ii" (−2) works to distinguish the form of the base, amino form (A and C) or keto form (G and U) (MK, FIG. 4D).

Figure 4E:
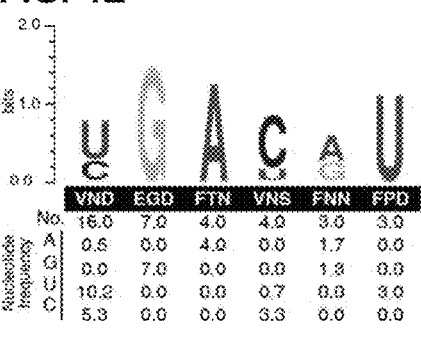

Combinations of the three amino acids (1, 4, and "ii") used 3 times or more were defined as triPPR codes among the RNA recognition codes of the PPR motifs, and P value was calculated for each of them to calculate the binding RNA base specifying capacity thereof. A part of the identified triPPR codes are shown in FIG. 4E.

Figure 7:
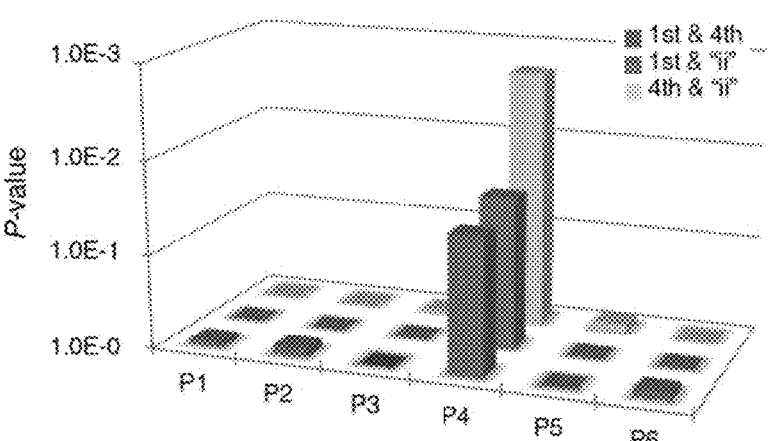
FIG. 7 shows the binding RNA base specifying capacities exerted by two amino acids. The binding RNA base specifying capacities exerted by different combinations of two amino acids (amino acids 1 and 4, 1 and "ii", and 4 and "ii") were analyzed on the basis of low randomness of amino acids and corresponding bases, and the results are shown in the same manner as that used in FIGS. 4A-4E.

Since the amino acids of the three positions were extremely diverse, the binding RNA base specifying capacity was calculated for two amino acids (1 and 4, 1 and "ii", or 4 and "ii"). As a result, a remarkable P value was calculated for the combination of amino acids 4 and "ii" (FIG. 7). Therefore, combinations of amino acids 4 and "ii" used 3 times or more were defined as diPPR codes among the RNA recognition codes of the PPR motifs. The identified triPPR codes and diPPR codes are shown in FIG. 8.

Example 3: Verification of Identified RNA Recognition Codes

Figure 9:
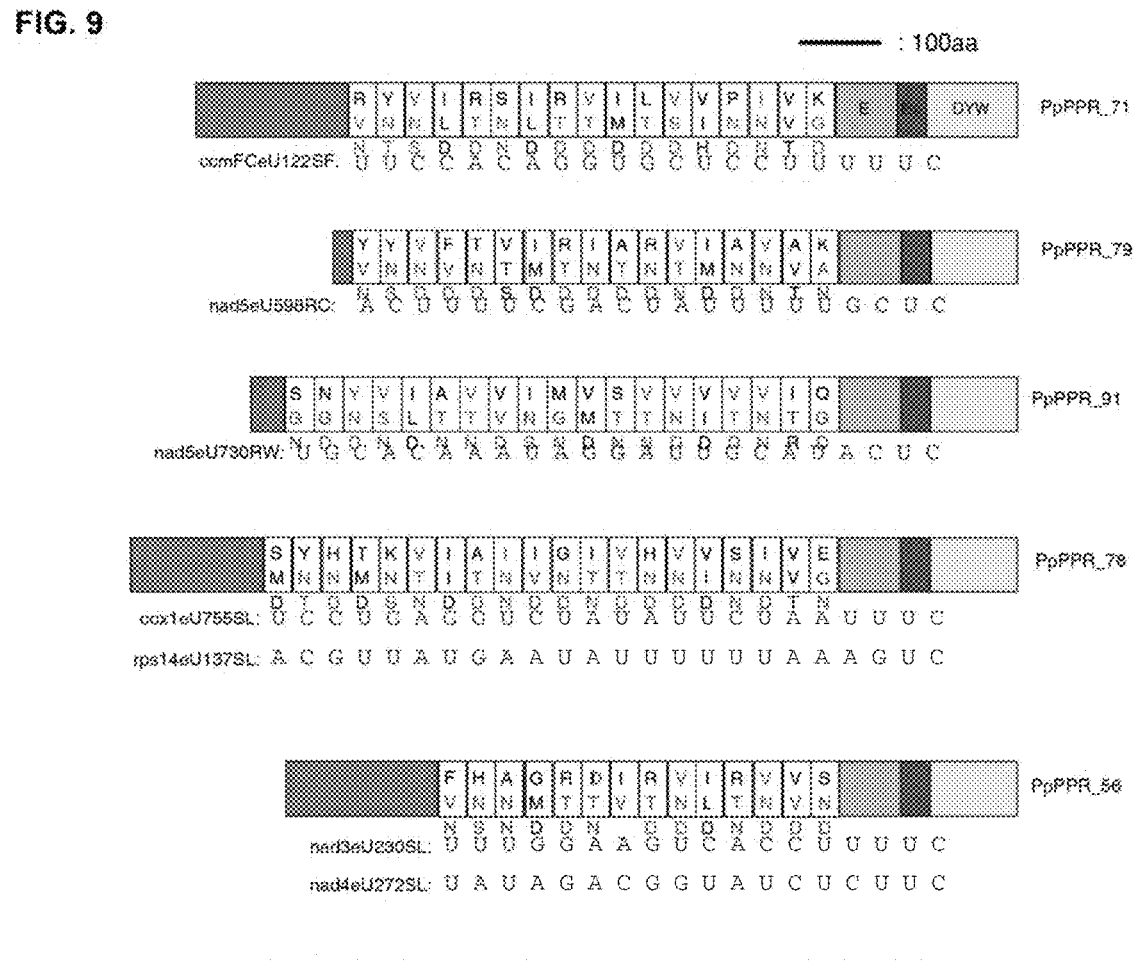
FIG. 9 shows the sequences of *Physcomitrella patens* subsp. *patens* RNA-editing PPR proteins and the RNA-editing sites on which the proteins act. Together with the motif structures of the proteins, the sequences of amino acids 1, 4, and "ii" (−2) in each PPR motif are shown. The letters in magenta and cyan colors (both are in dark gray in monochromatic indication) show the combinations of amino acids homologous to the triPPR or diPPR codes extracted from *Arabidopsis thaliana*. The additional motifs (E, E+, DYW) on the C terminus side are also shown. The sequences of the RNA-editing sites on which the proteins act (upstream sequences containing editable C) are shown in terms of the positions in alignment P4 shown in FIG. 4.

The RNA recognition codes for the PPR motifs identified by using the RNA-editing PPR proteins of *Arabidopsis thaliana* were verified. For the verification, the RNA-editing PPR proteins of *Physcomitrella patens* subsp. *patens* were used. It has already been elucidated that, in *Physcomitrella patens* subsp. *patens* (henceforth referred to as moss), RNA editing occurs at 13 sites in total (11 site in mitochondria, 2 sites in chloroplasts, SEQ ID NOS: 32 to 44 (see FIGS. 16A-16HH)). Further, it has also been elucidated that 6 PPR proteins (PpPPR_56, 71, 77, 78, 79, and 91) work for RNA editing at 9 sites, respectively. The proteins and corresponding RNA-editing sites are shown in FIG. 9.

Figure 10:
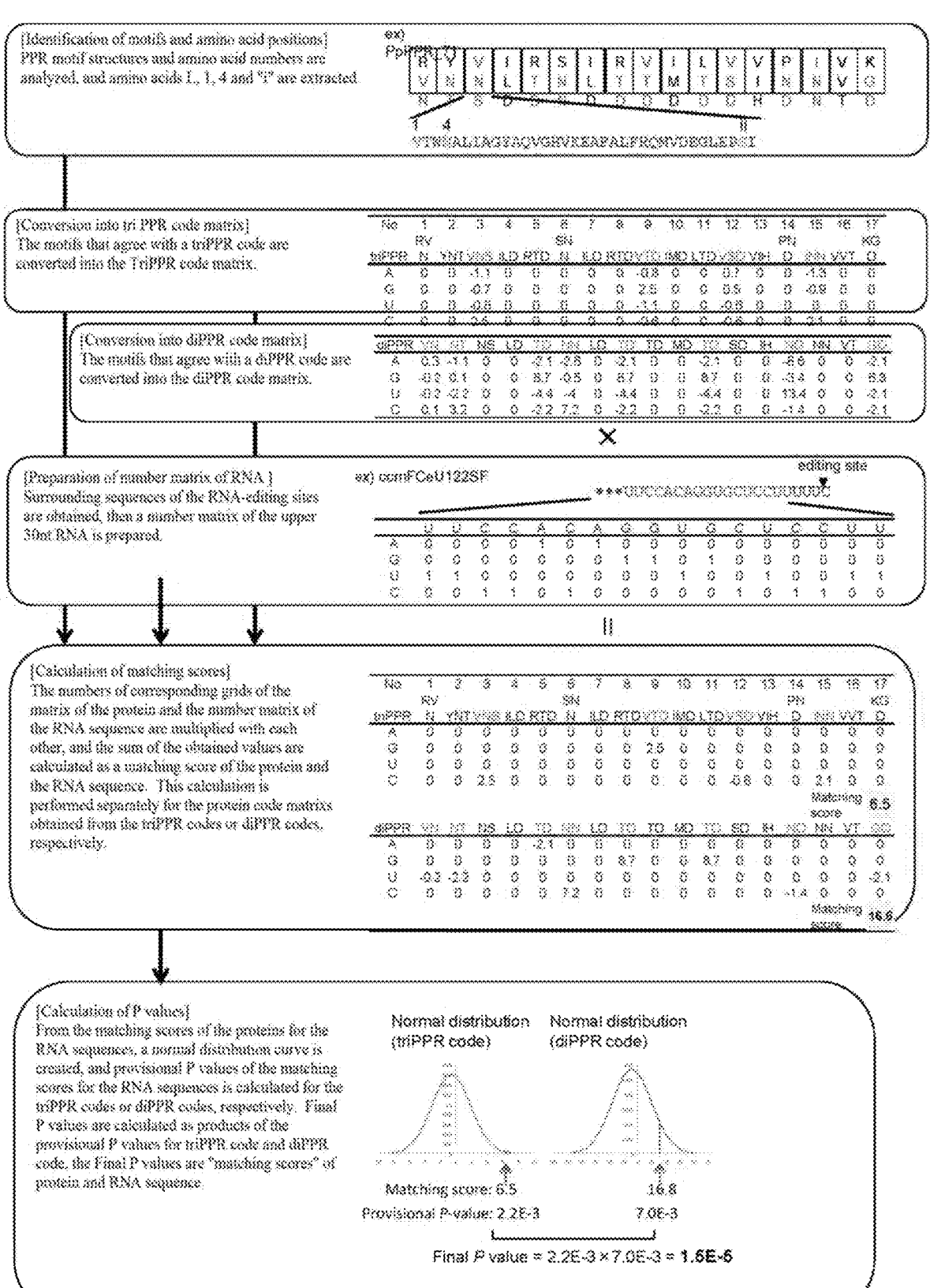
FIG. 10 shows a flowchart of a method for calculating matching score between a PPR protein and an RNA-editing site RNA sequence. From the Uniprot or PROSITE database, PPR models of proteins are obtained, and the amino acid numbers are given according to FIG. 1. Amino acids 1, 4, and "ii" are extracted. As an example, the moss PPR protein, PpPPR71, is shown. Then, the matching combinations of amino acids are converted into a triPPR code matrix. The motifs that could not be converted into the triPPR codes are then converted into a diPPR code matrix. In parallel, the RNA-editing site 30 nt (the last nucleotide is the editable C) are converted into an expression matrix. As an example, there is shown the ccmFCeU122SF sequence, on which the PpPPR71 protein acts. Then, products of numbers of corresponding grids of the protein code matrix and the RNA expression matrix are obtained, and matching scores are calculated from the sum of them. The last line of the protein code matrix should be matched to the line corresponding to the base 4 nucleotide before the editable C. This calculation is performed for protein code matrixes prepared from the triPPR codes and the diPPR codes. A provisional P value for each RNA sequence is calculated with each of the triPPR codes and diPPR codes using a normal distribution curve prepared from matching scores for a plurality of RNA sequences. The final matching score (P value) is calculated as a product of the provisional P values of the triPPR and diPPR codes.

The verification was performed as shown in FIG. 10. First, the amino acid sequence information of the moss PPR proteins was obtained from a non-patent paper (SEQ ID NOS: 26 to 31, FIGS. 2, 9, and 16A-16HH), and the three amino acids (1, 4, and "ii") were extracted from each PPR motif according to the PPR motif model defined as shown in FIGS. 1A-1C. When the combination of the extracted three amino acids agreed with any one of the triPPR codes identified from *Arabidopsis thaliana*, it was converted into a binding base scoring matrix represented by that code. Then, a PPR motif that could not be converted with any of the triPPR codes, but agreed with any one of the diPPR codes was converted into the binding nucleotide scoring matrix of diPPR code. In parallel, surrounding sequences of the RNA-editing sites (31-mer sequences having the editable C at the 3' end) were obtained from a non-patent paper (SEQ ID NOS: 32 to 44, FIGS. 2, 9 and 16), and converted into such a number matrix of the RNA sequence as shown in FIG. 10. The numbers of corresponding grids of the binding base scoring matrix of the protein and the number matrix of the RNA sequence were multiplied with each other, so as not to contradict to the above-mentioned alignment P4 (the last PPR motif corresponds to the base 4 nucleotides before the editable C), and the sum of the obtained values was calculated as a matching score of the protein and the RNA sequence. This calculation was performed for the triPPR codes, diPPR codes, and the PPR binding base scoring matrixes (PPR scoring matrixes) thereof.

For one kind of protein, this calculation was performed for all the RNA-editing sites of the moss (13 sites). Further, the same calculation was also performed for 34 RNA sequences of the RNA-editing sites of *Arabidopsis thaliana* chloroplast (FIG. 16, SEQ ID NOS: 45 to 78) as reference sequences of RNA-editing site surrounding sequences.

Then, from the matching scores of the proteins for the RNA sequences, a normal distribution curve was created, and provisional P values of the matching scores for the RNA sequences were calculated for the triPPR codes and diPPR codes, respectively.

Final P values (matching scores of protein and RNA sequence) were calculated as products of the provisional P values for triPPR code and diPPR code.

Figures 11A, 11B:
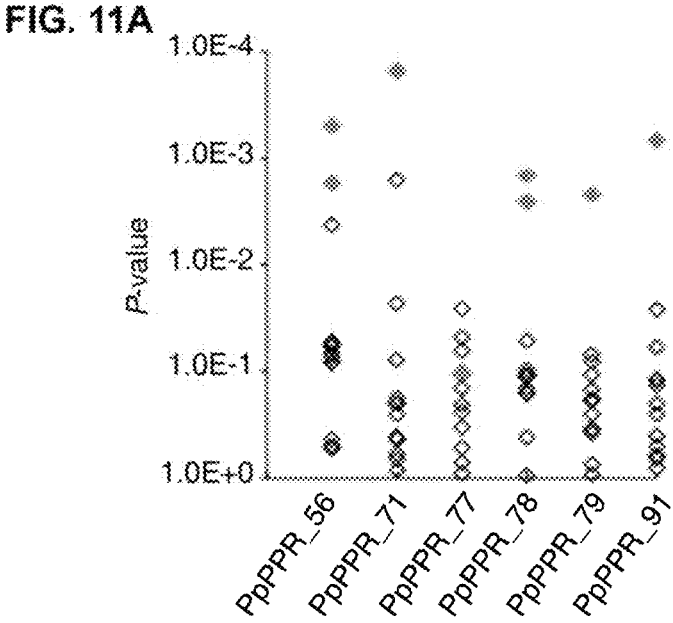
FIGS. 11A and 11B show prediction of the target RNA sequences of the PPR proteins using the PPR codes.

The matching scores of the moss PPR proteins and 13 moss RNA-editing sites are shown in FIGS. 11A and 11B. As a result of the analysis, 6 kinds of the proteins were computationally specified for the correct RNA-editing sites out of the 7 kinds of the proteins. That is, this analysis revealed that all the information for the binding RNA base specification performed by the PPR motif is contained in the three amino acids (1, 4, and "ii"). In other words, it was revealed that a PPR protein that binds to an intended RNA sequence can be searched for by referring to the information on the combinations of the two or three amino acids shown in FIG. 8 (triPPR and diPPR codes). At the same time, it was also shown that an artificial protein that binds to an intended RNA sequence can be synthesized by using or binding a PPR motif having such amino acid information.

Figure 12A:
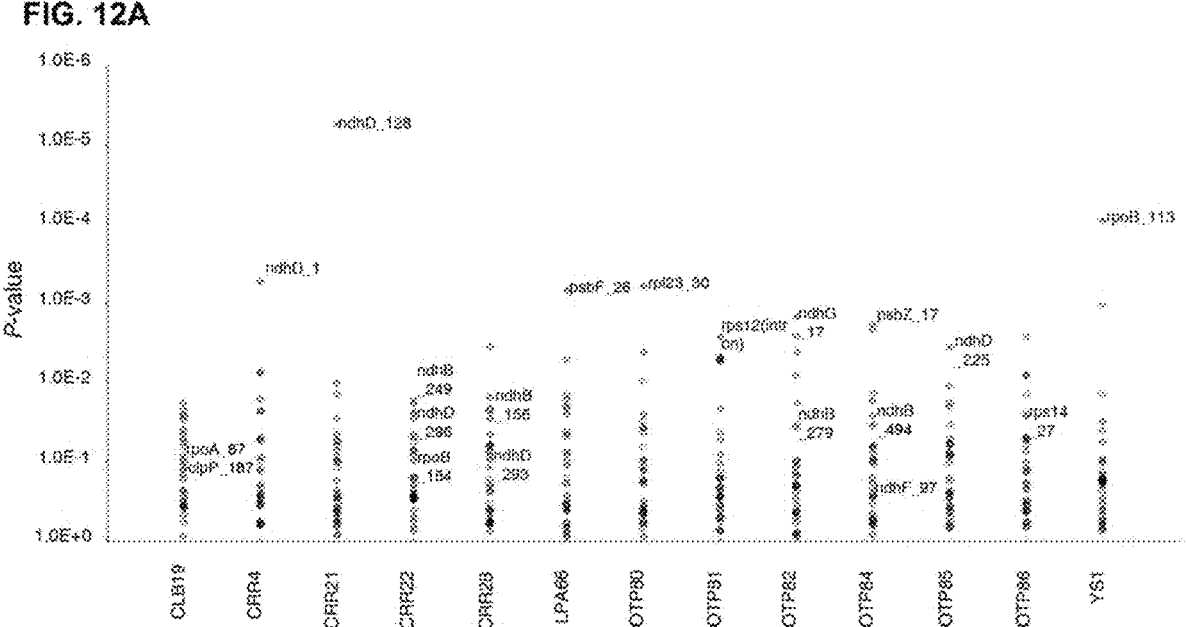
FIGS. 12A and 12B show verification of accuracy for prediction of RNA-editing sites using *Arabidopsis thaliana* RNA-editing proteins. The prediction accuracy was verified by using the *Arabidopsis thaliana* PPR proteins used for the code extraction.
Figure 12B:
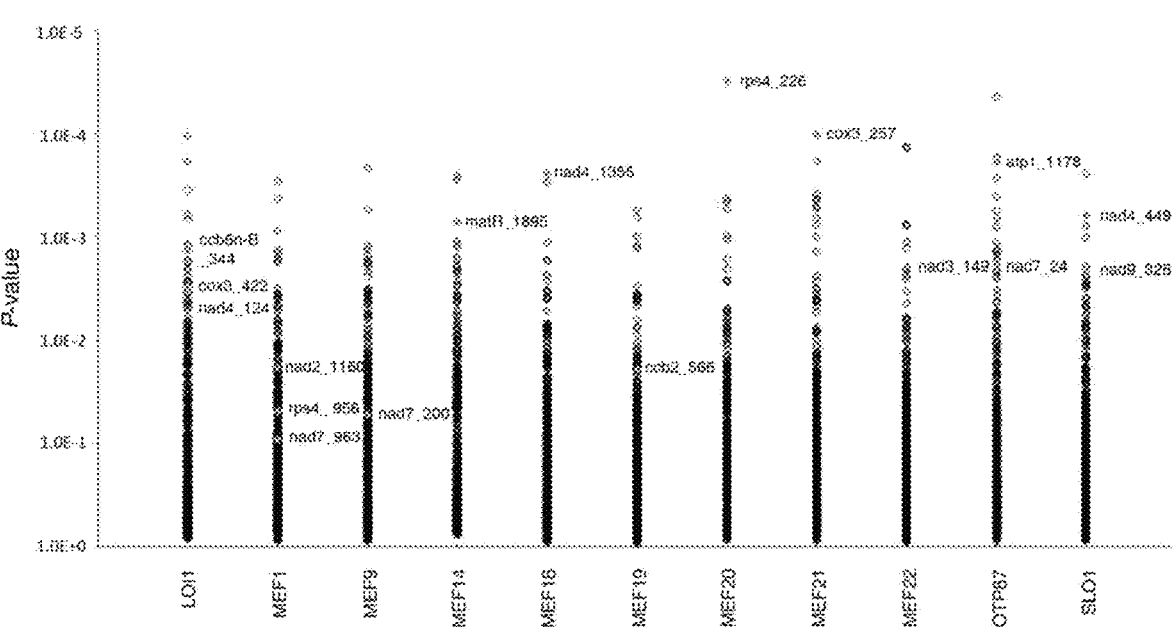

Example 4: Identification of Target Molecules of Unanalyzed RNA-Editing PPR Proteins Then, analysis was performed by using *Arabidopsis thaliana*, which has a larger number of RNA-editing sites compared with the moss (34 sites in chloroplastic genome (SEQ ID NOS: 45 to 78 (see FIGS. 16A-16HH)), and 488 sites in mitochondrial genome (SEQ ID NOS: 79 to 566 (see FIGS. 16A-16HH)), see FIGS. 6A-6C). In order to verify prediction accuracy, RNA-editing sites of 24 kinds of PPR proteins used for the code extraction were predicted. As a result, for the chloroplast-localized PPR proteins, at least one correct RNA-editing site was predicted with the highest P value for 10 kinds of proteins out of 13 kinds of the proteins. For mitochondria-localized PPR proteins, a correct RNA-editing site was predicted with a value within top 20 thereof for 8 kinds of proteins out of 11 kinds of the proteins (FIGS. 12A-12B). On the basis of the results of this verification of prediction accuracy, target RNA-editing sites of the PPR proteins of which function was unknown were predicted. An AHG11 mutant is a mutant having anomaly in the abscisic acid pathway, and the proteins encoded by the genes thereof (ahg11, at2g44880) have a typical RNA-editing PPR protein-like motif structure (FIG. 13, SEQ ID NO: 1 (see FIGS. 16A-16HH)). RNA-editing sites were predicted, and 405 sites for mitochondria and 30 sites for chloroplasts including those of values within the top 20 thereof were experimentally verified. As a result, it was revealed that only the RNA editing of mitochondria nad4_376 predicted with the 7th highest P value had anomaly in the mutant (FIGS. 13A-13D).

Then, it was attempted to identify target RNA sequences in the total genomes of the organelles i.e., a data set of about $3 \times 10^5$ RNA sequences. For this analysis, the probability matrix of PPR codes shown in FIG. 8 was used. Further, for the motifs having a combination of amino acids not agreeing with any of the diPPR and triPPR codes, background frequency was applied. The probability matrixes of the produced proteins were subjected to the FIMO analysis in MEME suite (http://meme.nbcr.net/meme4_6_1/fimo-intro.html) together with the chloroplast total nucleotide sequence of *Arabidopsis thaliana* (AP000423).

As a result, for CRR4 and CRR21, target RNA sequences thereof could be correctly predicted. Further, the codes were improved by extracting the PPR codes also from the moss PPR proteins (FIG. 15). As a result, the prediction accuracy was markedly improved for several proteins.

These results indicate that one correct target sequence can be identified from RNA sequences of several hundreds of thousands patterns by using the identified PPR codes. Conversely, by searching for a PPR motif having amino acids matching the code at the positions (1, 4, and "ii"), a protein that binds to the intended useful RNA sequence can be identified. Alternatively, it was shown that, by binding a PPR motif, an artificial RNA binding protein showing high sequence selectivity can be created. It will also be understood by those skilled in the art that, by obtaining a combination of amino acids at the concerned positions matching any of the PPR codes through introduction of mutation, intended RNA binding selectivity can be imparted. FIG. 15 shows evaluation of the binding RNA base selecting capacity of triPPR codes and diPPR codes based on the P values. It can be estimated that PPR codes that showed a significant P value (P<0.05) have high binding RNA base selecting capacity.

Example 5: Prediction of Target RNA Sequence of Radish Rf

Then, on the basis of the findings obtained by the present invention, functions of the PPR proteins that work as a fertility restoration factor for cytoplasmic male sterility were determined (Examples 5 to 9).

The cytoplasmic male sterility (CMS) is a characteristic that the male gamete comes to no longer normally function due to a mutation in a cytoplasmic genome, especially a mitochondrial genome. It is known that this characteristic is compensated by a fertility restoration gene (restorer of fertility, Rf), which often exists in the nucleus, and the male gamete is thereby made normal. This characteristic is used for the first filial hybrid breeding method, and is one of the agriculturally important characteristics. It is known that, in such a CMS-Rf system, the Rf gene codes for a PPR protein in many cases.

Sterility of the Ogura-type (synonym, Kosena-type) cytoplasm used in the first filial hybrid breeding method for radish or rapeseed originates in expression of the orf125 gene in a mitochondrial genome, and canceled by the presence of the nuclear-encoded orf687 gene, and the cytoplasm acquires fertility. The orf687 gene product is a PPR protein, and it is considered that it acts on RNA containing orf125 to inactivate the expression thereof, and the sterility is canceled as a result.

However, it has become clear from the past thremmatological analyses that amino acid polymorphism is observed for the orf687-like genes of various radish pedigrees, and that this amino acid polymorphism affects the function of the gene as a fertility restoration factor. However, any method for estimating functionality of a gene from the amino acid sequence encoded thereby has not been established.

Figure 19B:
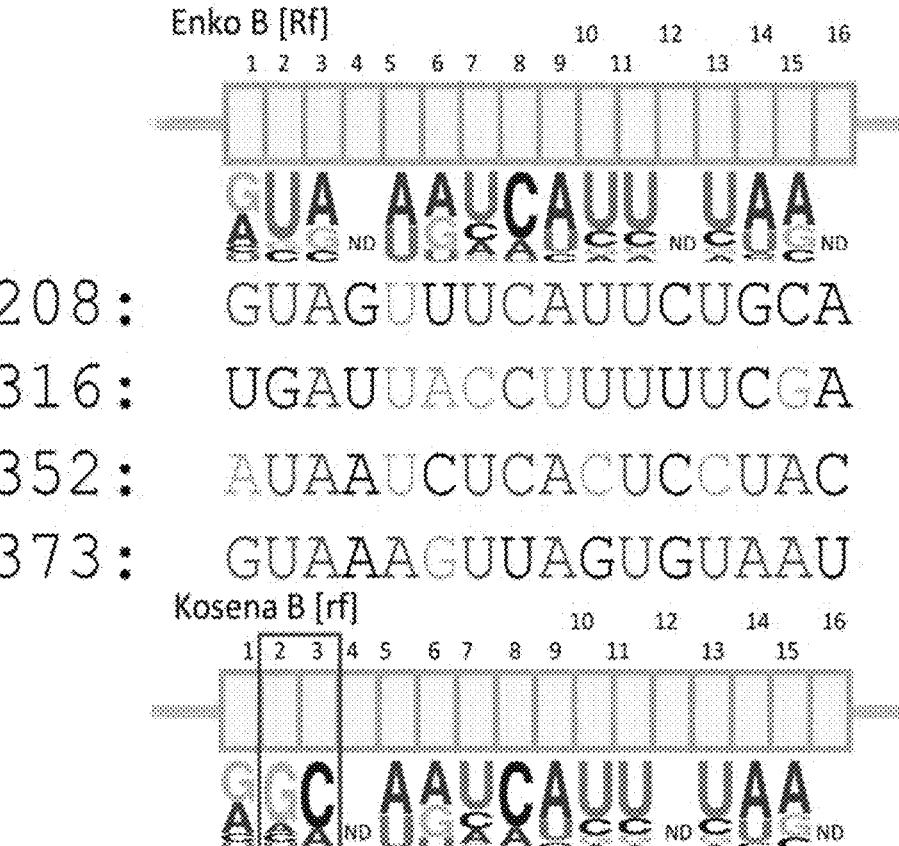

Therefore, a PPR motif was first specified in the amino acid sequence of the ORF687 protein of the radish variety Enko (named Enko B), which is known to function as a dominant Rf, amino acids responsible for the base specifying capacity (1, 4, and ii) were extracted from it, and converted into a PPR code, and then the target RNA sequence thereof was predicted for a transcription product containing the mitochondrial orf125 (FIGS. 19A-19B)

In parallel, three kinds of ORF687-like proteins, the ORF687 protein of the radish variety Enko (named Enko B), which is known to function as a dominant Rf, an ORF687-like protein that is similarly contained in Enko and well resembles the ORF687, but acts as a recessive gene (named Enko A), and a gene homologous to the Enko ORF687 existing in the genome of Kosena, which is a different radish variety (named Kosena B, recessive gene), are used as experimental materials, and the characteristics of them were biochemically analyzed.

(5-1) Preparation of the Genomic DNA from Radish

Radish was cultured on the Murashige and Skoog medium (containing 2% sucrose and 0.5% Gellangam) for three weeks. The green leaves (0.5 g) of the cultured plant were extracted with phenol/chloroform, and then ethanol was added to insolubilize DNA. The collected DNA was dissolved in 100 μl of the TE solution (10 mM Tris-HCl (pH 8.0), 1 mM EDTA), 10 units of RNase A (DNase-free, Takara Bio) was added to the mixture, and the reaction was allowed at 37° C. for 30 minutes. Then, the reaction mixture was extracted again with phenol/chloroform, and DNA was collected by ethanol precipitation. DNA was obtained in an amount of 10 μg.

(5-2) Cloning of Genes Coding for ORF687-Like Proteins

By performing PCR using radish genomic DNA as the template, oligonucleotide primers, Enko_B-F primer and Enko_B-R primer (SEQ ID NOS: 567 and 568, respectively), for Enko B, oligonucleotide primers, kosena_B-F primer and kosena_B-R primer (SEQ ID NOS: 569 and 570, respectively), for Kosena B, or oligonucleotide primers, Enko_A-F primer and Enko_A-R primer (SEQ ID NOS: 571 and 572, respectively), for Enko A, and KOD-FX (TOYOBO) as a DNA extension enzyme in 50 μl of a reaction mixture with 25 cycles of 95° C. for 30 seconds, 60° C. for 30 seconds, and 72° C. for 30 seconds, the genes were amplified, respectively.

The obtained DNA fragments were cloned by using the pBAD/Thio-TOPO vector (Invitrogen) according to the attached protocol. The DNA sequences were determined to confirm that the sequences were those homologous to the intended corresponding DNA sequences (Enko B (SEQ II) NO:573), Kosena B (SEQ ID NO: 574), Enko A (SEQ ID NO: 575)).

(5-3) Preparation of Recombinant ORF687-Like Proteins

The *Escherichia coli* TOP10 strain (Invitrogen) was transformed with the plasmids obtained above. The *Escherichia coli* strain was cultured at 37° C. in 300 ml of the LB medium containing ampicillin at a concentration of 100 μg/ml (300 mL of the medium contained in a 1-L conical flask). When the turbidity of the culture medium in terms of the absorbance at a wavelength of 600 nm reached 0.5, L-arabinose as an inducer was added at a final concentration of 0.2%, and culture was further continued for 4 hours.

The cells were collected by centrifugation, then suspended in 200 ml of Buffer A (50 mM Tris-HCl (pH 8.0), 500 mM KCl, 2 mM imidazole, 10 mM MgCl$_2$, 0.5% Triton X100, 10% glycerol) containing 1 mg/ml of lysozyme, and disrupted by ultrasonication and freezing/thawing. The cell suspension was centrifuged at 15,000×g for 20 minutes, and then the supernatant was collected as a crude extract.

This crude extract was applied to a column filled with a nickel column resin (ProBond A, Invitrogen) equilibrated with Buffer A.

After the column was sufficiently washed with Buffer A containing 20 mM imidazole, column chromatography was performed with two-step concentration gradient, in which the objective protein was eluted with Buffer A containing 200 mM imidazole. The obtained proteins were fusion proteins comprising the amino acid sequence of SEQ ID NO: 576 (Enko B), SEQ ID NO: 577 (Kosena B), or SEQ II) NO: 578 (Enko A), the amino acid sequence of thioredoxin for enhancing solubility on the N terminus side, and a histidine tag sequence on the C-terminus side. Each purified fraction in a volume of 100 μl was dialyzed against 500 mL of Buffer E (20 mM Tris-HCl (pH 7.9), 60 mM KCl, 12.5 mM MgCl$_2$, 0.1 mM EDTA, 17% glycerol, 2 mM DTT), and then used as a purified sample.

(5-4) Preparation of Substrate RNA

As the substrate RNA, three kinds of RNAs containing the sequence of a mitochondrial DNA of Ogura-type radish cytoplasm, RNAa, RNAb, and RNAc, were used.

The DNAs were amplified by PCR using oligonucleotide primers, A-F primer and A-R primer (SEQ ID NOS: 579 and 580, respectively), for RNAa, oligonucleotide primers, B-F primer and B-R primer (SEQ ID NOS: 581 and 582 respectively), for RNAb, or oligonucleotide primers, C-F primer and C-R primer (SEQ ID NOS: 583 and 584, respectively), for RNAc, and KODFX (TOYOBO) as a DNA extension enzyme, in 50 μl of a reaction mixture containing 10 ng of the aforementioned Ogura-type radish cytoplasm DNA as the template, with 25 cycles of 95° C. for 30 seconds, 60° C. for 30 seconds, and 72° C. for 30 seconds. To each of the forward primers (-F), the T7 promoter sequence for synthesizing the substrate RNA in vitro was added.

Each of the obtained DNA fragments was purified by developing it on agarose gel, and then excising a gel section containing it. By allowing a reaction using the purified DNA fragment as the template at 37° C. for 60 minutes in 20 μl of a reaction mixture containing NTP mix (10 nmol GTP, CPT, ATP, and 0.5 nmol UTP), 4 μl [32$^F$]α-UTP (GE Healthcare, 3000 Ci/mmol), and T7 RNA polymerase (Takara Bio), a substrate RNA was synthesized.

The substrate RNA was subjected to phenol/chloroform extraction and ethanol precipitation, and then the total amount thereof was developed by electrophoresis on denatured 6% polyacrylamide gel containing 6 M urea, and the $^{32}$P-labeled RNA was detected by exposing the gel to an X-ray film for 60 seconds.

Then, the section of the $^{32}$P-labeled RNA was excised from the gel, and immersed in 200 μl of a gel elution solution (0.3 M sodium acetate, 2.5 mM EDTA, 0.01% SDS) at 4° C. for 12 hours to elute the RNA from the gel. The radioactivity of 1 μl of the RNA fraction was measured, and the total amount of the synthesized RNA was calculated. The RNA solution was subjected to ethanol precipitation, and then the RNA was dissolved in ultrapure water at 2500 cpm/μl (1 fmol/μl). By this preparation method, about 100 μl of RNA of 2500 cpm/μl was usually obtained.

(5-5) Binding Experiment of Protein and RNA

Recombinant proteins of Enko B (Rf), Kosena B (if), and Enko A (if, ORF687-like protein existing in the Enko variety) were prepared, and the RNA binding activities thereof were verified.

The RNA binding activities of the prepared recombinant proteins (Enko B (SEQ ID NO: 576), Kosena B (SEQ ID NO: 577), and Enko A (SEQ ID NO: 578)) were analyzed by the gel shift assay. The aforementioned substrate RNA (BD 120, 375 pM, 7.5 fmol/20 μL) and 0 to 2500 nM of each recombinant protein were mixed in 20 μl of a reaction mixture (10 mM Tris-HCl (pH 7.9), 30 mM KCl, 6 mM MgCl$_2$, 2 mM DTT, 8% glycerol, 0.0067% Triton X-100), and the reaction was allowed at 25° C. for 15 minutes. Then, 4 μl of a 80% glycerol solution was added to the reaction mixture, 10 μL of the mixture was developed on 10% non-denatured polyacrylamide gel containing 1×TBE (89 mM Tris-HCl, 89 mM boric acid, 2 mM EDTA), and after the electrophoresis, the gel was dried.

The radioactivity of RNA in the gel was measured with Bioimaging Analyzer BAS2000 (Fuji Photo Film).

Example 6: RNA Binding Experiment Using Recombinant Proteins

Figure 17A:
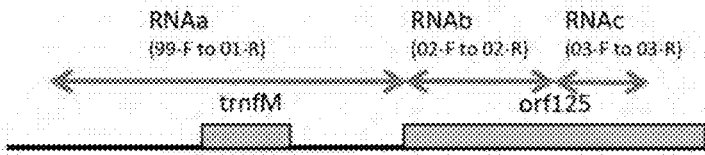
FIGS. 17A and 17B show analysis of the binding of the Enko B protein and RNA containing the cytoplasmic male sterility (CMS) gene.
Figure 17B:
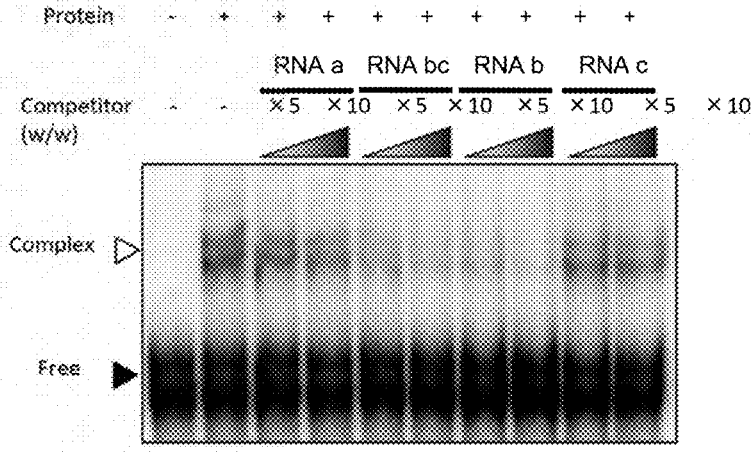

FIGS. 17A-17B show the analysis of binding of the Enko B protein and RNA containing the cytoplasmic male sterility (CMS) gene. FIG. 17A shows a schematic diagram around the mitochondrial orf125, and also schematically shows the regions of RNAa, RNAbc, RNAb, and RNAc used in the binding experiment. FIG. 17B shows binding of the Enko B protein and RNA. Enko B protein (1.4 nmol) and $^{32}$P-labeled RNAbc (0.1 ng) were reacted in the presence of non-labeled RNAa, RNAbc, RNAb, and RNAc (×5 and ×10 w/w with respect to RNAbc, used as a competitive inhibition substance) in 20 μL of a reaction mixture to perform the gel shift competition experiment. Complex 0 mentioned on the left side of the diagram indicates the complex of the protein and RNA, and Free (indicates RNA itself.

As shown in the drawings, the binding of the protein and RNA is visualized as a difference in the migration degree of the $^{32}$P-labeled RNA. This is because the molecular weight of the complex of the $^{32}$P-labeled RNA and the protein is larger than the molecular weight of the $^{32}$P-labeled RNA alone, and therefore the migration degree thereof in the electrophoresis becomes smaller.

In this experiment, a recombinant protein of Enko B was prepared, and binding thereof with a mitochondrial RNA containing orf125 was verified by competition gel shift assay. RI-labeled RNAb and the protein were mixed, and then non-labeled RNA was added. That is, a more reduced signal intensity of the band at the position indicated as Complex means that RNA at that position added as a competitor and the protein binds, i.e., the position corresponds to an RNA region to which Enko B binds with higher affinity. As a result, it was revealed that Enko B strongly binds to the region of RNAb.

The candidate sequence of No. 208 shows the most significant P value in the binding sequence prediction shown in FIGS. 19A-19B, and correctly locates at the 3' end of tRNA methionine. However, the analyses so far revealed that there is no difference in amount of tRNA and configuration of RNA containing orf125 (presence or absence of cleavage) between sterile and fertility-restored pedigrees, and the in vitro binding experiment (FIG. 17B) revealed that the RNAa sequence containing the sequence of No. 208 and Enko B do not bind. Therefore, it was judged that this region is not involved in fertility and sterility of Ogura-type cytoplasm.

Accordingly, further analysis was focused on the regions of Nos. 316, 352 and 373 contained in RNAb. RNAb consists of 125 b. Although it was attempted to narrow down the binding region to a 20 b order by using scanning mutation, it could not be limited to a single site (data are now shown). Therefore, it was considered that a plurality of binding sites for Enko B might exist in RNAb.

Example 7: RNA Binding Activity of Rf-Like Proteins

FIGS. 18A-18C binding of ORF687-like proteins and RNA. FIG. 18A shows the results of analysis of RNA binding characteristics of ORF687-like proteins performed by gel shift assay for binding of Enko B (Rf), Kosena B (rf), and Enko A (rf) with RNAb. FIG. 18B is shows the results of FIG. 18A in the form of graph, and dissociation constants (KD) of the proteins representing the RNA binding capacities thereof were calculated on the basis of this graph. FIG. 18C shows the results of calculation of the matching scores of Enko B (Rf), Kosena B (rf), and Enko A (rf), and potential binding sites thereof performed in the same manner as that used for obtaining the results shown in FIGS. 19A-19B.

As a result, in the non-competing state, all of the three kinds of proteins (Enko B, Kosena B, and Enko A) bound to RNAb with high affinity. As for Kosena B, the RNA binding activity was analyzed in the competing state, but definite difference of the activity was not observed compared with that observed for Enko B (FIGS. 18A and 18B).

Kosena B often shows an RNA binding activity slightly lower than that of Enko B (lower by about 2 times in terms of KD). However, 10 times or more of difference of the activity is detected in many cases for general RNA binding, and the above difference cannot be regarded as a significant difference.

The proteins do not show definite difference of matching scores for the corresponding regions also in the prediction based on the PPR codes (FIG. 18C). Therefore, it was decided to examine a possibility that the difference of Enko B and Kosena B might originate in difference of actions exerted after binding, not in simple difference in RNA binding affinity.

Further, prediction of binding sequences of a fertility restoration factor that acts on the Ogura-type cytoplasm are shown in FIGS. 19A-19B. FIG. 19A shows the results for prediction of binding of the Enko B protein using the PPR codes, and the structure of RNA containing the CMS gene orf125 is shown in the lower diagram of FIG. 19A. As for the regions from RNAa to RNAc shown in FIG. 19A, refer to FIG. 17. In FIG. 19A, the regions of Nos. 208, 230, 316, 352 and 373 are focused on, among the regions that showed a significantly high P value (FIG. 19A).

Further, sequence logos of the target RNA sequences predicted from the ORF687 protein sequence (sequences of the regions that showed a significant P value (Nos. 208, 316, 352, 373)), candidate binding RNA sequences, and sequence logos of the target RNA sequences predicted from the sequence of the ORF687-like protein of the radish variety having a recessive rf, Kosena (Kosena B) are shown in FIG. 18B. Further, the predicted binding base of Kosena B, which is a recessive if, is also shown.

It was revealed that the bases specified by EnkoB and Kosena B are different (UA in the case of Rf, and GC in the case of if), because of the amino acid polymorphism in the 2nd and 3rd PPR motifs. It could be predicted that this difference is directly linked with the functional difference between Rf and rf.

Example 8: Prediction and Analysis of RNA Structure

On the basis of computerized prediction and in vitro RNA binding experiment, there was contemplated a possibility that Rf binds the region of RNAb, especially the regions of Nos. 316, 352 and 373. On the basis of the in vitro analysis, there was also contemplated a possibility that RNAb has a plurality of binding sites. Therefore, the secondary structure of the RNAb sequence was predicted, and attention was paid to the regions.

Figure 20A:
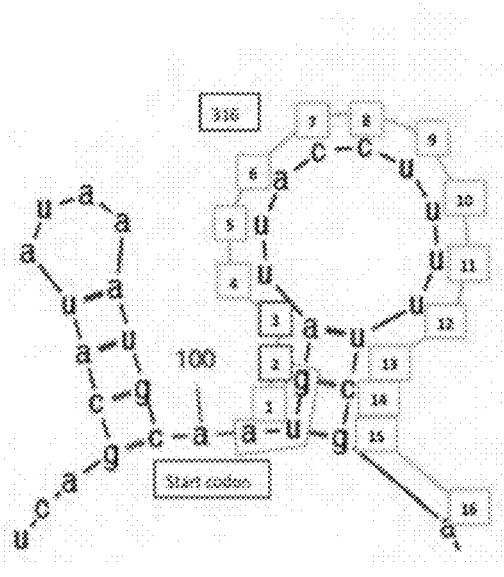
FIGS. 20A-20C show the secondary structure and structural change of the candidate binding RNA region of ORF687-like protein.
Figure 20B:
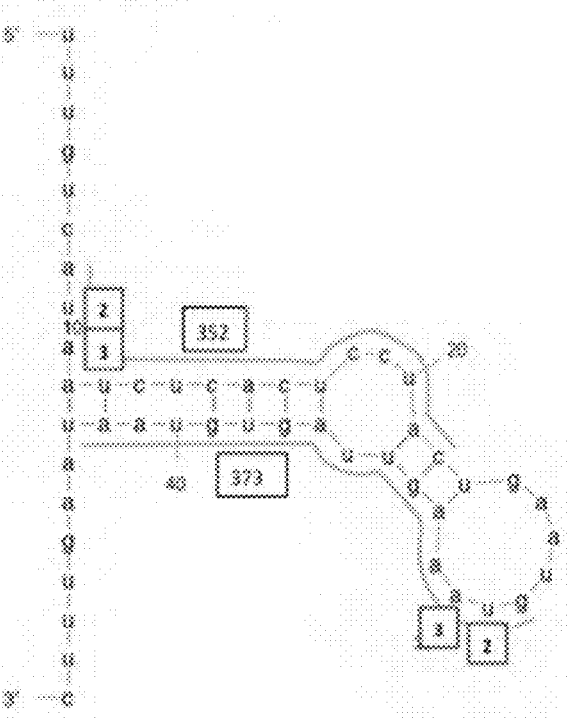
Figure 20C:
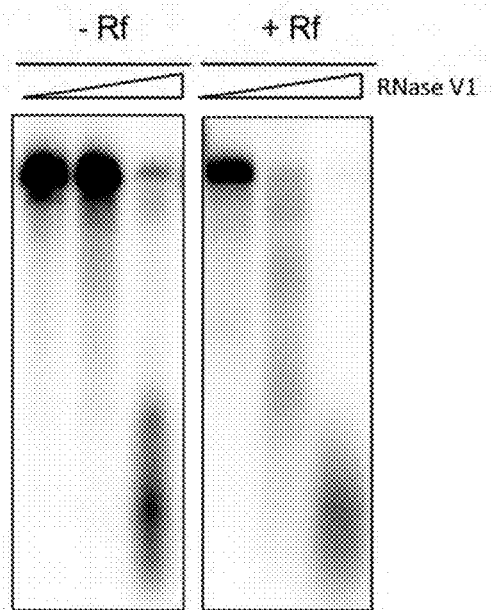

The results are shown in FIGS. 20A-20C. FIGS. 20A-20C show the secondary structure and structural change of the candidate binding RNA regions of ORF687-like protein. FIG. 20A shows the secondary structure of the region including the region of No. 306 and the predicted binding sites for the ORF687-like protein, and shows PPR motifs with boxes together with the corresponding bases. The 2nd and 3rd PPR motifs for which Enko B (Rf) and Kosena B (if) show a remarkable difference are emphasized. FIG. 20B shows the secondary structure of the region including the regions of Nos. 352 and 373 and the predicted binding sites for the ORF687-like protein. FIG. 20C shows results indicating structural change of RNAb induced by Enko B, which were obtained by mixing RNAb and Enko B protein, and then adding a double-strand selective RNase (RNase VD.

As a result, it was revealed that the No. 316 region corresponds to the stem loop structure immediately downstream from the start codon of orf125 (FIG. 20A). Further, the 2nd and 3rd PPR motifs showing polymorphism between Enko B and Kosena B located in the double-strand at the root of the stem loop. In particular, the base corresponding the 3rd PPR motif is A in Enko B, whereas it is C in Kosena B (refer to FIG. 19B). On the basis of these results, there was contemplated a working hypothesis that Enko B binds to the region concerned to promote formation of the stem loop structure, and thereby inhibit translation of orf125.

A double-strand structure is also predicted for the Nos. 352 and 373 regions, and it was contemplated that the Rf protein binds on the both sides (FIG. 20B). However, in such a case, it is expected that the structure will be destroyed by the binding of Rf (formation of single strand is promoted). Further, differences in corresponding base and structure were not contemplated for the 2nd and 3rd PPR motifs, for which Rf and rf show difference, and any specific molecular mechanism could not be predicted.

Therefore, internally-labeled RNA was mixed with the proteins, and RNase V1 was added to the mixture to decompose only the labeled RNA. RNase V1 is an RNase that selectively cleaves only double-strand regions of RNA. As a result, it was demonstrated that the substrate RNA is more quickly decomposed in the presence of the protein, namely, formation of double-stranded RNA is promoted in the presence of Rf (Enko B) (FIG. 20C). That is, it was considered that the translation inhibition based on the formation of double-stranded RNA in orf125 mRNA by Rf is the major cause of the fertility restoration in Ogura-type cytoplasmic male sterility.

Example 9: Determination of Function for Fertility Restoration Capacity of ORF687-Like Gene ORF687-like genes have so far been isolated from various radish varieties, and the functionality thereof as Rf is estimated on the basis of mating experiments. However, the encoded amino acid sequences are very alike, and therefore it is impossible to determine the functionality as Rf from the conservation characteristics of the whole amino acid sequences.

In this example, sequences of the ORF687-like proteins were first analyzed. Specifically, the protein sequences shown in SEQ ID NOS: 576 to 578 and 585 to 591 were used as materials, and the sequences of them as the PPR proteins were analyzed. By using all the sequences as query sequences for CLUSTALW (http://www.genomejp/tools/clustalw/), sequence alignment was obtained. By using the domain analysis software usable on the Web:

Pfam (http://pfam.sanger.ac.uk/),

InterProScan (http://www.ebi.ac.uk/Tools/InterProScan/), and

Prosite (http://www.expasy.org/prosite/), alignment of the ORF687-like proteins was created, and the PPR motif structures of the proteins were analyzed.

The results are shown in FIGS. 21A-21B. All the ORF687-like proteins each consist of 16 PPR motifs (FIGS. 21A-21B).

From the obtained PPR motif models, amino acids 1, 2, and "ii" (−2) according to the amino acid numbers shown in Non-patent document 5 were extracted, and used for determination of the function for the fertility restoration ability of the ORF-like proteins.

Thus, functions of the 9 kinds of Rf-like genes were determined by using the PPR codes. The amino acids responsible for the base specifying capacity (1, 4, and ii) were extracted in the same manner as that used for Enko B mentioned above, converted into PPR codes, and used for determination of the functionality thereof by using the amino acid species as RNA binding windows (FIG. 22). Although Enko B and Kosena B show a homology of 99.4% for the whole sequences, two of RNA binding windows show amino acid polymorphism, and it was considered that they were deeply involved in dominance and recessiveness for the fertility restoration by the ORF687-like genes (Non-patent reference 4). Further, the gene Comet B locating on the same locus as that of Enko B in the variety Comet shows a homology of 98.0% with respect to Enko B, and the RNA binding windows of them are completely the same. The finding that Comet B is a dominant gene obtained by the past mating tests could be verified. Further, Enko A is an overlapping gene locating near Enko B, and it was suggested also from the viewpoint of RNA recognition that it is a recessive gene. These data suggest that, for the dominance and recessiveness for the fertility restoration of the ORF687-like genes, it is important that the amino acids responsible for the base specifying capacity (1, 4, ii) are the same in all the corresponding PPR motifs in the ORF687-like genes, in particular, they have the same amino acids 4 ($A_4$), or the same amino acids "ii". Inter alia, it is considered that it is especially important that they have the same amino acids 4 ($A_4$). From this point of view, it was considered that the genes locating on the same locus as that of Enko B in various pedigrees of radish, of which information concerning fertility is unknown, rrORF690-1, rrORF690-2, PC PPR-A, and PC PPR-BL, have RNA binding windows different from those of Enko B, which is a dominant gene, and these genes are also recessive if.

The results described above suggest that the PPR codes used in the present invention can accelerate the determination of functions of industrially useful PPR proteins, which act as a fertility restoration factor. When a new pedigree is used for the first filial hybrid breeding method using the CMS-Rf system, whether candidate Rf gene sequences have fertility restoration ability can be determined from the sequences thereof by the above technique. The inventors of the present invention determined functions of the ORF687-like genes of 21 kinds of novel radish varieties, and successfully determined whether the fertility restoration ability of the ORF-like gene is dominant or recessive for 19 varieties (data are not shown). This technique can be applied not only to radish of the Ogura-type cytoplasm, but also to various cytoplasms and plant varieties containing a PPR protein as Rf.

REFERENCES CITED IN EXAMPLES

Reference 1: Small, I. D., and Peeters, N. (2000), The PPR motif—a TPR-related motif prevalent in plant organellar proteins, Trends Biochem. Sci., 25, 46-47

Reference 2: Lurin, C., Andres, C., Aubourg, S., Bellaoui, M., Bitton, F., Bruyere, C., Caboche, M., Debast, C., Gualberto, J., Hoffmann, B., et al. (2004), Genome-wide analysis of *Arabidopsis* pentatricopeptide repeat proteins reveals their essential role in organelle biogenesis, Plant Cell, 16, 2089-2103

Reference 3: Okuda, K., Myouga, F., Motohashi, R., Shinozaki, K., and Shikanai, T. (2007), Conserved domain structure of pentatricopeptide repeat proteins involved in chloroplast RNA editing, Proc. Natl. Acad. Sci. USA, 104, 8178-8183

Reference 4: Koizuka N, Imai R, Fujimoto H, Hayakawa T, Kimura Y, et al. (2003), Genetic characterization of a pentatricopeptide repeat protein gene, orf687, that restores fertility in the cytoplasmic male-sterile Kosena radish, Plant J., 34:407-415

Reference 5: Nakamura T, Yagi Y, Kobayashi K. (2012), Mechanistic insight into pentatricopeptide repeat proteins as sequence-specific RNA-binding proteins for organellar RNAs in plants, Plant & Cell Physiology, 53:1171-1179.

40

What is claimed is:

1. A method for modifying or disrupting an RNA having a target sequence, or imparting a novel function to an RNA having a target sequence, in a living body or cell, the method comprising:

determining a nucleic acid sequence coding for an amino acid sequence of a protein, cloning said nucleic acid sequence, and preparing a vector carrying a polynucleotide consisting of the nucleic acid sequence, wherein the protein contains one or more of PPR motifs, each consisting of a polypeptide of 30- to 38-amino acid length represented by the formula 1:

(HelixA)-X-(HelixB)-L                    (Formula 1)

wherein, in formula 1, Helix A is a moiety of 12-amino acid length capable of forming an α-helix structure, and is represented by the formula 2:

$A_1\text{-}A_2\text{-}A_3\text{-}A_4\text{-}A_5\text{-}A_6\text{-}A_7\text{-}A_8\text{-}A_9\text{-}A_{10}\text{-}A_{11}\text{-}A_{12}$    (Formula 2)

wherein, in the formula 2, $A_1$ to $A_{12}$ independently represent an amino acid;

wherein, in the formula 1, X is a moiety of 1- to 9-amino acid length and is optional;

wherein, in the formula 1, Helix B is a moiety of 11- to 13-amino acid length capable of forming an α-helix structure; and wherein, in the formula 1, L is a moiety of 2- to 7-amino acid length represented by the formula 3;

$L_{vii}\text{-}L_{vi}\text{-}L_v\text{-}L_{iv}\text{-}L_{iii}\text{-}L_{ii}\text{-}L_i$    (Formula 3)

wherein, in the formula 3, $L_i$ to $L_{vii}$ independently represent an amino acid, and $L_{iii}$ to $L_{vii}$ are optional, and wherein a combination of three amino acids $A_1$, $A_4$ and $L_{ii}$, or a combination of two amino acids $A_4$ and $L_{ii}$ corresponds to the target sequence;

preparing a cell containing the RNA having the target sequence; and introducing the vector into the cell, whereby the protein binds to the RNA having the target sequence.

2. The method according to claim 1, wherein the combination of the three amino acids $A_1$, $A_4$ and $L_{ii}$ is determined according to any one of the following propositions:

(3-1) when the three amino acids $A_1$, $A_4$, and $L_{ii}$ are valine, asparagine, and aspartic acid, respectively, the PPR motif can selectively bind to U (uracil);

(3-2) when the three amino acids $A_1$, $A_4$, and $L_{ii}$ are valine, threonine, and asparagine, respectively, the PPR motif can selectively bind to A (adenine);

(3-3) when the three amino acids $A_1$, $A_4$, and $L_{ii}$ are valine, asparagine, and asparagine, respectively, the PPR motif can selectively bind to C (cytosine);

(3-4) when the three amino acids $A_1$, $A_4$, and $L_{ii}$ are glutamic acid, glycine, and aspartic acid, respectively, the PPR motif can selectively bind to G (guanine);

(3-5) when the three amino acids $A_1$, $A_4$, and $L_{ii}$ are isoleucine, asparagine, and asparagine, respectively, the PPR motif can selectively bind to C or U;

(3-6) when the three amino acids $A_1$, $A_4$, and $L_{ii}$ are valine, threonine, and aspartic acid, respectively, the PPR motif can selectively bind to G;

(3-7) when the three amino acids $A_1$, $A_4$, and $L_{ii}$ are lysine, threonine, and aspartic acid, respectively, the PPR motif can selectively bind to G;

(3-8) when the three amino acids $A_1$, $A_4$, and $L_{ii}$ are phenylalanine, serine, and asparagine, respectively, the PPR motif can selectively bind to A;

(3-9) when the three amino acids $A_1$, $A_4$, and $L_{ii}$ are valine, asparagine, and serine, respectively, the PPR motif can selectively bind to C;

(3-10) when the three amino acids $A_1$, $A_4$, and $L_{ii}$ are phenylalanine, threonine, and asparagine, respectively, the PPR motif can selectively bind to A;

(3-11) when the three amino acids $A_1$, $A_4$, and $L_{ii}$ are isoleucine, asparagine, and aspartic acid, respectively, the PPR motif can selectively bind to U or A;

(3-12) when the three amino acids $A_1$, $A_4$, and $L_{ii}$ are threonine, threonine, and asparagine, respectively, the PPR motif can selectively bind to A;

(3-13) when the three amino acids $A_1$, $A_4$, and $L_{ii}$ are isoleucine, methionine, and aspartic acid, respectively, the PPR motif can selectively bind to U or C;

(3-14) when the three amino acids $A_1$, $A_4$, and $L_{ii}$ are phenylalanine, proline, and aspartic acid, respectively, the PPR motif can selectively bind to U;

(3-15) when the three amino acids $A_1$, $A_4$, and $L_{ii}$ are tyrosine, proline, and aspartic acid, respectively, the PPR motif can selectively bind to U; and (3-16) when the three amino acids $A_1$, $A_4$, and $L_{ii}$ are leucine, threonine, and aspartic acid, respectively, the PPR motif can selectively bind to G.

3. The method according to claim 1, wherein the combination of the two amino acids $A_4$ and $L_{ii}$ is determined according to any one of the following propositions:

(2-1) when $A_4$ and $L_{ii}$ are asparagine and aspartic acid, respectively, the motif can selectively bind to U;

(2-2) when $A_4$ and $L_{ii}$ are asparagine and asparagine, respectively, the motif can selectively bind to C;

(2-3) when $A_4$ and $L_{ii}$ are threonine and asparagine, respectively, the motif can selectively bind to A;

(2-4) when $A_4$ and $L_{ii}$ are threonine and aspartic acid, respectively, the motif can selectively bind to G;

(2-5) when $A_4$ and $L_{ii}$ are serine and asparagine, respectively, the motif can selectively bind to A;

(2-6) when $A_4$ and $L_{ii}$ are glycine and aspartic acid, respectively, the motif can selectively bind to G;

(2-7) when $A_4$ and $L_{ii}$ are asparagine and serine, respectively, the motif can selectively bind to C;

(2-8) when $A_4$ and $L_{ii}$ are proline and aspartic acid, respectively, the motif can selectively bind to U;

(2-9) when $A_4$ and $L_{ii}$ are glycine and asparagine, respectively, the motif can selectively bind to A;

(2-10) when $A_4$ and $L_{ii}$ are methionine and aspartic acid, respectively, the motif can selectively bind to U;

(2-11) when $A_4$ and $L_{ii}$ are leucine and aspartic acid, respectively, the motif can selectively bind to C; and (2-12) when $A_4$ and $L_{ii}$ are valine and threonine, respectively, the motif can selectively bind to U.

4. A method for modifying or disrupting an RNA having a target sequence, or imparting a novel function to an RNA having a target sequence, in a living body or cell, the method comprising:

preparing a vector carrying a polynucleotide consisting of a nucleic acid sequence coding for an amino acid sequence of a protein which contains one or more of PPR motifs, each consisting of a polypeptide of 30- to 38-amino acid length represented by the formula 1:

$$(\text{HelixA})\text{-X-}(\text{HelixB})\text{-L} \qquad (\text{Formula 1})$$

wherein, in formula 1, Helix A is a moiety of 12-amino acid length capable of forming an $\alpha$-helix structure, and is represented by the formula 2:

$$A_1\text{-}A_2\text{-}A_3\text{-}A_4\text{-}A_5\text{-}A_6\text{-}A_7\text{-}A_8\text{-}A_9\text{-}A_{10}\text{-}A_{11}\text{-}A_{12} \qquad (\text{Formula 2})$$

wherein, in the formula 2, $A_1$ to $A_{12}$ independently represent an amino acid;

wherein, in the formula 1, X is a moiety of 1- to 9-amino acid length and is optional;

wherein, in the formula 1, Helix B is a moiety of 11- to 13-amino acid length capable of forming an $\alpha$-helix structure; and wherein, in the formula 1, L is a moiety of 2- to 7-amino acid length represented by the formula 3;

$$L_{vii}\text{-}L_{vi}\text{-}L_{v}\text{-}L_{iv}\text{-}L_{iii}\text{-}L_{ii}\text{-}L_{i} \qquad (\text{Formula 3})$$

wherein, in the formula 3, $L_i$ to $L_{vii}$ independently represent an amino acid, and $L_{iii}$ to $L_{vii}$ are optional, and wherein a combination of three amino acids $A_1$, $A_4$ and $L_{ii}$, or a combination of two amino acids $A_4$ and $L_{ii}$ corresponds to the target sequence;

preparing a cell containing the RNA having the target sequence; and introducing the protein into the cell, whereby the protein binds to the RNA having the target sequence.

5. The method according to claim 4, wherein the combination of the three amino acids $A_1$, $A_4$ and $L_{ii}$ is determined according to any one of the following propositions:

(3-1) when the three amino acids $A_1$, $A_4$, and $L_{ii}$ are valine, asparagine, and aspartic acid, respectively, the PPR motif can selectively bind to U (uracil);

(3-2) when the three amino acids $A_1$, $A_4$, and $L_{ii}$ are valine, threonine, and asparagine, respectively, the PPR motif can selectively bind to A (adenine);

(3-3) when the three amino acids $A_1$, $A_4$, and $L_{ii}$ are valine, asparagine, and asparagine, respectively, the PPR motif can selectively bind to C (cytosine);

(3-4) when the three amino acids $A_1$, $A_4$, and $L_{ii}$ are glutamic acid, glycine, and aspartic acid, respectively, the PPR motif can selectively bind to G (guanine);

(3-5) when the three amino acids $A_1$, $A_4$, and $L_{ii}$ are isoleucine, asparagine, and asparagine, respectively, the PPR motif can selectively bind to C or U;

(3-6) when the three amino acids $A_1$, $A_4$, and $L_{ii}$ are valine, threonine, and aspartic acid, respectively, the PPR motif can selectively bind to G;

(3-7) when the three amino acids $A_1$, $A_4$, and $L_{ii}$ are lysine, threonine, and aspartic acid, respectively, the PPR motif can selectively bind to G;

(3-8) when the three amino acids $A_1$, $A_4$, and $L_{ii}$ are phenylalanine, serine, and asparagine, respectively, the PPR motif can selectively bind to A;

(3-9) when the three amino acids $A_1$, $A_4$, and $L_{ii}$ are valine, asparagine, and serine, respectively, the PPR motif can selectively bind to C;

(3-10) when the three amino acids $A_1$, $A_4$, and $L_{ii}$ are phenylalanine, threonine, and asparagine, respectively, the PPR motif can selectively bind to A;

(3-11) when the three amino acids $A_1$, $A_4$, and $L_{ii}$ are isoleucine, asparagine, and aspartic acid, respectively, the PPR motif can selectively bind to U or A;

(3-12) when the three amino acids $A_1$, $A_4$, and $L_{ii}$ are threonine, threonine, and asparagine, respectively, the PPR motif can selectively bind to A;

(3-13) when the three amino acids $A_1$, $A_4$, and $L_{ii}$ are isoleucine, methionine, and aspartic acid, respectively, the PPR motif can selectively bind to U or C;

(3-14) when the three amino acids $A_1$, $A_4$, and $L_{ii}$ are phenylalanine, proline, and aspartic acid, respectively, the PPR motif can selectively bind to U;

(3-15) when the three amino acids $A_1$, $A_4$, and $L_{ii}$ are tyrosine, proline, and aspartic acid, respectively, the PPR motif can selectively bind to U; and (3-16) when the three amino acids $A_1$, $A_4$, and $L_{ii}$ are leucine, threonine, and aspartic acid, respectively, the PPR motif can selectively bind to G.

6. The method according to claim 4, wherein the combination of the two amino acids $A_4$ and $L_{ii}$ is determined according to any one of the following propositions:

(2-1) when $A_4$ and $L_{ii}$ are asparagine and aspartic acid, respectively, the motif can selectively bind to U;

(2-2) when $A_4$ and $L_{ii}$ are asparagine and asparagine, respectively, the motif can selectively bind to C;

(2-3) when $A_4$ and $L_{ii}$ are threonine and asparagine, respectively, the motif can selectively bind to A;

(2-4) when $A_4$ and $L_{ii}$ are threonine and aspartic acid, respectively, the motif can selectively bind to G;

(2-5) when $A_4$ and $L_{ii}$ are serine and asparagine, respectively, the motif can selectively bind to A;

(2-6) when $A_4$ and $L_{ii}$ are glycine and aspartic acid, respectively, the motif can selectively bind to G;

(2-7) when $A_4$ and $L_{ii}$ are asparagine and serine, respectively, the motif can selectively bind to C;

(2-8) when $A_4$ and $L_{ii}$ are proline and aspartic acid, respectively, the motif can selectively bind to U;

(2-9) when $A_4$ and $L_{ii}$ are glycine and asparagine, respectively, the motif can selectively bind to A;

(2-10) when $A_4$ and $L_{ii}$ are methionine and aspartic acid, respectively, the motif can selectively bind to U;

(2-11) when $A_4$ and $L_{ii}$ are leucine and aspartic acid, respectively, the motif can selectively bind to C; and (2-12) when $A_4$ and $L_{ii}$ are valine and threonine, respectively, the motif can selectively bind to U.

7. A method for preparing a polynucleotide consisting of a nucleic acid sequence coding for an amino acid sequence of a complex comprising a region consisting of a PPR protein and a functional region, the PPR protein being able to bind to an RNA having a target sequence, the method comprising:

determining a nucleic acid sequence coding for an amino acid sequence of the complex, and cloning said nucleic acid sequence to obtain the polynucleotide consisting of said nucleic acid sequence, wherein the PPR protein contains one or more of PPR motifs, each consisting of a polypeptide of 30- to 38-amino acid length represented by the formula 1:

(HelixA)-X-(HelixB)-L          (Formula 1)

wherein, in formula 1, Helix A is a moiety of 12-amino acid length capable of forming an α-helix structure, and is represented by the formula 2:

$A_1$-$A_2$-$A_3$-$A_4$-$A_5$-$A_6$-$A_7$-$A_8$-$A_9$-$A_{10}$-$A_{11}$-$A_{12}$          (Formula 2)

wherein, in the formula 2, $A_1$ to $A_{12}$ independently represent an amino acid;

wherein, in the formula 1, X is a moiety of 1- to 9-amino acid length and is optional;

wherein, in the formula 1, Helix B is a moiety of 11- to 13-amino acid length capable of forming an α-helix structure; and wherein, in the formula 1, L is a moiety of 2- to 7-amino acid length represented by the formula 3;

$L_{vii}$-$L_{vi}$-$L_v$-$L_{iv}$-$L_{iii}$-$L_{ii}$-$L_i$          (Formula 3)

wherein, in the formula 3, L to $L_{vii}$ independently represent an amino acid, and $L_{iii}$ to $L_{vii}$ are optional, and wherein a combination of three amino acids $A_1$, $A_4$ and $L_{ii}$, or a combination of two amino acids $A_4$ and $L_{ii}$ corresponds to the target sequence.

8. The method according to claim 7, wherein the combination of the three amino acids $A_1$, $A_4$ and $L_{ii}$ is determined according to any one of the following propositions:

(3-1) when the three amino acids $A_1$, $A_4$, and $L_{ii}$ are valine, asparagine, and aspartic acid, respectively, the PPR motif can selectively bind to U (uracil);

(3-2) when the three amino acids $A_1$, $A_4$, and $L_{ii}$ are valine, threonine, and asparagine, respectively, the PPR motif can selectively bind to A (adenine);

(3-3) when the three amino acids $A_1$, $A_4$, and $L_{ii}$ are valine, asparagine, and asparagine, respectively, the PPR motif can selectively bind to C (cytosine);

(3-4) when the three amino acids $A_1$, $A_4$, and $L_{ii}$ are glutamic acid, glycine, and aspartic acid, respectively, the PPR motif can selectively bind to G (guanine);

(3-5) when the three amino acids $A_1$, $A_4$, and $L_{ii}$ are isoleucine, asparagine, and asparagine, respectively, the PPR motif can selectively bind to C or U;

(3-6) when the three amino acids $A_1$, $A_4$, and $L_{ii}$ are valine, threonine, and aspartic acid, respectively, the PPR motif can selectively bind to G;

(3-7) when the three amino acids $A_1$, $A_4$, and $L_{ii}$ are lysine, threonine, and aspartic acid, respectively, the PPR motif can selectively bind to G;

(3-8) when the three amino acids $A_1$, $A_4$, and $L_{ii}$ are phenylalanine, serine, and asparagine, respectively, the PPR motif can selectively bind to A;

(3-9) when the three amino acids $A_1$, $A_4$, and $L_{ii}$ are valine, asparagine, and serine, respectively, the PPR motif can selectively bind to C;

(3-10) when the three amino acids $A_1$, $A_4$, and $L_{ii}$ are phenylalanine, threonine, and asparagine, respectively, the PPR motif can selectively bind to A;

(3-11) when the three amino acids $A_1$, $A_4$, and $L_{ii}$ are isoleucine, asparagine, and aspartic acid, respectively, the PPR motif can selectively bind to U or A;

(3-12) when the three amino acids $A_1$, $A_4$, and $L_{ii}$ are threonine, threonine, and asparagine, respectively, the PPR motif can selectively bind to A;

(3-13) when the three amino acids $A_1$, $A_4$, and $L_{ii}$ are isoleucine, methionine, and aspartic acid, respectively, the PPR motif can selectively bind to U or C;

(3-14) when the three amino acids $A_1$, $A_4$, and $L_{ii}$ are phenylalanine, proline, and aspartic acid, respectively, the PPR motif can selectively bind to U;

(3-15) when the three amino acids $A_1$, $A_4$, and $L_{ii}$ are tyrosine, proline, and aspartic acid, respectively, the PPR motif can selectively bind to U; and (3-16) when the three amino acids $A_1$, $A_4$, and $L_{ii}$ are leucine, threonine, and aspartic acid, respectively, the PPR motif can selectively bind to G.

9. The method according to claim 7, wherein the combination of the two amino acids $A_4$ and $L_{ii}$ is determined according to any one of the following propositions:

(2-1) when $A_4$ and $L_{ii}$ are asparagine and aspartic acid, respectively, the motif can selectively bind to U;

(2-2) when $A_4$ and $L_{ii}$ are asparagine and asparagine, respectively, the motif can selectively bind to C;

(2-3) when $A_4$ and $L_{ii}$ are threonine and asparagine, respectively, the motif can selectively bind to A;

(2-4) when $A_4$ and $L_{ii}$ are threonine and aspartic acid, respectively, the motif can selectively bind to G;

(2-5) when $A_4$ and $L_{ii}$ are serine and asparagine, respectively, the motif can selectively bind to A;

(2-6) when $A_4$ and $L_{ii}$ are glycine and aspartic acid, respectively, the motif can selectively bind to G;

(2-7) when $A_4$ and $L_{ii}$ are asparagine and serine, respectively, the motif can selectively bind to C;

(2-8) when $A_4$ and $L_{ii}$ are proline and aspartic acid, respectively, the motif can selectively bind to U;

(2-9) when $A_4$ and $L_{ii}$ are glycine and asparagine, respectively, the motif can selectively bind to A;

(2-10) when $A_4$ and $L_{ii}$ are methionine and aspartic acid, respectively, the motif can selectively bind to U;

(2-11) when $A_4$ and $L_{ii}$ are leucine and aspartic acid, respectively, the motif can selectively bind to C; and (2-12) when $A_4$ and $L_{ii}$ are valine and threonine, respectively, the motif can selectively bind to U.

\* \* \* \* \*

SEQUENCE LISTING

```
Sequence total quantity: 591
SEQ ID NO: 1             moltype = AA  length = 555
FEATURE                  Location/Qualifiers
source                   1..555
                         mol_type = protein
                         organism = Arabidopsis thaliana
SEQUENCE: 1
MLRHAIETNV QIFTKFLVIS ASAVGIGYAR KLFDQRPQRD DSFLSNSMIK AYLETRQYPD  60
SFALYRDLRK ETCFAPDNFT FTTLTKSCSL SMCVYQGLQL HSQIWRFGFC ADMYVSTGVV  120
DMYAKFGKMG CARNAFDEMP HRSEVSWTAL ISGYIRCGEL DLASKLFDQM PHVKDVVIYN  180
AMMDGFVKSG DMTSARRLFD EMTHKTVITW TTMIHGYCNI KDIDAARKLF DAMPERNLVS  240
WNTMIGGYCQ NKQPQEGIRL FQEMQATTSL DPDDVTILSV LPAISDTGAL SLGEWCHCFV  300
QRKKLDKKVK VCTAILDMYS KCGEIEKAKR IFDEMPEKQV ASWNAMIHGY ALNGNARAAL  360
DLFVTMMIEE KPDEITMLAV ITACNHGGLV EEGRKWFHVM REMGLNAKIE HYGCMVDLLG  420
RAGSLKEAED LITNMPFEPN GIILSSFLSA CGQYKDIERA ERILKKAVEL EPQNDGNYVL  480
LRNLYAADKR WDDFGMVKNV MRKNQAKKEV GCSLIEINYI VSEFISGDTT HPHRRSIHLV  540
LGDLLMHMNE EKYNW                                                   555

SEQ ID NO: 2             moltype = AA  length = 500
FEATURE                  Location/Qualifiers
source                   1..500
                         mol_type = protein
                         organism = Arabidopsis thaliana
SEQUENCE: 2
MGLLPVVGIT SPALITHKNH ANPKIQRHNQ STSETTVSWT SRINLLTRNG RLAEAAKEFS  60
DMTLAGVEPN HITFIALLSG CGDFTSGSEA LGDLLHGYAC KLGLDRNHVM VGTAIIGMYS  120
KRGRFKKARL VFDYMEDKNS VTWNTMIDGY MRSGQVDNAA KMFDKMPERD LISWTAMING  180
FVKKGYQEEA LLWFREMQIS GVKPDYVAII AALNACTNLG ALSFGLWVHR YVLSQDFKNN  240
VRVSNSLIDL YCRCGCVEFA RQVFYNMEKR TVVSWNSVIV GFAANGNAHE SLVYFRKMQE  300
KGFKPDAVTF TGALTACSHV GLVEEGLRYF QIMKCDYRIS PRIEHYGCLV DLYSRAGRLE  360
DALKLVQSMP MKPNEVVIGS LLAACSNHGN NIVLAERLMK HLTDLNVKSH SNYVILSNMY  420
AADGKWEGAS KMRRKMKGLG LKKQPGFSSI EIDDCMHVFM AGDNAHVETT YIREVLELIS  480
SDLRLQGCVV ETLAGDLLNA                                              500

SEQ ID NO: 3             moltype = AA  length = 830
FEATURE                  Location/Qualifiers
source                   1..830
                         mol_type = protein
                         organism = Arabidopsis thaliana
SEQUENCE: 3
MASLPFNTIP NKVPFSVSSK PSSKHHDEQA HSPSSTSYFH RVSSLCKNGE IKEALSLVTE  60
MDFRNLRIGP EIYGEILQGC VYERDLSTGK QIHARILKNG DFYARNEYIE TKLVIFYAKC  120
DALEIAEVLF SKLRVRNVFS WAAIIGVKCR IGLCEGALMG FVEMLENEIF PDNFVVPNVC  180
KACGALKWSR FGRGVHGYVV KSGLEDCVFV ASSLADMYGK CGVLDDASKV FDEIPDRNAV  240
AWNALMVGYV QNGKNEEAIR LFSDMRKQGV EPTRVTVSTC LSASANMGGV EEGKQSHAIA  300
IVNGMELDNI LGTSLLNFYC KVGLIEYAEM VFDRMFEKDV VTWNLIISGY VQQGLVEDAI  360
YMCQLMRLEK LKYDCVTLAT LMSAAARTEN LKLGKEVQCY CIRHSFESDI VLASTVMDMY  420
AKCGSIVDAK KVFDSTVEKD LILWNTLLAA YAESGLSGEA LRLFYGMQLE GVPPNVITWN  480
LIILSLLRNG QVDEAKDMFL QMQSSGIIPN LISWTTMMNG MVQNGCSEEA ILFLRKMQES  540
GLRPNAFSIT VALSACAHLA SLHIGRTIHG YIIRNLQHSS LVSIETSLVD MYAKCGDINK  600
AEKVFGSKLY SELPLSNAMI SAYALYGNLK EAIALYRSLE GVGLKPDNIT ITNVLSACNH  660
AGDINQAIEI FTDIVSKRSM KPCLEHYGLM VDLLASAGET EKALRLIEEM PFKPDARMIQ  720
SLVASCNKQR KTELVDYLSR KLLESEPENS GNYVTISNAY AVEGSWDEVV KMREMMKAKG  780
LKKKPGCSWI QITGEEGVHV FVANDKTHTR INEIQMMLAL LLYDMGTGSK             830

SEQ ID NO: 4             moltype = AA  length = 809
FEATURE                  Location/Qualifiers
source                   1..809
                         mol_type = protein
                         organism = Arabidopsis thaliana
SEQUENCE: 4
MSSQLVQFST VPQIPNPPSR HRHFLSERNY IPANVYEHPA ALLLERCSSL KELRQILPLV  60
FKNGLYQEHF FQTKLVSLFC RYGSVDEARR VFEPIDSKLN VLYHTMLKGF AKVSDLDKAL  120
QFFVRMRYDD VEPVVYNFTY LLKVCGDEAE LRVGKEIHGL LVKSGFSLDL FAMTGLENMY  180
AKCRQVNEAR KVFDRMPERD LVSWNTIVAG YSQNGMARMA LEMVKSMCEE NLKPSFITIV  240
SVLPAVSALR LISVGKEIHG YAMRSGFDSL VNISTALVDM YAKCGSLETA RQLFDGMLER  300
```

-continued

```
NVVSWNSMID AYVQNENPKE AMLIFQKMLD EGVKPTDVSV MGALHACADL GDLERGRFIH   360
KLSVELGLDR NVSVVNSLIS MYCKCKEVDT AASMFGKLQS RTLVSWNAMI LGFAQNGRPI   420
DALNYFSQMR SRTVKPDTFT YVSVITAIAE LSITHHAKWI HGVVMRSCLD KNVFVTTALV   480
DMYAKCGAIM IARLIFDMMS ERHVTTWNAM IDGYGTHGFG KAALELFEEM QKGTIKPNGV   540
TFLSVISACS HSGLVEAGLK CFYMMKENYS IELSMDHYGA MVDLLGRAGR LNEAWDFIMQ   600
MPVKPAVNVY GAMLGACQIH KNVNFAEKAA ERLFELNPDD GGYHVLLANI YRAASMWEKV   660
GQVRVSMLRQ GLRKTPGCSM VEIKNEVHSF FSGSTAHPDS KKIYAFLEKL ICHIKEAGYV   720
PDTNLVLGVE NDVKEQLLST HSEKLAISFG LLNTTAGTTI HVRKNLRVCA DCHNATKYIS   780
LVTGREIVVR DMQRFHHFKN GACSCGDYW                                    809

SEQ ID NO: 5                moltype = AA   length = 638
FEATURE                     Location/Qualifiers
source                      1..638
                            mol_type = protein
                            organism = Arabidopsis thaliana
SEQUENCE: 5
MVVRSIIVSP PTTITYYHPM SIGLLVHPLS PHIPPASSPS ASTAGNHHQR IFSLAETCSD   60
MSQLKQLHAF TLRTTYPEEP ATLFLYGKIL QLSSSFSDVN YAFRVFDSIE NHSSFMWNTL   120
IRACAHDVSR KEEAFMLYRK MLERGESSPD KHTFPFVLKA CAYIFGFSEG KQVHCQIVKH   180
GFGGGDVYVNN GLIHLYGSCG CLDLARKVFD EMPERSLVSW NSMIDALVRF GEYDSALQLF   240
REMQRSFEPD GYTMQSVLSA CAGLGSLSLG TWAHAFLLRK CDVDVAMDVL VKNSLIEMYC   300
KCGSLRMAEQ VFQGMQKRDL ASWNAMILGF ATHGRAEEAM NFFDRMVDKR ENVRPNSVTF   360
VGLLIACNHR GFVNKGRQYF DMMVRDYCIE PALEHYGCIV DLIARAGYIT EAIDMVMSMP   420
MKPDAVIWRS LLDACCKKGA SVELSEEIAR NIIGTKEDNE SSNGNCSGAY VLLSRVYASA   480
SRWNDVGIVR KLMSEHGIRK EPGCSSIEIN GISHEFFAGD TSHPQTKQIY QQLKVIDDRL   540
RSIGYLPDRS QAPLVDATND GSKEYSLRLH SERLAIAFGL INLPPQTPIR IFKNLRVCND   600
CHEVTKLISK VFNTEIIVRD RVRFHHFKDG SCSCLDYW                          638

SEQ ID NO: 6                moltype = AA   length = 613
FEATURE                     Location/Qualifiers
source                      1..613
                            mol_type = protein
                            organism = Arabidopsis thaliana
SEQUENCE: 6
MLVFKSTMEC SISSTIHVLG SCKTSDDVNQ IHGRLIKTGI IKNSNLTTRI VLAFASSRRP   60
YLADFARCVF HEYHVCSFSF GEVEDPFLWN AVIKSHSHGK DPRQALLLLC LMLENGVSVD   120
KFSLSLVLKA CSRLGFVKGG MQIHGFLKKT GLWSDLFLQN CLIGLYLKCG CLGLSRQMFD   180
RMPKRDSVSY NSMIDGYVKC GLIVSARELF DLMPMEMKNL ISWNSMISGY AQTSDGVDIA   240
SKLFADMPEK DLISWNSMID GYVKHGRIED AKGLFDVMPR RDVVTWATMI DGYAKLGFVH   300
HAKTLFDQMP HRDVVAYNSM MAGYVQNKYH MEALEIFSDM EKESHLLPDD TTLVIVLPAI   360
AQLGRLSKAI DMHLYIVEKQ FYLGGKLGVA LIDMYSKCGS IQHAMLVFEG IENKSIDHWN   420
AMIGGLAIHG LGESAFDMLL QIERLSLKPD DITFVGVLNA CSHSGLVKEG LLCFELMRRK   480
HKIEPRLQHY GCMVDILSRS GSIELAKNLI EEMPVEPNDV IWRTFLTACS HHKEFETGEL   540
VAKHLILQAG YNPSSYVLLS NMYASFGMWK DVRRVRTMMK ERKIEKIPGC SWIELDGRVH   600
EFFVDSIEVS STL                                                    613

SEQ ID NO: 7                moltype = AA   length = 684
FEATURE                     Location/Qualifiers
source                      1..684
                            mol_type = protein
                            organism = Arabidopsis thaliana
SEQUENCE: 7
MSLLSADALG LLLKNAISAS SMRLGRVVHA RIVKTLDSPP PPFLANYLIN MYSKLDHPES   60
ARLVLRLTPA RNVVSWTSLI SGLAQNGHFS TALVEFFEMR REGVVPNDFT FPCAFKAVAS   120
LRLPVTGKQI HALAVKCGRI LDVFVGCSAF DMYCKTRLRD DARKLFDEIP ERNLETWNAF   180
ISNSVTDGRP REAIEAFIEF RRIDGHPNSI TFCAFLNACS DWLHLNLGMQ LHGLVLRSGF   240
DTDVSVCNGL IDFYGKCKQI RSSEIIFTEM GTKNAVSWCS LVAAYVQNHE DEKASVLYLR   300
SRKDIVETSD FMISSVLSAC AGMAGLELGR SIHAHAVKAC VERTIFVGSA LVDMYGKCGC   360
IEDSEQAFDE MPEKNLVTRN SLIGGYAHQG QVDMALALFE EMAPRGCGPT PNYMTFVSLL   420
SACSRAGAVE NGMKIFDSMR STYGIEPGAE HYSCIVDMLG RAGMVERAYE FIKKMPIQPT   480
ISVWGALQNA CRMHGKPQLG LLAAENLFKL DPKDSGNHVL LSNTFAAAGR WAEANTVREE   540
LKGVGIKKGA GYSWITVKNQ VHAFQAKDRS HILNKEIQTT LAKLRNEMEA AGYKPDLKLS   600
LYDLEEEEKA AEVSHHSEKL ALAFGLLSLP LSVPIRITKN LRICGDCHSF FKFVSGSVKR   660
EIIVRDNNRF HRFKDGICSC KDYW                                         684

SEQ ID NO: 8                moltype = AA   length = 646
FEATURE                     Location/Qualifiers
source                      1..646
                            mol_type = protein
                            organism = Arabidopsis thaliana
SEQUENCE: 8
MNPTQTLFSP GGNSPASSPA SHPSSLFPQI NNCRTIRDLS QIHAVFIKSG QMRDTLAAAE   60
ILRFCATSDL HHRDLLDYAHK IFNQMPQRNC FSWNTIIRGF SESDEDKALI AITLFYEMMS   120
DEFVEPNRFT FPSVLKACAK TGKIQEGKQI HGLALKYGFG GDEFVMSNLV RMYVMCGFMK   180
DARVLFYKNI IEKDMVVMTD RRKRDGEIVL WNVMIDGYMR LGDCKAARML FDKMRQRSVV   240
SWNTMISGYS LNGFFKDAVE VFREMKKGDI RPNYVTLVSV LPAISRLGSL ELGEWLHLYA   300
EDSGIRDDV LGSALIDMYS KCGIIEKAIH VFERLPRENV ITWSAMINGF AIHGQAGDAI   360
DCFCKMRQAG VRPSDVAYIN LLTACSHGGL VEEGRRYFSQ MVSVDGLEPR IEHYGCMVDL   420
LGRSGLLDEA EEFILNMPIK PDDVIWKALL GACRMQGNVE MGKRVANILM DMVPHDSGAY   480
```

```
VALSNMYASQ GNWSEVSEMR LRMKEKDIRK DPGCSLIDID GVLHEFVVED DSHPKAKEIN    540
SMLVEISDKL RLAGYRPITT QVLLNLEEED KENVLHYHSE KIATAFGLIS TSPGKPIRIV    600
KNLRICEDCH SSIKLISKVY KRKITVRDRK RFHHFQDGSC SCMDYW                   646

SEQ ID NO: 9              moltype = AA  length = 588
FEATURE                  Location/Qualifiers
source                   1..588
                         mol_type = protein
                         organism = Arabidopsis thaliana
SEQUENCE: 9
MALNSSAFFV PCHNYNQICD LLLSSARTRS TIKGLQLHGY VVKSGLSLIP LVANNLINFY     60
SKSQLPFDSR RAFEDSPQKS STTWSSIISC FAQNELPWMS LEFLKKMMAG NLRPDDHVLP    120
SATKSCAILS RCDIGRSVHC LSMKTGYDAD VFVGSSLVDM YAKCGEIVYA RKMFDEMPQR    180
NVVTWSGMMY GYAQMGENEE ALWLFKEALF ENLAVNDYSF SSVISVCANS TLLELGRQIH    240
GLSIKSSFDS SSFVGSSLVS LYSKCGVPEG AYQVFNEVPV KNLGIWNAML KAYAQHSHTQ    300
KVIELFKRMK LSGMKPNFIT FLNVLNACSH AGLVDEGRYY FDQMKESRIE PTDKHYASLV    360
DMLGRAGRLQ EALEVITNMP IDPTESVWGA LLTSCTVHKN TELAAFAADK VFELGPVSSG    420
MHISLSNAYA ADGRFEDAAK ARKLLRDRGE KKETGLSWVE ERNKVHTFAA GERRHEKSKE    480
IYEKLAELGE EMEKAGYIAD TSYVLREVDG DEKNQTIRYH SERLAIAFGL ITFPADRPIR    540
VMKNLRVCGD CHNAIKFMSV CTRRVIIVRD NNRFHRFEDG KCSCNDYW                 588

SEQ ID NO: 10             moltype = AA  length = 659
FEATURE                  Location/Qualifiers
source                   1..659
                         mol_type = protein
                         organism = Arabidopsis thaliana
SEQUENCE: 10
MKVRSKKALF CSVSRLLHTE RHTERQNLTT LFNRYVDKTD VFSWNSVIAD LARSGDSAEA     60
LLAFSSMRKL SLYPTRSSFP CAIKACSSLF DIFSGKQTHQ QAFVFGYQSD IFVSSALIVM    120
YSTCGKLEDA RKVFDEIPKR NIVSWTSMIR GYDLNGNALD AVSLFKDLLV DENDDDDAMF    180
LDSMGLVSVI SACSRVPAKG LTESIHSFVI KRGFDRGVSV GNTLLDAYAK GGEGGVAVAR    240
KIFDQIVDKD RVSYNSIMSV YAQGSMSNEA FEVFRRLVKN KVVTFNAITL STVLLAVSHS    300
GALRIGKCIH DQVIRMGLED DVIVGTSIID MYCKCGRVET ARKAFDRMKN KNVRSWTAMI    360
AGYGMHGHAA KALELFPAMI DSGVRPNYIT FVSVLAACSH AGLHVEGWRW FNAMKGRFGV    420
EPGLEHYGCM VDLLGRAGFL QKAYDLIQRM KMKPDSIIWS SLLAACRIHK NVELAEISVA    480
RLFELDSSNC GYYMLLSHIY ADAGRWKDVE RVRMIMKNRG LVKPPGFSLL ELNGEVHVFL    540
IGDEEHPQRE KIYEFLAELN RKLLEAGYVS NTSSVCHDVD EEEKEMTLRV HSEKLAIAFG    600
IMNTVPGSTV NVVKNLRVCS DCHNVIKLIS KIVDREFVVR DAKRFHHFKD GGCSCGDYW    659

SEQ ID NO: 11             moltype = AA  length = 685
FEATURE                  Location/Qualifiers
source                   1..685
                         mol_type = protein
                         organism = Arabidopsis thaliana
SEQUENCE: 11
MIKLIRFFRS RRCWVISLQA RCFSAPSRTH FDFSGESSDT ERALVSALGS CASSNDVTCG     60
RQIHCRVLKS GLDSNGYICN SVLNMYAKCR LLADAESVFR DHAKLDSASF NIMVDGYVRS    120
RRLWDALKLF DVMPERSCVS YTTLIKGYAQ NNQWSEAMEL FREMRNLGIM LNEVTLATVI    180
SACSHLGGIW DCRMLQSLAI KLKLEGRVFV STNLLHMYCL CLCLKDARKL FDEMPERNLV    240
TWNVMLNGYS KAGLIEQAEE LFDQITEKDI VSWGTMIDGC LRKNQLDEAL VYYTEMLRCG    300
MKPSEVMMVD LLSASARSVG SSKGLQLHGT IVKRGFDCYD FLQATIIHFY AVSNDIKLAL    360
QQFEASVKDH IASRNALIAG FVKNGMVEQA REVFDQTHDK DIFSWNAMIS GYAQSLSPQL    420
ALHLFREMIS SSQVKPDAIT MVSVFSAISS LGSLEEGKRA HDYLNFSTIP PNDNLTAAII    480
DMYAKCGSIE TALNIFHQTK NISSSTISPW NAIICGSATH GHAKLALDLY SDLQSLPIKP    540
NSITFVGVLS ACCHAGLVEL GKTYFESMKS DHGIEPDIKH YGCMVDLLGK AGRLEEAKEM    600
IKKMPVKADV MIWGMLLSAS RTHGNVEIAE LAATELAAID PSHGGCKVML SNVYADAGRW    660
EDVALVREEM RTRDVEWSRA FSGVV                                         685

SEQ ID NO: 12             moltype = AA  length = 565
FEATURE                  Location/Qualifiers
source                   1..565
                         mol_type = protein
                         organism = Arabidopsis thaliana
SEQUENCE: 12
MMKKHYKPIL SQLENCRSLV ELNQLHGLMI KSSVIRNVIP LSRLIDFCTT CPETMNLSYA     60
RSVFESIDCP SVYIWNSMIR GYSNSPNPDK ALIFYQEMLR KGYSPDYFTF PYVLKACSGL    120
RDIQFGSCVH GFVVKTGFEV NMYVSTCLLH MYMCCGEVNY GLRVFEDIPQ WNVVAWGSLI    180
SGFVNNNRFS DAIEAFREMQ SNGVKANETI MVDLLVACGR CKDIVTGKWF HGFLQGLGFD    240
PYFQSKVGFN VILATSLIDM YAKCGDLRTA RYLFDGMPER TLVSWNSIIT GYSQNGDAEE    300
ALCMFLDMLD LGIAPDKVTF LSVIRASMIQ GCSQLGQSIH AYVSKTGFVK DAAIVCALVN    360
MYAKTGDAES AKKAFEDLEK KDTIAWTVVI IGLASHGHGN EALSIFQRMQ EKGNATPDGI    420
TYLGVLYACS HIGLVEEGQR YFAEMRDLHG LEPTVEHYGC MVDILSRAGR FEEAERLVKT    480
MPVKPNVNIW GALLNGCDIH ENLELTDRIR SMVAEPEELG SGIYVLLSNI YAKAGRWADV    540
KLIRESMKSK RVDKVLGHSS VETMF                                         565

SEQ ID NO: 13             moltype = AA  length = 472
FEATURE                  Location/Qualifiers
source                   1..472
                         mol_type = protein
```

```
                           organism = Arabidopsis thaliana
SEQUENCE: 13
MSSVFPGPRF LSLLQQNSKT LIQAKQIHAQ LVINGCHDNS LFGKLIGHYC SKPSTESSSK    60
LAHLLVFPRF GHPDKFLFNT LLKCSKPEDS IRIFANYASK SSLLYLNERT FVFVLGACAR   120
SASSSALRVG RIVHGMVKKL GFLYESELIG TTLLHFYAKN GDLRYARKVF DEMPERTSVT   180
WNAMIGGYCS HKDKGNHNAR KAMVLFRRFS CCGSGVRPTD TTMVCVLSAI SQTGLLEIGS   240
LVHGYIEKLG FTPEVDVFIG TALVDMYSKC GCLNNAFSVF ELMKVKNVFT WTSMATGLAL   300
NGRGNETPNL LNRMAESGIK PNEITFTSLL SAYRHIGLVE EGIELFKSMK TRFGVTPVIE   360
HYGCIVDLLG KAGRIQEAYQ FILAMPIKPD AILLRSLCNA CSIYGETVMG EEIGKALLEI   420
EREDEKLSGS ECEDYVALSN VLAHKGKWVE VEKLRKEMKE RRIKTRPGYS FV           472

SEQ ID NO: 14            moltype = AA   length = 534
FEATURE                  Location/Qualifiers
source                   1..534
                         mol_type = protein
                         organism = Arabidopsis thaliana
SEQUENCE: 14
MAFHGIREVE NYFIPFLQRV KSRNEWKKIN ASIIIHGLSQ SSFMVTKMVD FCDKIEDMDY    60
ATRLFNQVSN PNVFLYNSII RAYTHNSLYC DVIRIYKQLL RKSFELPDRF TFPFMFKSCA   120
SLGSCYLGKQ VHGHLCKFGP RFHVVTENAL IDMYMKFDDL VDAHKVFDEM YERDVISWNS   180
LLSGYARLGQ MKKAKGLFHL MLDKTIVSWT AMISGYTGIG CYVEAMDFFR EMQLAGIEPD   240
EISLISVLPS CAQLGSLELG KWIHLYAERR GFLKQTGVLN ALIEMYSKCG VISQAIQLFG   300
QMEGKDVISW STMISGYAYH GNAHGAIETF NEMQRAKVKP NGITFLGLLS ACSHVGMWQE   360
GLRYFDMMRQ DYQIEPKIEH YGCLIDVLAR AGKLERAVEI TKTMPMKPDS KIWGSLLSSC   420
RTPGNLDVAL VAMDHLVELE PEDMGNYVLL ANIYADLGKW EDVSRLRKMI RNENMKKTPG   480
GSLIEVNNIV QEFVSGDNSK PFWTEISIVL QLFTSHQDQD VITNNNALAF IGIV          534

SEQ ID NO: 15            moltype = AA   length = 694
FEATURE                  Location/Qualifiers
source                   1..694
                         mol_type = protein
                         organism = Arabidopsis thaliana
SEQUENCE: 15
MSEASCLASP LLYTNSGIHS DSFYASLIDS ATHKAQLKQI HARLLVLGLQ FSGFLITKLI    60
HASSSFGDIT FARQVFDDLP RPQIFPWNAI IRGYSRNNHF QDALLMYSNM QLARVSPDSF   120
TFPHLLKACS GLSHLQMGRF VHAQVFRLGF DADVFVQNGL IALYAKCRRL GSARTVFEGL   180
PLPERTIVSW TAIVSAYAQN GEPMEALEIF SQMRKMDVKP DWVALVSVLN AFTCLQDLKQ   240
GRSIHASVVK MGLEIEPDLL ISLNTMYAKC GQVATAKILF DKMKSPNLIL WNAMISGYAK   300
NGYAREAIDM FHEMINKDVR PDTISITSAI SACAQVGSLE QARSMYEYVG RSDYRDDVFI   360
SSALIDMFAK CGSVEGARLV FDRTLDRDVV VWSAMIVGYG LHGRAREAIS LYRAMERGGV   420
HPNDVTFLGL LMACNHSGMV REGWWFFNRM ADHKINPQQQ HYACVIDLLG RAGHLDQAYE   480
VIKCMPVQPG VTVWGALLSA CKKHRHVELG EYAAQQLFSI DPSNTGHYVQ LSNLYAAARL   540
WDRVAEVRVR MKEKGLNKDV GCSWVEVRGR LEAFRVGDKS HPRYEEIERQ VEWIESRLKE   600
GGFVANKDAS LHDLNDEEAE ETLCSHSERI AIAYGLISTP QGTPLRITKN LRACVNCHAA   660
TKLISKLVDR EIVVRDTNRF HHFKDGVCSC GDYW                               694

SEQ ID NO: 16            moltype = AA   length = 656
FEATURE                  Location/Qualifiers
source                   1..656
                         mol_type = protein
                         organism = Arabidopsis thaliana
SEQUENCE: 16
MIRSRSVLLI FRKVLYQSSC LKCLLCANSF STSVSSSLGF RATNKELNQM IRSGYIAEAR    60
DIFEKLEARN TVTWNTMISG YVKRREMNQA RKLFDVMPKR DVVTWNTMIS GYVSCGGIRF   120
LEEARKLFDE MPSRDSFSWN TMISGYAKNR RIGEALLLFE KMPERNAVSW SAMITGFCQN   180
GEVDSAVVLF RKMPVKDSSP LCALVAGLIK NERLSEAAWV LGQYGSLVSG REDLVYAYNT   240
LIVGYGQRGQ VEAARCLFDQ IPDLCGDDHG GEFRERFCKN VVSWNSMIKA YLKVGDVVSA   300
RLLFDQMKDR DTISWNTMID GYVHVSRMED AFALFSEMPN RDAHSWNMMV SGYASVGNVE   360
LARHYFEKTP EKHTVSWNSI IAAYEKNKDY KEAVDLFIRM NIEGEKPDPH TLTSLLSAST   420
GLVNLRLGMQ MHQIVVKTVI PDVPVHNALI TMYSRCGEIM ESRRIFDEMK LKREVITWNA   480
MIGGYAFHGN ASEALNLFGS MKSNGIYPSH ITFVSVLNAC AHAGLVDEAK AQFVSMMSVY   540
KIEPQMEHYS SLVNVTSGQG QFEEAMYIIT SMPFEPDKTV WGALLDACRI YNNVGLAHVA   600
AEAMSRLEPE SSTPYVLLYN MYADMGLWDE ASQVRMNMES KRIKKERGSS WVDSST       656

SEQ ID NO: 17            moltype = AA   length = 544
FEATURE                  Location/Qualifiers
source                   1..544
                         mol_type = protein
                         organism = Arabidopsis thaliana
SEQUENCE: 17
MISSLAAITG GPSTFRRDPD SNTLRLSRRK TLISVLRSCK NIAHVPSIHA KIIRTFHDQD    60
AFVVFELIRV CSTLDSVDYA YDVFSYVSNP NVYLYTAMID GFVSSGRSAD GVSLYHRMIH   120
NSVLPDNYVI TSVLKACDLK VCREIHAQVL KLGFGSSRSV GLKMMEIYGK SGELVNAKKM   180
FDEMPRDRHV AATVMINCYS ECGFIKEALE LFQDVKIKDT VCWTAMIDGL VRNKEMNKAL   240
ELFREMQMEN VSANEFTAVC VLSACSDLGA LELGRWVHSF VENQRMELSN FVGNALINMY   300
SRCGDINEAR RVFRVMRDKD VISYNTMISG LAMHGASVEA INEFRDMVNR GFRPNQVTLV   360
ALLNACSHGG LLDIGLEVFN SMKRVFNVEP QIEHYGCIVD LLGRVGRLEE AYRFIENIPI   420
EPDHIMLGTL LSACKIHGNM ELGEKIAKRL FESENPDSGT YVLLSNLYAS SGKWKESTEI   480
RESMRDSGIE KEPGCSTIEV DNQIHEFLVG DIAHPHKEAI YQRLQELNRI LRFKENQIDI   540
```

```
IMGF                                                                                                 544

SEQ ID NO: 18           moltype = AA  length = 738
FEATURE                 Location/Qualifiers
source                  1..738
                        mol_type = protein
                        organism = Arabidopsis thaliana
SEQUENCE: 18
MAIFSTAQPL SLPRHPNFSN PNQPTTNNER SRHISLIERC VSLRQLKQTH GHMIRTGTFS   60
DPYSASKLFA MAALSSFASL EYARKVFDEI PKPNSFAWNT LIRAYASGPD PVLSIWAFLD  120
MVSESQCYPN KYTFPPLIKA AAEVSSLSLG QSLHGMAVKS AVGSDVFVAN SLIHCYFSCG  180
DLDSACKVFT TIKEKDVVSW NSMINGFVQK GSPDKALELF KKMESEDVKA SHVTMVGVLS  240
ACAKIRNLEF GRQVCSYIEE NRVNVNLTLA NAMLDMYTKC GSIEDAKRLF DAMEEKDNVT  300
WTTMLDGYAI SEDYEAAREV LNSMPQKDIV AWNALISAYE QNGKPNEALI VFHELQLQKN  360
MKLNQITLVS TLSACAQVGA LELGRWIHSY IKKHGIRMNF HVTSALIHMY SKCGDLEKSR  420
EVFNSVEKRD VFVWSAMIGG LAMHGCGNEA VDMFYKMQEA NVKPNGVTFT NVFCACSHTG  480
LVDEAESLFH QMESNYGIVP EEKHYACIVD VLGRSGYLEK AVKFIEAMPI PPSTSVWGAL  540
LGACKIHANL NLAEMACTRL LELEPRNDGA HVLLSNIYAK LGKWENVSEL RKHMRVTGLK  600
KEPGCSSIEI DGMIHEFLSG DNAHPMSEKV YGKLHEVMEK LKSNGYEPEI SQVLQIIEEE  660
EMKEQSLNLH SEKLAICYGL ISTEAPKVIR VIKNLRVCGD CHSVAKLISQ LYDREIIVRD  720
RYRFHHFRNG QCSCNDFW                                                738

SEQ ID NO: 19           moltype = AA  length = 741
FEATURE                 Location/Qualifiers
source                  1..741
                        mol_type = protein
                        organism = Arabidopsis thaliana
SEQUENCE: 19
MMLSCSPLTV PSSSYPFHFL PSSSDPPYDS IRNHPSLSLL HNCKTLQSLR IIHAQMIKIG   60
LHNTNYALSK LIEFCILSPH FEGLPYAISV FKTIQEPNLL IWNTMFRGHA LSSDPVSALK  120
LYVCMISLGL LPNSYTFPFV LKSCAKSKAF KEGQQIHGHV LKLGCDLDLY VHTSLISMYV  180
QNGRLEDAHK VFDKSPHRDV VSYTALIKGY ASRGYIENAQ KLFDEIPVKD VVSWNAMISG  240
YAETGNYKEA LELFKDMMKT NVRPDESTMV TVVSACAQSG SIELGRQVHL WIDDHGFGSN  300
LKIVNALIDL YSKCGELETA CGLFERLPYK DVISWNTLIG GYTHMNLYKE ALLLFQEMLR  360
SGETPNDVTM LSILPACAHL GAIDIGRWIH VYIDKRLKGV TNASSLRTSL IDMYAKCGDI  420
EAAHQVFNSI LHKSLSSWNA MIFGFAMHGR ADASFDLFSR MRKIGIQPDD ITFVGLLSAC  480
SHSGMLDLGR HIFRTMTQDY KMTPKLEHYG CMIDLLGHSG LFKEAEEMIN MMEMEPDGVI  540
WCSLLKACKM HGNVELGESF AENLIKIEPE NPGSYVLLSN IYASAGRWNE VAKTRALLND  600
KGMKKVPGCS SIEIDSVVHE FIIGDKFHPR NREIYGMLEE MEVLLEKAGF VPDTSEVLQE  660
MEEEWKEGAL RHHSEKLAIA FGLISTKPGT KLTIVKNLRV CRNCHEATKL ISKIYKREII  720
ARDRTRFHHF RDGVCSCNDY W                                            741

SEQ ID NO: 20           moltype = AA  length = 890
FEATURE                 Location/Qualifiers
source                  1..890
                        mol_type = protein
                        organism = Arabidopsis thaliana
SEQUENCE: 20
MSCPLAFTFS LPSIFPFPSQ LLPFSRHKHP YLLRATPTSA TEDVASAVSG APSIFISQSR   60
SPEWWIDLLR SKVRSNLLRE AVLTYVDMIV LGIKPDNYAF PALLKAVADL QDMELGKQIH  120
AHVFKGYGV DSVTVANTLV NLYRKCGDFG AVYKVFDRIS ERNQVSWNSL ISSLCSFEKW  180
EMALEAFRCM LDENVEPSSF TLVSVVTACS NLPMPEGLMM GKQVHAYGLR KGELNSFIIN  240
TLVAMYGKLG KLASSKVLLG SFGGRDLVTW NTVLSSLCQN EQLLEALEYL REMVLEGVEP  300
DEFTISSVLP ACSHLEMLRT GKELHAYALK NGSLDENSFV GSALVDMYCN CKQVLSGRRV  360
FDGMFDRKIG LWNAMIAGYS QNEHDKEALL LFIGMEESAG LLANSTTMAG VVPACVRSGA  420
FSRKEAIHGF VVKRGLDRDR FVQNTLMDMY SRLGKIDIAM RIFGKMEDRD LVTWNTMITG  480
YVFSEHHEDA LLLLHKMQNL ERKVSKGASR VSLKPNSITL MTILPSCAAL SALAKGKEIH  540
AYAIKNNLAT DVAVGSALVD MYAKCGCLQM SRKVFDQIPQ KNVITWNVII MAYGMHGNGQ  600
EAIDLLRMMM VQGVKPNEVT FISVFAACSH SGMVDEGLRI FYVMKPDYGV EPSSDHYACV  660
VDLLGRAGRI KEAYQLMNMM PRDFNKAGAW SSLLGASRIH NNLEIGEIAA QNLIQLEPNV  720
ASHYVLLANI YSSAGLWDKA TEVRRNMKEQ GVRKEPGCSW IEHGDEVHKF VAGDSSHPQS  780
EKLSGYLETL WERMRKEGYV PDTSCVLHNV EEDEKEILLC GHSEKLAIAF GILNTSPGTI  840
IRVAKNLRVC NDCHLATKFI SKIVDREIIL RDVRRFHRFK NGTCSCGDYW            890

SEQ ID NO: 21           moltype = AA  length = 603
FEATURE                 Location/Qualifiers
source                  1..603
                        mol_type = protein
                        organism = Arabidopsis thaliana
SEQUENCE: 21
MAISSASLIS SFSHAETFTK HSKIDTVNTQ NPILLISKCN SLRELMQIQA YAIKSHIEDV   60
SFVAKLINFC TESPTESSMS YARHLFEAMS EPDIVIFNSM ARGYSRFTNP LEVFSLFVEI  120
LEDGILPDNY TFPSLLKACA VAKALEEGRQ LHCLSMKLGL DDNVYVCPTL INMYTECEDV  180
DSARCVFDRI VEPCVVCYNA MITGYARRNR PNEALSLFRE MQGKYLKPNE ITLLSVLSSC  240
ALLGSLDLGK WIHKYAKKHS FCKYVKVNTA LIDMFAKCGS LDDAVSIFEK MRYKDTQAWS  300
AMIVAYANHG KAEKSMLMFE RMRSENVQPD EITFLGLLNA CSHTGRVEEG RKYFSQMVSK  360
FGIVPSIKHY GSMVDLLSRA GNLEDAYEFI DKLPISPTPM LWRILLAACS SHNNLDLAEK  420
VSERIFELDD SHGGDYVILS NLYARNKKWE YVDSLRKVMK DRKAVKVPGC SSIEVNNVVH  480
EFFSGDGVKS ATTKLHRALD EMVKELKLSG YVPDTSMVVH ANMNDQEKEI TLRYHSEKLA  540
```

```
ITFGLLNTPP GTTIRVVKNL RVCRDCHNAA KLISLIFGRK VVLRDVQRFH HFEDGKCSCG  600
DFW                                                                 603

SEQ ID NO: 22          moltype = AA  length = 960
FEATURE                Location/Qualifiers
source                 1..960
                       mol_type = protein
                       organism = Arabidopsis thaliana
SEQUENCE: 22
MEYAVTNMRL LSNMMYSASA ISFPRVRLHC SIPTEPSCRR NPFRQSNQPV QVPSPKLACF  60
DGVLTEAFQR LDVSENNSPV EAFAYVLELC GKRRAVSQGR QLHSRIFKTF PSFELDFLAG  120
KLVFMYGKCG SLDDAEKVFD EMPDRTAFAW NTMIGAYVSN GEPASALALY WNMRVEGVPL  180
GLSSFPALLK ACAKLRDIRS GSELHSLLVK LGYHSTGFIV NALVSMYAKN DDLSAARRLF  240
DGFQEKGDAV LWNSILSSYS TSGKSLETLE LFREMHMTGP APNSYTIVSA LTACDGFSYA  300
KLGKEIHASV LKSSTHSSEL YVCNALIAMY TRCGKMPQAE RILRQMNNAD VVTWNSLIKG  360
YVQNLMYKEA LEFFSDMIAA GHKSDEVSMT SIIAASGRLS NLLAGMELHA YVIKHGWDSN  420
LQVGNTLIDM YSKCNLTCYM GRAFLRMHDK DLISWTTVIA GYAQNDCHVE ALELFRDVAK  480
KRMEIDEMIL GSILRASSVL KSMLIVKEIH CHILRKGLLD TVIQNELVDV YGKCRNMGYA  540
TRVFESIKGK DVVSWTSMIS SSALNGNESE AVELFRRMVE TGLSADSVAL LCILSAAASL  600
SALNKGREIH CYLLRKGFCL EGSIAVAVVD MYACCGDLQS AKAVFDRIER KGLLQYTSMI  660
NAYGMHGCGK AAVELFDKMR HENVSPDHIS FLALLYACSH AGLLDEGRGF LKIMEHEYEL  720
EPWPEHYVCL VDMLGRANCV VEAFEFVKMM KTEPTAEVWK ALLAACRSHS EKEIGEIAAQ  780
RLLELEPKNP GNLVLVSNVF AEQGRWNDVE KVRAKMKASG MEKHPGCSWI EMDGKVHKFT  840
ARDKSHPESK EIYEKLSEVT RKLEREVGYV ADTKFVLHNV DEGEKVQMLH GHSERIAIAY  900
GLLRTPDRAC LRITKNLRVC RDCHTFCKLV SKLFRRDIVM RDANRFHHFE SGLCSCGDSW  960

SEQ ID NO: 23          moltype = AA  length = 895
FEATURE                Location/Qualifiers
source                 1..895
                       mol_type = protein
                       organism = Arabidopsis thaliana
SEQUENCE: 23
MNCLANESLN SLKISPFSTS RLLSSVTNFR NQLSFSSKDS SSSSAPFNPF RFFNDQSNSR  60
LCNLRTTKIL QAHLLRRYLL PFDVFLTKSL LSWYSNSGSM ADAAKLFDTI PQPDVVSCNI  120
MISGYKQHRL FEESLRFFSK MHFLGFEANE ISYGSVISAC SALQOAPLFSE LVCCHTIKMG  180
YFFYEVVESA LIDVFSKNLR FEDAYKVFRD SLSANVYCWN TIIAGALRNQ NYGAVFDLFH  240
EMCVGFQKPD SYTYSSVLAA CASLEKLRFG KVVQARVIKC GAEDVFVCTA IVDLYAKCGH  300
MAEAMEVFSR IPNPSVVSWT VMLSGYTKSN DAFSALEIFK EMRHSGVEIN NCTVTSVISA  360
CGRPSMVCEA SQVHAWVFKS GFYLDSSVAA ALISMYSKSG DIDLSEQVFE DLDDIQRQNI  420
VNVMITSFSQ SKKPGKAIRL FTRMLQEGLR TDEFSVCSLL SVLDCLNLGK QVHGYTLKSG  480
LVLDLTVGSS LFTLYSKCGS LEESYKLFQG IPFKDNACWA SMISGFNEYG YLREAIGLFS  540
EMLDDGTSPD ESTLAAVLTV CSSHPSLPRG KEIHGYTLRA GIDKGMDLGS ALVNMYSKCG  600
SLKLARQVYD RLPELDPVSC SSLISGYSQH GLIQDGFLLF RDMVMSGFTM DSFAISSILK  660
AAALSDESSL GAQVHAYITK IGLCTEPSVG SSLLTMYSKF GSIDDCCKAF SQINGPDLIA  720
WTALIASYAQ HGKANEALQV YNLMKEKGFK PDKVTFVGVL SACSHGGLVE ESYFHLNSMV  780
KDYGIEPENR HYVCMVDALG RSGRLREAES FINNMHIKPD ALVWGTLLAA CKIHGEVELG  840
KVAAKKAIEL EPSDAGAYIS LSNILAEVGE WDEVEETRKL MKGTGVQKEP GWSSV        895

SEQ ID NO: 24          moltype = AA  length = 681
FEATURE                Location/Qualifiers
source                 1..681
                       mol_type = protein
                       organism = Arabidopsis thaliana
SEQUENCE: 24
MNISKAKLLL LPPPLTPKLN RSLYSHSQRR TRSLPHHRDK PINWNSTHSF VLHNPLLSLL  60
EKCKLLLHLK QIQAQMIING LILDPFASSR LIAFCALSES RYLDYSVKIL KGIENPNIFS  120
WNVTIRGFSE SENPKESFLL YKQMLRHGCC ESRPDHFTYP VLFKVCADLR LSSLGHMILG  180
HVLKLRLELV SHVHNASIHM FASCGDMENA RKVFDESPVR DLVSWNCLIN GYKKIGEAEK  240
AIYVYKLMES EGVKPDDVTM IGLVSSCSML GDLNRGKEFY EYVKENGLRM TIPLVNALMD  300
MFSKCGDIHE ARRIFDNLEK RTIVSWTTMI SGYARCGLLD VSRKLFDDME EKDVVLWNAM  360
IGGSVQAKRG QDALALFQEM QTSNTKPDEI TMIHCLSACS QLGALDVGIW IHRYIEKYSL  420
SLNVALGTSL VDMYAKCGNI SEALSVFHGI QTRNSLTYTA IIGGLALHGD ASTAISYFNE  480
MIDAGIAPDE ITFIGLLSAC CHGGMIQTGR DYFSQMKSRF NLNPQLKHYS IMVDLLGRAG  540
LLEEADRLME SMPMEADAAV WGALLFGCRM HGNVELGEKA AKKLLELDPS DSGIYVLLDG  600
MYGEANMWED AKRARRMMNE RGVEKIPGCS SIEVNGIVCE FIVRDKSRPE SEKIYDRLHC  660
LGRHMRSSLS VLFSEYEITN N                                            681

SEQ ID NO: 25          moltype = AA  length = 842
FEATURE                Location/Qualifiers
source                 1..842
                       mol_type = protein
                       organism = Arabidopsis thaliana
SEQUENCE: 25
MAMLGNVLHL SPMVLATTTT TKPSLLNQSK CTKATPSSLK NCKTIDELKM FHRSLTKQGL  60
DNDVSTITKL VARSCELGTR ESLSFAKEVF ENSESYGTCF MYNSLIRGYA SSGLCNEAIL  120
LPLRMMNSGI SPDKYTFPFG LSACAKSRAK GNGIQIHGLI VKMGYAKDLF VQNSLVHFYA  180
ECGELDSARK VFDEMSERNV VSWTSMICGY ARRDFAKDAV DLFFRMVRDE EVTPNSVTMV  240
CVISACAKLE DLETGEKVYA FIRNSGIEVN DLMVSALVDM YMKCNAIDVA KRLFDEYGAS  300
NLDLCNAMAS NYVRQGLTRE ALGVFNLMMD SGVRPDRISM LSAISSCSQL RNILWGKSCH  360
```

```
GYVLRNGFES WDNICNALID MYMKCHRQDT AFRIFDRMSN KTVVTWNSIV AGYVENGEVD  420
AAWETFETMP EKNIVSWNTI ISGLVQGSLF EEAIEVFCSM QSQEGVNADG VTMMSIASAC  480
GHLGALDLAK WIYYYIEKNG IQLDVRLGTT LVDMFSRCGD PESAMSIFNS LTNRDVSAWT  540
AAIGAMAMAG NAERAIELFD DMIEQGLKPD GVAFVGALTA CSHGGLVQQG KEIFYSMLKL  600
HGVSPEDVHY GCMVDLLGRA GLLEEAVQLI EDMPMEPNDV IWNSLLAACR VQGNVEMAAY  660
AAEKIQVLAP ERTGSYVLLS NVYASAGRWN DMAKVRLSMK EKGLRKPPGT SSIQIRGKTH  720
EFTSGDESHP EMPNIEAMLD EVSQRASHLG HVPDLSNVLM DVDEKEKIFM LSRHSEKLAM  780
AYGLISSNKG TTIRIVKNLR VCSDCHSFAK FASKVYNREI ILRDNNRFHY IRQGKCSCGD  840
FW                                                                 842

SEQ ID NO: 26           moltype = AA  length = 859
FEATURE                 Location/Qualifiers
source                  1..859
                        mol_type = protein
                        organism = Physcomitrella patens
SEQUENCE: 26
MLHQGAGRAR GGLPSLLLGR RFDLWASFPW SFSSTSDDPS SRQSEENSQT IDELWEYFAG   60
PSQWWDNRIH KRNPRSPDLK HKVTGKALWI DGCFTPEWVK FQPVAQVGLQ SYATCTTKCT  120
EGGAQGKRQP KGNDGKLATA CESARVLGRI AQGGINMHVQ TANTLSEAIV VLMNRLQRGL  180
ITDSFMYVEV LKRCLKQKDL MAAKQVHDCI IKSRMEQNAH VMNNLLHVYI ECGRLQEARC  240
VFDALVKKSG ASWNAMIAGY VEHKHAEDAM RLFREMCHEG VQPNAGTYMI ILKACASLSA  300
LKWGKEVHAC IRHGGLESDV RVGTALLRMY GKCGSINEAR RIFDNLMNHD IISWTVMIGA  360
YAQSGNGKEA YRLMLQMEQE GFKPNAITYV SILNACASEG ALKWVKRVHR HALDAGLELD  420
VRVGTALVQM YAKSGSIDDA RVVFDRMKVR DVVSWNVMIG AFAEHGRGHE AYDLFLQMQT  480
EGCKPDAIMF LSILNACASA GALEWVKKIH RHALDSGLEV DVRVGTALVH MYSKSGSIDD  540
ARVVFDRMKV RNVVSWNAMI SGLAQHGLGQ DALEVFRRMT VHQKPDRVT FVAVLSACSH  600
AGLVDEGRSQ YLAMTQVYGI EPDVSHCNCM VDLLGRAGRL MEAKLFIDNM AVDPDEATWG  660
ALLGSCRTYG NVELGELVAK ERLKLDPKNA ATYVLLSNIY AEAGKWDMVS WVRTMMRERG  720
IRKEPGRSWI EVDNKIHDFL VADSSHPECK EINESKDKVI EKIKAEGYIP DTRLVLKNKN  780
MKDKELDICS HSEKLAIVYG LMHTPPGNPI RVFKNLRVCT DCHGATKLIS KVEGREIIVR  840
DANRFHHFKD GVCSCGDYW                                                859

SEQ ID NO: 27           moltype = AA  length = 833
FEATURE                 Location/Qualifiers
source                  1..833
                        mol_type = protein
                        organism = Physcomitrella patens
SEQUENCE: 27
MRVSTRIAAN IAVVRRRWFG SLQLPVPSAR FRSTFTRRVG ANDVLQRLGE GGNHIDSRTY   60
VKLFQRCTEL RDAALGKQVR DHIIQGGRQL NIYELNTLIK LYSICGNVTE ARQIFDSVEN  120
KTVVTWNALI AGYAQVGHVK EAFALFRQMV DEGLEPSIIT FLSVLDACSS PAGLNWGKEV  180
HAQVVTAGFV SDFRIGTALV SMYVKGGSMD DARQVFDGLH IRDVSTFNVM VGGYAKSGDV  240
EKAFELFYRM QQVGLKPNKI SFLSILDGCW TPEALAWGKA VHAQCMNAGL VDDIRVATSL  300
IRMYTTCGSI EGARRVFDNM KVRDVVSWTV MIEGYAENGN IEDAFGLFAT MQEEGIQPDR  360
ITYMHIMNAC AISANLNHAR EIHSQVDIAG FGTDLLVSTA LVHMYAKCGA IKDARQVFDA  420
MPRRDVVSWS AMIGAYVENG YGTEAFETFH LMKRSNIEPD GVTYINLLNA CGHLGALDVG  480
MEIYTQAIKA DLVSHVPLGN ALIIMNAKHG SVERARYIFD TMVRRDVITW NAMIGGYSLH  540
GNAREALYLF DRMLKERFRP NSVTFVGVLS ACSRAGFVDE GRRFFTYLLE GRGIVPTVKL  600
YGCMVDLLGR AGELDEAELL IKSMPVKPTS SIWSSLLVAC RIHGNLDVAE RAAERCLMID  660
PYDGAVYVQL SHMYAAAGMW ENVAKVRKVM ESRGIRKEQG CTWIEVAGKV HTFVVEDRSH  720
PLVGEIYAEL ARLMNAIKRE GYIPITQNVL HDVGEQQKEE AISYHSEKLA IAYGVLSLPS  780
GTPIRIYKNL RVCSDCHSAS KFISKVTGRE IIARDASRFH HFKDGVCSCG DYW          833

SEQ ID NO: 28           moltype = AA  length = 1204
FEATURE                 Location/Qualifiers
source                  1..1204
                        mol_type = protein
                        organism = Physcomitrella patens
SEQUENCE: 28
MYRCLWRSVI QTHKGSLGRV AGVREFSARP WPVEQNRSSI GAAGGESSNL VPVKVMRNER   60
HCGPDREDVS NTHQPRPTET DRATYVALLQ NCTRKRLLMR NERHCGPDRE DVSNTHQPRP  120
TETERATYVA LLQNCTRKRL LPEAKRIHAQ MVEAWVGPDI FLSNLLINMY VKCRSVLDAH  180
QVFKEMPRRD VISWNSLISC YAQQGFKKKA FQLFEEMQNA GFIPNKITYI SILTACYSPA  240
ELENGKKIHS QIIKAGYQRD PRVQNSLLSM YGKCGDLPRA RQVFAGISPR DVVSYNTMLG  300
LYAQKAYVKE CLGLFGQMSS EGISPDKVTY INLLDAFTTP SMLDEGKRIH KLTVEEGLNS  360
DIRVGTALVT MCVRCGDVDS AKQAFKGTAD RDVVVYNALI AALAQHGHNV EAFEQYYRMR  420
SDGVALNRTT YLSILNACST SKALEAGKLI HSHISEDGHS SDVQIGNALI SMYARCGDLP  480
KARELFYTMP KRDLISWNAI IAGYARREDR GEAMRLYKQM QSEGVKPGRV TFLHLLSACA  540
NSSAYADGKM IHEDILRSGI KSNGHLANAL MNMYRRCGSL MEAQNVFEGT QARDVISWNS  600
MIAGHAQHGS YETAYKLFQE MQNEELEPDN ITFASVLSGC KNPEALELGK QIHGRITESG  660
LQLDVNLGNA LINMYIRCGS LQDARNVFHS LQHRDVMSWT AMIGGCADQG EDMKAIELFW  720
QMQNEGFRPV KSTFSSILKV CTSSACLDEG KKVIAYILNS GYELDTGVGN ALISAYSKSG  780
SMTDAREVFD KMPSRDIVSW NKIIAGYAQN GLGQTAVEFA YQMQEQDVVP NKFSFVSLLN  840
ACSSFSALEE GKRVHAEIVK RKLQGDVRVG AALISMYAKC GSQGEAQEVF DNIIEKNVVT  900
WNAMINAYAQ HGLASKALGF FNCMEKEGIK PDGSTFTSIL SACNHAGLVL EGYQIFSSME  960
SEYGVLPTIE HYGCLVGLLG RARRFQEAET LINQMPFPPD AAVWETLLGA CRIHGNIALA  1020
EHAANNALKL NARNPAVYIL LSNVYAAAGR WDDVAKIRRV MEGRGIRKEP GRSWIEVDNI  1080
IHEFIAADRS HPETAEIYAE LKRLSVEMEE AGYFPDTQHV LHDLGKAHQE TSLCTHSERL  1140
AIAYGLIKTP PGTPIRIFKN LRICGDCHTA SKFISKLVGR EIIARDSNRF HSFKNGKCSC  1200
```

```
EDYW                                                                        1204

SEQ ID NO: 29            moltype = AA   length = 1042
FEATURE                  Location/Qualifiers
source                   1..1042
                         mol_type = protein
                         organism = Physcomitrella patens
SEQUENCE: 29
MSLPWGLDFT TVSTAKQTQA GFSVLKKEKH SLRDDLILAT SRQNDAGHKI DLVGDSARNF   60
LVKQIARDSD TLVRADLKKE CSRAYGKPSL LVEAHRSSSM HSQSRVQLCK WWFNTSGFRY   120
SNGKPRVNKL YFHTYKDEKI MIEKDGAVDV VQYLQQQGAQ VNSSDYMKML KRCIEVKDLV   180
AGRQVHQHII QHRTVPDQYT VNALINMYIQ CGSIEEARQV WKKLSYMERT VHSWNAMVVG   240
YIQYGYIEKA LKLLRQMQQH GLAPDRTTIM SFLSSCKSPG ALEWGREIHF QAMQAGLLFD   300
VKVANCILNM YAKCGSIEEA REVFDKMEKK SVVSWTITIG GYADCGRSET AFEIFQKMEQ   360
EGVVPNRITY ISVLNAFSSP AALKWGKAVH SRILNAGHES DTAVGTALVK MYAKCGSYKD   420
CRQVFEKLVN RDLIAWNTMI GGLAEGGYWE EASEVYNQMQ REGVMPNKIT YVILLNACVN   480
SAALHWGKEI HSRVAKAGFT SDIGVQNALI SMYSRCGSIK DARLVFDKMV RKDVISWTAM   540
IGGLAKSGFG AEALTVYQEM QQAGVEPNRV TYTSILNACS SPAALEWGRR IHQQVVEAGL   600
ATDAHVGNTL VNMYSMCGSV KDARQVFDRM IQRDIVAYNA MIGGYAAHNL GKEALKLFDR   660
LQEEGLKPDK VTYINMLNAC ANSGSLEWAR EIHTLVRKGG FFSDTSVGNA LVSTYAKCGS   720
FSDASIVFEK MTKRNVISWN AIIGGSAQHG RGQDALQLFE RMKMEGVKPD IVTFVSLLSA   780
CSHAGLLEEG RRYFCSMSQD FAIIPTIEHY GCMVDLLGRA GQLDEAEALI KTMPFQANTR   840
IWGALLGACR IHGNVPVAER AAESSLKLDL DNAVVYVALS HMYAAAGMWD SAAKLRKLME   900
QRGVTKEPGR SWIQVGDKLH YFVAEDRSHP QSEKIYAELD RLTHAMKMKG YVPDTRSVMH   960
DVDEGEKENA VCHHSERLAI AYGLISTPPG TRIHIFKNLR VCPDCHTATK FISKIVDREI   1020
IARDVNRFHH FKDGVCSCGD YW                                            1042

SEQ ID NO: 30            moltype = AA   length = 804
FEATURE                  Location/Qualifiers
source                   1..804
                         mol_type = protein
                         organism = Physcomitrella patens
SEQUENCE: 30
MIPTGKDGWY APADVLQYLH RKGPQVDSYD YVKLLQSCVK AKDLAVGKQV HEHILRCGVK   60
PNVYITNTLL KLYAHCGSVN EARQLFDKFS NKSVVSWNVM ISGYAHRGLA QEAFNLFTLM   120
QQERLEPDKF TFVSILSACS SPAVLNWGRE IHVRVMEAGL ANDTTVGNAL ISMYAKCGSV   180
RDARRVFDAM ASRDEVSWTT LTGAYAESGY GEESLKTYHA MLQERVRPSR ITYMNVLSAC   240
GSLAALEKGK QIHAHIVESE YHSDVRVSTA LTKMYMKCGA HKDAREVFEC LSYRDVIAWN   300
TMIRGFVDSG QLEEAHGTFH RMLEEGVAPD RATYTTVLSA CARPGGLARG KEIHARAAKD   360
GLVSDVRFGN ALINMYSKAG SMKDARQVFD RMPKRDVVSW TTLLGRYADC DQVVESFTTF   420
KQMLQQGVKA NKITYMCVLK ACSNPVALKW GKEIHAEVVK AGLLADLAVT NALMSMYFKC   480
GSVEDAIRVF EGMSMRDVVT WNTLIGGLGQ NGRGLEALQR YEVMKSEGMR PNAATFVNVL   540
SACRVCNLVE EGRRQFAFMS KDYGIVPTEK HYACMVDILA RAGHLREAED VILTIPLKPS   600
AAMWGALLAA CRIHCNVEIG ERAAEHCLKL EPQNAGLYVS LSAIYAAAGM WRDVAKLRKF   660
MKERGVKKEP GRSWIEIAGE VHSFVARDQS HPRTQEIYAE LETLKKQMKS LGYVPDTRFV   720
MHDLDDEGKE RAVCHHSEKL AIAYGLISTP PGTPIRISKN LRVCTDCHTA TKFISKITKR   780
EIIARDAHRF HHFKNGECSC GDYW                                          804

SEQ ID NO: 31            moltype = AA   length = 890
FEATURE                  Location/Qualifiers
source                   1..890
                         mol_type = protein
                         organism = Physcomitrella patens
SEQUENCE: 31
MLSRRFGLRR WKQVLQNYHV GAMTSIVYND GFASTGKELD GPTSVSGGEV WRLCKAGRLR   60
EAIQLLGIIK QRGLLVNSNT YGCVIEHCAK ARRFEDGKMV HKQLDELGVE IDIYLGNSLI   120
NFYSKFEDVA SAEQVFRRMT LRDVVTWSSM IAAYAGNNHP AKAFDTFERM TDANIEPNRI   180
TFLSILKACN NYSILEKGRK IHTIVKAMGM ETDVAVATAL ITMYSKCGEI SVACEVFHKM   240
TERNVVSWTA IIQANAQHRK LNEAFELYEQ MLQAGISPNA VTFVSLLNSC NTPEALNRGR   300
RIHSHISERG LETDMIVANA LITMYCKCNS VQEAREIFDR MSKRDVISWS AMIAGYAQSG   360
YKDKESIDEV FQLLERMRRE GVFPNKVTFM SILRACTAHG ALEQGRQIHA ELSKVGFELD   420
RSLQTAIFNM YAKCGSIYEA EQVFSKMANK NVVAWTSFLS MYIKCGDLSS AEKVFSEMPT   480
RNVVSWNLMI AGYAQNGDIV KVFELLSSMK AEGFQPDRVT VITILEACGA LAGLERGKLV   540
HAEAVKLGLE SDTVVATSLI GMYSKCGQVA EARTVFDKMS NRDTVAWNAM LAGYGQHGDG   600
LEAVDLFKRM LKERVSPNEI TLTAVISACS RAGLVQEGRE IFRMMQEDFK MTPRKQHYGC   660
MVDLLGRAGR LQEAEEFIQS MPCEPDISVW HALLGACKSH NNVQLAERAA HHILELEPSY   720
ASVYITLSNI YAQAGRWDDS TKVRRVMDDR GLKKDRGESS IEIDGRIHTF VAEDCAHPEI   780
DAIHAELETL TKEMKEAGYT PDMRFVLHDV DDVQKEKALC HHSEKLAIAY GLLKTPSGTP   840
IRIMKNLRVC GDCHTATKFI SKIRKREIVA RDANRFHYFN NGTCSCGDFW             890

SEQ ID NO: 32            moltype = RNA   length = 31
FEATURE                  Location/Qualifiers
source                   1..31
                         mol_type = genomic RNA
                         organism = Physcomitrella patens
SEQUENCE: 32
ctataggtat tggaaacgta tttagttctt c                                  31

SEQ ID NO: 33            moltype = RNA   length = 31
```

-continued

```
FEATURE             Location/Qualifiers
source              1..31
                    mol_type = other RNA
                    organism = Physcomitrella patens
SEQUENCE: 33
ctatttcaat ggttggtaag tagagatgtt c                                  31

SEQ ID NO: 34       moltype = RNA   length = 31
FEATURE             Location/Qualifiers
source              1..31
                    mol_type = other RNA
                    organism = Physcomitrella patens
SEQUENCE: 34
gtagagatgt ttccacaggt gctccttttt c                                  31

SEQ ID NO: 35       moltype = RNA   length = 31
FEATURE             Location/Qualifiers
source              1..31
                    mol_type = other RNA
                    organism = Physcomitrella patens
SEQUENCE: 35
atcccgatcc tgaggtctat attctaattt c                                  31

SEQ ID NO: 36       moltype = RNA   length = 31
FEATURE             Location/Qualifiers
source              1..31
                    mol_type = other RNA
                    organism = Physcomitrella patens
SEQUENCE: 36
acaattacta tcaaagctat tggacatcaa c                                  31

SEQ ID NO: 37       moltype = RNA   length = 31
FEATURE             Location/Qualifiers
source              1..31
                    mol_type = other RNA
                    organism = Physcomitrella patens
SEQUENCE: 37
cactttggct ttgaagcagc tgcttggtac c                                  31

SEQ ID NO: 38       moltype = RNA   length = 31
FEATURE             Location/Qualifiers
source              1..31
                    mol_type = other RNA
                    organism = Physcomitrella patens
SEQUENCE: 38
ttattatatt tgatttggaa gtcacctttt c                                  31

SEQ ID NO: 39       moltype = RNA   length = 31
FEATURE             Location/Qualifiers
source              1..31
                    mol_type = other RNA
                    organism = Physcomitrella patens
SEQUENCE: 39
attttttatat aggtatagac ggtatctctt c                                 31

SEQ ID NO: 40       moltype = RNA   length = 31
FEATURE             Location/Qualifiers
source              1..31
                    mol_type = other RNA
                    organism = Physcomitrella patens
SEQUENCE: 40
caaacagtag acttttcgac tatttttgct c                                  31

SEQ ID NO: 41       moltype = RNA   length = 31
FEATURE             Location/Qualifiers
source              1..31
                    mol_type = other RNA
                    organism = Physcomitrella patens
SEQUENCE: 41
ggaaaatctg cacaaatagg attgcatact c                                  31

SEQ ID NO: 42       moltype = RNA   length = 31
FEATURE             Location/Qualifiers
source              1..31
                    mol_type = other RNA
                    organism = Physcomitrella patens
SEQUENCE: 42
ctaaaacaaa tattttaata ataaaaaaat c                                  31
```

-continued

```
SEQ ID NO: 43            moltype = RNA   length = 31
FEATURE                  Location/Qualifiers
source                   1..31
                         mol_type = other RNA
                         organism = Physcomitrella patens
SEQUENCE: 43
aaaacaaata ttttaataat aaaaaaatca c                                   31

SEQ ID NO: 44            moltype = RNA   length = 31
FEATURE                  Location/Qualifiers
source                   1..31
                         mol_type = other RNA
                         organism = Physcomitrella patens
SEQUENCE: 44
atcaaatacg ttatgaatat tttttaaagt c                                   31

SEQ ID NO: 45            moltype = RNA   length = 31
FEATURE                  Location/Qualifiers
source                   1..31
                         mol_type = other RNA
                         organism = Arabidopsis thaliana
SEQUENCE: 45
aaatgagtag ttcagaaaga atcgagcttt c                                   31

SEQ ID NO: 46            moltype = RNA   length = 31
FEATURE                  Location/Qualifiers
source                   1..31
                         mol_type = other RNA
                         organism = Arabidopsis thaliana
SEQUENCE: 46
tttttttat cgatattctt gtttactact c                                    31

SEQ ID NO: 47            moltype = RNA   length = 31
FEATURE                  Location/Qualifiers
source                   1..31
                         mol_type = other RNA
                         organism = Arabidopsis thaliana
SEQUENCE: 47
gatttaatac cgatatttta gcaacaaatc c                                   31

SEQ ID NO: 48            moltype = RNA   length = 31
FEATURE                  Location/Qualifiers
source                   1..31
                         mol_type = other RNA
                         organism = Arabidopsis thaliana
SEQUENCE: 48
gtttttatgt cagcaacaga agcccaagct c                                   31

SEQ ID NO: 49            moltype = RNA   length = 31
FEATURE                  Location/Qualifiers
source                   1..31
                         mol_type = other RNA
                         organism = Arabidopsis thaliana
SEQUENCE: 49
ccaagatttt tcttgttctt atataattct c                                   31

SEQ ID NO: 50            moltype = RNA   length = 31
FEATURE                  Location/Qualifiers
source                   1..31
                         mol_type = other RNA
                         organism = Arabidopsis thaliana
SEQUENCE: 50
tgattgtatg tgtgatagca tctactatac c                                   31

SEQ ID NO: 51            moltype = RNA   length = 31
FEATURE                  Location/Qualifiers
source                   1..31
                         mol_type = other RNA
                         organism = Arabidopsis thaliana
SEQUENCE: 51
cctccactag caggtttttt tggaaaactc c                                   31

SEQ ID NO: 52            moltype = RNA   length = 31
FEATURE                  Location/Qualifiers
source                   1..31
                         mol_type = other RNA
                         organism = Arabidopsis thaliana
SEQUENCE: 52
ctcgaatttt cgatattcct ttttatttct c                                   31
```

-continued

```
SEQ ID NO: 53               moltype = RNA   length = 31
FEATURE                     Location/Qualifiers
source                      1..31
                            mol_type = other RNA
                            organism = Arabidopsis thaliana
SEQUENCE: 53
ctgttacttc gaaagtagct gcttcagctt c                                    31

SEQ ID NO: 54               moltype = RNA   length = 31
FEATURE                     Location/Qualifiers
source                      1..31
                            mol_type = other RNA
                            organism = Arabidopsis thaliana
SEQUENCE: 54
ttctttctgt tacttcgaaa gtagctgctt c                                    31

SEQ ID NO: 55               moltype = RNA   length = 31
FEATURE                     Location/Qualifiers
source                      1..31
                            mol_type = other RNA
                            organism = Arabidopsis thaliana
SEQUENCE: 55
gaattgggtt caagctttcc ctagcccctt c                                    31

SEQ ID NO: 56               moltype = RNA   length = 31
FEATURE                     Location/Qualifiers
source                      1..31
                            mol_type = other RNA
                            organism = Arabidopsis thaliana
SEQUENCE: 56
atgggtgggg caagctcttc tattctggtt c                                    31

SEQ ID NO: 57               moltype = RNA   length = 31
FEATURE                     Location/Qualifiers
source                      1..31
                            mol_type = other RNA
                            organism = Arabidopsis thaliana
SEQUENCE: 57
ctaacgattt aataactatc tttgtagctc c                                    31

SEQ ID NO: 58               moltype = RNA   length = 31
FEATURE                     Location/Qualifiers
source                      1..31
                            mol_type = other RNA
                            organism = Arabidopsis thaliana
SEQUENCE: 58
ttggcctaat tcttcttctg atgatcgatt c                                    31

SEQ ID NO: 59               moltype = RNA   length = 31
FEATURE                     Location/Qualifiers
source                      1..31
                            mol_type = other RNA
                            organism = Arabidopsis thaliana
SEQUENCE: 59
tccaaataat ttatgcagct tcaacatctc c                                    31

SEQ ID NO: 60               moltype = RNA   length = 31
FEATURE                     Location/Qualifiers
source                      1..31
                            mol_type = other RNA
                            organism = Arabidopsis thaliana
SEQUENCE: 60
tcggtacaat ccaaataatt tatgcagctt c                                    31

SEQ ID NO: 61               moltype = RNA   length = 31
FEATURE                     Location/Qualifiers
source                      1..31
                            mol_type = other RNA
                            organism = Arabidopsis thaliana
SEQUENCE: 61
ttggatttct tattgctttt gccgtcaaat c                                    31

SEQ ID NO: 62               moltype = RNA   length = 31
FEATURE                     Location/Qualifiers
source                      1..31
                            mol_type = other RNA
                            organism = Arabidopsis thaliana
SEQUENCE: 62
```

```
tgttagcaat gtacagcggt caaataggat c                                    31

SEQ ID NO: 63            moltype = RNA   length = 31
FEATURE                  Location/Qualifiers
source                   1..31
                         mol_type = other RNA
                         organism = Arabidopsis thaliana
SEQUENCE: 63
ctttggacct ggtgtatctt gtctttacca c                                    31

SEQ ID NO: 64            moltype = RNA   length = 31
FEATURE                  Location/Qualifiers
source                   1..31
                         mol_type = other RNA
                         organism = Arabidopsis thaliana
SEQUENCE: 64
actttatcga tccacttact tctattatgt c                                    31

SEQ ID NO: 65            moltype = RNA   length = 31
FEATURE                  Location/Qualifiers
source                   1..31
                         mol_type = other RNA
                         organism = Arabidopsis thaliana
SEQUENCE: 65
tacatgattt tcttttagtt tttctgggat c                                    31

SEQ ID NO: 66            moltype = RNA   length = 31
FEATURE                  Location/Qualifiers
source                   1..31
                         mol_type = other RNA
                         organism = Arabidopsis thaliana
SEQUENCE: 66
aaaaacatat tttattgagt cccttcatgc c                                    31

SEQ ID NO: 67            moltype = RNA   length = 31
FEATURE                  Location/Qualifiers
source                   1..31
                         mol_type = other RNA
                         organism = Arabidopsis thaliana
SEQUENCE: 67
ggcattccat taataacagg ccgttttgat c                                    31

SEQ ID NO: 68            moltype = RNA   length = 31
FEATURE                  Location/Qualifiers
source                   1..31
                         mol_type = other RNA
                         organism = Arabidopsis thaliana
SEQUENCE: 68
ctgttcatgg actagctgta cctaccgttt c                                    31

SEQ ID NO: 69            moltype = RNA   length = 31
FEATURE                  Location/Qualifiers
source                   1..31
                         mol_type = other RNA
                         organism = Arabidopsis thaliana
SEQUENCE: 69
tggcagtttt tgcattaatt attacttcat c                                    31

SEQ ID NO: 70            moltype = RNA   length = 31
FEATURE                  Location/Qualifiers
source                   1..31
                         mol_type = other RNA
                         organism = Arabidopsis thaliana
SEQUENCE: 70
atcaatatac ttttaatgtc gaatcaggat c                                    31

SEQ ID NO: 71            moltype = RNA   length = 31
FEATURE                  Location/Qualifiers
source                   1..31
                         mol_type = other RNA
                         organism = Arabidopsis thaliana
SEQUENCE: 71
tagaaggaac atgtattaca cgtgcaaaat c                                    31

SEQ ID NO: 72            moltype = RNA   length = 31
FEATURE                  Location/Qualifiers
source                   1..31
                         mol_type = other RNA
                         organism = Arabidopsis thaliana
```

-continued

```
SEQUENCE: 72
ataacccaga aataattcgt gtatatattt c                                    31

SEQ ID NO: 73              moltype = RNA   length = 31
FEATURE                    Location/Qualifiers
source                     1..31
                           mol_type = other RNA
                           organism = Arabidopsis thaliana
SEQUENCE: 73
ggaaacaaaa aatatctatt ctagttctat c                                   31

SEQ ID NO: 74              moltype = RNA   length = 31
FEATURE                    Location/Qualifiers
source                     1..31
                           mol_type = other RNA
                           organism = Arabidopsis thaliana
SEQUENCE: 74
acattccttt aatgaattcc cttggaactt c                                   31

SEQ ID NO: 75              moltype = RNA   length = 31
FEATURE                    Location/Qualifiers
source                     1..31
                           mol_type = other RNA
                           organism = Arabidopsis thaliana
SEQUENCE: 75
aaaaacctac tttcttacga ttacgaggtt c                                   31

SEQ ID NO: 76              moltype = RNA   length = 31
FEATURE                    Location/Qualifiers
source                     1..31
                           mol_type = other RNA
                           organism = Arabidopsis thaliana
SEQUENCE: 76
gacataaaaa ggaaattctt tttgaaatat c                                   31

SEQ ID NO: 77              moltype = RNA   length = 31
FEATURE                    Location/Qualifiers
source                     1..31
                           mol_type = other RNA
                           organism = Arabidopsis thaliana
SEQUENCE: 77
aatggaaaat tcatggaaaa ttacaatccc c                                   31

SEQ ID NO: 78              moltype = RNA   length = 31
FEATURE                    Location/Qualifiers
source                     1..31
                           mol_type = other RNA
                           organism = Arabidopsis thaliana
SEQUENCE: 78
aaaaaaaata tcatttgatt cgtcgatcct c                                   31

SEQ ID NO: 79              moltype = RNA   length = 31
FEATURE                    Location/Qualifiers
source                     1..31
                           mol_type = other RNA
                           organism = Arabidopsis thaliana
SEQUENCE: 79
ttatcgcgga attagacctg ctattaacgt c                                   31

SEQ ID NO: 80              moltype = RNA   length = 31
FEATURE                    Location/Qualifiers
source                     1..31
                           mol_type = other RNA
                           organism = Arabidopsis thaliana
SEQUENCE: 80
tgaaagctat gaaacaagta tgcggtagtt c                                   31

SEQ ID NO: 81              moltype = RNA   length = 31
FEATURE                    Location/Qualifiers
source                     1..31
                           mol_type = other RNA
                           organism = Arabidopsis thaliana
SEQUENCE: 81
tcaatagagg tgcaaggctg acagaagtac c                                   31

SEQ ID NO: 82              moltype = RNA   length = 31
FEATURE                    Location/Qualifiers
source                     1..31
                           mol_type = other RNA
```

```
                           organism = Arabidopsis thaliana
SEQUENCE: 82
acagaatctc tcaatatgag aaagccattc c                                            31

SEQ ID NO: 83              moltype = RNA   length = 31
FEATURE                    Location/Qualifiers
source                     1..31
                           mol_type = other RNA
                           organism = Arabidopsis thaliana
SEQUENCE: 83
gtggattaac taacgaaaga aaaatggaac c                                            31

SEQ ID NO: 84              moltype = RNA   length = 31
FEATURE                    Location/Qualifiers
source                     1..31
                           mol_type = other RNA
                           organism = Arabidopsis thaliana
SEQUENCE: 84
atcggaaact tctatttctc attcacaaat c                                            31

SEQ ID NO: 85              moltype = RNA   length = 31
FEATURE                    Location/Qualifiers
source                     1..31
                           mol_type = other RNA
                           organism = Arabidopsis thaliana
SEQUENCE: 85
tggcgcgaaa tccatcattg gctaaacaat c                                            31

SEQ ID NO: 86              moltype = RNA   length = 31
FEATURE                    Location/Qualifiers
source                     1..31
                           mol_type = other RNA
                           organism = Arabidopsis thaliana
SEQUENCE: 86
ctctaaccga agctattgca ttgtttgccc c                                            31

SEQ ID NO: 87              moltype = RNA   length = 31
FEATURE                    Location/Qualifiers
source                     1..31
                           mol_type = other RNA
                           organism = Arabidopsis thaliana
SEQUENCE: 87
ctcaacccga gatgttagaa ggtgcaaaat c                                            31

SEQ ID NO: 88              moltype = RNA   length = 31
FEATURE                    Location/Qualifiers
source                     1..31
                           mol_type = other RNA
                           organism = Arabidopsis thaliana
SEQUENCE: 88
caataggtgc cggagctgct acaattgctt c                                            31

SEQ ID NO: 89              moltype = RNA   length = 31
FEATURE                    Location/Qualifiers
source                     1..31
                           mol_type = other RNA
                           organism = Arabidopsis thaliana
SEQUENCE: 89
ccttaatgct aggttttgaa aaagactttt c                                            31

SEQ ID NO: 90              moltype = RNA   length = 31
FEATURE                    Location/Qualifiers
source                     1..31
                           mol_type = other RNA
                           organism = Arabidopsis thaliana
SEQUENCE: 90
taggttttga aaaagacttt tcatgtcatt c                                            31

SEQ ID NO: 91              moltype = RNA   length = 31
FEATURE                    Location/Qualifiers
source                     1..31
                           mol_type = other RNA
                           organism = Arabidopsis thaliana
SEQUENCE: 91
aaagactttt catgtcattc ccatttaggt c                                            31

SEQ ID NO: 92              moltype = RNA   length = 31
FEATURE                    Location/Qualifiers
source                     1..31
```

-continued

```
                              mol_type = other RNA
                              organism = Arabidopsis thaliana
SEQUENCE: 92
aagactttc atgtcattcc catttaggtc c                                    31

SEQ ID NO: 93          moltype = RNA   length = 31
FEATURE                Location/Qualifiers
source                 1..31
                              mol_type = other RNA
                              organism = Arabidopsis thaliana
SEQUENCE: 93
ttttcatgtc attcccattt aggtccgatt c                                   31

SEQ ID NO: 94          moltype = RNA   length = 31
FEATURE                Location/Qualifiers
source                 1..31
                              mol_type = other RNA
                              organism = Arabidopsis thaliana
SEQUENCE: 94
atgtcattcc catttaggtc cgattcggat c                                   31

SEQ ID NO: 95          moltype = RNA   length = 31
FEATURE                Location/Qualifiers
source                 1..31
                              mol_type = other RNA
                              organism = Arabidopsis thaliana
SEQUENCE: 95
agaagaagta aggaaatgag acgacttttt c                                   31

SEQ ID NO: 96          moltype = RNA   length = 31
FEATURE                Location/Qualifiers
source                 1..31
                              mol_type = other RNA
                              organism = Arabidopsis thaliana
SEQUENCE: 96
tgtcattccc atttaggtcc gattcggatc c                                   31

SEQ ID NO: 97          moltype = RNA   length = 31
FEATURE                Location/Qualifiers
source                 1..31
                              mol_type = other RNA
                              organism = Arabidopsis thaliana
SEQUENCE: 97
attcccattt aggtccgatt cggatccctc c                                   31

SEQ ID NO: 98          moltype = RNA   length = 31
FEATURE                Location/Qualifiers
source                 1..31
                              mol_type = other RNA
                              organism = Arabidopsis thaliana
SEQUENCE: 98
ttaggtccga ttcggatccc tccgttgttt c                                   31

SEQ ID NO: 99          moltype = RNA   length = 31
FEATURE                Location/Qualifiers
source                 1..31
                              mol_type = other RNA
                              organism = Arabidopsis thaliana
SEQUENCE: 99
cgattcggat ccctccgttg tttccttttc c                                   31

SEQ ID NO: 100         moltype = RNA   length = 31
FEATURE                Location/Qualifiers
source                 1..31
                              mol_type = other RNA
                              organism = Arabidopsis thaliana
SEQUENCE: 100
attcggatcc ctccgttgtt tccttttcct c                                   31

SEQ ID NO: 101         moltype = RNA   length = 31
FEATURE                Location/Qualifiers
source                 1..31
                              mol_type = other RNA
                              organism = Arabidopsis thaliana
SEQUENCE: 101
tccctccgtt gtttcctttt cctcctgcac c                                   31

SEQ ID NO: 102         moltype = RNA   length = 31
FEATURE                Location/Qualifiers
```

-continued

```
source                    1..31
                          mol_type = other RNA
                          organism = Arabidopsis thaliana
SEQUENCE: 102
ccgttgtttc cttttcctcc tgcacctttt c                                   31

SEQ ID NO: 103            moltype = RNA   length = 31
FEATURE                   Location/Qualifiers
source                    1..31
                          mol_type = other RNA
                          organism = Arabidopsis thaliana
SEQUENCE: 103
cgttgtttcc ttttcctcct gcaccttttc c                                   31

SEQ ID NO: 104            moltype = RNA   length = 31
FEATURE                   Location/Qualifiers
source                    1..31
                          mol_type = other RNA
                          organism = Arabidopsis thaliana
SEQUENCE: 104
gaaatgagac gactttttct tgaactatat c                                   31

SEQ ID NO: 105            moltype = RNA   length = 31
FEATURE                   Location/Qualifiers
source                    1..31
                          mol_type = other RNA
                          organism = Arabidopsis thaliana
SEQUENCE: 105
aagatcctac ttctacaatt ggtgggtcac c                                   31

SEQ ID NO: 106            moltype = RNA   length = 31
FEATURE                   Location/Qualifiers
source                    1..31
                          mol_type = other RNA
                          organism = Arabidopsis thaliana
SEQUENCE: 106
ttggtgggtc accgggttat tcaaataagt c                                   31

SEQ ID NO: 107            moltype = RNA   length = 31
FEATURE                   Location/Qualifiers
source                    1..31
                          mol_type = other RNA
                          organism = Arabidopsis thaliana
SEQUENCE: 107
ttttctgtgg ttttcccatg ttacaacttt c                                   31

SEQ ID NO: 108            moltype = RNA   length = 31
FEATURE                   Location/Qualifiers
source                    1..31
                          mol_type = other RNA
                          organism = Arabidopsis thaliana
SEQUENCE: 108
tcgtaccaat tcggtcgatc cggaatggat c                                   31

SEQ ID NO: 109            moltype = RNA   length = 31
FEATURE                   Location/Qualifiers
source                    1..31
                          mol_type = other RNA
                          organism = Arabidopsis thaliana
SEQUENCE: 109
ggtcgatccg gaatggatcg gttaaacatt c                                   31

SEQ ID NO: 110            moltype = RNA   length = 31
FEATURE                   Location/Qualifiers
source                    1..31
                          mol_type = other RNA
                          organism = Arabidopsis thaliana
SEQUENCE: 110
gtcgatccgg aatggatcgg ttaaacattc c                                   31

SEQ ID NO: 111            moltype = RNA   length = 31
FEATURE                   Location/Qualifiers
source                    1..31
                          mol_type = other RNA
                          organism = Arabidopsis thaliana
SEQUENCE: 111
attccattag ggagcctggt cttgactctt c                                   31

SEQ ID NO: 112            moltype = RNA   length = 31
```

```
FEATURE              Location/Qualifiers
source               1..31
                     mol_type = other RNA
                     organism = Arabidopsis thaliana
SEQUENCE: 112
gtcttgactc ttctgtgtgg tattcattct c                                      31

SEQ ID NO: 113       moltype = RNA   length = 31
FEATURE              Location/Qualifiers
source               1..31
                     mol_type = other RNA
                     organism = Arabidopsis thaliana
SEQUENCE: 113
tgactcttct gtgtggtatt cattctcgtt c                                      31

SEQ ID NO: 114       moltype = RNA   length = 31
FEATURE              Location/Qualifiers
source               1..31
                     mol_type = other RNA
                     organism = Arabidopsis thaliana
SEQUENCE: 114
gaatcacatc cagcagtggt tggaacagct c                                      31

SEQ ID NO: 115       moltype = RNA   length = 31
FEATURE              Location/Qualifiers
source               1..31
                     mol_type = other RNA
                     organism = Arabidopsis thaliana
SEQUENCE: 115
tccagcagtg gttggaacag ctcgcaaaat c                                      31

SEQ ID NO: 116       moltype = RNA   length = 31
FEATURE              Location/Qualifiers
source               1..31
                     mol_type = other RNA
                     organism = Arabidopsis thaliana
SEQUENCE: 116
ccagcagtgg ttggaacagc tcgcaaaatc c                                      31

SEQ ID NO: 117       moltype = RNA   length = 31
FEATURE              Location/Qualifiers
source               1..31
                     mol_type = other RNA
                     organism = Arabidopsis thaliana
SEQUENCE: 117
gttggaacag ctcgcaaaat ccaaccactt c                                      31

SEQ ID NO: 118       moltype = RNA   length = 31
FEATURE              Location/Qualifiers
source               1..31
                     mol_type = other RNA
                     organism = Arabidopsis thaliana
SEQUENCE: 118
cttcacctac tttattgccc ctaaccgttt c                                      31

SEQ ID NO: 119       moltype = RNA   length = 31
FEATURE              Location/Qualifiers
source               1..31
                     mol_type = other RNA
                     organism = Arabidopsis thaliana
SEQUENCE: 119
tcacctactt tattgcccct aaccgtttct c                                      31

SEQ ID NO: 120       moltype = RNA   length = 31
FEATURE              Location/Qualifiers
source               1..31
                     mol_type = other RNA
                     organism = Arabidopsis thaliana
SEQUENCE: 120
ctattgaaac agaatggttt catgttcttt c                                      31

SEQ ID NO: 121       moltype = RNA   length = 31
FEATURE              Location/Qualifiers
source               1..31
                     mol_type = other RNA
                     organism = Arabidopsis thaliana
SEQUENCE: 121
ttgaaacaga atggtttcat gttctttcat c                                      31
```

-continued

```
SEQ ID NO: 122           moltype = RNA   length = 31
FEATURE                  Location/Qualifiers
source                   1..31
                         mol_type = other RNA
                         organism = Arabidopsis thaliana
SEQUENCE: 122
ggtttcatgt tctttcatcg attggttatt c                                      31

SEQ ID NO: 123           moltype = RNA   length = 31
FEATURE                  Location/Qualifiers
source                   1..31
                         mol_type = other RNA
                         organism = Arabidopsis thaliana
SEQUENCE: 123
ttcatgttct ttcatcgatt ggttattcct c                                      31

SEQ ID NO: 124           moltype = RNA   length = 31
FEATURE                  Location/Qualifiers
source                   1..31
                         mol_type = other RNA
                         organism = Arabidopsis thaliana
SEQUENCE: 124
tctcctccac accaatcacg agtttttctt c                                      31

SEQ ID NO: 125           moltype = RNA   length = 31
FEATURE                  Location/Qualifiers
source                   1..31
                         mol_type = other RNA
                         organism = Arabidopsis thaliana
SEQUENCE: 125
ctccacacca atcacgagtt tttcttcatt c                                      31

SEQ ID NO: 126           moltype = RNA   length = 31
FEATURE                  Location/Qualifiers
source                   1..31
                         mol_type = other RNA
                         organism = Arabidopsis thaliana
SEQUENCE: 126
cacaccaatc acgagttttt cttcattcct c                                      31

SEQ ID NO: 127           moltype = RNA   length = 31
FEATURE                  Location/Qualifiers
source                   1..31
                         mol_type = other RNA
                         organism = Arabidopsis thaliana
SEQUENCE: 127
caccaatcac gagtttttct tcattcctct c                                      31

SEQ ID NO: 128           moltype = RNA   length = 31
FEATURE                  Location/Qualifiers
source                   1..31
                         mol_type = other RNA
                         organism = Arabidopsis thaliana
SEQUENCE: 128
tcttggttgt tcttaacagc gatggctatt c                                      31

SEQ ID NO: 129           moltype = RNA   length = 31
FEATURE                  Location/Qualifiers
source                   1..31
                         mol_type = other RNA
                         organism = Arabidopsis thaliana
SEQUENCE: 129
catttaagtc ttggggtagc accactagat c                                      31

SEQ ID NO: 130           moltype = RNA   length = 31
FEATURE                  Location/Qualifiers
source                   1..31
                         mol_type = other RNA
                         organism = Arabidopsis thaliana
SEQUENCE: 130
attctcgtat tctctatgta catgttcctg c                                      31

SEQ ID NO: 131           moltype = RNA   length = 31
FEATURE                  Location/Qualifiers
source                   1..31
                         mol_type = other RNA
                         organism = Arabidopsis thaliana
SEQUENCE: 131
cgtattctct atgtacatgt cctgcggct c                                       31
```

-continued

```
SEQ ID NO: 132            moltype = RNA   length = 31
FEATURE                   Location/Qualifiers
source                    1..31
                          mol_type = other RNA
                          organism = Arabidopsis thaliana
SEQUENCE: 132
ttcctattaa caaaacatcc cctttatctt c                              31

SEQ ID NO: 133            moltype = RNA   length = 31
FEATURE                   Location/Qualifiers
source                    1..31
                          mol_type = other RNA
                          organism = Arabidopsis thaliana
SEQUENCE: 133
acgttgttta ccttagttac tggggggttt c                              31

SEQ ID NO: 134            moltype = RNA   length = 31
FEATURE                   Location/Qualifiers
source                    1..31
                          mol_type = other RNA
                          organism = Arabidopsis thaliana
SEQUENCE: 134
gggatgctcg tttgacctct gtattcatct c                              31

SEQ ID NO: 135            moltype = RNA   length = 31
FEATURE                   Location/Qualifiers
source                    1..31
                          mol_type = other RNA
                          organism = Arabidopsis thaliana
SEQUENCE: 135
gctcgtttga cctctgtatt catctcgttt c                              31

SEQ ID NO: 136            moltype = RNA   length = 31
FEATURE                   Location/Qualifiers
source                    1..31
                          mol_type = other RNA
                          organism = Arabidopsis thaliana
SEQUENCE: 136
atctcgtttc ttatttacct gggtgcactg c                              31

SEQ ID NO: 137            moltype = RNA   length = 31
FEATURE                   Location/Qualifiers
source                    1..31
                          mol_type = other RNA
                          organism = Arabidopsis thaliana
SEQUENCE: 137
cactgcgttt tcaaaagctt cctgtcgaac c                              31

SEQ ID NO: 138            moltype = RNA   length = 31
FEATURE                   Location/Qualifiers
source                    1..31
                          mol_type = other RNA
                          organism = Arabidopsis thaliana
SEQUENCE: 138
aaaagcttcc tgtcgaaccg gcttctattt c                              31

SEQ ID NO: 139            moltype = RNA   length = 31
FEATURE                   Location/Qualifiers
source                    1..31
                          mol_type = other RNA
                          organism = Arabidopsis thaliana
SEQUENCE: 139
cttcctgtcg aaccggcttc tatttcaatt c                              31

SEQ ID NO: 140            moltype = RNA   length = 31
FEATURE                   Location/Qualifiers
source                    1..31
                          mol_type = other RNA
                          organism = Arabidopsis thaliana
SEQUENCE: 140
ctgtcgaacc ggcttctatt tcaattcgtg c                              31

SEQ ID NO: 141            moltype = RNA   length = 31
FEATURE                   Location/Qualifiers
source                    1..31
                          mol_type = other RNA
                          organism = Arabidopsis thaliana
SEQUENCE: 141
```

-continued

```
aaccggcttc tatttcaatt cgtgctggac c                              31

SEQ ID NO: 142          moltype = RNA   length = 31
FEATURE                 Location/Qualifiers
source                  1..31
                        mol_type = other RNA
                        organism = Arabidopsis thaliana
SEQUENCE: 142
ggcttctatt tcaattcgtg ctggaccgat c                              31

SEQ ID NO: 143          moltype = RNA   length = 31
FEATURE                 Location/Qualifiers
source                  1..31
                        mol_type = other RNA
                        organism = Arabidopsis thaliana
SEQUENCE: 143
ctggaccgat cgatatacca ataataaagt c                              31

SEQ ID NO: 144          moltype = RNA   length = 31
FEATURE                 Location/Qualifiers
source                  1..31
                        mol_type = other RNA
                        organism = Arabidopsis thaliana
SEQUENCE: 144
taaagtcttc agtcaactgg tggaatacat c                              31

SEQ ID NO: 145          moltype = RNA   length = 31
FEATURE                 Location/Qualifiers
source                  1..31
                        mol_type = other RNA
                        organism = Arabidopsis thaliana
SEQUENCE: 145
catcgcatca acctgggagc attagccgat c                              31

SEQ ID NO: 146          moltype = RNA   length = 31
FEATURE                 Location/Qualifiers
source                  1..31
                        mol_type = other RNA
                        organism = Arabidopsis thaliana
SEQUENCE: 146
attagccgat ctggtacatc aatacatgtt c                              31

SEQ ID NO: 147          moltype = RNA   length = 31
FEATURE                 Location/Qualifiers
source                  1..31
                        mol_type = other RNA
                        organism = Arabidopsis thaliana
SEQUENCE: 147
gatctggtac atcaatacat gttcctatgc c                              31

SEQ ID NO: 148          moltype = RNA   length = 31
FEATURE                 Location/Qualifiers
source                  1..31
                        mol_type = other RNA
                        organism = Arabidopsis thaliana
SEQUENCE: 148
ttccaatctt gtctaacttt gctaacttcc c                              31

SEQ ID NO: 149          moltype = RNA   length = 31
FEATURE                 Location/Qualifiers
source                  1..31
                        mol_type = other RNA
                        organism = Arabidopsis thaliana
SEQUENCE: 149
tcttgtctaa ctttgctaac ttccccttct c                              31

SEQ ID NO: 150          moltype = RNA   length = 31
FEATURE                 Location/Qualifiers
source                  1..31
                        mol_type = other RNA
                        organism = Arabidopsis thaliana
SEQUENCE: 150
gtctaacttt gctaacttcc ccttctcaac c                              31

SEQ ID NO: 151          moltype = RNA   length = 31
FEATURE                 Location/Qualifiers
source                  1..31
                        mol_type = other RNA
                        organism = Arabidopsis thaliana
```

-continued

```
SEQUENCE: 151
tctaactttg ctaacttccc cttctcaacc c                                    31

SEQ ID NO: 152         moltype = RNA   length = 31
FEATURE                Location/Qualifiers
source                 1..31
                       mol_type = other RNA
                       organism = Arabidopsis thaliana
SEQUENCE: 152
ctttgctaac ttcccttct caacccgtat c                                     31

SEQ ID NO: 153         moltype = RNA   length = 31
FEATURE                Location/Qualifiers
source                 1..31
                       mol_type = other RNA
                       organism = Arabidopsis thaliana
SEQUENCE: 153
gtatcttgtt tgttctggaa acacgtcttc c                                    31

SEQ ID NO: 154         moltype = RNA   length = 31
FEATURE                Location/Qualifiers
source                 1..31
                       mol_type = other RNA
                       organism = Arabidopsis thaliana
SEQUENCE: 154
tgtttgttct ggaaacacgt cttcctattc c                                    31

SEQ ID NO: 155         moltype = RNA   length = 31
FEATURE                Location/Qualifiers
source                 1..31
                       mol_type = other RNA
                       organism = Arabidopsis thaliana
SEQUENCE: 155
cgtcttccta ttccatcttt tctcgaatct c                                    31

SEQ ID NO: 156         moltype = RNA   length = 31
FEATURE                Location/Qualifiers
source                 1..31
                       mol_type = other RNA
                       organism = Arabidopsis thaliana
SEQUENCE: 156
ctattgaaat ggttcgtcag tagagatgtt c                                    31

SEQ ID NO: 157         moltype = RNA   length = 31
FEATURE                Location/Qualifiers
source                 1..31
                       mol_type = other RNA
                       organism = Arabidopsis thaliana
SEQUENCE: 157
agcacggctg aagtggctat acatacaaat c                                    31

SEQ ID NO: 158         moltype = RNA   length = 31
FEATURE                Location/Qualifiers
source                 1..31
                       mol_type = other RNA
                       organism = Arabidopsis thaliana
SEQUENCE: 158
atacaaatct atttacggat ctatatgctt c                                    31

SEQ ID NO: 159         moltype = RNA   length = 31
FEATURE                Location/Qualifiers
source                 1..31
                       mol_type = other RNA
                       organism = Arabidopsis thaliana
SEQUENCE: 159
aagttccaga acaggaggtt ggtataccac c                                    31

SEQ ID NO: 160         moltype = RNA   length = 31
FEATURE                Location/Qualifiers
source                 1..31
                       mol_type = other RNA
                       organism = Arabidopsis thaliana
SEQUENCE: 160
gtagagatgt tcccacgggt gccccttttt c                                    31

SEQ ID NO: 161         moltype = RNA   length = 31
FEATURE                Location/Qualifiers
source                 1..31
                       mol_type = other RNA
```

-continued

```
                       organism = Arabidopsis thaliana
SEQUENCE: 161
tagagatgtt cccacgggtg ccccttttc c                                  31

SEQ ID NO: 162         moltype = RNA   length = 31
FEATURE                Location/Qualifiers
source                 1..31
                       mol_type = other RNA
                       organism = Arabidopsis thaliana
SEQUENCE: 162
ataatgaaac tgcctttat tttttttatt c                                  31

SEQ ID NO: 163         moltype = RNA   length = 31
FEATURE                Location/Qualifiers
source                 1..31
                       mol_type = other RNA
                       organism = Arabidopsis thaliana
SEQUENCE: 163
taggatttat gttggcttcg ttgggaggct c                                 31

SEQ ID NO: 164         moltype = RNA   length = 31
FEATURE                Location/Qualifiers
source                 1..31
                       mol_type = other RNA
                       organism = Arabidopsis thaliana
SEQUENCE: 164
cagctccaaa aggataagtt gcgttggaat c                                 31

SEQ ID NO: 165         moltype = RNA   length = 31
FEATURE                Location/Qualifiers
source                 1..31
                       mol_type = other RNA
                       organism = Arabidopsis thaliana
SEQUENCE: 165
cttttttccaa tggtactata attcctattc c                                31

SEQ ID NO: 166         moltype = RNA   length = 31
FEATURE                Location/Qualifiers
source                 1..31
                       mol_type = other RNA
                       organism = Arabidopsis thaliana
SEQUENCE: 166
atggtactat aattcctatt cctatctctt c                                 31

SEQ ID NO: 167         moltype = RNA   length = 31
FEATURE                Location/Qualifiers
source                 1..31
                       mol_type = other RNA
                       organism = Arabidopsis thaliana
SEQUENCE: 167
actataattc ctattcctat ctcttcattc c                                 31

SEQ ID NO: 168         moltype = RNA   length = 31
FEATURE                Location/Qualifiers
source                 1..31
                       mol_type = other RNA
                       organism = Arabidopsis thaliana
SEQUENCE: 168
cctatctctt cattccctct tttggtctat c                                 31

SEQ ID NO: 169         moltype = RNA   length = 31
FEATURE                Location/Qualifiers
source                 1..31
                       mol_type = other RNA
                       organism = Arabidopsis thaliana
SEQUENCE: 169
cttattttt ttcgttcccg ttcttcattt c                                  31

SEQ ID NO: 170         moltype = RNA   length = 31
FEATURE                Location/Qualifiers
source                 1..31
                       mol_type = other RNA
                       organism = Arabidopsis thaliana
SEQUENCE: 170
ttattttttt tcgttcccgt tcttcatttc c                                 31

SEQ ID NO: 171         moltype = RNA   length = 31
FEATURE                Location/Qualifiers
source                 1..31
```

```
                          mol_type = other RNA
                          organism = Arabidopsis thaliana
SEQUENCE: 171
caaggggggac ttctcatatt tagaatcttt c                               31

SEQ ID NO: 172         moltype = RNA   length = 31
FEATURE                Location/Qualifiers
source                 1..31
                       mol_type = other RNA
                       organism = Arabidopsis thaliana
SEQUENCE: 172
ttctgcggtg tgctctgttt actattcttt c                               31

SEQ ID NO: 173         moltype = RNA   length = 31
FEATURE                Location/Qualifiers
source                 1..31
                       mol_type = other RNA
                       organism = Arabidopsis thaliana
SEQUENCE: 173
gtgctctgtt tactattctt tcgtactttc c                               31

SEQ ID NO: 174         moltype = RNA   length = 31
FEATURE                Location/Qualifiers
source                 1..31
                       mol_type = other RNA
                       organism = Arabidopsis thaliana
SEQUENCE: 174
ttttcttttt tattattttt atggtcgtgc c                               31

SEQ ID NO: 175         moltype = RNA   length = 31
FEATURE                Location/Qualifiers
source                 1..31
                       mol_type = other RNA
                       organism = Arabidopsis thaliana
SEQUENCE: 175
gcacccccat ttagatttag aaagaagggt c                               31

SEQ ID NO: 176         moltype = RNA   length = 31
FEATURE                Location/Qualifiers
source                 1..31
                       mol_type = other RNA
                       organism = Arabidopsis thaliana
SEQUENCE: 176
tccatttgtg ggaatttgat gatctataaa c                               31

SEQ ID NO: 177         moltype = RNA   length = 31
FEATURE                Location/Qualifiers
source                 1..31
                       mol_type = other RNA
                       organism = Arabidopsis thaliana
SEQUENCE: 177
agaaacaacc accagcgttt ggtgcagcac c                               31

SEQ ID NO: 178         moltype = RNA   length = 31
FEATURE                Location/Qualifiers
source                 1..31
                       mol_type = other RNA
                       organism = Arabidopsis thaliana
SEQUENCE: 178
ggtgcattct tctttctttc cttggtcttt c                               31

SEQ ID NO: 179         moltype = RNA   length = 31
FEATURE                Location/Qualifiers
source                 1..31
                       mol_type = other RNA
                       organism = Arabidopsis thaliana
SEQUENCE: 179
tctttccttg gtctttcgtt ctgtcatatt c                               31

SEQ ID NO: 180         moltype = RNA   length = 31
FEATURE                Location/Qualifiers
source                 1..31
                       mol_type = other RNA
                       organism = Arabidopsis thaliana
SEQUENCE: 180
ccaattacaa cgtattaacc gctaatgcac c                               31

SEQ ID NO: 181         moltype = RNA   length = 31
FEATURE                Location/Qualifiers
```

-continued

```
source                   1..31
                         mol_type = other RNA
                         organism = Arabidopsis thaliana
SEQUENCE: 181
aatcatgagg gtagtatttt attatggtgt c                                    31

SEQ ID NO: 182          moltype = RNA   length = 31
FEATURE                 Location/Qualifiers
source                   1..31
                         mol_type = other RNA
                         organism = Arabidopsis thaliana
SEQUENCE: 182
agggtagtat tttattatgg tgtcggatcc c                                    31

SEQ ID NO: 183          moltype = RNA   length = 31
FEATURE                 Location/Qualifiers
source                   1..31
                         mol_type = other RNA
                         organism = Arabidopsis thaliana
SEQUENCE: 183
tgtcggatcc caaatttta tggatttttt c                                     31

SEQ ID NO: 184          moltype = RNA   length = 31
FEATURE                 Location/Qualifiers
source                   1..31
                         mol_type = other RNA
                         organism = Arabidopsis thaliana
SEQUENCE: 184
cagagccata atgtcttaaa acaaggaggc c                                    31

SEQ ID NO: 185          moltype = RNA   length = 31
FEATURE                 Location/Qualifiers
source                   1..31
                         mol_type = other RNA
                         organism = Arabidopsis thaliana
SEQUENCE: 185
atagggaaag tctttttttt ttttttgtct c                                    31

SEQ ID NO: 186          moltype = RNA   length = 31
FEATURE                 Location/Qualifiers
source                   1..31
                         mol_type = other RNA
                         organism = Arabidopsis thaliana
SEQUENCE: 186
aagtcttttt tttttttttg tctcgaactt c                                    31

SEQ ID NO: 187          moltype = RNA   length = 31
FEATURE                 Location/Qualifiers
source                   1..31
                         mol_type = other RNA
                         organism = Arabidopsis thaliana
SEQUENCE: 187
acttcgtgaa gaactcaatt ttatctctcc c                                    31

SEQ ID NO: 188          moltype = RNA   length = 31
FEATURE                 Location/Qualifiers
source                   1..31
                         mol_type = other RNA
                         organism = Arabidopsis thaliana
SEQUENCE: 188
tatatgaatt ctttcattat tcgttatttc c                                    31

SEQ ID NO: 189          moltype = RNA   length = 31
FEATURE                 Location/Qualifiers
source                   1..31
                         mol_type = other RNA
                         organism = Arabidopsis thaliana
SEQUENCE: 189
gttctacgaa cccttgttga ttctgaactt c                                    31

SEQ ID NO: 190          moltype = RNA   length = 31
FEATURE                 Location/Qualifiers
source                   1..31
                         mol_type = other RNA
                         organism = Arabidopsis thaliana
SEQUENCE: 190
gaaaattaaa aatcctctgg acgcttggcg c                                    31

SEQ ID NO: 191          moltype = RNA   length = 31
```

-continued

```
FEATURE                 Location/Qualifiers
source                  1..31
                        mol_type = other RNA
                        organism = Arabidopsis thaliana
SEQUENCE: 191
aaattaaaaa tcctctggac gcttggcgct c                                 31

SEQ ID NO: 192          moltype = RNA   length = 31
FEATURE                 Location/Qualifiers
source                  1..31
                        mol_type = other RNA
                        organism = Arabidopsis thaliana
SEQUENCE: 192
ggagctcttg gcattgcttt gtttttctct c                                 31

SEQ ID NO: 193          moltype = RNA   length = 31
FEATURE                 Location/Qualifiers
source                  1..31
                        mol_type = other RNA
                        organism = Arabidopsis thaliana
SEQUENCE: 193
gagctcttgg cattgctttg tttttctctc c                                 31

SEQ ID NO: 194          moltype = RNA   length = 31
FEATURE                 Location/Qualifiers
source                  1..31
                        mol_type = other RNA
                        organism = Arabidopsis thaliana
SEQUENCE: 194
gcattgcttt gtttttctct cctttcctat c                                 31

SEQ ID NO: 195          moltype = RNA   length = 31
FEATURE                 Location/Qualifiers
source                  1..31
                        mol_type = other RNA
                        organism = Arabidopsis thaliana
SEQUENCE: 195
tctttgtttg taccgaaccg cttgcagaat c                                 31

SEQ ID NO: 196          moltype = RNA   length = 31
FEATURE                 Location/Qualifiers
source                  1..31
                        mol_type = other RNA
                        organism = Arabidopsis thaliana
SEQUENCE: 196
ccgaaccgct tgcagaatca aatcctgttc c                                 31

SEQ ID NO: 197          moltype = RNA   length = 31
FEATURE                 Location/Qualifiers
source                  1..31
                        mol_type = other RNA
                        organism = Arabidopsis thaliana
SEQUENCE: 197
aatcaaatcc tgttccacaa gatcctatat c                                 31

SEQ ID NO: 198          moltype = RNA   length = 31
FEATURE                 Location/Qualifiers
source                  1..31
                        mol_type = other RNA
                        organism = Arabidopsis thaliana
SEQUENCE: 198
gatgccgccg aaaagaatgg aacgctgctt c                                 31

SEQ ID NO: 199          moltype = RNA   length = 31
FEATURE                 Location/Qualifiers
source                  1..31
                        mol_type = other RNA
                        organism = Arabidopsis thaliana
SEQUENCE: 199
gttggtggtt tttaaccgta ggcatcttgc c                                 31

SEQ ID NO: 200          moltype = RNA   length = 31
FEATURE                 Location/Qualifiers
source                  1..31
                        mol_type = other RNA
                        organism = Arabidopsis thaliana
SEQUENCE: 200
ggaagttggt gggcttatca tgaattaggt c                                 31
```

-continued

```
SEQ ID NO: 201          moltype = RNA   length = 31
FEATURE                 Location/Qualifiers
source                  1..31
                        mol_type = other RNA
                        organism = Arabidopsis thaliana
SEQUENCE: 201
catgaattag gtcggggtgg ctggtggttt c                                          31

SEQ ID NO: 202          moltype = RNA   length = 31
FEATURE                 Location/Qualifiers
source                  1..31
                        mol_type = other RNA
                        organism = Arabidopsis thaliana
SEQUENCE: 202
gatcccgtag aaaatgcttc ttttatgcct c                                          31

SEQ ID NO: 203          moltype = RNA   length = 31
FEATURE                 Location/Qualifiers
source                  1..31
                        mol_type = other RNA
                        organism = Arabidopsis thaliana
SEQUENCE: 203
tcttttatgc ctcgggtatt agccacagct c                                          31

SEQ ID NO: 204          moltype = RNA   length = 31
FEATURE                 Location/Qualifiers
source                  1..31
                        mol_type = other RNA
                        organism = Arabidopsis thaliana
SEQUENCE: 204
acagctcgta ttcattctgt aattttaccc c                                          31

SEQ ID NO: 205          moltype = RNA   length = 31
FEATURE                 Location/Qualifiers
source                  1..31
                        mol_type = other RNA
                        organism = Arabidopsis thaliana
SEQUENCE: 205
taattttacc ccttcttcat tcttggacct c                                          31

SEQ ID NO: 206          moltype = RNA   length = 31
FEATURE                 Location/Qualifiers
source                  1..31
                        mol_type = other RNA
                        organism = Arabidopsis thaliana
SEQUENCE: 206
ggacctcgtt tcttaatatt gtgacttttc c                                          31

SEQ ID NO: 207          moltype = RNA   length = 31
FEATURE                 Location/Qualifiers
source                  1..31
                        mol_type = other RNA
                        organism = Arabidopsis thaliana
SEQUENCE: 207
ttaatattgt gacttttcca tgctgtgtct c                                          31

SEQ ID NO: 208          moltype = RNA   length = 31
FEATURE                 Location/Qualifiers
source                  1..31
                        mol_type = other RNA
                        organism = Arabidopsis thaliana
SEQUENCE: 208
accttttcaa tacggtccgg attgctagct c                                          31

SEQ ID NO: 209          moltype = RNA   length = 31
FEATURE                 Location/Qualifiers
source                  1..31
                        mol_type = other RNA
                        organism = Arabidopsis thaliana
SEQUENCE: 209
ggtggttctt ccttctaatg accggcatat c                                          31

SEQ ID NO: 210          moltype = RNA   length = 31
FEATURE                 Location/Qualifiers
source                  1..31
                        mol_type = other RNA
                        organism = Arabidopsis thaliana
SEQUENCE: 210
ttcgtaatgg aaagaaagag accactactt c                                          31
```

-continued

```
SEQ ID NO: 211            moltype = RNA   length = 31
FEATURE                   Location/Qualifiers
source                    1..31
                          mol_type = other RNA
                          organism = Arabidopsis thaliana
SEQUENCE: 211
agacttacat cacgatatct ttttcttcct c                                 31

SEQ ID NO: 212            moltype = RNA   length = 31
FEATURE                   Location/Qualifiers
source                    1..31
                          mol_type = other RNA
                          organism = Arabidopsis thaliana
SEQUENCE: 212
tttgaaaatg attgttctaa aatggttatt c                                 31

SEQ ID NO: 213            moltype = RNA   length = 31
FEATURE                   Location/Qualifiers
source                    1..31
                          mol_type = other RNA
                          organism = Arabidopsis thaliana
SEQUENCE: 213
ttgaaaatga ttgttctaaa atggttattc c                                 31

SEQ ID NO: 214            moltype = RNA   length = 31
FEATURE                   Location/Qualifiers
source                    1..31
                          mol_type = other RNA
                          organism = Arabidopsis thaliana
SEQUENCE: 214
attgttcatg gaactactat cgagattctt c                                 31

SEQ ID NO: 215            moltype = RNA   length = 31
FEATURE                   Location/Qualifiers
source                    1..31
                          mol_type = other RNA
                          organism = Arabidopsis thaliana
SEQUENCE: 215
tggaactact atcgagattc ttcggaccat c                                 31

SEQ ID NO: 216            moltype = RNA   length = 31
FEATURE                   Location/Qualifiers
source                    1..31
                          mol_type = other RNA
                          organism = Arabidopsis thaliana
SEQUENCE: 216
gaaaatgatt gttctaaaat ggttattcct c                                 31

SEQ ID NO: 217            moltype = RNA   length = 31
FEATURE                   Location/Qualifiers
source                    1..31
                          mol_type = other RNA
                          organism = Arabidopsis thaliana
SEQUENCE: 217
ttcttcggac catctttcct agtatcatct c                                 31

SEQ ID NO: 218            moltype = RNA   length = 31
FEATURE                   Location/Qualifiers
source                    1..31
                          mol_type = other RNA
                          organism = Arabidopsis thaliana
SEQUENCE: 218
actatcaaag ctattggaca tcaatggtat c                                 31

SEQ ID NO: 219            moltype = RNA   length = 31
FEATURE                   Location/Qualifiers
source                    1..31
                          mol_type = other RNA
                          organism = Arabidopsis thaliana
SEQUENCE: 219
ttccagaaga agatctagaa ttgggtcaat c                                 31

SEQ ID NO: 220            moltype = RNA   length = 31
FEATURE                   Location/Qualifiers
source                    1..31
                          mol_type = other RNA
                          organism = Arabidopsis thaliana
SEQUENCE: 220
```

-continued

```
tacgtattat tgtaacatct gctgatgtac c                           31

SEQ ID NO: 221        moltype = RNA   length = 31
FEATURE               Location/Qualifiers
source                1..31
                      mol_type = other RNA
                      organism = Arabidopsis thaliana
SEQUENCE: 221
atgtacctca tagttgggct gtaccttcct c                           31

SEQ ID NO: 222        moltype = RNA   length = 31
FEATURE               Location/Qualifiers
source                1..31
                      mol_type = other RNA
                      organism = Arabidopsis thaliana
SEQUENCE: 222
gtgagatttg tggaactaat catgccttta c                           31

SEQ ID NO: 223        moltype = RNA   length = 31
FEATURE               Location/Qualifiers
source                1..31
                      mol_type = other RNA
                      organism = Arabidopsis thaliana
SEQUENCE: 223
gtgatgcagc ggaaccatgg caattaggat c                           31

SEQ ID NO: 224        moltype = RNA   length = 31
FEATURE               Location/Qualifiers
source                1..31
                      mol_type = other RNA
                      organism = Arabidopsis thaliana
SEQUENCE: 224
gcctttacgt ctatcgtcgt agaagctgtt c                           31

SEQ ID NO: 225        moltype = RNA   length = 31
FEATURE               Location/Qualifiers
source                1..31
                      mol_type = other RNA
                      organism = Arabidopsis thaliana
SEQUENCE: 225
gaagctgttc ctaggaaaga ttatggttct c                           31

SEQ ID NO: 226        moltype = RNA   length = 31
FEATURE               Location/Qualifiers
source                1..31
                      mol_type = other RNA
                      organism = Arabidopsis thaliana
SEQUENCE: 226
accaccgtag gaggtgtgat gtacatgcac c                           31

SEQ ID NO: 227        moltype = RNA   length = 31
FEATURE               Location/Qualifiers
source                1..31
                      mol_type = other RNA
                      organism = Arabidopsis thaliana
SEQUENCE: 227
gacatcatac caaagtcgta caattaggac c                           31

SEQ ID NO: 228        moltype = RNA   length = 31
FEATURE               Location/Qualifiers
source                1..31
                      mol_type = other RNA
                      organism = Arabidopsis thaliana
SEQUENCE: 228
aagtcgtaca attaggacct cgatatggtt c                           31

SEQ ID NO: 229        moltype = RNA   length = 31
FEATURE               Location/Qualifiers
source                1..31
                      mol_type = other RNA
                      organism = Arabidopsis thaliana
SEQUENCE: 229
ttatgttctt ttttgctttt ttttgggctt c                           31

SEQ ID NO: 230        moltype = RNA   length = 31
FEATURE               Location/Qualifiers
source                1..31
                      mol_type = other RNA
                      organism = Arabidopsis thaliana
```

-continued

```
SEQUENCE: 230
tgttcttttt tgctttttt tgggcttctt c                                      31

SEQ ID NO: 231          moltype = RNA   length = 31
FEATURE                 Location/Qualifiers
source                  1..31
                        mol_type = other RNA
                        organism = Arabidopsis thaliana
SEQUENCE: 231
atccttggga aatcccttt cttaataccc c                                      31

SEQ ID NO: 232          moltype = RNA   length = 31
FEATURE                 Location/Qualifiers
source                  1..31
                        mol_type = other RNA
                        organism = Arabidopsis thaliana
SEQUENCE: 232
aaatcccttt tcttaatacc cctattctcc c                                      31

SEQ ID NO: 233          moltype = RNA   length = 31
FEATURE                 Location/Qualifiers
source                  1..31
                        mol_type = other RNA
                        organism = Arabidopsis thaliana
SEQUENCE: 233
ttcggatagt atttatggtt ctaccttttt c                                      31

SEQ ID NO: 234          moltype = RNA   length = 31
FEATURE                 Location/Qualifiers
source                  1..31
                        mol_type = other RNA
                        organism = Arabidopsis thaliana
SEQUENCE: 234
gctccatttg ttactattgg acaaatttct c                                      31

SEQ ID NO: 235          moltype = RNA   length = 31
FEATURE                 Location/Qualifiers
source                  1..31
                        mol_type = other RNA
                        organism = Arabidopsis thaliana
SEQUENCE: 235
agcaatctta gttattggtg ggggttcggt c                                      31

SEQ ID NO: 236          moltype = RNA   length = 31
FEATURE                 Location/Qualifiers
source                  1..31
                        mol_type = other RNA
                        organism = Arabidopsis thaliana
SEQUENCE: 236
tatatgcatg ctaatggggc aagtatgttt c                                      31

SEQ ID NO: 237          moltype = RNA   length = 31
FEATURE                 Location/Qualifiers
source                  1..31
                        mol_type = other RNA
                        organism = Arabidopsis thaliana
SEQUENCE: 237
gtttaccttc atatttttcg tggtctatat c                                      31

SEQ ID NO: 238          moltype = RNA   length = 31
FEATURE                 Location/Qualifiers
source                  1..31
                        mol_type = other RNA
                        organism = Arabidopsis thaliana
SEQUENCE: 238
gccaccttaa atcgttttt tagtcttcat c                                      31

SEQ ID NO: 239          moltype = RNA   length = 31
FEATURE                 Location/Qualifiers
source                  1..31
                        mol_type = other RNA
                        organism = Arabidopsis thaliana
SEQUENCE: 239
tttattttag taggcgccag tcttcttcat c                                      31

SEQ ID NO: 240          moltype = RNA   length = 31
FEATURE                 Location/Qualifiers
source                  1..31
                        mol_type = other RNA
```

-continued

```
                           organism = Arabidopsis thaliana
SEQUENCE: 240
attgtgccgg aatggtattt cctaccgatc c                                  31

SEQ ID NO: 241            moltype = RNA   length = 31
FEATURE                   Location/Qualifiers
source                    1..31
                          mol_type = other RNA
                          organism = Arabidopsis thaliana
SEQUENCE: 241
acaaagcggg aggtgtagcc gcaatagcac c                                  31

SEQ ID NO: 242            moltype = RNA   length = 31
FEATURE                   Location/Qualifiers
source                    1..31
                          mol_type = other RNA
                          organism = Arabidopsis thaliana
SEQUENCE: 242
agccgcaata gcaccagttt ttatatgtct c                                  31

SEQ ID NO: 243            moltype = RNA   length = 31
FEATURE                   Location/Qualifiers
source                    1..31
                          mol_type = other RNA
                          organism = Arabidopsis thaliana
SEQUENCE: 243
tatgtgcgta gttcaagttt tcgaccgatt c                                  31

SEQ ID NO: 244            moltype = RNA   length = 31
FEATURE                   Location/Qualifiers
source                    1..31
                          mol_type = other RNA
                          organism = Arabidopsis thaliana
SEQUENCE: 244
acactgggcg ggatctatca gcagcgaatt c                                  31

SEQ ID NO: 245            moltype = RNA   length = 31
FEATURE                   Location/Qualifiers
source                    1..31
                          mol_type = other RNA
                          organism = Arabidopsis thaliana
SEQUENCE: 245
ctgggcggga tctatcagca gcgaattccc c                                  31

SEQ ID NO: 246            moltype = RNA   length = 31
FEATURE                   Location/Qualifiers
source                    1..31
                          mol_type = other RNA
                          organism = Arabidopsis thaliana
SEQUENCE: 246
gaggtatcat tagccgaaga agaccctggc c                                  31

SEQ ID NO: 247            moltype = RNA   length = 31
FEATURE                   Location/Qualifiers
source                    1..31
                          mol_type = other RNA
                          organism = Arabidopsis thaliana
SEQUENCE: 247
acgtcagcga cgaagacatc gtaaattggt c                                  31

SEQ ID NO: 248            moltype = RNA   length = 31
FEATURE                   Location/Qualifiers
source                    1..31
                          mol_type = other RNA
                          organism = Arabidopsis thaliana
SEQUENCE: 248
cgtcagcgac gaagacatcg taaattggtc c                                  31

SEQ ID NO: 249            moltype = RNA   length = 31
FEATURE                   Location/Qualifiers
source                    1..31
                          mol_type = other RNA
                          organism = Arabidopsis thaliana
SEQUENCE: 249
taaattggtc cgcgggcatc gcgataagtc c                                  31

SEQ ID NO: 250            moltype = RNA   length = 31
FEATURE                   Location/Qualifiers
source                    1..31
```

-continued

```
                              mol_type = other RNA
                              organism = Arabidopsis thaliana
SEQUENCE: 250
gcgataagtc ctctgtccta ctacaggtgc c                                        31

SEQ ID NO: 251         moltype = RNA   length = 31
FEATURE                Location/Qualifiers
source                 1..31
                       mol_type = other RNA
                       organism = Arabidopsis thaliana
SEQUENCE: 251
aacctttatc aagtccgaac gattgtcgac c                                        31

SEQ ID NO: 252         moltype = RNA   length = 31
FEATURE                Location/Qualifiers
source                 1..31
                       mol_type = other RNA
                       organism = Arabidopsis thaliana
SEQUENCE: 252
cgaatataat cctcaagtac tccaaagact c                                        31

SEQ ID NO: 253         moltype = RNA   length = 31
FEATURE                Location/Qualifiers
source                 1..31
                       mol_type = other RNA
                       organism = Arabidopsis thaliana
SEQUENCE: 253
tttcacacca tcgaccgaca tcgactcatc c                                        31

SEQ ID NO: 254         moltype = RNA   length = 31
FEATURE                Location/Qualifiers
source                 1..31
                       mol_type = other RNA
                       organism = Arabidopsis thaliana
SEQUENCE: 254
aagagatcga cgatcccaag ttcttttact c                                        31

SEQ ID NO: 255         moltype = RNA   length = 31
FEATURE                Location/Qualifiers
source                 1..31
                       mol_type = other RNA
                       organism = Arabidopsis thaliana
SEQUENCE: 255
tcccacacag tgtactacta tcggccctac c                                        31

SEQ ID NO: 256         moltype = RNA   length = 31
FEATURE                Location/Qualifiers
source                 1..31
                       mol_type = other RNA
                       organism = Arabidopsis thaliana
SEQUENCE: 256
acgaaattcc gattgttcag agagtcagat c                                        31

SEQ ID NO: 257         moltype = RNA   length = 31
FEATURE                Location/Qualifiers
source                 1..31
                       mol_type = other RNA
                       organism = Arabidopsis thaliana
SEQUENCE: 257
tgaaagaggc gatcagaatg gtactcgaat c                                        31

SEQ ID NO: 258         moltype = RNA   length = 31
FEATURE                Location/Qualifiers
source                 1..31
                       mol_type = other RNA
                       organism = Arabidopsis thaliana
SEQUENCE: 258
tcggattgtt acaacctcta gcagatggtt c                                        31

SEQ ID NO: 259         moltype = RNA   length = 31
FEATURE                Location/Qualifiers
source                 1..31
                       mol_type = other RNA
                       organism = Arabidopsis thaliana
SEQUENCE: 259
ccagatcatg agtaaataaa aaatcgaaaa c                                        31

SEQ ID NO: 260         moltype = RNA   length = 31
FEATURE                Location/Qualifiers
```

-continued

```
source                  1..31
                        mol_type = other RNA
                        organism = Arabidopsis thaliana
SEQUENCE: 260
gtggctacat ttatgttaag tctggtcgct c                               31

SEQ ID NO: 261          moltype = RNA   length = 31
FEATURE                 Location/Qualifiers
source                  1..31
                        mol_type = other RNA
                        organism = Arabidopsis thaliana
SEQUENCE: 261
ccttttgatt atggtatggt attgtcagat c                               31

SEQ ID NO: 262          moltype = RNA   length = 31
FEATURE                 Location/Qualifiers
source                  1..31
                        mol_type = other RNA
                        organism = Arabidopsis thaliana
SEQUENCE: 262
cttttgatta tggtatggta ttgtcagatc c                               31

SEQ ID NO: 263          moltype = RNA   length = 31
FEATURE                 Location/Qualifiers
source                  1..31
                        mol_type = other RNA
                        organism = Arabidopsis thaliana
SEQUENCE: 263
ctaggtgttt atggaattat tatagcgggt c                               31

SEQ ID NO: 264          moltype = RNA   length = 31
FEATURE                 Location/Qualifiers
source                  1..31
                        mol_type = other RNA
                        organism = Arabidopsis thaliana
SEQUENCE: 264
attcttatta ctgtactaat atgtgtaggt c                               31

SEQ ID NO: 265          moltype = RNA   length = 31
FEATURE                 Location/Qualifiers
source                  1..31
                        mol_type = other RNA
                        organism = Arabidopsis thaliana
SEQUENCE: 265
tcttattact gtactaatat gtgtaggtcc c                               31

SEQ ID NO: 266          moltype = RNA   length = 31
FEATURE                 Location/Qualifiers
source                  1..31
                        mol_type = other RNA
                        organism = Arabidopsis thaliana
SEQUENCE: 266
cttattactg tactaatatg tgtaggtccc c                               31

SEQ ID NO: 267          moltype = RNA   length = 31
FEATURE                 Location/Qualifiers
source                  1..31
                        mol_type = other RNA
                        organism = Arabidopsis thaliana
SEQUENCE: 267
ctgtactaat atgtgtaggt ccccgtaatt c                               31

SEQ ID NO: 268          moltype = RNA   length = 31
FEATURE                 Location/Qualifiers
source                  1..31
                        mol_type = other RNA
                        organism = Arabidopsis thaliana
SEQUENCE: 268
agattgtcat ggcgcaaaag cagatatggt c                               31

SEQ ID NO: 269          moltype = RNA   length = 31
FEATURE                 Location/Qualifiers
source                  1..31
                        mol_type = other RNA
                        organism = Arabidopsis thaliana
SEQUENCE: 269
ggcgcaaaag cagatatggt ctggtattcc c                               31

SEQ ID NO: 270          moltype = RNA   length = 31
```

-continued

```
FEATURE                Location/Qualifiers
source                 1..31
                       mol_type = other RNA
                       organism = Arabidopsis thaliana
SEQUENCE: 270
attccctgt tccctgtatt ggttatgttc c                                    31

SEQ ID NO: 271         moltype = RNA   length = 31
FEATURE                Location/Qualifiers
source                 1..31
                       mol_type = other RNA
                       organism = Arabidopsis thaliana
SEQUENCE: 271
ttccctgtat tggttatgtt ccttatttct c                                   31

SEQ ID NO: 272         moltype = RNA   length = 31
FEATURE                Location/Qualifiers
source                 1..31
                       mol_type = other RNA
                       organism = Arabidopsis thaliana
SEQUENCE: 272
cgtttgatct cccagaagcg gaagctgaat c                                   31

SEQ ID NO: 273         moltype = RNA   length = 31
FEATURE                Location/Qualifiers
source                 1..31
                       mol_type = other RNA
                       organism = Arabidopsis thaliana
SEQUENCE: 273
gctataatgt agaatattct tcaatggggt c                                   31

SEQ ID NO: 274         moltype = RNA   length = 31
FEATURE                Location/Qualifiers
source                 1..31
                       mol_type = other RNA
                       organism = Arabidopsis thaliana
SEQUENCE: 274
agtatgccaa tatgatctta atgagtggtc c                                   31

SEQ ID NO: 275         moltype = RNA   length = 31
FEATURE                Location/Qualifiers
source                 1..31
                       mol_type = other RNA
                       organism = Arabidopsis thaliana
SEQUENCE: 275
taatgagtgg tccatgcaca ttgttctttc c                                   31

SEQ ID NO: 276         moltype = RNA   length = 31
FEATURE                Location/Qualifiers
source                 1..31
                       mol_type = other RNA
                       organism = Arabidopsis thaliana
SEQUENCE: 276
catgcacatt gttctttcca ggaggttggc c                                   31

SEQ ID NO: 277         moltype = RNA   length = 31
FEATURE                Location/Qualifiers
source                 1..31
                       mol_type = other RNA
                       organism = Arabidopsis thaliana
SEQUENCE: 277
ttgttctttc caggaggttg gccgcctatc c                                   31

SEQ ID NO: 278         moltype = RNA   length = 31
FEATURE                Location/Qualifiers
source                 1..31
                       mol_type = other RNA
                       organism = Arabidopsis thaliana
SEQUENCE: 278
atcttcccat tttcaagaag atcccgggct c                                   31

SEQ ID NO: 279         moltype = RNA   length = 31
FEATURE                Location/Qualifiers
source                 1..31
                       mol_type = other RNA
                       organism = Arabidopsis thaliana
SEQUENCE: 279
ggctcgatct ggtttagtat caaggttctt c                                   31
```

-continued

```
SEQ ID NO: 280          moltype = RNA    length = 31
FEATURE                 Location/Qualifiers
source                  1..31
                        mol_type = other RNA
                        organism = Arabidopsis thaliana
SEQUENCE: 280
tatcgttatg atcaattaat gggacttggc c                                            31

SEQ ID NO: 281          moltype = RNA    length = 31
FEATURE                 Location/Qualifiers
source                  1..31
                        mol_type = other RNA
                        organism = Arabidopsis thaliana
SEQUENCE: 281
cggaaagtgt tcttgcctct atcattagct c                                            31

SEQ ID NO: 282          moltype = RNA    length = 31
FEATURE                 Location/Qualifiers
source                  1..31
                        mol_type = other RNA
                        organism = Arabidopsis thaliana
SEQUENCE: 282
ttcttgcctc tatcattagc tcgggtagtc c                                            31

SEQ ID NO: 283          moltype = RNA    length = 31
FEATURE                 Location/Qualifiers
source                  1..31
                        mol_type = other RNA
                        organism = Arabidopsis thaliana
SEQUENCE: 283
taatgacgat ggatgcattc gccatagttt c                                            31

SEQ ID NO: 284          moltype = RNA    length = 31
FEATURE                 Location/Qualifiers
source                  1..31
                        mol_type = other RNA
                        organism = Arabidopsis thaliana
SEQUENCE: 284
tgggcgctct agccaaaacg aatcctattt c                                            31

SEQ ID NO: 285          moltype = RNA    length = 31
FEATURE                 Location/Qualifiers
source                  1..31
                        mol_type = other RNA
                        organism = Arabidopsis thaliana
SEQUENCE: 285
accccgtta gccggctttt gtagcaaatt c                                             31

SEQ ID NO: 286          moltype = RNA    length = 31
FEATURE                 Location/Qualifiers
source                  1..31
                        mol_type = other RNA
                        organism = Arabidopsis thaliana
SEQUENCE: 286
gctttgggtt gtggggctta ctttctagcc c                                            31

SEQ ID NO: 287          moltype = RNA    length = 31
FEATURE                 Location/Qualifiers
source                  1..31
                        mol_type = other RNA
                        organism = Arabidopsis thaliana
SEQUENCE: 287
ctttgggttg tggggcttac tttctagccc c                                            31

SEQ ID NO: 288          moltype = RNA    length = 31
FEATURE                 Location/Qualifiers
source                  1..31
                        mol_type = other RNA
                        organism = Arabidopsis thaliana
SEQUENCE: 288
ccagtgggag tagtgactag cgttataggt c                                            31

SEQ ID NO: 289          moltype = RNA    length = 31
FEATURE                 Location/Qualifiers
source                  1..31
                        mol_type = other RNA
                        organism = Arabidopsis thaliana
SEQUENCE: 289
tactagcaat gacttccttt ttcattactt c                                            31
```

-continued

```
SEQ ID NO: 290          moltype = RNA   length = 31
FEATURE                 Location/Qualifiers
source                  1..31
                        mol_type = other RNA
                        organism = Arabidopsis thaliana
SEQUENCE: 290
tagcaatgac ttccttttc attacttcat c                                    31

SEQ ID NO: 291          moltype = RNA   length = 31
FEATURE                 Location/Qualifiers
source                  1..31
                        mol_type = other RNA
                        organism = Arabidopsis thaliana
SEQUENCE: 291
tctcagttac tcatcaaatg gcactcagtt c                                   31

SEQ ID NO: 292          moltype = RNA   length = 31
FEATURE                 Location/Qualifiers
source                  1..31
                        mol_type = other RNA
                        organism = Arabidopsis thaliana
SEQUENCE: 292
tcttttagg agggacaatt ttacatattt c                                    31

SEQ ID NO: 293          moltype = RNA   length = 31
FEATURE                 Location/Qualifiers
source                  1..31
                        mol_type = other RNA
                        organism = Arabidopsis thaliana
SEQUENCE: 293
cggctggtac catttcgatg tgtttcgatt c                                   31

SEQ ID NO: 294          moltype = RNA   length = 31
FEATURE                 Location/Qualifiers
source                  1..31
                        mol_type = other RNA
                        organism = Arabidopsis thaliana
SEQUENCE: 294
ctggtaccat ttcgatgtgt ttcgattctt c                                   31

SEQ ID NO: 295          moltype = RNA   length = 31
FEATURE                 Location/Qualifiers
source                  1..31
                        mol_type = other RNA
                        organism = Arabidopsis thaliana
SEQUENCE: 295
ttgatgcttt tgaattcatt gtattaattc c                                   31

SEQ ID NO: 296          moltype = RNA   length = 31
FEATURE                 Location/Qualifiers
source                  1..31
                        mol_type = other RNA
                        organism = Arabidopsis thaliana
SEQUENCE: 296
gcttttgaat tcattgtatt aattccactt c                                   31

SEQ ID NO: 297          moltype = RNA   length = 31
FEATURE                 Location/Qualifiers
source                  1..31
                        mol_type = other RNA
                        organism = Arabidopsis thaliana
SEQUENCE: 297
gaattcattg tattaattcc acttcctact c                                   31

SEQ ID NO: 298          moltype = RNA   length = 31
FEATURE                 Location/Qualifiers
source                  1..31
                        mol_type = other RNA
                        organism = Arabidopsis thaliana
SEQUENCE: 298
actcgcggta tgctctttat gatctcggct c                                   31

SEQ ID NO: 299          moltype = RNA   length = 31
FEATURE                 Location/Qualifiers
source                  1..31
                        mol_type = other RNA
                        organism = Arabidopsis thaliana
SEQUENCE: 299
```

-continued

```
ctttatgatc tcggctcatg atttaattgc c                                    31

SEQ ID NO: 300           moltype = RNA   length = 31
FEATURE                  Location/Qualifiers
source                   1..31
                         mol_type = other RNA
                         organism = Arabidopsis thaliana
SEQUENCE: 300
atttaattgc catgtattta gctattgagc c                                    31

SEQ ID NO: 301           moltype = RNA   length = 31
FEATURE                  Location/Qualifiers
source                   1..31
                         mol_type = other RNA
                         organism = Arabidopsis thaliana
SEQUENCE: 301
aagaaagtct gaattttcca cggaagccgg c                                    31

SEQ ID NO: 302           moltype = RNA   length = 31
FEATURE                  Location/Qualifiers
source                   1..31
                         mol_type = other RNA
                         organism = Arabidopsis thaliana
SEQUENCE: 302
gaaagtctga attttccacg gaagccggct c                                    31

SEQ ID NO: 303           moltype = RNA   length = 31
FEATURE                  Location/Qualifiers
source                   1..31
                         mol_type = other RNA
                         organism = Arabidopsis thaliana
SEQUENCE: 303
ctcgaaatat ttgatcttag gtgcattttc c                                    31

SEQ ID NO: 304           moltype = RNA   length = 31
FEATURE                  Location/Qualifiers
source                   1..31
                         mol_type = other RNA
                         organism = Arabidopsis thaliana
SEQUENCE: 304
ttcctctgga atattattgt ttggttgttc c                                    31

SEQ ID NO: 305           moltype = RNA   length = 31
FEATURE                  Location/Qualifiers
source                   1..31
                         mol_type = other RNA
                         organism = Arabidopsis thaliana
SEQUENCE: 305
cacacatgtt caatcttttt ttagcggttt c                                    31

SEQ ID NO: 306           moltype = RNA   length = 31
FEATURE                  Location/Qualifiers
source                   1..31
                         mol_type = other RNA
                         organism = Arabidopsis thaliana
SEQUENCE: 306
ccacttcgat caattagcca agattttgac c                                    31

SEQ ID NO: 307           moltype = RNA   length = 31
FEATURE                  Location/Qualifiers
source                   1..31
                         mol_type = other RNA
                         organism = Arabidopsis thaliana
SEQUENCE: 307
gatctagtgg tatttttatg gggattctgt c                                    31

SEQ ID NO: 308           moltype = RNA   length = 31
FEATURE                  Location/Qualifiers
source                   1..31
                         mol_type = other RNA
                         organism = Arabidopsis thaliana
SEQUENCE: 308
tcctttctat tgcgcctaaa atctctattt c                                    31

SEQ ID NO: 309           moltype = RNA   length = 31
FEATURE                  Location/Qualifiers
source                   1..31
                         mol_type = other RNA
                         organism = Arabidopsis thaliana
```

-continued

```
SEQUENCE: 309
tctctatttc tgctaatatt ttacgtgttt c                              31

SEQ ID NO: 310           moltype = RNA   length = 31
FEATURE                  Location/Qualifiers
source                   1..31
                         mol_type = other RNA
                         organism = Arabidopsis thaliana
SEQUENCE: 310
ccccagagat ctttatcatt aatgcaacct c                              31

SEQ ID NO: 311           moltype = RNA   length = 31
FEATURE                  Location/Qualifiers
source                   1..31
                         mol_type = other RNA
                         organism = Arabidopsis thaliana
SEQUENCE: 311
cccagagatc tttatcatta atgcaacctc c                              31

SEQ ID NO: 312           moltype = RNA   length = 31
FEATURE                  Location/Qualifiers
source                   1..31
                         mol_type = other RNA
                         organism = Arabidopsis thaliana
SEQUENCE: 312
ccgccatggc ccaaacgaaa gtcaaaagac c                              31

SEQ ID NO: 313           moltype = RNA   length = 31
FEATURE                  Location/Qualifiers
source                   1..31
                         mol_type = other RNA
                         organism = Arabidopsis thaliana
SEQUENCE: 313
gcccaaacga aagtcaaaag acctctagct c                              31

SEQ ID NO: 314           moltype = RNA   length = 31
FEATURE                  Location/Qualifiers
source                   1..31
                         mol_type = other RNA
                         organism = Arabidopsis thaliana
SEQUENCE: 314
catagttcaa ttggacatgt aggttatatt c                              31

SEQ ID NO: 315           moltype = RNA   length = 31
FEATURE                  Location/Qualifiers
source                   1..31
                         mol_type = other RNA
                         organism = Arabidopsis thaliana
SEQUENCE: 315
gttcaattgg acatgtaggt tatattcgta c                              31

SEQ ID NO: 316           moltype = RNA   length = 31
FEATURE                  Location/Qualifiers
source                   1..31
                         mol_type = other RNA
                         organism = Arabidopsis thaliana
SEQUENCE: 316
tgtcggccta cgaatgtggt ttcgatcctt c                              31

SEQ ID NO: 317           moltype = RNA   length = 31
FEATURE                  Location/Qualifiers
source                   1..31
                         mol_type = other RNA
                         organism = Arabidopsis thaliana
SEQUENCE: 317
ttttatcttg tttcaatttt attttttaatc c                             31

SEQ ID NO: 318           moltype = RNA   length = 31
FEATURE                  Location/Qualifiers
source                   1..31
                         mol_type = other RNA
                         organism = Arabidopsis thaliana
SEQUENCE: 318
tttatcttgt ttcaatttta tttttaatcc c                              31

SEQ ID NO: 319           moltype = RNA   length = 31
FEATURE                  Location/Qualifiers
source                   1..31
                         mol_type = other RNA
```

-continued

```
                        organism = Arabidopsis thaliana
SEQUENCE: 319
gaagtaacct ttttctttcc ttgggcagta c                                   31

SEQ ID NO: 320          moltype = RNA   length = 31
FEATURE                 Location/Qualifiers
source                  1..31
                        mol_type = other RNA
                        organism = Arabidopsis thaliana
SEQUENCE: 320
taaccttttt ctttccttgg gcagtacctc c                                   31

SEQ ID NO: 321          moltype = RNA   length = 31
FEATURE                 Location/Qualifiers
source                  1..31
                        mol_type = other RNA
                        organism = Arabidopsis thaliana
SEQUENCE: 321
ctgtaatgat gtcagaattt gcaccaattt c                                   31

SEQ ID NO: 322          moltype = RNA   length = 31
FEATURE                 Location/Qualifiers
source                  1..31
                        mol_type = other RNA
                        organism = Arabidopsis thaliana
SEQUENCE: 322
gatttctata tgaatggaaa aggggtgctt c                                   31

SEQ ID NO: 323          moltype = RNA   length = 31
FEATURE                 Location/Qualifiers
source                  1..31
                        mol_type = other RNA
                        organism = Arabidopsis thaliana
SEQUENCE: 323
ctatatgaat ggaaaagggg tgcttcggat c                                   31

SEQ ID NO: 324          moltype = RNA   length = 31
FEATURE                 Location/Qualifiers
source                  1..31
                        mol_type = other RNA
                        organism = Arabidopsis thaliana
SEQUENCE: 324
ttagtgatta gtctgctagt ttctttgatc c                                   31

SEQ ID NO: 325          moltype = RNA   length = 31
FEATURE                 Location/Qualifiers
source                  1..31
                        mol_type = other RNA
                        organism = Arabidopsis thaliana
SEQUENCE: 325
gattagtctg ctagtttctt tgatcctact c                                   31

SEQ ID NO: 326          moltype = RNA   length = 31
FEATURE                 Location/Qualifiers
source                  1..31
                        mol_type = other RNA
                        organism = Arabidopsis thaliana
SEQUENCE: 326
gcgagaaaac aaagtgggct gtaatgatgt c                                   31

SEQ ID NO: 327          moltype = RNA   length = 31
FEATURE                 Location/Qualifiers
source                  1..31
                        mol_type = other RNA
                        organism = Arabidopsis thaliana
SEQUENCE: 327
tttctttgat cctactcggt gttccttttc c                                   31

SEQ ID NO: 328          moltype = RNA   length = 31
FEATURE                 Location/Qualifiers
source                  1..31
                        mol_type = other RNA
                        organism = Arabidopsis thaliana
SEQUENCE: 328
acatacaggg aattggaggt agcattctac c                                   31

SEQ ID NO: 329          moltype = RNA   length = 31
FEATURE                 Location/Qualifiers
source                  1..31
```

-continued

```
                          mol_type = other RNA
                          organism = Arabidopsis thaliana
SEQUENCE: 329
attctaccga tgttaagtca tggactggtt c                               31

SEQ ID NO: 330          moltype = RNA   length = 31
FEATURE                 Location/Qualifiers
source                  1..31
                        mol_type = other RNA
                        organism = Arabidopsis thaliana
SEQUENCE: 330
ttcttttcat tccaaattca agaatacgac c                               31

SEQ ID NO: 331          moltype = RNA   length = 31
FEATURE                 Location/Qualifiers
source                  1..31
                        mol_type = other RNA
                        organism = Arabidopsis thaliana
SEQUENCE: 331
ccgacataag actcgacttg ttagatatta c                               31

SEQ ID NO: 332          moltype = RNA   length = 31
FEATURE                 Location/Qualifiers
source                  1..31
                        mol_type = other RNA
                        organism = Arabidopsis thaliana
SEQUENCE: 332
tacggaggtt tagtgagcac catgccgaat c                               31

SEQ ID NO: 333          moltype = RNA   length = 31
FEATURE                 Location/Qualifiers
source                  1..31
                        mol_type = other RNA
                        organism = Arabidopsis thaliana
SEQUENCE: 333
cggaggttta gtgagcacca tgccgaatct c                               31

SEQ ID NO: 334          moltype = RNA   length = 31
FEATURE                 Location/Qualifiers
source                  1..31
                        mol_type = other RNA
                        organism = Arabidopsis thaliana
SEQUENCE: 334
gaggtttagt gagcaccatg ccgaatctct c                               31

SEQ ID NO: 335          moltype = RNA   length = 31
FEATURE                 Location/Qualifiers
source                  1..31
                        mol_type = other RNA
                        organism = Arabidopsis thaliana
SEQUENCE: 335
ccatgccgaa tctctctacc attttctttt c                               31

SEQ ID NO: 336          moltype = RNA   length = 31
FEATURE                 Location/Qualifiers
source                  1..31
                        mol_type = other RNA
                        organism = Arabidopsis thaliana
SEQUENCE: 336
tcttttcttt tactttggcc aatatgagtt c                               31

SEQ ID NO: 337          moltype = RNA   length = 31
FEATURE                 Location/Qualifiers
source                  1..31
                        mol_type = other RNA
                        organism = Arabidopsis thaliana
SEQUENCE: 337
tggtactagc agctttatcg gggaatttct c                               31

SEQ ID NO: 338          moltype = RNA   length = 31
FEATURE                 Location/Qualifiers
source                  1..31
                        mol_type = other RNA
                        organism = Arabidopsis thaliana
SEQUENCE: 338
tcaagaatac gaccgatacg attaattggt c                               31

SEQ ID NO: 339          moltype = RNA   length = 31
FEATURE                 Location/Qualifiers
```

-continued

```
source                1..31
                      mol_type = other RNA
                      organism = Arabidopsis thaliana
SEQUENCE: 339
aacctgattt cctccataaa ttctccgatt c                                   31

SEQ ID NO: 340        moltype = RNA   length = 31
FEATURE               Location/Qualifiers
source                1..31
                      mol_type = other RNA
                      organism = Arabidopsis thaliana
SEQUENCE: 340
aattctccga ttcaaatggc agagaagttt c                                   31

SEQ ID NO: 341        moltype = RNA   length = 31
FEATURE               Location/Qualifiers
source                1..31
                      mol_type = other RNA
                      organism = Arabidopsis thaliana
SEQUENCE: 341
ttccatattt atacctttc ttgttggact c                                    31

SEQ ID NO: 342        moltype = RNA   length = 31
FEATURE               Location/Qualifiers
source                1..31
                      mol_type = other RNA
                      organism = Arabidopsis thaliana
SEQUENCE: 342
atatttatac cttttcttgt tggactcgtt c                                   31

SEQ ID NO: 343        moltype = RNA   length = 31
FEATURE               Location/Qualifiers
source                1..31
                      mol_type = other RNA
                      organism = Arabidopsis thaliana
SEQUENCE: 343
tttcttgttg gactcgttcg gatgggtgtt c                                   31

SEQ ID NO: 344        moltype = RNA   length = 31
FEATURE               Location/Qualifiers
source                1..31
                      mol_type = other RNA
                      organism = Arabidopsis thaliana
SEQUENCE: 344
ttcggatggg tgttcacccc aaagtgttcc c                                   31

SEQ ID NO: 345        moltype = RNA   length = 31
FEATURE               Location/Qualifiers
source                1..31
                      mol_type = other RNA
                      organism = Arabidopsis thaliana
SEQUENCE: 345
gtgcctctct tattactttt ttgtattctc c                                   31

SEQ ID NO: 346        moltype = RNA   length = 31
FEATURE               Location/Qualifiers
source                1..31
                      mol_type = other RNA
                      organism = Arabidopsis thaliana
SEQUENCE: 346
ctcttattac tttttgtat tctcctgttc c                                    31

SEQ ID NO: 347        moltype = RNA   length = 31
FEATURE               Location/Qualifiers
source                1..31
                      mol_type = other RNA
                      organism = Arabidopsis thaliana
SEQUENCE: 347
cttattactt ttttgtattc tcctgttcct c                                   31

SEQ ID NO: 348        moltype = RNA   length = 31
FEATURE               Location/Qualifiers
source                1..31
                      mol_type = other RNA
                      organism = Arabidopsis thaliana
SEQUENCE: 348
ggatacaatt cgactcttct acggccaaat c                                   31

SEQ ID NO: 349        moltype = RNA   length = 31
```

-continued

| FEATURE | Location/Qualifiers |
|---|---|
| source | 1..31 |
| | mol_type = other RNA |
| | organism = Arabidopsis thaliana |

SEQUENCE: 349
ctatgttaga acatttctgt gaatgctatt c                                        31

| SEQ ID NO: 350 | moltype = RNA   length = 31 |
| FEATURE | Location/Qualifiers |
| source | 1..31 |
| | mol_type = other RNA |
| | organism = Arabidopsis thaliana |

SEQUENCE: 350
tgaccacatt tctgatccct atttgcattt c                                        31

| SEQ ID NO: 351 | moltype = RNA   length = 31 |
| FEATURE | Location/Qualifiers |
| source | 1..31 |
| | mol_type = other RNA |
| | organism = Arabidopsis thaliana |

SEQUENCE: 351
gtatgagaag ttatgggaaa gagtatatta c                                        31

| SEQ ID NO: 352 | moltype = RNA   length = 31 |
| FEATURE | Location/Qualifiers |
| source | 1..31 |
| | mol_type = other RNA |
| | organism = Arabidopsis thaliana |

SEQUENCE: 352
gggaaagagt atattacagc atttttaatt c                                        31

| SEQ ID NO: 353 | moltype = RNA   length = 31 |
| FEATURE | Location/Qualifiers |
| source | 1..31 |
| | mol_type = other RNA |
| | organism = Arabidopsis thaliana |

SEQUENCE: 353
aattcgtgaa tttctaatga tcgccgtgtt c                                        31

| SEQ ID NO: 354 | moltype = RNA   length = 31 |
| FEATURE | Location/Qualifiers |
| source | 1..31 |
| | mol_type = other RNA |
| | organism = Arabidopsis thaliana |

SEQUENCE: 354
attcgtgaat ttctaatgat cgccgtgttc c                                        31

| SEQ ID NO: 355 | moltype = RNA   length = 31 |
| FEATURE | Location/Qualifiers |
| source | 1..31 |
| | mol_type = other RNA |
| | organism = Arabidopsis thaliana |

SEQUENCE: 355
atgatcgccg tgttccgcat gctagatctt c                                        31

| SEQ ID NO: 356 | moltype = RNA   length = 31 |
| FEATURE | Location/Qualifiers |
| source | 1..31 |
| | mol_type = other RNA |
| | organism = Arabidopsis thaliana |

SEQUENCE: 356
atgctagatc ttctactatt ctatgttttt c                                        31

| SEQ ID NO: 357 | moltype = RNA   length = 31 |
| FEATURE | Location/Qualifiers |
| source | 1..31 |
| | mol_type = other RNA |
| | organism = Arabidopsis thaliana |

SEQUENCE: 357
tgctagatct tctactattc tatgtttttc c                                        31

| SEQ ID NO: 358 | moltype = RNA   length = 31 |
| FEATURE | Location/Qualifiers |
| source | 1..31 |
| | mol_type = other RNA |
| | organism = Arabidopsis thaliana |

SEQUENCE: 358
tactattcta tgttttccc gaaagcgtgc c                                         31

-continued

```
SEQ ID NO: 359            moltype = RNA   length = 31
FEATURE                   Location/Qualifiers
source                    1..31
                          mol_type = other RNA
                          organism = Arabidopsis thaliana
SEQUENCE: 359
tccaaacagg aaccaccgat ttacaaatat c                                   31

SEQ ID NO: 360            moltype = RNA   length = 31
FEATURE                   Location/Qualifiers
source                    1..31
                          mol_type = other RNA
                          organism = Arabidopsis thaliana
SEQUENCE: 360
agcggcgcca aatctttcta tggattgctt c                                   31

SEQ ID NO: 361            moltype = RNA   length = 31
FEATURE                   Location/Qualifiers
source                    1..31
                          mol_type = other RNA
                          organism = Arabidopsis thaliana
SEQUENCE: 361
ttattctgtg tcctgtgcta ggaagcatta c                                   31

SEQ ID NO: 362            moltype = RNA   length = 31
FEATURE                   Location/Qualifiers
source                    1..31
                          mol_type = other RNA
                          organism = Arabidopsis thaliana
SEQUENCE: 362
cggcaggatc cgtcatcttg gcaggaattc c                                   31

SEQ ID NO: 363            moltype = RNA   length = 31
FEATURE                   Location/Qualifiers
source                    1..31
                          mol_type = other RNA
                          organism = Arabidopsis thaliana
SEQUENCE: 363
ttggcaggaa ttcctttaaa atttggaacc c                                   31

SEQ ID NO: 364            moltype = RNA   length = 31
FEATURE                   Location/Qualifiers
source                    1..31
                          mol_type = other RNA
                          organism = Arabidopsis thaliana
SEQUENCE: 364
tacccatgtt tcccgaagcg acactttgtt c                                   31

SEQ ID NO: 365            moltype = RNA   length = 31
FEATURE                   Location/Qualifiers
source                    1..31
                          mol_type = other RNA
                          organism = Arabidopsis thaliana
SEQUENCE: 365
tcctgtgcta ggaagcatta ctcttctttt c                                   31

SEQ ID NO: 366            moltype = RNA   length = 31
FEATURE                   Location/Qualifiers
source                    1..31
                          mol_type = other RNA
                          organism = Arabidopsis thaliana
SEQUENCE: 366
ttgctataat atatacttcc ttgaccactt c                                   31

SEQ ID NO: 367            moltype = RNA   length = 31
FEATURE                   Location/Qualifiers
source                    1..31
                          mol_type = other RNA
                          organism = Arabidopsis thaliana
SEQUENCE: 367
tgaatctggt gactattggt atgtttagtc c                                   31

SEQ ID NO: 368            moltype = RNA   length = 31
FEATURE                   Location/Qualifiers
source                    1..31
                          mol_type = other RNA
                          organism = Arabidopsis thaliana
SEQUENCE: 368
aatagacgaa atattcctat tatgtcaatg c                                   31
```

```
SEQ ID NO: 369            moltype = RNA   length = 31
FEATURE                   Location/Qualifiers
source                    1..31
                          mol_type = other RNA
                          organism = Arabidopsis thaliana
SEQUENCE: 369
atattcctat tatgtcaatg ccaattgaat c                                      31

SEQ ID NO: 370            moltype = RNA   length = 31
FEATURE                   Location/Qualifiers
source                    1..31
                          mol_type = other RNA
                          organism = Arabidopsis thaliana
SEQUENCE: 370
caattgaatc aatgttatta gctgtgaatt c                                      31

SEQ ID NO: 371            moltype = RNA   length = 31
FEATURE                   Location/Qualifiers
source                    1..31
                          mol_type = other RNA
                          organism = Arabidopsis thaliana
SEQUENCE: 371
attcgaactt tttggtattt tccgtttctt c                                      31

SEQ ID NO: 372            moltype = RNA   length = 31
FEATURE                   Location/Qualifiers
source                    1..31
                          mol_type = other RNA
                          organism = Arabidopsis thaliana
SEQUENCE: 372
cggatgatat gatgggtcaa gtatttgctt c                                      31

SEQ ID NO: 373            moltype = RNA   length = 31
FEATURE                   Location/Qualifiers
source                    1..31
                          mol_type = other RNA
                          organism = Arabidopsis thaliana
SEQUENCE: 373
tgatgggtca agtatttgct tcattggttc c                                      31

SEQ ID NO: 374            moltype = RNA   length = 31
FEATURE                   Location/Qualifiers
source                    1..31
                          mol_type = other RNA
                          organism = Arabidopsis thaliana
SEQUENCE: 374
tcaaatattt cacattttct atgattattt c                                      31

SEQ ID NO: 375            moltype = RNA   length = 31
FEATURE                   Location/Qualifiers
source                    1..31
                          mol_type = other RNA
                          organism = Arabidopsis thaliana
SEQUENCE: 375
ttttctatga ttatttctat tttaggtatt c                                      31

SEQ ID NO: 376            moltype = RNA   length = 31
FEATURE                   Location/Qualifiers
source                    1..31
                          mol_type = other RNA
                          organism = Arabidopsis thaliana
SEQUENCE: 376
ggggaatcct ccttaataga cgaaatattc c                                      31

SEQ ID NO: 377            moltype = RNA   length = 31
FEATURE                   Location/Qualifiers
source                    1..31
                          mol_type = other RNA
                          organism = Arabidopsis thaliana
SEQUENCE: 377
tccttaatag acgaaatatt cctattatgt c                                      31

SEQ ID NO: 378            moltype = RNA   length = 31
FEATURE                   Location/Qualifiers
source                    1..31
                          mol_type = other RNA
                          organism = Arabidopsis thaliana
SEQUENCE: 378
```

-continued

```
tgggaacttt gctttctggt tgggaagtgt c                              31

SEQ ID NO: 379          moltype = RNA   length = 31
FEATURE                 Location/Qualifiers
source                  1..31
                        mol_type = other RNA
                        organism = Arabidopsis thaliana
SEQUENCE: 379
gtttaggtac caatttttgg gccaattccc c                              31

SEQ ID NO: 380          moltype = RNA   length = 31
FEATURE                 Location/Qualifiers
source                  1..31
                        mol_type = other RNA
                        organism = Arabidopsis thaliana
SEQUENCE: 380
tatctttgat tgcttttat gaagtcgcac c                               31

SEQ ID NO: 381          moltype = RNA   length = 31
FEATURE                 Location/Qualifiers
source                  1..31
                        mol_type = other RNA
                        organism = Arabidopsis thaliana
SEQUENCE: 381
ccgaatccga gtttgctgct ccaaccatta c                              31

SEQ ID NO: 382          moltype = RNA   length = 31
FEATURE                 Location/Qualifiers
source                  1..31
                        mol_type = other RNA
                        organism = Arabidopsis thaliana
SEQUENCE: 382
ccaaactaat acctattctg tttagtactt c                              31

SEQ ID NO: 383          moltype = RNA   length = 31
FEATURE                 Location/Qualifiers
source                  1..31
                        mol_type = other RNA
                        organism = Arabidopsis thaliana
SEQUENCE: 383
caggtgcttt tgttgcgtat aatgtaaatc c                              31

SEQ ID NO: 384          moltype = RNA   length = 31
FEATURE                 Location/Qualifiers
source                  1..31
                        mol_type = other RNA
                        organism = Arabidopsis thaliana
SEQUENCE: 384
ctttcaaact agtacttttt gtaatcgact c                              31

SEQ ID NO: 385          moltype = RNA   length = 31
FEATURE                 Location/Qualifiers
source                  1..31
                        mol_type = other RNA
                        organism = Arabidopsis thaliana
SEQUENCE: 385
agttttgaat gactttctag tcagatcgtt c                              31

SEQ ID NO: 386          moltype = RNA   length = 31
FEATURE                 Location/Qualifiers
source                  1..31
                        mol_type = other RNA
                        organism = Arabidopsis thaliana
SEQUENCE: 386
atcattatgc ctttgcaatg ttacttggtt c                              31

SEQ ID NO: 387          moltype = RNA   length = 31
FEATURE                 Location/Qualifiers
source                  1..31
                        mol_type = other RNA
                        organism = Arabidopsis thaliana
SEQUENCE: 387
tacttggttc aactctattt gtgacctttt c                              31

SEQ ID NO: 388          moltype = RNA   length = 31
FEATURE                 Location/Qualifiers
source                  1..31
                        mol_type = other RNA
                        organism = Arabidopsis thaliana
```

```
SEQUENCE: 388
cttggttcaa ctctatttgt gacctttct c                                              31

SEQ ID NO: 389          moltype = RNA   length = 31
FEATURE                 Location/Qualifiers
source                  1..31
                        mol_type = other RNA
                        organism = Arabidopsis thaliana
SEQUENCE: 389
tctatttgtg accttttctc gtatgtggga c                                             31

SEQ ID NO: 390          moltype = RNA   length = 31
FEATURE                 Location/Qualifiers
source                  1..31
                        mol_type = other RNA
                        organism = Arabidopsis thaliana
SEQUENCE: 390
actctctatc ttcttgggta gataatcgat c                                             31

SEQ ID NO: 391          moltype = RNA   length = 31
FEATURE                 Location/Qualifiers
source                  1..31
                        mol_type = other RNA
                        organism = Arabidopsis thaliana
SEQUENCE: 391
atgcttcttg gggcttcttg ttcgatagcc c                                             31

SEQ ID NO: 392          moltype = RNA   length = 31
FEATURE                 Location/Qualifiers
source                  1..31
                        mol_type = other RNA
                        organism = Arabidopsis thaliana
SEQUENCE: 392
cgaccgtagt gatgttaatt gtggttacat c                                             31

SEQ ID NO: 393          moltype = RNA   length = 31
FEATURE                 Location/Qualifiers
source                  1..31
                        mol_type = other RNA
                        organism = Arabidopsis thaliana
SEQUENCE: 393
agccctcgat ttatgtgtta tttatccatt c                                             31

SEQ ID NO: 394          moltype = RNA   length = 31
FEATURE                 Location/Qualifiers
source                  1..31
                        mol_type = other RNA
                        organism = Arabidopsis thaliana
SEQUENCE: 394
gttatttatc cattcttact tttttttatgc c                                            31

SEQ ID NO: 395          moltype = RNA   length = 31
FEATURE                 Location/Qualifiers
source                  1..31
                        mol_type = other RNA
                        organism = Arabidopsis thaliana
SEQUENCE: 395
ttatgccaat gttggtgact ggagataact c                                             31

SEQ ID NO: 396          moltype = RNA   length = 31
FEATURE                 Location/Qualifiers
source                  1..31
                        mol_type = other RNA
                        organism = Arabidopsis thaliana
SEQUENCE: 396
ttacacgact tcaggcagat aaagcagcta c                                             31

SEQ ID NO: 397          moltype = RNA   length = 31
FEATURE                 Location/Qualifiers
source                  1..31
                        mol_type = other RNA
                        organism = Arabidopsis thaliana
SEQUENCE: 397
taggtgattt tggattagct cttgggattt c                                             31

SEQ ID NO: 398          moltype = RNA   length = 31
FEATURE                 Location/Qualifiers
source                  1..31
                        mol_type = other RNA
```

-continued

```
                            organism = Arabidopsis thaliana
SEQUENCE: 398
gattttggat tagctcttgg gatttcgggt c                                      31

SEQ ID NO: 399          moltype = RNA   length = 31
FEATURE                 Location/Qualifiers
source                  1..31
                        mol_type = other RNA
                        organism = Arabidopsis thaliana
SEQUENCE: 399
caaacagtag acttttcaac cattttttgct c                                     31

SEQ ID NO: 400          moltype = RNA   length = 31
FEATURE                 Location/Qualifiers
source                  1..31
                        mol_type = other RNA
                        organism = Arabidopsis thaliana
SEQUENCE: 400
acttttcaac cattttttgct cgtgctagtg c                                     31

SEQ ID NO: 401          moltype = RNA   length = 31
FEATURE                 Location/Qualifiers
source                  1..31
                        mol_type = other RNA
                        organism = Arabidopsis thaliana
SEQUENCE: 401
cttttcaacc attttttgctc gtgctagtgc c                                     31

SEQ ID NO: 402          moltype = RNA   length = 31
FEATURE                 Location/Qualifiers
source                  1..31
                        mol_type = other RNA
                        organism = Arabidopsis thaliana
SEQUENCE: 402
gtgctagtgc ccccagaaat tcttggattt c                                      31

SEQ ID NO: 403          moltype = RNA   length = 31
FEATURE                 Location/Qualifiers
source                  1..31
                        mol_type = other RNA
                        organism = Arabidopsis thaliana
SEQUENCE: 403
aatgccataa gtcttatttg tattttactt c                                      31

SEQ ID NO: 404          moltype = RNA   length = 31
FEATURE                 Location/Qualifiers
source                  1..31
                        mol_type = other RNA
                        organism = Arabidopsis thaliana
SEQUENCE: 404
gtgctgttgg gaaatccgcg cagataggat c                                      31

SEQ ID NO: 405          moltype = RNA   length = 31
FEATURE                 Location/Qualifiers
source                  1..31
                        mol_type = other RNA
                        organism = Arabidopsis thaliana
SEQUENCE: 405
aatccgcgca gataggatcg catacttggt c                                      31

SEQ ID NO: 406          moltype = RNA   length = 31
FEATURE                 Location/Qualifiers
source                  1..31
                        mol_type = other RNA
                        organism = Arabidopsis thaliana
SEQUENCE: 406
ctatggaggg tcccactcca gtatccgctt c                                      31

SEQ ID NO: 407          moltype = RNA   length = 31
FEATURE                 Location/Qualifiers
source                  1..31
                        mol_type = other RNA
                        organism = Arabidopsis thaliana
SEQUENCE: 407
atagcaaggt gctccccttt atttgaatac c                                      31

SEQ ID NO: 408          moltype = RNA   length = 31
FEATURE                 Location/Qualifiers
source                  1..31
```

-continued

```
                          mol_type = other RNA
                          organism = Arabidopsis thaliana
SEQUENCE: 408
acccacctac ggctttgatt gttattactt c                                               31

SEQ ID NO: 409          moltype = RNA   length = 31
FEATURE                 Location/Qualifiers
source                  1..31
                        mol_type = other RNA
                        organism = Arabidopsis thaliana
SEQUENCE: 409
ctttgattgt tattacttct gcaggagcta c                                               31

SEQ ID NO: 410          moltype = RNA   length = 31
FEATURE                 Location/Qualifiers
source                  1..31
                        mol_type = other RNA
                        organism = Arabidopsis thaliana
SEQUENCE: 410
cattccgttt tgtttcccat cccagtcttt c                                               31

SEQ ID NO: 411          moltype = RNA   length = 31
FEATURE                 Location/Qualifiers
source                  1..31
                        mol_type = other RNA
                        organism = Arabidopsis thaliana
SEQUENCE: 411
taggtctcga cttcttcgct atgatcttcc c                                               31

SEQ ID NO: 412          moltype = RNA   length = 31
FEATURE                 Location/Qualifiers
source                  1..31
                        mol_type = other RNA
                        organism = Arabidopsis thaliana
SEQUENCE: 412
gacttcttcg ctatgatctt cccagtagtt c                                               31

SEQ ID NO: 413          moltype = RNA   length = 31
FEATURE                 Location/Qualifiers
source                  1..31
                        mol_type = other RNA
                        organism = Arabidopsis thaliana
SEQUENCE: 413
cagtagttca tataggagct atagccgttt c                                               31

SEQ ID NO: 414          moltype = RNA   length = 31
FEATURE                 Location/Qualifiers
source                  1..31
                        mol_type = other RNA
                        organism = Arabidopsis thaliana
SEQUENCE: 414
gtaccatgat actttctgtt ttgtcgagcc c                                               31

SEQ ID NO: 415          moltype = RNA   length = 31
FEATURE                 Location/Qualifiers
source                  1..31
                        mol_type = other RNA
                        organism = Arabidopsis thaliana
SEQUENCE: 415
cattgggcaa tttactttat acctactatt c                                               31

SEQ ID NO: 416          moltype = RNA   length = 31
FEATURE                 Location/Qualifiers
source                  1..31
                        mol_type = other RNA
                        organism = Arabidopsis thaliana
SEQUENCE: 416
tatacctact attctgtctg gtttttggtt c                                               31

SEQ ID NO: 417          moltype = RNA   length = 31
FEATURE                 Location/Qualifiers
source                  1..31
                        mol_type = other RNA
                        organism = Arabidopsis thaliana
SEQUENCE: 417
gccctgcttt ggtctctggt ttgatggttg c                                               31

SEQ ID NO: 418          moltype = RNA   length = 31
FEATURE                 Location/Qualifiers
```

-continued

```
source                    1..31
                          mol_type = other RNA
                          organism = Arabidopsis thaliana
SEQUENCE: 418
gctaaaaatc cggtacattc cgttttgttt c                                  31

SEQ ID NO: 419           moltype = RNA   length = 31
FEATURE                  Location/Qualifiers
source                   1..31
                         mol_type = other RNA
                         organism = Arabidopsis thaliana
SEQUENCE: 419
ctaaaaatcc ggtacattcc gttttgtttc c                                  31

SEQ ID NO: 420           moltype = RNA   length = 31
FEATURE                  Location/Qualifiers
source                   1..31
                         mol_type = other RNA
                         organism = Arabidopsis thaliana
SEQUENCE: 420
atccggtaca ttccgttttg tttcccatcc c                                  31

SEQ ID NO: 421           moltype = RNA   length = 31
FEATURE                  Location/Qualifiers
source                   1..31
                         mol_type = other RNA
                         organism = Arabidopsis thaliana
SEQUENCE: 421
ctttctggtc agtaatggaa gcaatcgtcc c                                  31

SEQ ID NO: 422           moltype = RNA   length = 31
FEATURE                  Location/Qualifiers
source                   1..31
                         mol_type = other RNA
                         organism = Arabidopsis thaliana
SEQUENCE: 422
gtcagtaatg gaagcaatcg tccctaccgt c                                  31

SEQ ID NO: 423           moltype = RNA   length = 31
FEATURE                  Location/Qualifiers
source                   1..31
                         mol_type = other RNA
                         organism = Arabidopsis thaliana
SEQUENCE: 423
cctaccgtcg taaataaga gcacccggct c                                   31

SEQ ID NO: 424           moltype = RNA   length = 31
FEATURE                  Location/Qualifiers
source                   1..31
                         mol_type = other RNA
                         organism = Arabidopsis thaliana
SEQUENCE: 424
accgtcgtaa aataagagca cccggctctg c                                  31

SEQ ID NO: 425           moltype = RNA   length = 31
FEATURE                  Location/Qualifiers
source                   1..31
                         mol_type = other RNA
                         organism = Arabidopsis thaliana
SEQUENCE: 425
gtaaataag agcacccggc tctgcccatt c                                   31

SEQ ID NO: 426           moltype = RNA   length = 31
FEATURE                  Location/Qualifiers
source                   1..31
                         mol_type = other RNA
                         organism = Arabidopsis thaliana
SEQUENCE: 426
ccggctctgc ccattcacaa ggactcgatt c                                  31

SEQ ID NO: 427           moltype = RNA   length = 31
FEATURE                  Location/Qualifiers
source                   1..31
                         mol_type = other RNA
                         organism = Arabidopsis thaliana
SEQUENCE: 427
gactcgattc tatgtccaaa catcacatgc c                                  31

SEQ ID NO: 428           moltype = RNA   length = 31
```

-continued

```
FEATURE              Location/Qualifiers
source               1..31
                     mol_type = other RNA
                     organism = Arabidopsis thaliana
SEQUENCE: 428
gtccaaacat cacatgccag cagatgtggt c                               31

SEQ ID NO: 429       moltype = RNA   length = 31
FEATURE              Location/Qualifiers
source               1..31
                     mol_type = other RNA
                     organism = Arabidopsis thaliana
SEQUENCE: 429
tggtggaacg tgcggaacca catattggat c                               31

SEQ ID NO: 430       moltype = RNA   length = 31
FEATURE              Location/Qualifiers
source               1..31
                     mol_type = other RNA
                     organism = Arabidopsis thaliana
SEQUENCE: 430
acaaaactta tcttcaagct ttaccttatt c                               31

SEQ ID NO: 431       moltype = RNA   length = 31
FEATURE              Location/Qualifiers
source               1..31
                     mol_type = other RNA
                     organism = Arabidopsis thaliana
SEQUENCE: 431
atcttcaagc tttaccttat tctgatcgtt c                               31

SEQ ID NO: 432       moltype = RNA   length = 31
FEATURE              Location/Qualifiers
source               1..31
                     mol_type = other RNA
                     organism = Arabidopsis thaliana
SEQUENCE: 432
tcaagcttta ccttattctg atcgttcaga c                               31

SEQ ID NO: 433       moltype = RNA   length = 31
FEATURE              Location/Qualifiers
source               1..31
                     mol_type = other RNA
                     organism = Arabidopsis thaliana
SEQUENCE: 433
ctttccatg acgactagga aaaggcaaat c                                31

SEQ ID NO: 434       moltype = RNA   length = 31
FEATURE              Location/Qualifiers
source               1..31
                     mol_type = other RNA
                     organism = Arabidopsis thaliana
SEQUENCE: 434
tatgtttcta tgatggccca agaacacgct c                               31

SEQ ID NO: 435       moltype = RNA   length = 31
FEATURE              Location/Qualifiers
source               1..31
                     mol_type = other RNA
                     organism = Arabidopsis thaliana
SEQUENCE: 435
ctatgatggc ccaagaacac gctcattctt c                               31

SEQ ID NO: 436       moltype = RNA   length = 31
FEATURE              Location/Qualifiers
source               1..31
                     mol_type = other RNA
                     organism = Arabidopsis thaliana
SEQUENCE: 436
ttacgagctc aatatatacg agtgttattc c                               31

SEQ ID NO: 437       moltype = RNA   length = 31
FEATURE              Location/Qualifiers
source               1..31
                     mol_type = other RNA
                     organism = Arabidopsis thaliana
SEQUENCE: 437
gagtgttatt ccgtgaaata actcgaattt c                               31
```

-continued

```
SEQ ID NO: 438            moltype = RNA    length = 31
FEATURE                   Location/Qualifiers
source                    1..31
                          mol_type = other RNA
                          organism = Arabidopsis thaliana
SEQUENCE: 438
tccgtgaaat aactcgaatt tcaaatcatt c                                  31

SEQ ID NO: 439            moltype = RNA    length = 31
FEATURE                   Location/Qualifiers
source                    1..31
                          mol_type = other RNA
                          organism = Arabidopsis thaliana
SEQUENCE: 439
ctaggaaaag gcaaatcaaa aattttactt c                                  31

SEQ ID NO: 440            moltype = RNA    length = 31
FEATURE                   Location/Qualifiers
source                    1..31
                          mol_type = other RNA
                          organism = Arabidopsis thaliana
SEQUENCE: 440
cttctcgtat cgatgaatta gaagagatgt c                                  31

SEQ ID NO: 441            moltype = RNA    length = 31
FEATURE                   Location/Qualifiers
source                    1..31
                          mol_type = other RNA
                          organism = Arabidopsis thaliana
SEQUENCE: 441
tggggattca gtggtgtaat gttaagaggt c                                  31

SEQ ID NO: 442            moltype = RNA    length = 31
FEATURE                   Location/Qualifiers
source                    1..31
                          mol_type = other RNA
                          organism = Arabidopsis thaliana
SEQUENCE: 442
tgttaagagg tccaggggta tgctgggatt c                                  31

SEQ ID NO: 443            moltype = RNA    length = 31
FEATURE                   Location/Qualifiers
source                    1..31
                          mol_type = other RNA
                          organism = Arabidopsis thaliana
SEQUENCE: 443
gattcgcgaa gagcagcacc ttacgatgtt c                                  31

SEQ ID NO: 444            moltype = RNA    length = 31
FEATURE                   Location/Qualifiers
source                    1..31
                          mol_type = other RNA
                          organism = Arabidopsis thaliana
SEQUENCE: 444
gagcagcacc ttacgatgtt catgaccaat c                                  31

SEQ ID NO: 445            moltype = RNA    length = 31
FEATURE                   Location/Qualifiers
source                    1..31
                          mol_type = other RNA
                          organism = Arabidopsis thaliana
SEQUENCE: 445
gcaccttacg atgttcatga ccaatcggat c                                  31

SEQ ID NO: 446            moltype = RNA    length = 31
FEATURE                   Location/Qualifiers
source                    1..31
                          mol_type = other RNA
                          organism = Arabidopsis thaliana
SEQUENCE: 446
cttgacgtac cagtaggtac cagaggagat c                                  31

SEQ ID NO: 447            moltype = RNA    length = 31
FEATURE                   Location/Qualifiers
source                    1..31
                          mol_type = other RNA
                          organism = Arabidopsis thaliana
SEQUENCE: 447
gacctcaaca tcctgctgct catggtgttt c                                  31
```

-continued

```
SEQ ID NO: 448            moltype = RNA   length = 31
FEATURE                   Location/Qualifiers
source                    1..31
                          mol_type = other RNA
                          organism = Arabidopsis thaliana
SEQUENCE: 448
cagaggagat cgctatgatc gttactgtat c                                  31

SEQ ID NO: 449            moltype = RNA   length = 31
FEATURE                   Location/Qualifiers
source                    1..31
                          mol_type = other RNA
                          organism = Arabidopsis thaliana
SEQUENCE: 449
agatcgctat gatcgttact gtatccgtat c                                  31

SEQ ID NO: 450            moltype = RNA   length = 31
FEATURE                   Location/Qualifiers
source                    1..31
                          mol_type = other RNA
                          organism = Arabidopsis thaliana
SEQUENCE: 450
gatgtcgaat gaaactatcc atggaatcct c                                  31

SEQ ID NO: 451            moltype = RNA   length = 31
FEATURE                   Location/Qualifiers
source                    1..31
                          mol_type = other RNA
                          organism = Arabidopsis thaliana
SEQUENCE: 451
ccatttcgaa ctttatacag aaggtttttc c                                  31

SEQ ID NO: 452            moltype = RNA   length = 31
FEATURE                   Location/Qualifiers
source                    1..31
                          mol_type = other RNA
                          organism = Arabidopsis thaliana
SEQUENCE: 452
aattgcatac ctatacaagg gttcaagttt c                                  31

SEQ ID NO: 453            moltype = RNA   length = 31
FEATURE                   Location/Qualifiers
source                    1..31
                          mol_type = other RNA
                          organism = Arabidopsis thaliana
SEQUENCE: 453
caagtttcga tcgatatttg cggagttgat c                                  31

SEQ ID NO: 454            moltype = RNA   length = 31
FEATURE                   Location/Qualifiers
source                    1..31
                          mol_type = other RNA
                          organism = Arabidopsis thaliana
SEQUENCE: 454
accagtgcag acgaagtaac acgaatatct c                                  31

SEQ ID NO: 455            moltype = RNA   length = 31
FEATURE                   Location/Qualifiers
source                    1..31
                          mol_type = other RNA
                          organism = Arabidopsis thaliana
SEQUENCE: 455
ccggtagtaa gtctatttcc atcagccggc c                                  31

SEQ ID NO: 456            moltype = RNA   length = 31
FEATURE                   Location/Qualifiers
source                    1..31
                          mol_type = other RNA
                          organism = Arabidopsis thaliana
SEQUENCE: 456
tcatcaatca tccggatcta cgccgtatat c                                  31

SEQ ID NO: 457            moltype = RNA   length = 31
FEATURE                   Location/Qualifiers
source                    1..31
                          mol_type = other RNA
                          organism = Arabidopsis thaliana
SEQUENCE: 457
```

-continued

```
ggtttcgagg gtcatccatt acgaaaagac c                                          31

SEQ ID NO: 458           moltype = RNA   length = 31
FEATURE                  Location/Qualifiers
source                   1..31
                         mol_type = other RNA
                         organism = Arabidopsis thaliana
SEQUENCE: 458
aaatggaaag atcggaacat gggaatagat c                                          31

SEQ ID NO: 459           moltype = RNA   length = 31
FEATURE                  Location/Qualifiers
source                   1..31
                         mol_type = other RNA
                         organism = Arabidopsis thaliana
SEQUENCE: 459
cttggaaaaa atcgtagttc agattcaagt c                                          31

SEQ ID NO: 460           moltype = RNA   length = 31
FEATURE                  Location/Qualifiers
source                   1..31
                         mol_type = other RNA
                         organism = Arabidopsis thaliana
SEQUENCE: 460
cttggaaaaa atcgtagttc agattcaagt c                                          31

SEQ ID NO: 461           moltype = RNA   length = 31
FEATURE                  Location/Qualifiers
source                   1..31
                         mol_type = other RNA
                         organism = Arabidopsis thaliana
SEQUENCE: 461
tggtttgaca tggtttacgt gttactggtt c                                          31

SEQ ID NO: 462           moltype = RNA   length = 31
FEATURE                  Location/Qualifiers
source                   1..31
                         mol_type = other RNA
                         organism = Arabidopsis thaliana
SEQUENCE: 462
ggtttgacat ggtttacgtg ttactggttc c                                          31

SEQ ID NO: 463           moltype = RNA   length = 31
FEATURE                  Location/Qualifiers
source                   1..31
                         mol_type = other RNA
                         organism = Arabidopsis thaliana
SEQUENCE: 463
cgtgttactg gttcccggaa gagttaatat c                                          31

SEQ ID NO: 464           moltype = RNA   length = 31
FEATURE                  Location/Qualifiers
source                   1..31
                         mol_type = other RNA
                         organism = Arabidopsis thaliana
SEQUENCE: 464
gttactggtt cccggaagag ttaatatctc c                                          31

SEQ ID NO: 465           moltype = RNA   length = 31
FEATURE                  Location/Qualifiers
source                   1..31
                         mol_type = other RNA
                         organism = Arabidopsis thaliana
SEQUENCE: 465
tcccggaaga gttaatatct ccattagcgt c                                          31

SEQ ID NO: 466           moltype = RNA   length = 31
FEATURE                  Location/Qualifiers
source                   1..31
                         mol_type = other RNA
                         organism = Arabidopsis thaliana
SEQUENCE: 466
ggaagagtta atatctccat tagcgtcacc c                                          31

SEQ ID NO: 467           moltype = RNA   length = 31
FEATURE                  Location/Qualifiers
source                   1..31
                         mol_type = other RNA
                         organism = Arabidopsis thaliana
```

-continued

```
SEQUENCE: 467
cgtcaccctt tcttaccctg ccttttgact c                                    31

SEQ ID NO: 468            moltype = RNA   length = 31
FEATURE                   Location/Qualifiers
source                    1..31
                          mol_type = other RNA
                          organism = Arabidopsis thaliana
SEQUENCE: 468
ggagaacaaa ggacgaaata caatcgattc c                                    31

SEQ ID NO: 469            moltype = RNA   length = 31
FEATURE                   Location/Qualifiers
source                    1..31
                          mol_type = other RNA
                          organism = Arabidopsis thaliana
SEQUENCE: 469
gaacaaagga cgaaatacaa tcgattcctc c                                    31

SEQ ID NO: 470            moltype = RNA   length = 31
FEATURE                   Location/Qualifiers
source                    1..31
                          mol_type = other RNA
                          organism = Arabidopsis thaliana
SEQUENCE: 470
aatacaatcg attcctccat ttaagtggtt c                                    31

SEQ ID NO: 471            moltype = RNA   length = 31
FEATURE                   Location/Qualifiers
source                    1..31
                          mol_type = other RNA
                          organism = Arabidopsis thaliana
SEQUENCE: 471
tacaatcgat tcctccattt aagtggttct c                                    31

SEQ ID NO: 472            moltype = RNA   length = 31
FEATURE                   Location/Qualifiers
source                    1..31
                          mol_type = other RNA
                          organism = Arabidopsis thaliana
SEQUENCE: 472
attcctccat ttaagtggtt ctcgcttctt c                                    31

SEQ ID NO: 473            moltype = RNA   length = 31
FEATURE                   Location/Qualifiers
source                    1..31
                          mol_type = other RNA
                          organism = Arabidopsis thaliana
SEQUENCE: 473
tctcgcttct tcttgttcct gttcctaact c                                    31

SEQ ID NO: 474            moltype = RNA   length = 31
FEATURE                   Location/Qualifiers
source                    1..31
                          mol_type = other RNA
                          organism = Arabidopsis thaliana
SEQUENCE: 474
ctcgcttctt cttgttcctg ttcctaactc c                                    31

SEQ ID NO: 475            moltype = RNA   length = 31
FEATURE                   Location/Qualifiers
source                    1..31
                          mol_type = other RNA
                          organism = Arabidopsis thaliana
SEQUENCE: 475
cgcttcttct tgttcctgtt cctaactcct c                                    31

SEQ ID NO: 476            moltype = RNA   length = 31
FEATURE                   Location/Qualifiers
source                    1..31
                          mol_type = other RNA
                          organism = Arabidopsis thaliana
SEQUENCE: 476
ttcttcttgt tcctgttcct aactcctccc c                                    31

SEQ ID NO: 477            moltype = RNA   length = 31
FEATURE                   Location/Qualifiers
source                    1..31
                          mol_type = other RNA
```

```
                        organism = Arabidopsis thaliana
SEQUENCE: 477
cccgggtcgt tcccaatgtt tggcactttc c                                    31

SEQ ID NO: 478         moltype = RNA   length = 31
FEATURE                Location/Qualifiers
source                 1..31
                       mol_type = other RNA
                       organism = Arabidopsis thaliana
SEQUENCE: 478
cttcgtgggt gcaacatcaa caaattcgct c                                    31

SEQ ID NO: 479         moltype = RNA   length = 31
FEATURE                Location/Qualifiers
source                 1..31
                       mol_type = other RNA
                       organism = Arabidopsis thaliana
SEQUENCE: 479
atgatcaagt tacaacctaa gatctatgac c                                    31

SEQ ID NO: 480         moltype = RNA   length = 31
FEATURE                Location/Qualifiers
source                 1..31
                       mol_type = other RNA
                       organism = Arabidopsis thaliana
SEQUENCE: 480
atgaccatat tatgttaact gttcgtattt c                                    31

SEQ ID NO: 481         moltype = RNA   length = 31
FEATURE                Location/Qualifiers
source                 1..31
                       mol_type = other RNA
                       organism = Arabidopsis thaliana
SEQUENCE: 481
attatgttaa ctgttcgtat ttcgttcatt c                                    31

SEQ ID NO: 482         moltype = RNA   length = 31
FEATURE                Location/Qualifiers
source                 1..31
                       mol_type = other RNA
                       organism = Arabidopsis thaliana
SEQUENCE: 482
tcgtatttcg ttcattccat cggtatgctc c                                    31

SEQ ID NO: 483         moltype = RNA   length = 31
FEATURE                Location/Qualifiers
source                 1..31
                       mol_type = other RNA
                       organism = Arabidopsis thaliana
SEQUENCE: 483
cccaggtacc tgtaattgtg atctgtttgc c                                    31

SEQ ID NO: 484         moltype = RNA   length = 31
FEATURE                Location/Qualifiers
source                 1..31
                       mol_type = other RNA
                       organism = Arabidopsis thaliana
SEQUENCE: 484
gtacctgtaa ttgtgatctg tttgccagaa c                                    31

SEQ ID NO: 485         moltype = RNA   length = 31
FEATURE                Location/Qualifiers
source                 1..31
                       mol_type = other RNA
                       organism = Arabidopsis thaliana
SEQUENCE: 485
tacctgtaat tgtgatctgt ttgccagaac c                                    31

SEQ ID NO: 486         moltype = RNA   length = 31
FEATURE                Location/Qualifiers
source                 1..31
                       mol_type = other RNA
                       organism = Arabidopsis thaliana
SEQUENCE: 486
tatatatatc ctatgaattt aatttcgcat c                                    31

SEQ ID NO: 487         moltype = RNA   length = 31
FEATURE                Location/Qualifiers
source                 1..31
```

```
                           mol_type = other RNA
                           organism = Arabidopsis thaliana
SEQUENCE: 487
acgaacaatc gtcgtttttt gatggttttt c                                   31

SEQ ID NO: 488            moltype = RNA   length = 31
FEATURE                   Location/Qualifiers
source                    1..31
                           mol_type = other RNA
                           organism = Arabidopsis thaliana
SEQUENCE: 488
aatcgtcgtt ttttgatggt ttttccgctt c                                   31

SEQ ID NO: 489            moltype = RNA   length = 31
FEATURE                   Location/Qualifiers
source                    1..31
                           mol_type = other RNA
                           organism = Arabidopsis thaliana
SEQUENCE: 489
tggttttttcc gcttctcaca gctgctcttt c                                  31

SEQ ID NO: 490            moltype = RNA   length = 31
FEATURE                   Location/Qualifiers
source                    1..31
                           mol_type = other RNA
                           organism = Arabidopsis thaliana
SEQUENCE: 490
ggttttttccg cttctcacag ctgctctttc c                                  31

SEQ ID NO: 491            moltype = RNA   length = 31
FEATURE                   Location/Qualifiers
source                    1..31
                           mol_type = other RNA
                           organism = Arabidopsis thaliana
SEQUENCE: 491
ttccacacct ccggatatct ggtgccaaat c                                   31

SEQ ID NO: 492            moltype = RNA   length = 31
FEATURE                   Location/Qualifiers
source                    1..31
                           mol_type = other RNA
                           organism = Arabidopsis thaliana
SEQUENCE: 492
cctccggata tctggtgcca aatcgtcgcc c                                   31

SEQ ID NO: 493            moltype = RNA   length = 31
FEATURE                   Location/Qualifiers
source                    1..31
                           mol_type = other RNA
                           organism = Arabidopsis thaliana
SEQUENCE: 493
ggatatctgg tgccaaatcg tcgcccgttt c                                   31

SEQ ID NO: 494            moltype = RNA   length = 31
FEATURE                   Location/Qualifiers
source                    1..31
                           mol_type = other RNA
                           organism = Arabidopsis thaliana
SEQUENCE: 494
tgataataga gttggctatt tttgtggcat c                                   31

SEQ ID NO: 495            moltype = RNA   length = 31
FEATURE                   Location/Qualifiers
source                    1..31
                           mol_type = other RNA
                           organism = Arabidopsis thaliana
SEQUENCE: 495
attctaggag aagttcgaat ccgttccgtt c                                   31

SEQ ID NO: 496            moltype = RNA   length = 31
FEATURE                   Location/Qualifiers
source                    1..31
                           mol_type = other RNA
                           organism = Arabidopsis thaliana
SEQUENCE: 496
cctttgcacg agtcagaaac cgatgtattt c                                   31

SEQ ID NO: 497            moltype = RNA   length = 31
FEATURE                   Location/Qualifiers
```

-continued

```
source                  1..31
                        mol_type = other RNA
                        organism = Arabidopsis thaliana
SEQUENCE: 497
aaagctttat aaagccttt gtaaagatcc c                                               31

SEQ ID NO: 498         moltype = RNA   length = 31
FEATURE                Location/Qualifiers
source                 1..31
                       mol_type = other RNA
                       organism = Arabidopsis thaliana
SEQUENCE: 498
gtacaaaact gggtttggga agatatggca c                                              31

SEQ ID NO: 499         moltype = RNA   length = 31
FEATURE                Location/Qualifiers
source                 1..31
                       mol_type = other RNA
                       organism = Arabidopsis thaliana
SEQUENCE: 499
agatatggca ctaaaagttg taaagctggt c                                              31

SEQ ID NO: 500         moltype = RNA   length = 31
FEATURE                Location/Qualifiers
source                 1..31
                       mol_type = other RNA
                       organism = Arabidopsis thaliana
SEQUENCE: 500
tatttaacca taaaatcgat tatgctcctg c                                              31

SEQ ID NO: 501         moltype = RNA   length = 31
FEATURE                Location/Qualifiers
source                 1..31
                       mol_type = other RNA
                       organism = Arabidopsis thaliana
SEQUENCE: 501
ataaaatcga ttatgctcct gcggaagtat c                                              31

SEQ ID NO: 502         moltype = RNA   length = 31
FEATURE                Location/Qualifiers
source                 1..31
                       mol_type = other RNA
                       organism = Arabidopsis thaliana
SEQUENCE: 502
ggattgctcg tgtgtccacg ggacaaatcc c                                              31

SEQ ID NO: 503         moltype = RNA   length = 31
FEATURE                Location/Qualifiers
source                 1..31
                       mol_type = other RNA
                       organism = Arabidopsis thaliana
SEQUENCE: 503
gacaagccgc tacattagcg gctcataaac c                                              31

SEQ ID NO: 504         moltype = RNA   length = 31
FEATURE                Location/Qualifiers
source                 1..31
                       mol_type = other RNA
                       organism = Arabidopsis thaliana
SEQUENCE: 504
ccgctacatt agcggctcat aaaccatgtt c                                              31

SEQ ID NO: 505         moltype = RNA   length = 31
FEATURE                Location/Qualifiers
source                 1..31
                       mol_type = other RNA
                       organism = Arabidopsis thaliana
SEQUENCE: 505
ctgcggaagt atctactcgt tacggaatct c                                              31

SEQ ID NO: 506         moltype = RNA   length = 31
FEATURE                Location/Qualifiers
source                 1..31
                       mol_type = other RNA
                       organism = Arabidopsis thaliana
SEQUENCE: 506
atgaccctaa tcgttcttct cagatcgctc c                                              31

SEQ ID NO: 507         moltype = RNA   length = 31
```

-continued

```
FEATURE              Location/Qualifiers
source               1..31
                     mol_type = other RNA
                     organism = Arabidopsis thaliana
SEQUENCE: 507
aagttcgctc cgccgcgcaa gatcctcgaa c                               31

SEQ ID NO: 508       moltype = RNA   length = 31
FEATURE              Location/Qualifiers
source               1..31
                     mol_type = other RNA
                     organism = Arabidopsis thaliana
SEQUENCE: 508
aacgcatagc attctctggg cacataggat c                               31

SEQ ID NO: 509       moltype = RNA   length = 31
FEATURE              Location/Qualifiers
source               1..31
                     mol_type = other RNA
                     organism = Arabidopsis thaliana
SEQUENCE: 509
aaaaatggaa aattggctat ggagattccg c                               31

SEQ ID NO: 510       moltype = RNA   length = 31
FEATURE              Location/Qualifiers
source               1..31
                     mol_type = other RNA
                     organism = Arabidopsis thaliana
SEQUENCE: 510
ctctccgagg gcatggaatg tctaattttt c                               31

SEQ ID NO: 511       moltype = RNA   length = 31
FEATURE              Location/Qualifiers
source               1..31
                     mol_type = other RNA
                     organism = Arabidopsis thaliana
SEQUENCE: 511
atggaatgtc taatttttcg gtcagaatct c                               31

SEQ ID NO: 512       moltype = RNA   length = 31
FEATURE              Location/Qualifiers
source               1..31
                     mol_type = other RNA
                     organism = Arabidopsis thaliana
SEQUENCE: 512
ttccactcaa ttttcattac gaagatgtat c                               31

SEQ ID NO: 513       moltype = RNA   length = 31
FEATURE              Location/Qualifiers
source               1..31
                     mol_type = other RNA
                     organism = Arabidopsis thaliana
SEQUENCE: 513
ttcattacga agatgtatca cgtcaagatc c                               31

SEQ ID NO: 514       moltype = RNA   length = 31
FEATURE              Location/Qualifiers
source               1..31
                     mol_type = other RNA
                     organism = Arabidopsis thaliana
SEQUENCE: 514
cttcggccaa cacacaagat gagactttac c                               31

SEQ ID NO: 515       moltype = RNA   length = 31
FEATURE              Location/Qualifiers
source               1..31
                     mol_type = other RNA
                     organism = Arabidopsis thaliana
SEQUENCE: 515
gatgtatcac gtcaagatcc gttgctcaaa c                               31

SEQ ID NO: 516       moltype = RNA   length = 31
FEATURE              Location/Qualifiers
source               1..31
                     mol_type = other RNA
                     organism = Arabidopsis thaliana
SEQUENCE: 516
atgtatcacg tcaagatccg ttgctcaaac c                               31
```

-continued

```
SEQ ID NO: 517          moltype = RNA   length = 31
FEATURE                 Location/Qualifiers
source                  1..31
                        mol_type = other RNA
                        organism = Arabidopsis thaliana
SEQUENCE: 517
tcacgtcaag atccgttgct caaaccgaat c                                  31

SEQ ID NO: 518          moltype = RNA   length = 31
FEATURE                 Location/Qualifiers
source                  1..31
                        mol_type = other RNA
                        organism = Arabidopsis thaliana
SEQUENCE: 518
atcacgccaa cgttatggaa gttcctggat c                                  31

SEQ ID NO: 519          moltype = RNA   length = 31
FEATURE                 Location/Qualifiers
source                  1..31
                        mol_type = other RNA
                        organism = Arabidopsis thaliana
SEQUENCE: 519
ataaatgtcc ccagaaaaca ggagtatgcc c                                  31

SEQ ID NO: 520          moltype = RNA   length = 31
FEATURE                 Location/Qualifiers
source                  1..31
                        mol_type = other RNA
                        organism = Arabidopsis thaliana
SEQUENCE: 520
cgagaacacc gaaaaaacct aattccgctc c                                  31

SEQ ID NO: 521          moltype = RNA   length = 31
FEATURE                 Location/Qualifiers
source                  1..31
                        mol_type = other RNA
                        organism = Arabidopsis thaliana
SEQUENCE: 521
cggttgagca atcgacatga tatatttgct c                                  31

SEQ ID NO: 522          moltype = RNA   length = 31
FEATURE                 Location/Qualifiers
source                  1..31
                        mol_type = other RNA
                        organism = Arabidopsis thaliana
SEQUENCE: 522
ttgctcacat cccgggcgaa ggtcataatt c                                  31

SEQ ID NO: 523          moltype = RNA   length = 31
FEATURE                 Location/Qualifiers
source                  1..31
                        mol_type = other RNA
                        organism = Arabidopsis thaliana
SEQUENCE: 523
tgttaataag aggaggtaga gtgaaagatt c                                  31

SEQ ID NO: 524          moltype = RNA   length = 31
FEATURE                 Location/Qualifiers
source                  1..31
                        mol_type = other RNA
                        organism = Arabidopsis thaliana
SEQUENCE: 524
gtagagtgaa agattcgcca ggtgtaaaat c                                  31

SEQ ID NO: 525          moltype = RNA   length = 31
FEATURE                 Location/Qualifiers
source                  1..31
                        mol_type = other RNA
                        organism = Arabidopsis thaliana
SEQUENCE: 525
tagagtgaaa gattcgccag gtgtaaaatc c                                  31

SEQ ID NO: 526          moltype = RNA   length = 31
FEATURE                 Location/Qualifiers
source                  1..31
                        mol_type = other RNA
                        organism = Arabidopsis thaliana
SEQUENCE: 526
ggaccgtact cgagctttgg ataaatgtcc c                                  31
```

-continued

```
SEQ ID NO: 527          moltype = RNA   length = 31
FEATURE                 Location/Qualifiers
source                  1..31
                        mol_type = other RNA
                        organism = Arabidopsis thaliana
SEQUENCE: 527
caatcaatta agggtcaaat gttggaacct c                              31

SEQ ID NO: 528          moltype = RNA   length = 31
FEATURE                 Location/Qualifiers
source                  1..31
                        mol_type = other RNA
                        organism = Arabidopsis thaliana
SEQUENCE: 528
gaaagagagg aattccgtac aggtacaact c                              31

SEQ ID NO: 529          moltype = RNA   length = 31
FEATURE                 Location/Qualifiers
source                  1..31
                        mol_type = other RNA
                        organism = Arabidopsis thaliana
SEQUENCE: 529
gtatcaagat gtcaatctga gatcttattt c                              31

SEQ ID NO: 530          moltype = RNA   length = 31
FEATURE                 Location/Qualifiers
source                  1..31
                        mol_type = other RNA
                        organism = Arabidopsis thaliana
SEQUENCE: 530
gtacaggtac aactcttatt tttacgaagt c                              31

SEQ ID NO: 531          moltype = RNA   length = 31
FEATURE                 Location/Qualifiers
source                  1..31
                        mol_type = other RNA
                        organism = Arabidopsis thaliana
SEQUENCE: 531
tttttacgaa gtcaaaaaaa tgcgatcttt c                              31

SEQ ID NO: 532          moltype = RNA   length = 31
FEATURE                 Location/Qualifiers
source                  1..31
                        mol_type = other RNA
                        organism = Arabidopsis thaliana
SEQUENCE: 532
gtcagtcaaa ataaaatctg tttatcaaag c                              31

SEQ ID NO: 533          moltype = RNA   length = 31
FEATURE                 Location/Qualifiers
source                  1..31
                        mol_type = other RNA
                        organism = Arabidopsis thaliana
SEQUENCE: 533
aaaataaaat ctgtttatca aagcgcttct c                              31

SEQ ID NO: 534          moltype = RNA   length = 31
FEATURE                 Location/Qualifiers
source                  1..31
                        mol_type = other RNA
                        organism = Arabidopsis thaliana
SEQUENCE: 534
aaataaaatc tgtttatcaa agcgcttctc c                              31

SEQ ID NO: 535          moltype = RNA   length = 31
FEATURE                 Location/Qualifiers
source                  1..31
                        mol_type = other RNA
                        organism = Arabidopsis thaliana
SEQUENCE: 535
aggggtggag ggaatccgta tatgtttttc c                              31

SEQ ID NO: 536          moltype = RNA   length = 31
FEATURE                 Location/Qualifiers
source                  1..31
                        mol_type = other RNA
                        organism = Arabidopsis thaliana
SEQUENCE: 536
```

```
aaactaaatg ctataagcat agaaaaactt c                                      31

SEQ ID NO: 537          moltype = RNA   length = 31
FEATURE                 Location/Qualifiers
source                  1..31
                        mol_type = other RNA
                        organism = Arabidopsis thaliana
SEQUENCE: 537
actaaatgct ataagcatag aaaaacttct c                                      31

SEQ ID NO: 538          moltype = RNA   length = 31
FEATURE                 Location/Qualifiers
source                  1..31
                        mol_type = other RNA
                        organism = Arabidopsis thaliana
SEQUENCE: 538
tatttaacca taaaatcgat tatgctcctg c                                      31

SEQ ID NO: 539          moltype = RNA   length = 31
FEATURE                 Location/Qualifiers
source                  1..31
                        mol_type = other RNA
                        organism = Arabidopsis thaliana
SEQUENCE: 539
ataaaatcga ttatgctcct gcggaagtat c                                      31

SEQ ID NO: 540          moltype = RNA   length = 31
FEATURE                 Location/Qualifiers
source                  1..31
                        mol_type = other RNA
                        organism = Arabidopsis thaliana
SEQUENCE: 540
ctgcggaagt atctactcgt tacggaatct c                                      31

SEQ ID NO: 541          moltype = RNA   length = 31
FEATURE                 Location/Qualifiers
source                  1..31
                        mol_type = other RNA
                        organism = Arabidopsis thaliana
SEQUENCE: 541
ttcggctttc gtctcggtag gtgtattatt c                                      31

SEQ ID NO: 542          moltype = RNA   length = 31
FEATURE                 Location/Qualifiers
source                  1..31
                        mol_type = other RNA
                        organism = Arabidopsis thaliana
SEQUENCE: 542
accgattacc ctcgataaag aagaatcttt c                                      31

SEQ ID NO: 543          moltype = RNA   length = 31
FEATURE                 Location/Qualifiers
source                  1..31
                        mol_type = other RNA
                        organism = Arabidopsis thaliana
SEQUENCE: 543
taccctcgat aaagaagaat ctttctaaat c                                      31

SEQ ID NO: 544          moltype = RNA   length = 31
FEATURE                 Location/Qualifiers
source                  1..31
                        mol_type = other RNA
                        organism = Arabidopsis thaliana
SEQUENCE: 544
agcgttcctg atagaaaatg acgactcctt c                                      31

SEQ ID NO: 545          moltype = RNA   length = 31
FEATURE                 Location/Qualifiers
source                  1..31
                        mol_type = other RNA
                        organism = Arabidopsis thaliana
SEQUENCE: 545
cttggaaaaa atcgtagttc agattcaagt c                                      31

SEQ ID NO: 546          moltype = RNA   length = 31
FEATURE                 Location/Qualifiers
source                  1..31
                        mol_type = other RNA
                        organism = Arabidopsis thaliana
```

-continued

```
SEQUENCE: 546
gttctcgtat cgcttttttt gtagaaagct c                              31

SEQ ID NO: 547          moltype = RNA   length = 31
FEATURE                 Location/Qualifiers
source                  1..31
                        mol_type = other RNA
                        organism = Arabidopsis thaliana
SEQUENCE: 547
catatccctc acgacataag attaaaagat c                              31

SEQ ID NO: 548          moltype = RNA   length = 31
FEATURE                 Location/Qualifiers
source                  1..31
                        mol_type = other RNA
                        organism = Arabidopsis thaliana
SEQUENCE: 548
atatccctca cgacataaga ttaaaagatc c                              31

SEQ ID NO: 549          moltype = RNA   length = 31
FEATURE                 Location/Qualifiers
source                  1..31
                        mol_type = other RNA
                        organism = Arabidopsis thaliana
SEQUENCE: 549
acgacataag attaaaagat ccaaaccttc c                              31

SEQ ID NO: 550          moltype = RNA   length = 31
FEATURE                 Location/Qualifiers
source                  1..31
                        mol_type = other RNA
                        organism = Arabidopsis thaliana
SEQUENCE: 550
ataagattaa aagatccaaa ccttcctctt c                              31

SEQ ID NO: 551          moltype = RNA   length = 31
FEATURE                 Location/Qualifiers
source                  1..31
                        mol_type = other RNA
                        organism = Arabidopsis thaliana
SEQUENCE: 551
aagagatcta ttaagaagag aaagatttat c                              31

SEQ ID NO: 552          moltype = RNA   length = 31
FEATURE                 Location/Qualifiers
source                  1..31
                        mol_type = other RNA
                        organism = Arabidopsis thaliana
SEQUENCE: 552
tatatacaat tacaaactac acgaaagttg c                              31

SEQ ID NO: 553          moltype = RNA   length = 31
FEATURE                 Location/Qualifiers
source                  1..31
                        mol_type = other RNA
                        organism = Arabidopsis thaliana
SEQUENCE: 553
atacaattac aaactacacg aaagttgccc c                              31

SEQ ID NO: 554          moltype = RNA   length = 31
FEATURE                 Location/Qualifiers
source                  1..31
                        mol_type = other RNA
                        organism = Arabidopsis thaliana
SEQUENCE: 554
ttacaaacta cacgaaagtt gccccttttt c                              31

SEQ ID NO: 555          moltype = RNA   length = 31
FEATURE                 Location/Qualifiers
source                  1..31
                        mol_type = other RNA
                        organism = Arabidopsis thaliana
SEQUENCE: 555
gaacaaaacg aacttcatat atcccttttc c                              31

SEQ ID NO: 556          moltype = RNA   length = 31
FEATURE                 Location/Qualifiers
source                  1..31
                        mol_type = other RNA
```

-continued

```
                         organism = Arabidopsis thaliana
SEQUENCE: 556
gaacttcata tatcccttttt ccactcaatc c                                 31

SEQ ID NO: 557          moltype = RNA   length = 31
FEATURE                 Location/Qualifiers
source                  1..31
                        mol_type = other RNA
                        organism = Arabidopsis thaliana
SEQUENCE: 557
tcaatccaga aacaagattt gacgttattc c                                  31

SEQ ID NO: 558          moltype = RNA   length = 31
FEATURE                 Location/Qualifiers
source                  1..31
                        mol_type = other RNA
                        organism = Arabidopsis thaliana
SEQUENCE: 558
acaagatttg acgttattcc gcttcgtctc c                                  31

SEQ ID NO: 559          moltype = RNA   length = 31
FEATURE                 Location/Qualifiers
source                  1..31
                        mol_type = other RNA
                        organism = Arabidopsis thaliana
SEQUENCE: 559
ttcttgaaac tattcctcaa gcaaggcagc c                                  31

SEQ ID NO: 560          moltype = RNA   length = 31
FEATURE                 Location/Qualifiers
source                  1..31
                        mol_type = other RNA
                        organism = Arabidopsis thaliana
SEQUENCE: 560
aaataaggag atctttctat aaagaaattt c                                  31

SEQ ID NO: 561          moltype = RNA   length = 31
FEATURE                 Location/Qualifiers
source                  1..31
                        mol_type = other RNA
                        organism = Arabidopsis thaliana
SEQUENCE: 561
cattaagatt tcaaacttgt cgtctacttt c                                  31

SEQ ID NO: 562          moltype = RNA   length = 31
FEATURE                 Location/Qualifiers
source                  1..31
                        mol_type = other RNA
                        organism = Arabidopsis thaliana
SEQUENCE: 562
caaacttgtc gtctactttc aggaaatgtt c                                  31

SEQ ID NO: 563          moltype = RNA   length = 31
FEATURE                 Location/Qualifiers
source                  1..31
                        mol_type = other RNA
                        organism = Arabidopsis thaliana
SEQUENCE: 563
tcaaaaggat cgaactacct actcattatt c                                  31

SEQ ID NO: 564          moltype = RNA   length = 31
FEATURE                 Location/Qualifiers
source                  1..31
                        mol_type = other RNA
                        organism = Arabidopsis thaliana
SEQUENCE: 564
gaactaccta ctcattattc ggaggttaat c                                  31

SEQ ID NO: 565          moltype = RNA   length = 31
FEATURE                 Location/Qualifiers
source                  1..31
                        mol_type = other RNA
                        organism = Arabidopsis thaliana
SEQUENCE: 565
ttaatcatag aacaccaaaa gctgtggtat c                                  31

SEQ ID NO: 566          moltype = RNA   length = 31
FEATURE                 Location/Qualifiers
source                  1..31
```

```
                          mol_type = other RNA
                          organism = Arabidopsis thaliana
SEQUENCE: 566
taagctatag gataagctta gagaaatgtt c                                        31

SEQ ID NO: 567           moltype = DNA   length = 32
FEATURE                  Location/Qualifiers
misc_feature             1..32
                         note = Enko_B-F primer
source                   1..32
                         mol_type = other DNA
                         organism = synthetic construct
SEQUENCE: 567
cgcgaattca gcggagagag ttgcgaagca gg                                       32

SEQ ID NO: 568           moltype = DNA   length = 31
FEATURE                  Location/Qualifiers
misc_feature             1..31
                         note = Enko_B-R primer
source                   1..31
                         mol_type = other DNA
                         organism = synthetic construct
SEQUENCE: 568
cgcgtcgact catcccccaa atgatagatc c                                        31

SEQ ID NO: 569           moltype = DNA   length = 32
FEATURE                  Location/Qualifiers
misc_feature             1..32
                         note = Kosena_B-F primer
source                   1..32
                         mol_type = other DNA
                         organism = synthetic construct
SEQUENCE: 569
cgcgaattca gcggagagag ttgcgaagca gg                                       32

SEQ ID NO: 570           moltype = DNA   length = 31
FEATURE                  Location/Qualifiers
misc_feature             1..31
                         note = Kosena_B-R primer
source                   1..31
                         mol_type = other DNA
                         organism = synthetic construct
SEQUENCE: 570
cgcgtcgact catcccccaa atgatagatc c                                        31

SEQ ID NO: 571           moltype = DNA   length = 38
FEATURE                  Location/Qualifiers
misc_feature             1..38
                         note = Enko A-F primer
source                   1..38
                         mol_type = other DNA
                         organism = synthetic construct
SEQUENCE: 571
cgcgaattca gcagggatgg agagagtggc gaagcagg                                 38

SEQ ID NO: 572           moltype = DNA   length = 54
FEATURE                  Location/Qualifiers
misc_feature             1..54
                         note = Enko A-R primer
source                   1..54
                         mol_type = other DNA
                         organism = synthetic construct
SEQUENCE: 572
cgcgtcgact tcatcctcca actgatatcc cacactcatc tgcagatcct caag              54

SEQ ID NO: 573           moltype = DNA   length = 2064
FEATURE                  Location/Qualifiers
source                   1..2064
                         mol_type = genomic DNA
                         organism = Raphanus sativus
SEQUENCE: 573
atgttggcta gggtttgtgg attcaagtgt tcttcttctc ctgctgagtc tgcggctaga  60
ttgttctgta cgagatcgat tcgtgatact ctggccaagg caagcggaga gagttgcgaa  120
gcaggttttg gaggagagag tttgaagctg caaagtgggt ttcatgaaat caaaggttta  180
gaggatgcga ttgatttgtt cagtgacatg cttcgatctc gtcctttacc ttctgtggtt  240
gatttctgta aattgatggg tgtggtggtg agaatggaac gcccggatct tgtgatttct  300
ctctatcaga agatggaaag gaaacagatt cgatgtgata tatacagctt caatattctg  360
ataaaatgtt tctgcagctg ctctaagctc ccctttgctt tgtctacatt tggtaagatc  420
accaagcttg gactccaccc tgatgttgtt accttcacca ccctgctcca tggattatgt  480
```

```
gtggaagata gggtttctga agccttggat ttttttcatc aaatgtttga aacgacatgt   540
aggcccaatg tcgtaacctt caccactttg atgaacggtc tttgccgcga gggtagaatt   600
gtcgaagccg tagctctgct tgatcggatg atggaagatg gtctccagcc tacccagatt   660
acttatggaa caatcgtaga tgggatgtgt aagaagggag atactgtgtc tgcactgaat   720
ctgctgagga agatggagga ggtgagccac atcataccca atgttgtaat ctatagtgca   780
atcattgata gcctttgtaa agacggacgt catagcgatg cacaaaatct tttcactgaa   840
atgcaagaga aaggaatctt tcccgattta tttacctaca acagtatgat agttggtttt   900
tgtagctctg gtagatggag cgacgcggag cagttgttgc aagaaatgtt agaaaggaag   960
atcagccctg atgttgtaac ttataatgct ttgatcaatg catttgtcaa ggaaggcaag  1020
ttctttgagg ctgaagaatt atacgatgag atgcttccaa ggggtataat ccctaataca  1080
atcacatata gttcaatgat cgatggattt tgcaaacaga atcgtcttga tgctgctgag  1140
cacatgtttt atttgatggc taccaagggc tgctctccca acctaatcac tttcaatact  1200
ctcatagacg gatattgtgg ggctaagagg atagatgatg gaatggaact tctccatgag  1260
atgactgaaa caggattagt tgctgacaca actacttaca acactcttat tcacgggttc  1320
tatctggtgg gcgatcttaa tgctgctcta gaccttttac aagagatgat ctctagtggt  1380
ttgtgccctg atatcgttac ttgtgacact ttgctggatg gtctctgcga taatgggaaa  1440
ctaaaagatg cattggaaat gtttaaggtt atgcagaaga gtaagaagga tcttgatgct  1500
agtcacccct tcaatggtgt ggaacctgat gttcaaactt acaatatatt gatcagcggc  1560
ttgatcaatg aagggaagtt tttagaggcc gaggaattat acggaggat gccccacagg  1620
ggtatagtcc cagatactat cacctatagc tcaatgatcg atggattatg caagcagagc  1680
cgcctagatg aggctacaca aatgtttgat tcgatgggta gcaagagctt ctctccaaac  1740
gtagtgacct ttactacact cattaatggc tactgtaagg caggaaaggt tgatgatggg  1800
ctggagcttt tctgcgagat gggtcgaaga gggatagttg ctaacgcaat tacttacatc  1860
actttgattt gtggttttcg taaagtgggg aatattaatg gggctctaga cattttccag  1920
gagatgattt caagtggtgt gtatcctgat accattacca tccgcaatat gctgactggt  1980
ttatggagta aagaggaact aaaaagggca gtggcaatgc ttgagaaact gcagatgagt  2040
atggatctat catttggggg atga                                        2064
```

SEQ ID NO: 574           moltype = DNA   length = 2064
FEATURE                  Location/Qualifiers
source                   1..2064
                         mol_type = genomic DNA
                         organism = Raphanus sativus
SEQUENCE: 574

```
atgttggcta gggtttgtgg attcaagtgt tcttcttctc ctgctgagtc tgcggctaga   60
ttgttctgta cgagatcgat tcgtgatact ctggccaagg caagcggaga gagttgcgaa   120
gcaggttttg gaggagagag tttgaagctg caaagtgggt ttcatgaaat caaaggttta   180
gaggatgcga ttgatttgtt cagtgacatg cttcgatctc gtcctttacc ttctgtggtt   240
gatttctata aattgatggg tgtggtggtg agaatggaac gcccggatct tgtgatttct   300
ctctatcaga agatggaaag gaaacagatt cgatgtgata tatacagctt caccattctg   360
ataaaatgtt tctgcagctg ctctaagctc ccctttgctt tgtctacatt tggtaagatc   420
accaagcttg gactccaccc tgatgttgtt accttcaaca ccctgctcca cggattgtgc   480
gtggaagata gggtttctga agctttgaat ttgtttcaat aaatgtttga aacgacatgt   540
aggcccaatg tcgtaacctt caccactttg atgaacggtc tttgccgcga gggtagaatt   600
gtcgaagccg tagctctgct tgatcggatg atggaagatg gtctccagcc tacccagatt   660
acttatggaa caatcgtaga tgggatgtgt aagaagggag atactgtgtc tgcattgaat   720
cttctgagga agatggagga ggtgagccac atcataccca atgttgtaat ctatagtgca   780
atcattgata gcctttgtaa agacggacgt catagcgatg cacaaaatct tttcactgaa   840
atgcaagaga aaggaatctt tcccgattta tttacctaca acagtatgat agttggtttt   900
tgtagctctg gtagatggag cgacgcggag cagttgttgc aagaaatgtt agaaaggaag   960
atcagccctg atgttgtaac ttataatgct ttgatcaatg catttgtcaa ggaaggcaag  1020
ttctttgagg ctgaagaatt atacgatgag atgcttccaa ggggtataat ccctaataca  1080
atcacatata gttcaatgat cgatggattt tgcaaacaga atcgtcttga tgctgctgag  1140
cacatgtttt atttgatggc taccaagggc tgctctccca acctaatcac tttcaatact  1200
ctcatagacg gatattgtgg ggctaagagg atagatgatg gaatggaact tctccatgag  1260
atgactgaaa caggattagt tgctgacaca actacttaca acactcttat tcacgggttc  1320
tatctggtgg gcgatcttaa tgctgctcta gaccttttac aagagatgat ctctagtggt  1380
ttgtgccctg atatcgttac ttgtgacact ttgctggatg gtctctgcga taatgggaaa  1440
ctaaaagatg cattggaaat gtttaaggtt atgcagaaga gtaagaagga tcttgatgct  1500
agtcacccct tcaatggtgt ggaacctgat gttcaaactt acaatatatt gatcagcggc  1560
ttgatcaatg aagggaagtt tttagaggcc gaggaattat acggaggat gccccacagg  1620
ggtatagtcc cagatactat cacctatagc tcaatgatcg atggattatg caagcagagc  1680
cgcctagatg aggctacaca aatgtttgat tcgatgggta gcaagagctt ctctccaaac  1740
gtagtgacct ttactacact cattaatggc tactgtaagg caggaaaggt tgatgatggg  1800
ctggagcttt tctgcgagat gggtcgaaga gggatagttg ctaacgcaat tacttacatc  1860
actttgattt gtggttttcg taaagtgggg aatattaatg gggctctaga cattttccag  1920
gagatgattt caagtggtgt gtatcctgat accattacca tccgcaatat gctgactggt  1980
ttatggagta aagaggaact aaaaagggca gtggcaatgc ttgagaaact gcagatgagt  2040
atggatctat catttggggg atga                                        2064
```

SEQ ID NO: 575           moltype = DNA   length = 2061
FEATURE                  Location/Qualifiers
source                   1..2061
                         mol_type = genomic DNA
                         organism = Raphanus sativus
SEQUENCE: 575

```
atgttggcta gggtttgcag attcgagtct tcctcttcgt cttctgtgtc tgcggctaga   60
tttttctgta cgggatcgat tcgtcatgct ctggccgaga aaagcaggga tggagagagt   120
ggcgaagcag gttttagagg agagagtttg aaactgcgaa gtggatctta tgaaatcaaa   180
```

```
gggttagagg atgcgattga tttgttcagt gacatgcttc gatctcgtcc tttaccttct  240
gtgattgatt tcaacaagct aatgggtgcg gtggtgagaa tggaacgccc ggatcttgtg  300
atttctctct atcaaaagat ggaaaggaaa cagattcgat gtgatatata cagcttcacc  360
attctgataa aatgtttctg cagttgctct aagctcccct ttgctttgtc tacatttggt  420
aagctcacca agcttggact ccaccctgat gttgttacct tcaccaccct gctccacgga  480
ttatgtcttg atcacagggt ttctgaagcc ttggatttgt ttcatcaaat ttgtagacca  540
gatgtcctaa cgttcaccac gctgatgaat ggtctttgcc gcgagggtcg agttgtcgaa  600
gccgtagctc tgcttgatcg gatggtggaa aatggtctcc agcctgacca gattacttac  660
ggaacatttg tagatgggat gtgtaagatg ggcgacactg tgtctgcatt gaatcttctg  720
aggaagatgg aggagataag ccacatcaaa cccaatgtgg ttatctatag tgccatcatt  780
gatggccttt gtaaagatgg acgccatagc gattctcata atcttttcat tgaaatgcaa  840
gacaagggaa tctttccaaa tatagttacc tacaactgta tgatcggtgg attttgcatc  900
tctggtagat ggagtgcagc ccagcggttg ttgcaagaaa tgttagaaag gaagatcagc  960
cctaatgttg taacttataa tgctttgatc aatgcatttg tcaaggaagg caagttcctc  1020
gaggctgcag aattatacga tgagatgctt ccaaggggta tcattcctaa tacaatcaca  1080
tataattcaa tgatcgatgg gttttgcaaa caggatcgtc ttgatgctgc tgaggacatg  1140
ttttatttga tggctaccaa gggctgctct ccggacgtat tcactttcac tactctcata  1200
gacggatatt gtggggctaa gaggatagat gatggaatgg aacttctcca tgagatgcct  1260
agaagaggat tagttgctaa cacagttact tacaacactc ttattcacgg gttctgtctg  1320
gtgggcgatc ttaatgctgc tctagacctt tcacagcaga tgatttctag tggtgtgtgc  1380
cctgatatcg ttacttgtaa cactttgctg gacggtctct gcgataatgg gaaactaaaa  1440
gatgcattgg aaatgtttaa ggctatgcag aagagtaaga tggatcttga tgctagtcac  1500
cccttcaatg gtgtgtgaacc tgatgttcta acttacaata tattgatctg cggcttgatc  1560
aatgaaggga agtttttaga ggccgaggaa ttatacgagg agatgccaca cagaggtata  1620
gtcccagata ctatcaccta tagctcaatg atcgatggac tatgcaagca gagccgccta  1680
gatgaggcta cacaaatgtt tgtttcgatg ggtagcaaga gcttctctcc caacgtagtg  1740
acatttaaca cactcattaa tggctactgt aaggcaggaa gggttgatga tgggctggag  1800
cttttctgcg agatgggtcg aagagggata gttgctgatg caattattta catcactttg  1860
atttatggtt ttcgtaaagt gggtaatatt aatggggctc tagacatttt ccaggagatg  1920
atttcaagtg gtgtgtatcc tgataccatt actatccgca atatgctgac tggttttttgg  1980
agtaaagagg aactagaaag ggcagtggca atgcttgagg atctgcagat gagtgtgggg  2040
tatcagttgg aggatgaatg a                                            2061
```

SEQ ID NO: 576                moltype = AA   length = 687
FEATURE                       Location/Qualifiers
source                        1..687
                              mol_type = protein
                              organism = Raphanus sativus
SEQUENCE: 576
MLARVCGFKC SSSPAESAAR LFCTRSIRDT LAKASGESCE AGFGGESLKL QSGFHEIKGL    60
EDAIDLFSDM LRSRPLPSVV DFCKLMGVVV RMERPDLVIS LYQKMERKQI RCDIYSFNIL   120
IKCFCSCSKL PFALSTFGKI TKLGLHPDVV TFTTLLHGLC VEDRVSEALD FFHQMFETTC   180
RPNVVTFTTL MNGLCREGRI VEAVALLDRM MEDGLQPTQI TYGTIVDGMC KKGDTVSALN   240
LLRKMEEVSH IIPNVVIYSA IIDSLCKDGR HSDAQNLFTE MQEKGIFPDL FTYNSMIVGF   300
CSSGRWSDAE QLLQEMLERK ISPDVVTYNA LINAFVKEGK FFEAEELYDE MLPRGIIPNT   360
ITYSSMIDGF CKQNRLDAAE HMFYLMATKG CSPNLITFNT LIDGYCGAKR IDDGMELLHE   420
MTETGLVADT TTYNTLIHGF YLVGDLNAAL DLLQEMISSG LCPDIVTCDT LLDGLCDNGK   480
LKDALEMFKV MQKSKKDLDA SHPFNGVEPD VQTYNILISG LINEGKFLEA EELYEEMPHR   540
GIVPDTITYS SMIDGLCKQS RLDEATQMFD SMGSKSFSPN VVTFTTLING YCKAGRVDDG   600
LELFCEMGRR GIVANAITYI TLICGFRKVG NINGALDIFQ EMISSGVYPD TITIRNMLTG   660
LWSKEELKRA VAMLEKLQMS MDLSFGG                                       687

SEQ ID NO: 577                moltype = AA   length = 687
FEATURE                       Location/Qualifiers
source                        1..687
                              mol_type = protein
                              organism = Raphanus sativus
SEQUENCE: 577
MLARVCGFKC SSSPAESAAR LFCTRSIRDT LAKASGESCE AGFGGESLKL QSGFHEIKGL    60
EDAIDLFSDM LRSRPLPSVV DFCKLMGVVV RMERPDLVIS LYQKMERKQI RCDIYSFTIL   120
IKCFCSCSKL PFALSTFGKI TKLGLHPDVV TFNTLLHGLC VEDRVSEALN LFHQMFETTC   180
RPNVVTFTTL MNGLCREGRI VEAVALLDRM MEDGLQPTQI TYGTIVDGMC KKGDTVSALN   240
LLRKMEEVSH IIPNVVIYSA IIDSLCKDGR HSDAQNLFTE MQEKGIFPDL FTYNSMIVGF   300
CSSGRWSDAE QLLQEMLERK ISPDVVTYNA LINAFVKEGK FFEAEELYDE MLPRGIIPNT   360
ITYSSMIDGF CKQNRLDAAE HMFYLMATKG CSPNLITFNT LIDGYCGAKR IDDGMELLHE   420
MTETGLVADT TTYNTLIHGF YLVGDLNAAL DLLQEMISSG LCPDIVTCDT LLDGLCDNGK   480
LKDALEMFKV MQKSKKDLDA SHPFNGVEPD VQTYNILISG LINEGKFLEA EELYEEMPHR   540
GIVPDTITYS SMIDGLCKQS RLDEATQMFD SMGSKSFSPN VVTFTTLING YCKAGRVDDG   600
LELFCEMGRR GIVANAITYI TLICGFRKVG NINGALDIFQ EMISSGVYPD TITIRNMLTG   660
LWSKEELKRA VAMLEKLQMS MDLSFGG                                       687

SEQ ID NO: 578                moltype = AA   length = 686
FEATURE                       Location/Qualifiers
source                        1..686
                              mol_type = protein
                              organism = Raphanus sativus
SEQUENCE: 578
MLARVCRFES SSSSSVSAAR FFCTGSIRHA LAEKSRDGES GEAGFRGESL KLRSGSYEIK    60
GLEDAIDLFS DMLRSRPLPS VIDFNKLMGA VVRMERPDLV ISLYQKMERK QIRCDIYSFT   120
```

-continued

```
ILIKCFCSCS KLPFALSTFG KLTKLGLHPD VVTFTTLLHG LCLDHRVSEA LDLFHQICRP   180
DVLTFTTLMN GLCREGRVVE AVALLDRMVE NGLQPDQITY GTFVDGMCKM GDTVSALNLL   240
RKMEEISHIK PNVVIYSAII DGLCKDGRHS DSHNLFIEMQ DKGIFPNIVT YNCMIGGFCI   300
SGRWSAAQRL LQEMLERKIS PNVVTYNALI NAFVKEGKFF EAAELYDEML PRGIIPNTIT   360
YNSMIDGFCK QDRLDAAEDM FYLMATKGCS PDVFTFTTLI DGYCGAKRID DGMELLHEMP   420
RRGLVANTVT YNTLIHGFCL VGDLNAALDL SQQMISSGVC PDIVTCNTLL DGLCDNGKLK   480
DALEMFKAMQ KSKMDLDASH PFNGVEPDVL TYNILICGLI NEGKFLEAEE LYEEMPHRGI   540
VPDTITYSSM IDGLCKQSRL DEATQMFVSM GSKSFSPNVV TFNTLINGYC KAGRVDDGLE   600
LFCEMGRRGI VADAIIYITL IYGFRKVGNI NGALDIFQEM ISSGVYPDTI TIRNMLTGFW   660
SKEELERAVA MLEDLQMSVG YQLEDE                                        686

SEQ ID NO: 579              moltype = DNA   length = 41
FEATURE                     Location/Qualifiers
misc_feature                1..41
                            note = A-F primer primer
source                      1..41
                            mol_type = other DNA
                            organism = synthetic construct
SEQUENCE: 579
aatacgactc actatagaag aagaagctgc tttgtggagt g                         41

SEQ ID NO: 580              moltype = DNA   length = 24
FEATURE                     Location/Qualifiers
misc_feature                1..24
                            note = A-R primer primer
source                      1..24
                            mol_type = other DNA
                            organism = synthetic construct
SEQUENCE: 580
tgcatttata tgctgaagaa aagc                                             24

SEQ ID NO: 581              moltype = DNA   length = 48
FEATURE                     Location/Qualifiers
misc_feature                1..48
                            note = B-F primer primer
source                      1..48
                            mol_type = other DNA
                            organism = synthetic construct
SEQUENCE: 581
tagataatac gactcactat aggggatgatt acctttttcg aaaaattg                  48

SEQ ID NO: 582              moltype = DNA   length = 38
FEATURE                     Location/Qualifiers
misc_feature                1..38
                            note = B-R primer primer
source                      1..38
                            mol_type = other DNA
                            organism = synthetic construct
SEQUENCE: 582
aaaccagctt agccaaatat gggccattag caaataag                              38

SEQ ID NO: 583              moltype = DNA   length = 42
FEATURE                     Location/Qualifiers
misc_feature                1..42
                            note = C-F primer primer
source                      1..42
                            mol_type = other DNA
                            organism = synthetic construct
SEQUENCE: 583
aatacgactc actatagtat ttggctaagc tggttttcta ac                        42

SEQ ID NO: 584              moltype = DNA   length = 27
FEATURE                     Location/Qualifiers
misc_feature                1..27
                            note = C-R primer primer
source                      1..27
                            mol_type = other DNA
                            organism = synthetic construct
SEQUENCE: 584
gacacctagc cacccatact gaaattc                                          27

SEQ ID NO: 585              moltype = AA   length = 667
FEATURE                     Location/Qualifiers
source                      1..667
                            mol_type = protein
                            organism = Raphanus sativus
SEQUENCE: 585
MLARVCRFES SSSVPAARLF CTRSIRHTLA KKSSGKAGGF GGERLKLQSG FHEIKGLDDA    60
IDLFGYMVRS RPLPCVIDFC KLLGVVVRME RPDVVISLHR KMEMRRIPCN IYSFTILIKC   120
```

```
FCSCSKLPFA LSTFGKITKL GFHPSLVTFS TLLHGLCVED RVSEALHFFH QICKPNVIAF    180
TTLMNGLCRE GRVVEAVALL DRMVEDGLQP NQITYGTIVD GMCKMGDTVS ALNLLRKMEE    240
VSRIKPNVVI YSAIIDGLWK DGRQTDAQNL FSEMQEKGIS PNLFTYNCMI NGFCSSGRWS    300
EAQRLLREMF ERKMSPDVVT FSVLINALVK EGKFFEAEEL YNEMLPRGII PNTITYNSMI    360
DGFSKQNRLD AAERMFYLMA TKGCSPDVIT FSILIDGYCG AKRVDDGMKL LHEMSRRGLV    420
ANTITYTTLI HGFCQLGNLN AALDLLQEMI SSGVCPNVVT CNTLLDGLCN NGKLKDALEM    480
FKVMQKSKMD LDASHPFNDV EPDVQTYNIL ICGLINEGKF SEAEELYEEM PHRGLVPDTI    540
TYNSVIDGLC KQSRLDEATQ MFDSMGSKGF SPDVVTFTTL INGYCKVGRV GDGLEVFCEM    600
GRRGIVANAI TYRTLIHGFC QVGNINGALD IFQEMISSGV YPDTITIRNM LTGLWSKEEL    660
KRAVQCL                                                              667

SEQ ID NO: 586          moltype = AA  length = 683
FEATURE                 Location/Qualifiers
source                  1..683
                        mol_type = protein
                        organism = Raphanus sativus
SEQUENCE: 586
MLARVCRFES SSSSSVSAAR FFCTGSIRHA LAEKSRDGES GEAGFRGESL KLRSGSYEIK    60
GLEDAIDLFS DMLRSRPLPS VIDFNKLMGA VVRMERPDLV ISLYQKMERK QIRCDIYSFT    120
ILIKCFCSCS KLPFALSTFG KLTKLGLHPD VVTFTTLLHG LCLDHRVSEA LDLFHQICRP    180
DVLTFTTLMN GLCREGRVVE AVALLDRMVE NGLQPDQITY GTFVDGMCKM GDTVSALNLL    240
RKMEEISHIK PNVVIYSAII DGLCKDGRHS DSHNLFIEMQ DKGIFPNIVT YNCMIGGFCI    300
SGRWSAAQRL LQEMLERKIS PNVVTYNALI NAFVKEGKFF EAAELYDEML PRGIIPNTIT    360
YNSMIDGFCK QDRLDAAEDM FYLMATKGCS PDVFTFTTLI DGYCGAKRID DGMELLHEMP    420
RRGLVANTVT YNTLIHGFCL VGDLNAALDL SQQMISSGVC PDIVTCNTLL DGLCDNGKLK    480
DALEMFKAMQ KSKMDLDASH PFNGVEPDVL TYNILICGLI NEGKFLEAEE LYEEMPHRGI    540
VPDTITYSSM IDGLCKQSRL DEATQMFVSM GSKSFSPNVV TFNTLINGYC KAGRVDDGLE    600
LFCEMGRRGI VADAIIYITL IYGFRKVGNI NGALDIFQEM ISSGVYPDTI TIRNMLTGFW    660
SKEELERAVA MLEDLQRYQL EDE                                            683

SEQ ID NO: 587          moltype = AA  length = 687
FEATURE                 Location/Qualifiers
source                  1..687
                        mol_type = protein
                        organism = Raphanus sativus
SEQUENCE: 587
MLARVCGFKC SSSPAESAAR LFCTRSIRDT LAKASGESCE AGFGGESLKL QSGFHEIKGL    60
EDAIDLFSDM LRSRPLPSVV DFCKLMGVVV RMKRPDVVIS LHKKVEMRRI PCDAYSFNIL    120
IKCFCSCSKL PFALSTFGKI TKLGLHPDVV TFTTLLHGLC VEDRVSEALN LFHQMFETTC    180
RPNVVTFTTL MNGLCREGRI VEAVALLDRM MEDGLQPTQI TYGTIVDGMC KKGDTVSALN    240
LLRKMEEVSH IIPNVVIYSA IIDSLCKDGR HSDAQNLFTE MQEKGIFPDL FTYNSMIVGF    300
CSSGRWSDAE QLLQEMLERK ISPDVVTYNA LINAFVKEGK FFEAEELYDE MLPRGIIPNT    360
ITYSSMIDGF CKQNRLDAAE NMFYLMATKG CSPNLITFNT LIDGYCGAKR IDDGMELLHE    420
MTETGLVADT TTYNTLIHGF CLVGDLNAAL DLLQEMISSG LCPDIVTCDT LLDGLCDNGK    480
LKDALEMFKV MQKSKKDLDA SHPFNGVEPD VQTYNILISG LINEGKFLEA EELYEEMPHR    540
GIVPDTITYS SMIDGLCKQS RLDEATQMFD SMGSKSFSPN VVTFTTLING YCKAGRVDDG    600
LELFCEMGRR GIVANAITYI TLICGFRKVG NINGALDIFQ EMISSGVYPD TITIRNMLTG    660
LWSKEELKRA VAMLEKLQMS MDLSFGG                                        687

SEQ ID NO: 588          moltype = AA  length = 690
FEATURE                 Location/Qualifiers
source                  1..690
                        mol_type = protein
                        organism = Raphanus sativus
SEQUENCE: 588
MLARVCRFES SSSSSVSAAR MFCTGSIRHA LAKKGRDGES GEAGFGGESL KLRSGFHEIK    60
GLEDAIDLFS DMLRSRPLPS VIDFNKLMGV VVRMERPDLV ISLYQKMERK QIPCDVYSFN    120
ILIKCFCSCS KLPFALSTFG KITKLGLHPD VATFNTLLHG LCLDKRVSEA LDLFHQMFET    180
TCRPNIITFT TLMNGLCYEG RVVEAVALLD RMLEDGLQPD QITYGTIVDG MCKMGDTVSA    240
LNLLRKMEEL SHIKPNVVIY SAIIDGLWKD GRHTDAQNLF SEMQEKGIFP NLFTYTCMIN    300
GFCDSGRWSE AQQLLQEMLV RKISPNVVTY SALINAFVKE GKFFEAEELY DEMLPRGIIP    360
STVTYSSMID GFCKQNRLDA AEHMFYLMPT KGCSPNLITF NTLIAGYCRA KRVDDGMELL    420
HEMTETGLVA DTTTYNTLIH GFCLVDDLNA ALDLSQQMIS SGVCPDIVTC NTLLDGLCDN    480
GKLKDALEMF KAMQKSKMDF DASHPFNDVE PDVLTYNILI SGLINDGKFL GAEELYEEMP    540
HRGIVPDTFT YNSMICGLCK QNRLDEAKQM SDSMGSKSFS PNVVTFNTLI NGYCKAGRVD    600
DGLELFCGMG QRGIVANAIT YITLIHGFRK VDNINGALDI FQEMISSGVY PDTITIRNML    660
TGLWSKEELK RAVAMLEDLQ MSVGYQLEDE                                     690

SEQ ID NO: 589          moltype = AA  length = 690
FEATURE                 Location/Qualifiers
source                  1..690
                        mol_type = protein
                        organism = Raphanus sativus
SEQUENCE: 589
MLARVCRFES SSSSSVSAAR MFCTGSIRHA LAKKGRDGES GEAGFGGESL KLRSGFHEIK    60
GLEDAIDLFS DMLRSRPLPS VIDFNKLMGV VVRMERPDLV ISLYQKMERK QIPCDVYSFN    120
ILIKCFCSCS KLPFALSTFG KITKLGLHPD VATFNTLLHG LCLDKRVSEA LDLFHQMFET    180
TCRPNIITFT TLMNGLCYEG RVVEAVALLD RMLEDGLQPD QITYGTIVDG MCKMGDTVSA    240
LNLLRKMEEL SHIKPNVVIY SAIIDGLWKD GRHTDAQNLF SEMQEKGIFP NLFTYTCMIN    300
```

-continued

```
GFCDSGRWSE AQQLLQEMLV RKISPNVVTY SALINAFVKE GKFFEAEELY DEMLPRGIIP  360
STVTYSSMID GFCKQNRLDA AEHMFYLMPT KGCSPNLITF NTLIAGYCRA KRVDDGMELL  420
HEMTETGLVA DTTTYNTLIH GFCLVDDLNA ALDLSQQMIS SGVCPDIVTC NTLLDGLCDN  480
GKLKDALEMF KAMQKSKMDF DASHPFNDVE PDVLTYNILI SGLINDGKFL GAEELYEEMP  540
HRGIVPDTVT YNSVINGLCK QSRLNEAKQM SDSMGSRSFS PNVVTFNTLI NGYCKAGRVD  600
DGLELFCEMG RRGVVANAIT YITLIHGFSK VGNINGALDI FQEMMASGVY PDTITIRNML  660
TGLWSKEEVK RAVAMLEDLQ MSVGYQLEDE                                   690

SEQ ID NO: 590        moltype = AA  length = 683
FEATURE               Location/Qualifiers
source                1..683
                      mol_type = protein
                      organism = Raphanus sativus
SEQUENCE: 590
MLARVYRSGS SSSPAVSAAR LFCTRSIRHA LAKKSRDGES GFGGESLKLR SGFHEIKGLE  60
DAIDLFGDMV RSRPLPSVID FCKLMGVVVR MGRLDVVISL HRKMEMGRVP CNAYSFTILM  120
KCFCSCSKLP FALSTFGKIT KLGLHPDVVT FNTLLHGLCV EDRVSEALYL FHQMCKPNVV  180
TFTTLMKGLC REGRVVEAVA LLDRMVEDGL QPNQITYGTI VDGMCKMGDS VSALDLLRKM  240
EEVSHIKPDV VIYSAIIDGL WKDGRHTDAQ NLFSEMQDKR IFPDLFTYSC MIDGFCSSGR  300
WSEAQQLLQE MLERKISPDV VTYNALINAF VKEGKFFEAE ELYDEMLPRG IIPNTITYSS  360
MIDGFCKQNR LDAAEHMFYL MATKGCSPDV FTFNTLIDGY CGAKRIDDGM ELLHEMTEAG  420
LVANTVTYTT LIHGFCQVGD LNSAQDLLQE MISSGVCPNV VTCNTLLDGL CDNGKLKDAL  480
KMFKAMQKSK KNFDASHPFN GVEPDVLTYN ILICGLINEG KFIEAEELYE EMPHRGIVPD  540
TITYSSMIDG LCKQSRLDEA TQMSDSMGSK SFSPNVVTFN TLINGYCKAG RVDDGLELFC  600
EMGRRGIVAN AITYITLIYG SRKVGNINGA LDIFQEMISS GVYPDTITIR NMLTGLWSKE  660
ELERAVAMLE VLQMSVGYQL EDE                                          683

SEQ ID NO: 591        moltype = AA  length = 686
FEATURE               Location/Qualifiers
source                1..686
                      mol_type = protein
                      organism = Raphanus sativus
SEQUENCE: 591
MLARVCRFES SSSSSVSAAR LLCTRSIHLP LAEKSRDGEN GEAGSGGESL KLQSGSYEIK  60
GLEDAIDLFS DMLRSRPLPS VIDFNKLMGA VVRMERPDLV ISLYQKMERK QIRCDIYSFT  120
ILIKCFCSCS KLPVALSTFG KLTKLGLHPD VVTFTTLLHG LCVEDRVSEA LDLFHQMCKP  180
NVVTFNTLMN GLCREGRVVE AVALLDQMVE NGLQPDQITY GTIVDGMCKM GDTVSALNLL  240
RKMEEVSHII PNVVIYSAII DGLCKDGRHS DAHNLFIEMQ DKGIFPNIVT YNCMIGGFCI  300
SGRWSAAQRL LQEMLVRKIS PNVVTYNALI NAFVKEGKFF EAEELYDEML PRGIIPNTIT  360
YNSMIDGFCK QNRLDAAEHM FYVMATKGCS PDVFTFNTLI DGYCGAKRID DGMELLHEMT  420
ETGLVADTTT YNTLIHGFCL VGDLNAALDL LQEMVSSGVC PDIVTCNTLL DGLCDNGKLK  480
DALEMFKAMQ KSKMYIDASH PFNGVEPDVL TYNILICGLI NEGKFLEAEE LYEEMPHRGI  540
VPDTITYSSM IDGLCKQSRL DEATQMFVSM GSKSFSPNVV TFNTLINGYC KAGRVDDGLE  600
LFCEMGRRGI VADAITYITL IYGFRKVGNI NGALDIFQEM MASGVYPDTI TIRNMLTGLW  660
SKEELKRAVA MLEDLQMSVG YQLEDE                                       686
```